(12) United States Patent
Tyte et al.

(10) Patent No.: US 8,754,242 B2
(45) Date of Patent: *Jun. 17, 2014

(54) HERBICIDES

(75) Inventors: Melloney Tyte, Bracknell (GB);
Christopher John Matthews, Bracknell (GB); Gavin John Hall, Bracknell (GB); William Guy Whittingham, Bracknell (GB); Jeffrey Steven Wailes, Bracknell (GB); James Nicholas Scutt, Bracknell (GB); Stephane André Marie Jeanmart, Bracknell (GB); Russell Colin Viner, Bracknell (GB)

(73) Assignees: Syngenta Crop Protection LLC, Greensboro, NC (US); Syngenta Limited, Guildford, Surrey (GB)

( * ) Notice: Subject to any disclaimer, the term of this patent is extended or adjusted under 35 U.S.C. 154(b) by 964 days.

This patent is subject to a terminal disclaimer.

(21) Appl. No.: 12/672,165

(22) PCT Filed: Aug. 6, 2008

(86) PCT No.: PCT/EP2008/006467
§ 371 (c)(1),
(2), (4) Date: Jul. 11, 2011

(87) PCT Pub. No.: WO2009/019005
PCT Pub. Date: Feb. 12, 2009

(65) Prior Publication Data
US 2012/0094832 A1    Apr. 19, 2012

(30) Foreign Application Priority Data

Aug. 8, 2007 (GB) .................................. 0715454.5

(51) Int. Cl.
  *C07D 493/08*  (2006.01)
  *C07D 407/04*  (2006.01)
  *A01N 43/08*  (2006.01)
  *A01N 43/12*  (2006.01)
  *A01N 43/90*  (2006.01)

(52) U.S. Cl.
  USPC ........... 549/300; 549/200; 549/229; 549/263; 504/116.1; 504/140; 504/209; 504/283; 504/291; 504/294; 504/297; 504/354; 504/288; 514/449; 514/461; 514/468; 514/675; 514/680

(58) Field of Classification Search
  USPC .............. 549/300, 200, 229, 263; 504/116.1, 504/140, 209, 283, 288, 291, 294, 297, 504/354; 514/449, 461, 468, 675, 680
  See application file for complete search history.

(56) References Cited

U.S. PATENT DOCUMENTS

| | | | |
|---|---|---|---|
| 4,175,135 A | 11/1979 | Haines | |
| 4,209,532 A | 6/1980 | Wheeler | |
| 4,256,659 A | 3/1981 | Wheeler | |
| 4,283,348 A | 8/1981 | Wheeler | |
| 4,338,122 A | 7/1982 | Wheeler | |
| 4,371,711 A | 2/1983 | Saito et al. | |
| 4,409,153 A | 10/1983 | Hodakowski | |
| 4,489,012 A | 12/1984 | Hodakowski | |
| 4,526,723 A | 7/1985 | Wheeler et al. | |
| 4,551,547 A | 11/1985 | Wheeler | |
| 4,659,372 A | 4/1987 | Wheeler | |
| 5,808,135 A * | 9/1998 | Fischer et al. | ................. 560/129 |
| 5,840,661 A | 11/1998 | Fischer et al. | |
| 6,251,833 B1 | 6/2001 | Erdelen et al. | |
| 6,358,887 B1 | 3/2002 | Fischer et al. | |
| 6,458,965 B1 | 10/2002 | Lieb et al. | |
| 6,515,184 B1 | 2/2003 | Fischer et al. | |
| 6,569,810 B1 | 5/2003 | Fischer et al. | |
| 6,642,180 B1 | 11/2003 | Fischer et al. | |
| 6,894,005 B1 | 5/2005 | Maetzke et al. | |
| 8,058,210 B2 | 11/2011 | Lieb et al. | |
| 8,084,649 B2 | 12/2011 | Muehlebach et al. | |
| 8,530,388 B2 | 9/2013 | Whittingham et al. | |
| 8,530,667 B2 | 9/2013 | Jeanmart et al. | |
| 2003/0199572 A1 | 10/2003 | Lieb et al. | |
| 2003/0216260 A1 | 11/2003 | Ruther et al. | |

(Continued)

FOREIGN PATENT DOCUMENTS

| | | |
|---|---|---|
| CA | 2322158 | 8/2000 |
| CA | 2325526 | 9/2000 |

(Continued)

OTHER PUBLICATIONS

Walter Ried, et al: "Ringerweiterungen and Umlagerungen von 3-Alkyl-4-phenylcyclobutendionen;" Chemische Berichte., vol. 115, 1982, pp. 783-790, XP002545737, Verlag Chemie GMBH, Weinheim, p. 785; compound.
Organometallics, vol. 18, No. 21, 1999, pp. 4429-4436, XP002545728, ACS, Washington, DC, p. 4430; compounds 4D-4H.
M. Muehlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.
J. Wenger and T. Nidermann, "Chapter 9: Acetyl-CoA Carboxylase Inhibitors", in Modern Crop Protection Compounds, ed. W. Kraemer et al., Wiley-VCH Verlag, Weinheim, 2007, pp. 335-357.
J. Wenger, T. Nidermann and C. Mathews, "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

*Primary Examiner* — Jane C Oswecki
(74) *Attorney, Agent, or Firm* — R. Kody Jones

(57) ABSTRACT

Compounds of formula (I) wherein the substituents are as defined in claim 1, are suitable for use as herbicides.

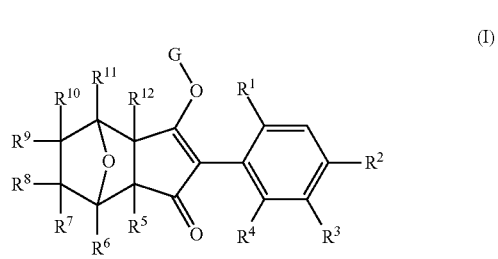

20 Claims, No Drawings

(56) References Cited

U.S. PATENT DOCUMENTS

| | | |
|---|---|---|
| 2005/0164883 A1 | 7/2005 | Maetzke et al. |
| 2006/0058194 A1 | 3/2006 | Fischer et al. |
| 2006/0166829 A1 | 7/2006 | Fischer et al. |
| 2007/0015664 A1 | 1/2007 | Fischer et al. |
| 2007/0298968 A1 | 12/2007 | Bretschneider et al. |
| 2007/0298969 A1 | 12/2007 | Fischer et al. |
| 2008/0167188 A1 | 7/2008 | Fischer et al. |
| 2009/0137393 A1 | 5/2009 | Fischer et al. |
| 2009/0227563 A1 | 9/2009 | Fischer et al. |
| 2009/0239906 A1 | 9/2009 | Fischer et al. |
| 2009/0298828 A1 | 12/2009 | Fischer et al. |
| 2009/0305891 A1 | 12/2009 | Fischer et al. |
| 2010/0009850 A1 | 1/2010 | Fischer et al. |
| 2010/0113270 A1 | 5/2010 | Mathews et al. |
| 2010/0210466 A1 | 8/2010 | Muehlebach et al. |
| 2010/0216638 A1 | 8/2010 | Mathews et al. |
| 2010/0298140 A1 | 11/2010 | Jeanmart et al. |
| 2011/0263428 A1 | 10/2011 | Jeanmart et al. |
| 2012/0021912 A1 | 1/2012 | Mathews et al. |
| 2012/0028800 A1 | 2/2012 | Mathews et al. |
| 2012/0065064 A1 | 3/2012 | Taylor et al. |
| 2012/0065066 A1 | 3/2012 | Mathews et al. |
| 2012/0142529 A1 | 6/2012 | Tyte et al. |

FOREIGN PATENT DOCUMENTS

| | | |
|---|---|---|
| CA | 2382432 | 2/2002 |
| CA | 2382435 | 2/2002 |
| CA | 2404868 | 9/2002 |
| CA | 2456776 | 2/2004 |
| CA | 2636352 | 7/2008 |
| DE | 2813341 | 4/1983 |
| WO | 96/01798 | 1/1996 |
| WO | 96/03366 | 2/1996 |
| WO | 9603366 | 2/1996 |
| WO | 96/25395 | 8/1996 |
| WO | 96/35664 | 11/1996 |
| WO | 97/14667 | 4/1997 |
| WO | 98/39281 | 9/1998 |
| WO | 99/43649 | 9/1999 |
| WO | 99/47525 | 9/1999 |
| WO | 99/48869 | 9/1999 |
| WO | 9948869 | 9/1999 |
| WO | 00/15615 | 3/2000 |
| WO | 00/47585 | 8/2000 |
| WO | 01/09092 | 2/2001 |
| WO | 01/17972 | 3/2001 |
| WO | 01/17973 | 3/2001 |
| WO | 01/74770 | 10/2001 |
| WO | 0174770 | 10/2001 |
| WO | 03/013249 | 2/2003 |
| WO | 2004/037749 | 5/2004 |
| WO | 2004/058712 | 7/2004 |
| WO | 2004058712 | 7/2004 |
| WO | 2004/080962 | 9/2004 |
| WO | 2004/111042 | 12/2004 |
| WO | 2005/092897 | 10/2005 |
| WO | 2005/123667 | 12/2005 |
| WO | 2005123667 | 12/2005 |
| WO | 2006/024411 | 3/2006 |
| WO | 2007/068427 | 6/2007 |
| WO | 2007/080066 | 7/2007 |
| WO | 2007/096058 | 8/2007 |
| WO | 2007/121868 | 11/2007 |
| WO | 2007/140881 | 12/2007 |
| WO | 2008/071405 | 6/2008 |
| WO | 2008/110307 | 9/2008 |
| WO | 2008/110308 | 9/2008 |
| WO | 2008/145336 | 12/2008 |
| WO | 2009019015 | 2/2009 |
| WO | 2009030450 | 3/2009 |
| WO | 2010000773 | 1/2010 |
| WO | 2010133232 | 11/2010 |

* cited by examiner

HERBICIDES

This application is a 371 of International Application No. PCT/EP2008/006467 filed Aug. 6, 2008, which claims priority to GB 0715454.5 filed Aug. 8, 2007, the contents of which are incorporated herein by reference.

The present invention relates to novel, herbicidally active cyclopentanedione compounds, and derivatives thereof, to processes for their preparation, to compositions comprising those compounds, and to their use in controlling weeds, especially in crops of useful plants, or in inhibiting undesired plant growth.

Cyclopentanedione compounds having herbicidal action are described, for example, in WO 01/74770 and WO 96/03366.

Novel cyclopentanedione compounds, and derivatives thereof, having herbicidal and growth-inhibiting properties have now been found.

The present invention accordingly relates to compounds of formula I

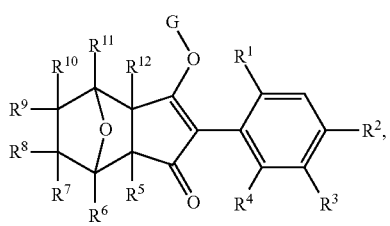

(I)

wherein
G is hydrogen or an alkali metal, alkaline earth metal, sulfonium, ammonium or a latentiating group,
$R^1$ is methyl, ethyl, n-propyl, isopropyl, cyclopropyl, halomethyl, haloethyl, vinyl, ethynyl, halogen, $C_1$-$C_2$alkoxy or $C_1$-$C_2$haloalkoxy,
$R^2$, $R^3$ and $R^4$ are independently of each other hydrogen, methyl, ethyl, n-propyl, isopropyl, cyclopropyl, halomethyl, haloethyl, vinyl, ethynyl, halogen, $C_1$-$C_2$alkoxy or $C_1$-$C_2$ haloalkoxy,
$R^5$ and $R^{12}$ are independently of each other hydrogen, $C_1$-$C_3$alkyl, $C_1$-$C_3$haloalkyl, $C_1$-$C_3$alkyoxy, $C_1$-$C_3$alkylthio, halogen or $C_1$-$C_6$alkoxycarbonyl, or
$R^5$ and $R^{12}$ join together to form a 3-7 membered carbocyclic ring, optionally containing an oxygen or sulfur atom, and
$R^6$, $R^7$, $R^8$, $R^9$, $R^{10}$ and $R^{11}$ are independently of each other hydrogen or a substituent, or $R^7$ and $R^8$, or $R^9$ and $R^{10}$, together with the carbon atoms to which they are attached form a keto, an optionally substituted alkenyl or optionally substituted imino unit, or any two of $R^7$, $R^8$, $R^9$ and $R^{10}$ together form a 3-8 membered carbocyclic ring optionally containing a heteroatom selected from O, S or N and optionally substituted, or $R^7$ and $R^{10}$ together form a bond.

In the substituent definitions of the compounds of the formula I, each alkyl moiety either alone or as part of a larger group (such as alkoxy, alkylthio, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$ alkyl groups, but are preferably $C_1$-$C_4$ alkyl or $C_1$-$C_3$ alkyl groups, and, more preferably, $C_1$-$C_2$alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy ($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, mercapto, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$) alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$) alkylsilyl, aryldi($C_{1-4}$)alkylsilyl, triarylsilyl, aryl($C_{1-4}$)alkylthio($C_{1-4}$)alkyl, aryloxy($C_{1-4}$)alkyl, formyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-4}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, $C_{1-6}$alkyliminooxy, $C_{3-6}$alkenyloxyimino, aryloxyimino, aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$) alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms. It is to be understood that the alkenyl units formed by $R^7$ together with $R^8$ are directly attached to the bridged cyclohexane ring by a double bond.

When present, the optional substituents on alkenyl or alkynyl include those optional substituents given above for an alkyl moiety.

Halogen is fluorine, chlorine, bromine or iodine.

Haloalkyl groups are alkyl groups which are substituted with one or more of the same or different halogen atoms and are, for example, $CF_3$, $CF_2C_1$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" refers to ring systems which may be mono-, bi- or tricyclic. Examples of such rings include phenyl, naphthyl, anthracenyl, indenyl or phenanthrenyl. A preferred aryl group is phenyl.

The term "heteroaryl" preferably refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

Preferred examples of heteroaromatic radicals include pyridyl, pyrimidinyl, triazinyl, thienyl, furyl, oxazolyl, isoxazolyl, 2,1,3-benzoxadiazolyl and thiazolyl.

Another group of preferred heteroaryls comprises furyl, thienyl, pyrazolyl, 1,2,3-triazolyl, 1,2,4-triazolyl, pyridyl, pyrimidinyl, pyridazinyl, pyrazinyl, quinolinyl, isoquinolinyl, cinnolinyl, quinazolinyl or quinoxalinyl.

The term "heterocyclyl" preferably refers to a non-aromatic preferably monocyclic or bicyclic ring systems containing up to 7 atoms including one or more (preferably one or two) heteroatoms selected from O, S and N. Examples of such rings include 1,3-dioxolane, oxetane, tetrahydrofuran, morpholine, thiomorpholin and piperazine. When present, the optional substituents on heterocyclyl include $C_{1-6}$ alkyl and $C_{1-6}$ haloalkyl as well as those optional substituents given above for an alkyl moiety.

Cycloalkyl includes preferably cyclopropyl, cyclobutyl, cyclopentyl and cyclohexyl. Cycloalkylalkyl is preferentially cyclopropylmethyl. Cycloalkenyl includes preferably cyclopentenyl and cyclohexenyl. When present, the optional substituents on cycloalkyl or cycloalkenyl include $C_{1-3}$ alkyl as well as those optional substituents given above for an alkyl moiety.

Carbocyclic rings such as those formed by $R^7$ together with $R^8$ include aryl, cycloalkyl or carbocyclic groups, and cycloalkenyl groups.

When present, the optional substituents on aryl, heteroaryl and carbocycles are preferably selected independently, from halogen, nitro, cyano, rhodano, isothiocyanato, $C_{1-6}$ alkyl, $C_{1-6}$ haloalkyl, $C_{1-6}$ alkoxy-$(C_{1-6})$alkyl, $C_{2-6}$ alkenyl, $C_{2-4}$ haloalkenyl, $C_{2-4}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy$(C_{1-10})$alkoxy, tri$(C_{1-4})$alkylsilyl$(C_{1-4})$alkoxy, $C_{1-6}$ alkoxycarbonyl$(C_{1-10})$alkoxy, $C_{1-10}$ haloalkoxy, aryl$(C_{1-4})$alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, mercapto, $C_{1-10}$ alkylthio, $C_{1-10}$ haloalkylthio, aryl$(C_{1-4})$alkylthio, $C_{3-7}$ cycloalkylthio (where the cycloalkyl group is optionally substituted with $C_{1-6}$ alkyl or halogen), tri$(C_{1-4})$-alkylsilyl$(C_{1-6})$alkylthio, arylthio, $C_{1-4}$ alkylsulfonyl, $C_{1-6}$ haloalkylsulfonyl, $C_{1-6}$ alkylsulfinyl, $C_{1-6}$ haloalkylsulfinyl, arylsulfonyl, tri$(C_{1-4})$alkylsilyl, aryldi$(C_{1-4})$-alkysilyl, $(C_{1-4})$alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di$(C_{1-6}$ alkyl)-aminocarbonyl, N—$(C_{1-3}$ alkyl)-N—$(C_{1-3}$ alkoxy)aminocarbonyl, $C_{1-6}$ alkylcarbonyloxy, arylcarbonyloxy, di$(C_{1-6})$alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di$(C_{1-6})$alkylamino, $C_{1-6}$ alkylcarbonylamino, N—$(C_{1-6})$alkylcarbonyl-N—$(C_{1-6})$alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include arylcarbonylamino (where the aryl group is substituted by $C_{1-6}$ alkyl or halogen), $(C_{1-6})$alkoxycarbonylamino$(C_{1-6})$alkoxycarbonyl-N—$(C_{1-6})$alkylamino, aryloxycarbonylamino (where the aryl group is substituted by $C_{1-6}$ alkyl or halogen), aryloxycarbonyl-N—$(C_{1-6})$alkylamino, (where the aryl group is substituted by $C_{1-6}$ alkyl or halogen), arylsulphonylamino (where the aryl group is substituted by $C_{1-6}$ alkyl or halogen), arylsulphonyl-N—$(C_{1-6})$alkylamino (where the aryl group is substituted by $C_{1-6}$ alkyl or halogen), aryl-N—$(C_{1-6})$alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonylamino, di$(C_{1-6})$alkylaminocarbonylamino, arylaminocarbonylamino where the aryl group is substituted by $C_{1-6}$ alkyl or halogen), aryl-N—$(C_{1-6})$alkylamino-carbonylamino where the aryl group is substituted by $C_{1-6}$ alkyl or halogen), $C_{1-6}$ alkylaminocarbonyl-N—$(C_{1-6})$alkylamino, di$(C_{1-6})$alkylaminocarbonyl-N—$(C_{1-6})$alkylamino, arylaminocarbonyl-N—$(C_{1-6})$alkylamino where the aryl group is substituted by $C_{1-6}$ alkyl or halogen) and aryl-N—$(C_{1-6})$alkylaminocarbonyl-N—$(C_{1-6})$alkylamino where the aryl group is substituted by $C_{1-6}$ alkyl or halogen).

For substituted heterocyclyl groups it is preferred that one or more substituents are independently selected from halogen, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $(C_{1-6})$alkyl groups. When heterocyclic rings are formed by joining two groups on an N atom, the resulting rings are suitably pyrrolidine, piperidine, thiomorpholine and morpholine each of which may be substituted by one or two independently selected $(C_{1-6})$ alkyl groups.

It should be understood that the term "substituent" in the definitions of $R^6$ to $R^{11}$ comprises preferably all substitutents given above for "aryl", "heteroaryl" and "heterocyclyl".

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$- alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

Preferably, in the compounds of the formula I, $R^6$ and $R^{11}$ are independently of each other hydrogen, halogen, formyl, cyano or nitro or $R^6$ and $R^{11}$ are independently of each other $C_1$-$C_6$alkyl, $C_2$-$C_6$alkenyl, $C_2$-$C_6$alkynyl, $C_1$-$C_6$alkoxy, $C_3$-$C_7$ cycloalkyl, $C_3$-$C_7$ cycloalkenyl, phenyl, heteroaryl or a 3-7 membered heterocyclyl, where all these substituents are optionally substituted, or $R^6$ and $R^{11}$ are independently of each other a group $COR^{13}$, $CO_2R^{14}$ or $CONR^{15}R^{16}$, $CR^{17}=NOR^{18}$, $CR^{19}=NNR^{20}R^{21}$, $NHR^{22}$, $NR^{22}R^{23}$ or $OR^{24}$, wherein $R^{13}$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted, $R^{14}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted, $R^{15}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, phenyl, heteroaryl or a 3-7 membered heterocyclyl, where all these substituents are optionally substituted, $R^{16}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, phenylsulfonyl, heteroarylsulfonyl, amino, $C_1$-$C_6$alkylamino, $diC_1$-$C_6$alkylamino, phenyl, heteroaryl or a 3-7 membered heterocyclyl, where all these substituents are optionally substituted, or $R^{15}$ and $R^{16}$ may be joined to form an optionally substituted 3-7 membered ring, optionally containing an oxygen, sulfur or nitrogen atom, $R^{17}$ and $R^{19}$ are independently of each other hydrogen, $C_1$-$C_3$alkyl or $C_3$-$C_6$cycloalkyl, $R^{18}$, $R^{20}$ and $R^{21}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, aminocarbonyl, $C_1$-$C_6$alkylaminocarbonyl, $diC_1$-$C_6$alkylaminocarbonyl, phenyl or heteroaryl, where all these substituents are optionally substituted, $R^{22}$ is $C_1$-$C_6$alkylcarbonyl, $C_1$-$C_6$alkoxycarbonyl, $C_1$-$C_6$alkylthiocarbonyl, $C_1$-$C_6$alkylaminocarbonyl, $diC_1$-$C_6$alkylaminocarbonyl, $C_1$-$C_6$alkylsulfonyl, phenylcarbonyl, phenoxycarbonyl, phenylaminocarbonyl, phenylthiocarbonyl, phenylsulfonyl, heteroarylcarbonyl, heteroaryloxycarbonyl, heteroarylaminocarbonyl, heteroarylthiocarbonyl or heteroarylsulfonyl, where all these substituents are optionally substituted, $R^{23}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, $diC_1$-$C_6$alkylaminocarbonyl, $C_1$-$C_6$alkylsulfonyl, phenyl or heteroaryl, where all these substituents are optionally substituted, or $R^{22}$ and $R^{23}$ may be joined to form an optionally substituted 3-7 membered ring, optionally containing an oxygen, sulfur or nitrogen atom, where all these substituents are optionally substituted, and $R^{24}$ is $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, aminocarbonyl, $C_1$-$C_6$alkylaminocarbonyl, $diC_1$-$C_6$alkylaminocarbonyl, tri ($C_1$-$C_6$alkyl)silyl, phenyl or heteroaryl, where all these substituents are optionally substituted.

More preferably, $R^6$ and $R^{11}$ are independently of each other hydrogen, halogen, cyano, optionally substituted $C_1$-$C_6$alkyl or a group $COR^{13}$, $CO_2R^{14}$ or $CONR^{15}R^{16}$, $CR^{17}=NOR^{18}$ or $CR^{19}=NNR^{20}R^{21}$, wherein $R^{13}$, $R^{14}$, $R^{15}$ and $R^{16}$ are $C_1$-$C_6$alkyl, $R^{17}$ and $R^{19}$ are hydrogen or $C_1$-$C_3$ alkyl, $R^{18}$ is $C_1$-$C_3$ alkyl, and $R^{20}$ and $R^{21}$ are independently of each other hydrogen or $C_1$-$C_3$alkyl.

In particular, $R^6$ and $R^{11}$ are independently of each other hydrogen, methyl or methyl substituted by $C_1$-$C_3$alkoxy.

Preferably, $R^7$, $R^8$, $R^9$ and $R^{10}$ are independently of each other hydrogen, halogen, hydroxyl, formyl, amino, cyano or nitro, or $R^7$, $R^8$, $R^9$ and $R^{10}$ are independently of each other $C_1$-$C_6$alkyl, $C_2$-$C_6$alkenyl, $C_2$-$C_6$alkynyl, $C_1$-$C_6$alkoxy, $C_1$-$C_6$alkoxyC_1$-$C_6$alkyl, $C_1$-$C_6$alkylthio, $C_1$-$C_6$alkylsulfinyl, $C_1$-$C_6$alkylsulfonyl, $C_1$-$C_6$alkylthioC_1$-$C_6$alkyl, $C_1$-$C_6$alkylsulfinylC_1$-$C_6$alkyl, $C_1$-$C_6$alkylsulfonylC_1$-$C_6$alkyl, $C_3$-$C_7$ cycloalkyl, $C_4$-$C_7$cycloalkenyl, tri($C_1$-$C_6$alkyl)silyl, aryl, heteroaryl or a 3-7 membered heterocyclyl, where all these substituents are optionally substituted, or $R^7$, $R^8$, $R^9$ and $R^{10}$ are independently of each other a group $COR^{13}$, $CO_2R^{14}$ or $CONR^{15}R^{16}$, $CR^{17}$=$NOR^{18}$, $CR^{19}$=$NNR^{20}R^{21}$, $NR^{22}R^{23}$ or $OR^{24}$, wherein $R^{13}$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted, $R^{14}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted, $R^{15}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, phenyl, heteroaryl or a 3-7 membered heterocyclyl, where all these substituents are optionally substituted, $R^{16}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, amino, $C_1$-$C_6$alkylamino, di$C_1$-$C_6$alkylamino, phenyl, heteroaryl or a 3-7 membered heterocyclyl, where all these substituents are optionally substituted, or $R^{15}$ and $R^{16}$ may be joined to form an optionally substituted 3-7 membered ring, optionally containing an oxygen, sulfur or nitrogen atom, $R^{17}$ and $R^{19}$ are independently of each other hydrogen, $C_1$-$C_3$alkyl or $C_3$-$C_6$cycloalkyl, $R^{18}$, $R^{20}$ and $R^{21}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, phenyl or heteroaryl, where all these substituents are optionally substituted, $R^{22}$ and $R^{23}$ are independently of each other $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl or $R^{22}$ and $R^{23}$ may be joined to form an optionally substituted 3-7 membered ring, optionally containing an oxygen, sulfur or nitrogen atom, where all these substituents are optionally substituted, and $R^{24}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, tri($C_1$-$C_6$alkyl)silyl, phenyl or heteroaryl, where all these substituents are optionally substituted.

More preferably, $R^7$, $R^8$, $R^9$ and $R^{10}$ are hydrogen.

It is also preferred that one of $R^7$, $R^8$, $R^9$ and $R^{10}$ is methyl or ethyl.

It is also preferred that one of $R^7$, $R^8$, $R^9$ and $R^{10}$ is an optionally substituted aryl or heteroaryl and more preferably optionally substituted phenyl, naphthyl, furyl, thienyl, pyrazolyl, 1,2,3-triazolyl, 1,2,4-triazolyl, pyridyl, pyrimidinyl, pyridazinyl, pyrazinyl, quinolinyl, isoquinolinyl, cinnolinyl, quinazolinyl or quinoxalinyl.

In particular, one of $R^7$, $R^8$, $R^9$ and $R^{10}$ is pyridyl or pyridyl substituted by trifluoromethyl or halogen.

It is also preferred that $R^7$ and $R^{10}$ form a bond.

Preferably, $R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, 3-7 membered heterocyclyl, optionally substituted phenyl or optionally substituted heteroaryl, or $CR^{17}$=$NOR^{18}$, wherein $R^{17}$ is hydrogen or $C_1$-$C_3$ alkyl and $R^{18}$ is $C_1$-$C_3$ alkyl.

In another group of preferred compounds of the formula I, $R^7$ and $R^8$, or $R^9$ and $R^{10}$, together form a unit =O, or form a unit =$CR^{25}R^{26}$, or form a unit =$NR^{27}$, or any two of $R^7$, $R^8$, $R^9$ and $R^{10}$ form a 3-8 membered ring, optionally containing a heteroatom selected from O, S or N and optionally substituted by $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, $C_1$-$C_3$haloalkyl, halogen, phenyl, phenyl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, $C_1$-$C_4$alkoxycarbonyl, aminocarbonyl, $C_1$-$C_6$alkylaminocarbonyl, di$C_1$-$C_6$alkylaminocarbonyl, halogen, cyano or by nitro, heteroaryl or heteroaryl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, halogen, cyano or by nitro, wherein $R^{25}$ and $R^{26}$ are independently of each other hydrogen, halogen, cyano or nitro, or $R^{25}$ and $R^{26}$ are independently of each other $C_1$-$C_6$alkyl, $C_1$-$C_6$alkoxy, $C_1$-$C_6$alkylamino, di$C_1$-$C_6$alkylamino, $C_1$-$C_6$alkylcarbonyl, $C_1$-$C_6$alkoxycarbonyl, $C_1$-$C_6$alkylaminocarbonyl, di$C_1$-$C_6$alkylaminocarbonyl, N-phenyl-N—$C_1$-$C_6$alkylaminocarbonyl, N-phenyl$C_1$-$C_6$alkyl-N—$C_1$-$C_6$alkylaminocarbonyl, N-heteroaryl-N—$C_1$-$C_6$alkylaminocarbonyl, N-heteroaryl$C_1$-$C_6$alkyl-N—$C_1$-$C_6$alkylaminocarbonyl, phenyl, heteroaryl, $C_3$-$C_6$cycloalkyl or 3-7 membered heterocyclyl, where all these substituents are optionally substituted, or $R^{25}$ and $R^{26}$ may be joined together to form a 5-8 membered ring optionally containing a heteroatom selected from O, S or N and optionally substituted by $C_1$-$C_2$alkyl or $C_1$-$C_2$alkoxy, $R^{27}$ is nitro or cyano, or $R^{27}$ is $C_1$-$C_6$alkylamino, di$C_1$-$C_6$alkylamino, $C_1$-$C_6$alkoxy, $C_3$-$C_6$alkenyloxy, $C_3$-$C_6$alkynyloxy, phenoxy, phenylamino, N-phenyl-N—$C_1$-$C_6$alkylamino, N-phenyl$C_1$-$C_6$alkyl-N—$C_1$-$C_6$alkylamino heteroaryloxy, heteroarylamino, N-heteroaryl-N—$C_1$-$C_6$alkylamino or N-heteroaryl$C_1$-$C_6$alkyl-N—$C_1$-$C_6$alkylamino, where all these substituents are optionally substituted, where, more preferably, $R^7$ and $R^8$, or $R^9$ and $R^{10}$, together form a unit =O or =$NR^{27}$, wherein $R^{27}$ is $C_{1-3}$alkoxy or $C_2$-$C_3$ alkenyloxy.

More preferably, $R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, 3-7 membered heterocyclyl, optionally substituted phenyl or optionally substituted heteroaryl.

In particular, $R^7$, $R^8$, $R^9$ and $R^{10}$ are independently of each other hydrogen, methyl, ethyl or optionally substituted phenyl.

In particular, one of $R^7$, $R^8$, $R^9$ and $R^{10}$ is optionally substituted heteroaryl, preferably optionally substituted furyl, thienyl, pyrazolyl, 1,2,4-triazolyl, pyridyl, pyrimidinyl, pyridazinyl, pyrazinyl, quinolinyl, isoquinolinyl, cinnolinyl, quinazolinyl or quinoxalinyl, and more preferably pyridyl substituted once or twice by trifluoromethyl or halogen.

In another group of preferred compounds of the formula I, $R^1$, $R^2$ and $R^4$ are methyl and $R^3$ is hydrogen.

In another group of preferred compounds of the formula I, $R^1$, $R^2$ and $R^4$ are methyl and $R^3$ is hydrogen, and $R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, 3-7 membered heterocyclyl, optionally substituted aryl or optionally substituted heteroaryl, preferably optionally substituted heteroaryl, and in particular pyridyl substituted once or twice by trifluoromethyl or halogen.

In another group of preferred compounds of the formula I, $R^5$ and $R^{12}$ are independently of each other hydrogen or $C_1$-$C_3$alkyl, where hydrogen is more preferred.

In another group of preferred compounds of the formula I, $R^1$ is methyl, ethyl, vinyl, ethynyl, cyclopropyl, difluoromethoxy, trifluoromethoxy or $C_1$-$C_2$ alkoxy and $R^2$, $R^3$ and $R^4$ are independently of each other hydrogen, methyl, ethyl, vinyl or ethynyl.

Preferably in this group, $R^1$ is ethyl and $R^2$, $R^3$ and $R^4$ are independently of each other hydrogen, methyl or ethyl.

Preferably in this group, $R^1$, $R^2$ and $R^4$ are methyl and $R^3$ is hydrogen.

The latentiating group G is preferably selected from the groups $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_6$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_6$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_6$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_6$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_2$-$C_3$alkylthio, $C_1$-$C_3$alkylsulfinyl, $C_1$-$C_3$alkylsulfonyl, halogen, cyano, or by nitro), $C_2$-$C_6$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_2$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_6$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_6$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_8$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_5$dialkylamino $R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_6$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_6$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_8$alkylaminocarbonyl$C_1$-$C_8$alkyl, $C_2$-$C_8$dialkylaminocarbonyl$C_1$-$C_8$alkyl, $C_1$-$C_8$alkylcarbonylamino$C_1$-$C_8$alkyl, N—$C_1$-$C_8$alkylcarbonyl-N—$C_1$-$C_5$alkylamino$C_1$-$C_3$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_6$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$, $X^b$ and $R^b$ are as defined above.

It is preferred that G is hydrogen, an alkali metal or alkaline earth metal, where hydrogen is especially preferred.

It should be understood that in those compounds of formula I where G is a metal, ammonium (such as $NH_4+$; $N(alkyl)_4+$) or sulfonium (such as $S(alkyl)_3+$) cation, the corresponding negative charge is largely delocalised across the O—C=C—C=O unit.

Depending on the nature of the substituents, compounds of formula I may exist in different isomeric forms. When G is hydrogen, for example, compounds of formula I may exist in different tautomeric forms.

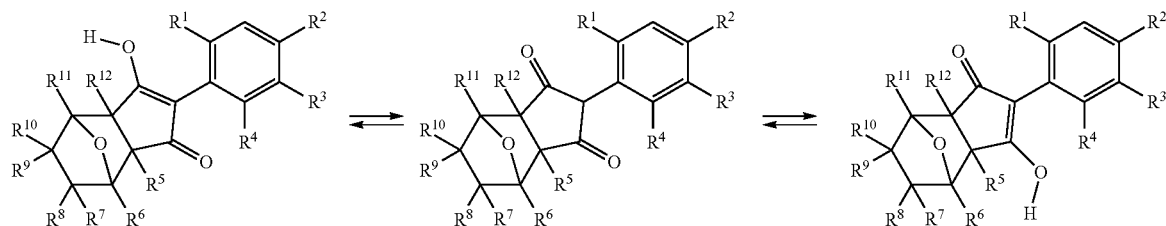

This invention covers all such isomers and tautomers and mixtures thereof in all proportions. Also, when substituents contain double bonds, cis- and trans-isomers can exist. These isomers, too, are within the scope of the claimed compounds of the formula I.

A compound of formula I wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula I wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as phenyl$C_1$-$C_6$alkyl, chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, HO—C $(X^a)R^a$, wherein $X^a$ is oxygen, an acid chloride, Cl—$C(X^a)$ $R^a$, wherein $X^a$ is oxygen, or acid anhydride, $[R^aC(X^a)]_2O$, wherein $X^a$ is oxygen, or an isocyanate, $R^c$N=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride, Cl—$C(X^d)$—$N(R^d)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^c$N=C=S, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base.

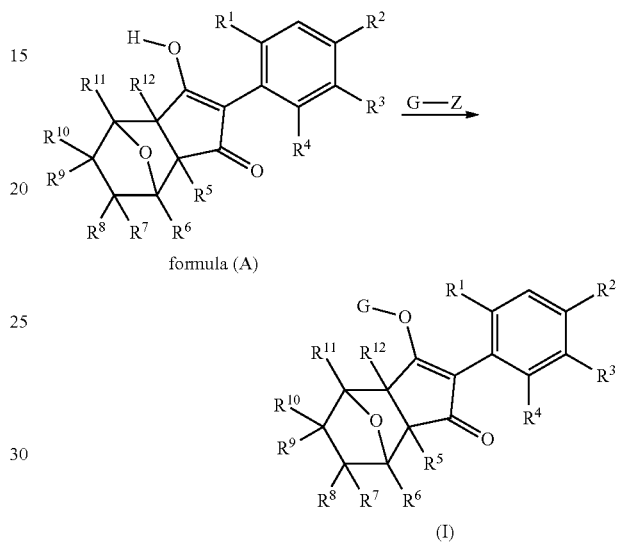

formula (A)

Depending on the nature of the substituents $R^1$ to $R^{12}$, and of the group G, isomeric compounds of formula I may be formed. For example, a compound of formula (A) wherein $R^5$ and $R^{12}$ are different may give rise to a compound of formula (1a) or to a compound of formula (1b), or to a mixture of compounds of formula (1a) and formula (1b).

formula (Ia)

formula (Ib)

The O-alkylation of cyclic 1,3-diones is known; suitable methods are described, for example, by T. Wheeler U.S. Pat. No. 4,436,666. Alternative procedures have been reported by M. Pizzorno and S. Albonico, Chem. Ind. (London), (1972), 425; H. Born et al., J. Chem. Soc., (1953), 1779; M. Constantino et al., Synth. Commun., (1992), 22 (19), 2859; Y. Tian et al., Synth. Commun., (1997), 27 (9), 1577, S. Chandra Roy et al., Chem. Letters, (2006), 35 (1), 16, and P. Zubaidha et al., Tetrahedron Lett., (2004), 45, 7187.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N, N'-dicyclohexylcarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598 and T. Isobe and T. Ishikawa, J. Org. Chem., (1999), 64 (19), 6984.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197.

A compound of formula (A) may be prepared by the cyclisation of a compound of formula (B), wherein R is hydrogen or an alkyl group, preferably in the presence of an acid or base, and optionally in the presence of a suitable solvent, by analogous methods to those described by T. Wheeler, U.S. Pat. No. 4,209,532. The compounds of formula (B) have been particularly designed as intermediates in the synthesis of the compounds of the formula I. A compound of formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

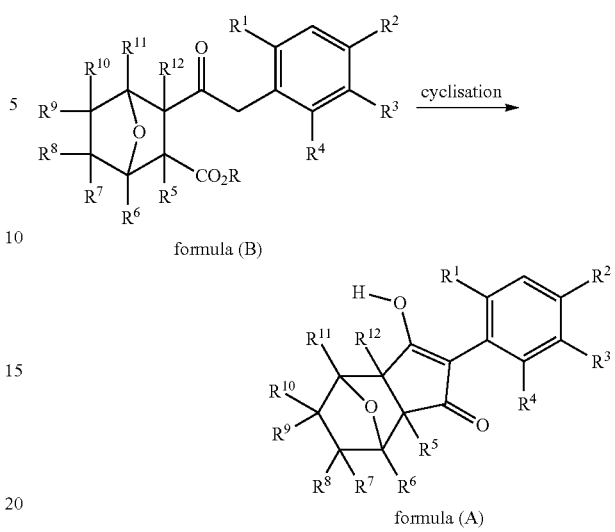

formula (B)

formula (A)

A compound of formula (B) wherein R is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, toluene, dimethylsulfoxide or N,N-dimethylformamide.

A compound of formula (B), wherein R is H, may be prepared by saponification of a compound of formula (C) wherein R' is alkyl (preferably methyl or ethyl), under standard conditions, followed by acidification of the reaction mixture to effect decarboxylation, by similar processes to those described, for example, by T. Wheeler, U.S. Pat. No. 4,209,532.

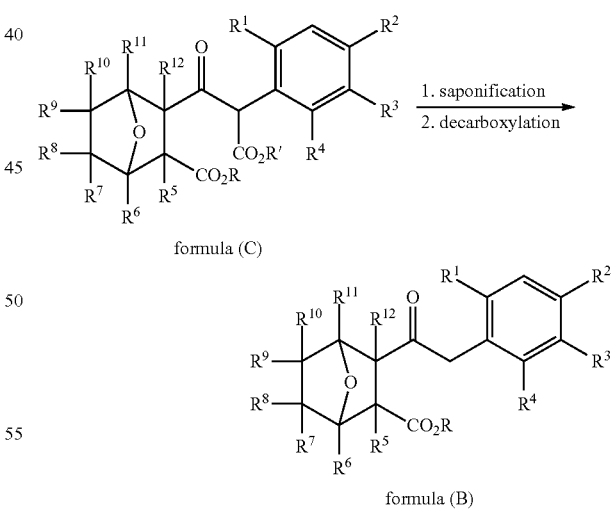

formula (C)

formula (B)

A compound of formula (B), wherein R is H, may be esterified to a compound of formula (B), wherein R is alkyl, under standard conditions, for example by heating with an alkyl alcohol, ROH, in the presence of an acid catalyst.

A compound of formula (C), wherein R is alkyl, may be prepared by treating a compound of formula (D) with a suitable carboxylic acid chloride of formula (E) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, a compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F):

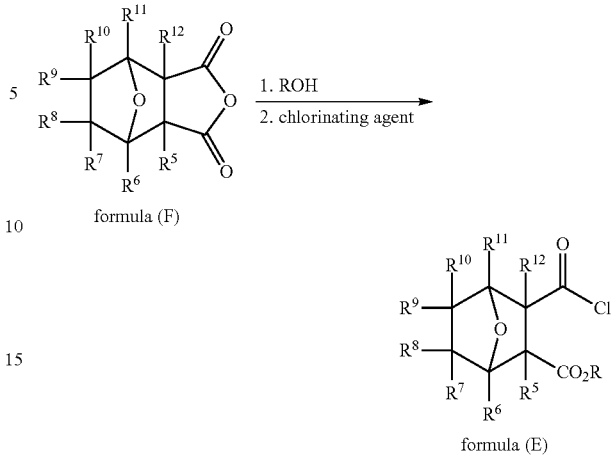

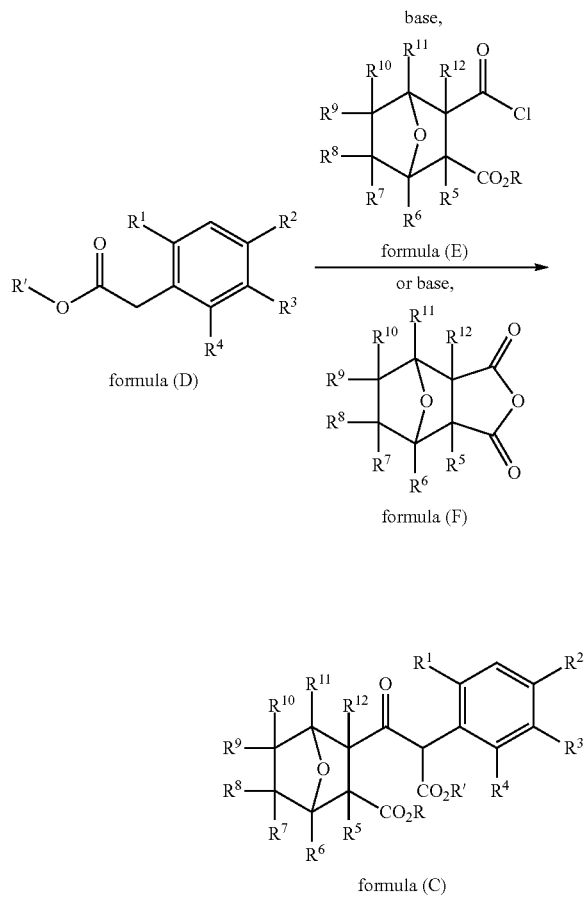

A compound of formula (F) wherein $R^7$ and $R^{10}$ are hydrogen may be prepared by the reduction of a compound of formula (G) under known conditions (see, for example, Y. Baba, N. Hirukawa and M. Sodeoka, Bioorg. Med. Chem. (2005), 13 (17), 5164, M. Hart et al., Bioorg. Med. Chem. Letters, (2004), 14 (18), 1969, Y. Baba, N. Hirukawa, N. Tanohira and M. Sodeoka, J. Am. Chem. Soc., (2003), 125, 9740).

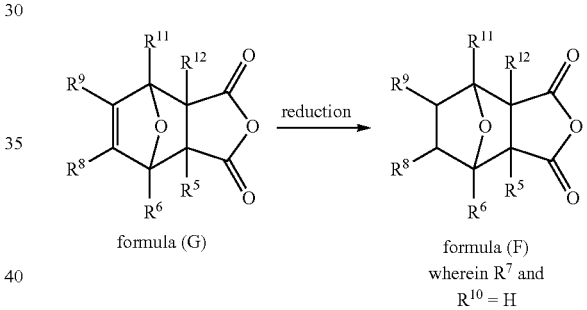

A compound of formula (G) may be prepared by reacting a compound of formula (H) with an anhydride of formula (J), optionally in the presence of a Lewis acid catalyst, and according to procedures described, for example, by O. Diels and K. Alder, Liebigs Ann. Chem., (1931), 490, 257, K. Potts and E. Walsh, J. Org. Chem., (1984), 49 (21), 4099, J. Jurczak, T. Kozluk, S. Filipek and S. Eugster, Helv. Chim. Acta, (1982), 65, 1021, W. Dauben, C. Kessel and K. Takemura, J. Am. Chem. Soc., (1980), 102, 6893, A. Pelter and B. Singaram, Tetrahedron Lett., (1982), 23, 245, M. Lee and C. Hemdon, J. Org. Chem., (1978), 43, 518, B. Fisher and J. Hodge, J. Org. Chem. (1964), 29, 776, G. D'Alelio, C. Williams and C. Wilson, J. Org. Chem., (1960), 25, 1028, Z. Song, M. Ho and H. Wong, J. Org. Chem., (1994), 59 (14), 3917-3926, W. Tochtermann, S. Bruhn and C. Wolff, Tetrahedron Lett., (1994), 35(8), 1165, W. Dauben, J. Lam and Z. Guo, J. Org. Chem., (1996), 61 (14), 4816, M. Sodeoka, Y. Baba, S. Kobayashi and N. Hirukawa, Bioorg. Med. Chem. Lett., (1997), 7 (14), 1833, M. Avalos, R. Babiano, J. Bravo, P. Cintas, J. Jimenez and J. Palacios, Tetrahedron Lett., (1998), 39(50), 9301, J. Auge, R. Gil, S. Kalsey and N. Lubin-Germain, Synlett, (2000), 6, 877, I. Hemeon, C. Deamicis, H. Jenkins, P. Scammells and R. Singer, Synlett, (2002), 11, 1815, M. Essers, B. Wibbeling and G. Haufe, Tetrahedron Lett., Compounds of formula (D) are known compounds, or may be prepared from known compounds by known methods.

A compound of formula (E) may be prepared from a compound of formula (F) by treatment with an alkyl alcohol, R—OH, in the presence of a base, such as dimethylaminopyridine or an alkaline metal alkoxide (see, for example, S. Buser and A. Vasella, Helv. Chim. Acta, (2005), 88, 3151, M. Hart et al., Bioorg. Med. Chem. Letters, (2004), 14, 1969), followed by treatment of the resulting acid with a chlorinating reagent such as oxalyl chloride or thionyl chloride under known conditions (see, for example, C. Santelli-Rouvier. Tetrahedron Lett., (1984), 25 (39), 4371; D. Walba and M. Wand, Tetrahedron Lett., (1982), 23 (48), 4995; J. Cason, Org. Synth. Coll. Vol. III, (169), 1955).

(2001), 42 (32), 5429, P. Vogel et al., Tetrahedron Asymmetry, (1996), 7 (11), 3153, Y. Baba, N. Hirukawa, N. Tanohira and M. Sodeoka, J. Am. Chem. Soc., (2003), 125, 9740, L. Ghosez et al., Tetrahedron Lett., (1988), 29 (36), 4573, H. Kotsuki, S. Kitagawa and H. Nishizawa, J. Org. Chem., (1978), 43 (7), 1471, Y. Li et al., J. Org. Chem., (1997), 62 (23), 7926, M. Drew et al., J. Chem. Soc. Perkin Trans. 1, (1985), 1277, R. McDonald and C. Reineke, J. Org. Chem., (1967), 32, 1878, R. Fleming and B. Murray, J. Org. Chem., (1979), 44 (13), 2280, M. Goldstein and G. Thayer Jr. J. Am. Chem. Soc., (1965), 87 (9), 1925 and G. Keglevich et al., J. Organomet. Chem., (1999), 579, 182, and references therein.

Compounds of formula (H) and formula (J) are known compounds, or may be made from known compounds by known methods.

Compounds of formula (G) are alkenes, and as such undergo further reactions typical of alkenes to give additional compounds of formula (F) according to known procedures. Examples of such reactions include, but are not restricted to, halogenation, epoxidation, cyclopropanation, dihydroxylation, hydroarylation, hydrovinylation and hydration of alkenes. In turn, the products from these reactions may be transformed into additional compounds of formula (F) by methods described, for example by J. March, Advanced Organic Chemistry, third edition, John Wiley and Sons. Compounds of formula (G) wherein $R^8$ or $R^9$ are $C_1$-$C_6$alkoxy are enol ethers, and these may be hydrolysed to the corresponding ketone using standard procedures to give additional compounds of formula (F). Certain compounds of formula (F), for example where $R^7$ is a halogen, may be converted into compounds of formula (G) by known methods.

A compound of formula (G) may also be prepared by reacting a compound of formula (H) with a compound of formula (K), wherein R" is hydrogen or an alkyl group, to give a compound of formula (L) and cyclising a compound of formula (L) under known conditions (see, for example, P. Sprague et al., J. Med. Chem., (1985), 28, 1580, A. Guzaev and M. Manoharan, J. Am. Chem. Soc., (2003), 125, 2380, and A. Marchand and R. Allen, J. Org. Chem., (1975), 40 (17), 2551.

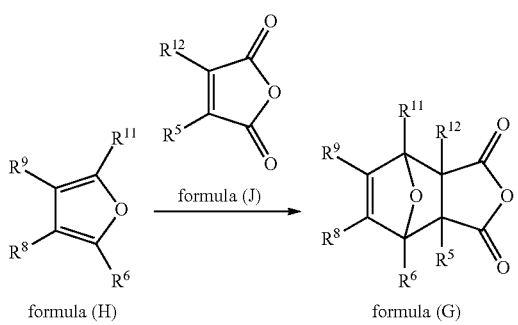

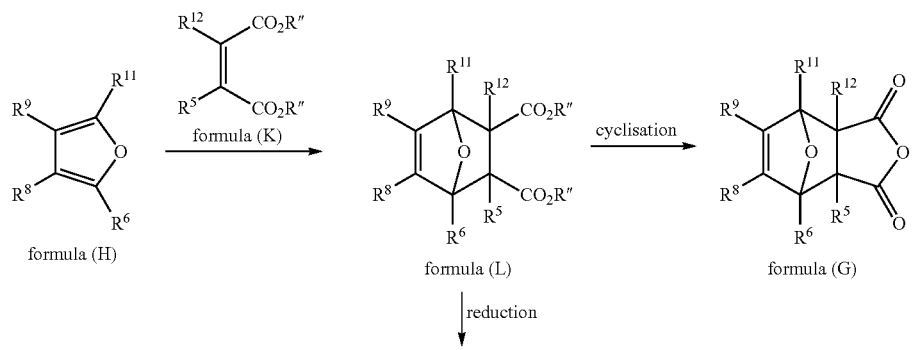

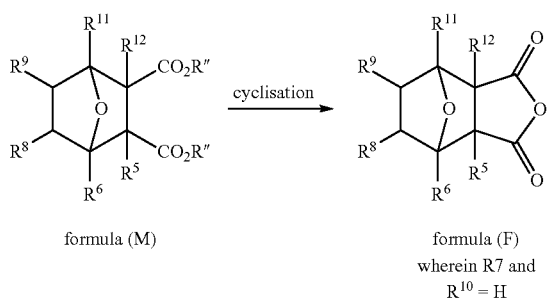

A compound of formula (L) may also be reduced to a compound of formula (M), and a compound of formula (M) cyclised to a compound of formula (F) wherein $R^7$ and $R^{10}$ are hydrogen, under conditions similar to those described previously.

Compounds of formula (K) are known compounds, or may be prepared from known compounds by known methods.

Additional compounds of formula (A) may be prepared by reacting an iodonium ylide of formula (N), wherein Ar is an optionally substituted phenyl group, and an aryl boronic acid of formula (O), in the presence of a suitable palladium catalyst, a base and in a suitable solvent.

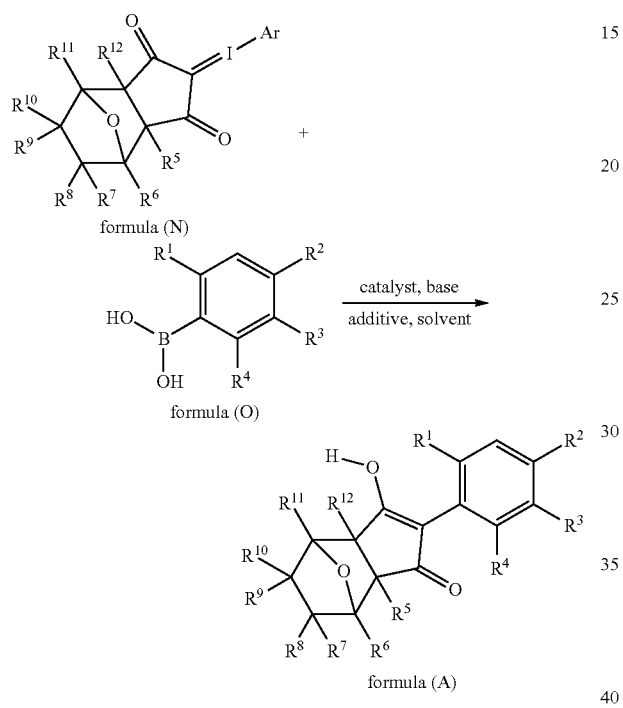

Suitable palladium catalysts are generally palladium(II) or palladium(0) complexes, for example palladium(II)dihalides, palladium(II)acetate, palladium(II) sulfate, bis(triphenylphosphine)-palladium(II) dichloride, bis(tricyclopentylphosphine)palladium(II)dichloride, bis(tricyclohexylphosphine)palladium(II) dichloride, bis(dibenzylideneacetone)palladium(0) or tetrakis-(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II)dichloride ($PdCl_2$) or palladium(II)acetate ($Pd(OAc)_2$), together with the desired ligand, for example triphenyl-phosphine ($PPh_3$), tricyclopentylphosphine, tricyclohexylphosphine, 2-dicyclohexylphosphino-2',6'-dimethoxybiphenyl or 2-dicyclohexylphosphino-2',4',6'-triisopropylbiphenyl and the selected solvent, with a compound of formula (N), the arylboronic acid of formula (O), and a base. Also suitable are bidendate ligands, for example 1,1'-bis(diphenylphosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula (N). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of formula (N) may be prepared from a compound of formula (P) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis, (1983), 392, R. M. Moriarty et al., J. Am. Chem. Soc, (1985), 107, 1375, or of Z. Yang et al., Org. Lett., (2002), 4 (19), 3333.

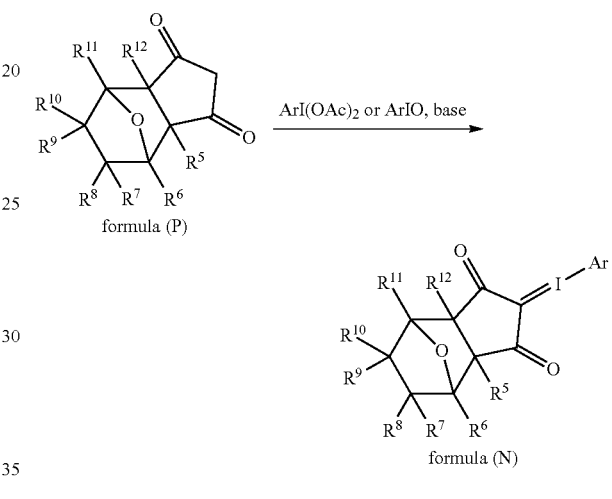

A compound of formula (P) wherein $R^7$ and $R^{10}$ are hydrogen may be prepared by reduction of a compound of formula (Q) under known conditions.

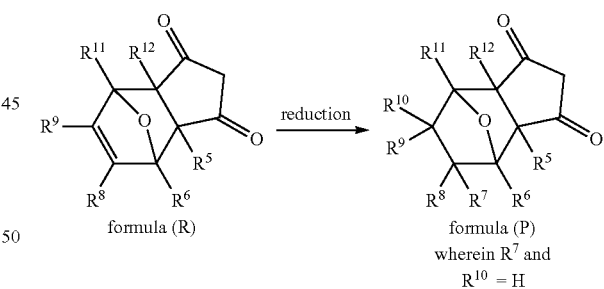

Compounds of formula (R) are alkenes, and as such undergo further reactions typical of alkenes to give additional compounds of formula (P) according to known procedures. Examples of such reactions include, but are not restricted to, halogenation, epoxidation, cyclopropanation, dihydroxylation, hydroarylation, hydrovinylation and hydration of alkenes. In turn, the products of these reactions may be transformed into additional compounds of formula (P) by methods described, for example by J. March, Advanced Organic Chemistry, third edition, John Wiley and Sons. Compounds of formula (R) wherein $R^8$ or $R^9$ are $C_1$-$C_6$alkoxy are enol ethers, and these may be hydrolysed to the corresponding ketone using standard procedures. In turn, the ketone may be further transformed, for example by ketalisation, oximation, reduction and the like under known conditions to give additional compounds of formula (P).

A compound of formula (R) may be prepared by reacting a compound of formula (S) with a cyclopentenedione of formula (T), optionally in the presence of a Lewis acid catalyst, according to procedures described, for example by B. Zwanenburg et al., Tetrahedron (1989), 45 (22), 7109 and by M. Oda et al., Chem. Lett., (1977), 307.

alkyl, and Hal is a halogen (preferably bromine or iodine), by coupling with an aryl boronic acid of formula (O), in the presence of a suitable palladium catalyst and a base and preferably in the presence of a suitable ligand, and in a suitable solvent. Preferably the palladium catalyst is palladium acetate, the base is potassium phosphate, the ligand is 2-dicyclohexylphosphino-2',6'-dimethoxybiphenyl and the solvent is toluene.

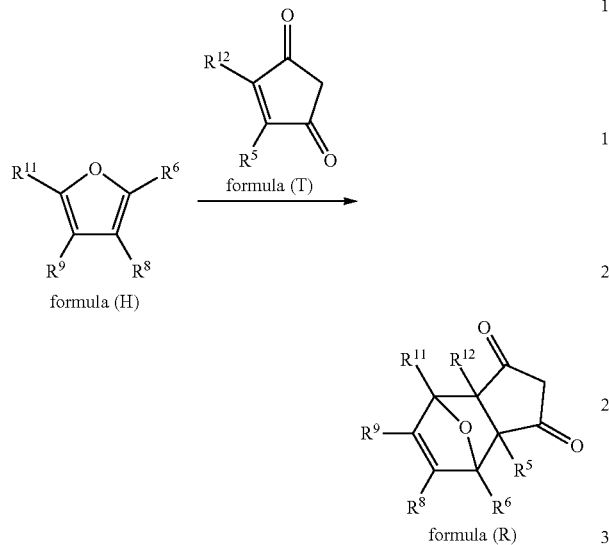

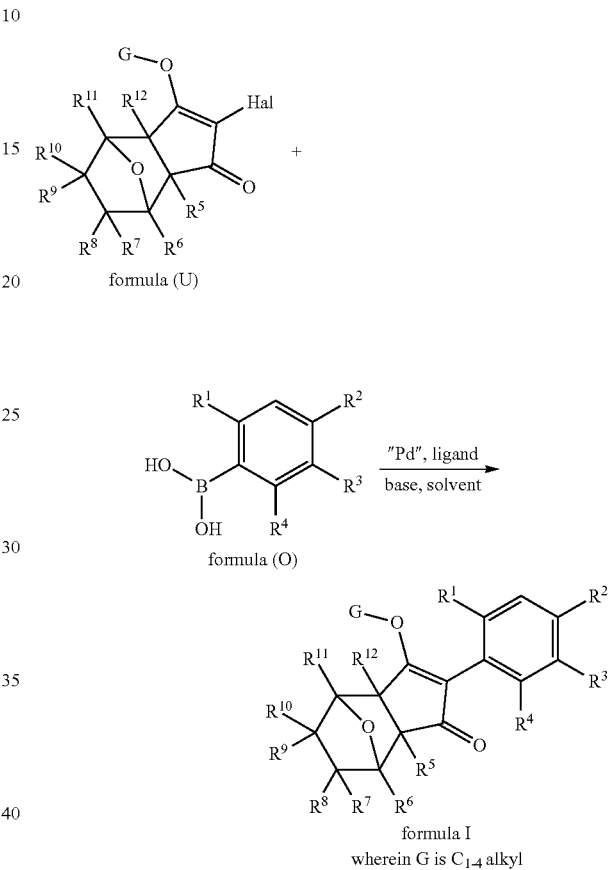

Compounds of formula (H) and formula (T) are known compounds or may be made from known compounds by known methods.

In a further approach, a compound of formula (A) may be prepared from a compound of formula I, wherein G is $C_{1-4}$ alkyl, by hydrolysis, preferably in the presence of an acid catalyst such as hydrochloric acid and optionally in the presence of a suitable solvent such as tetrahydrofuran, acetone or 4-methylpentan-2-one.

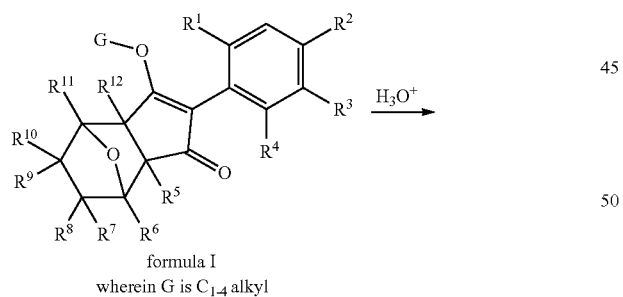

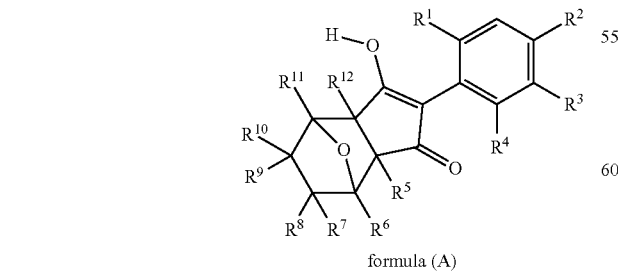

A compound of formula I wherein G is $C_{1-4}$ alkyl, may be prepared from a compound of formula (U), wherein G is $C_{1-4}$ A compound of formula (U) may be prepared by halogenation of a compound of formula (P), followed by reaction of the resulting halide of formula (V) with a $C_{1-4}$ alkyl halide or tri-$C_{1-4}$-alkylorthoformate under known conditions (for example by the procedures of R. Shepherd and A. White, J. Chem. Soc. Perkin Trans. 1 (1987), 2153, and Y.-L. Lin et at., Bioorg. Med. Chem. (2002), 10, 685). Alternatively, a compound of formula (U) may be prepared by reaction of a compound of formula (P) with a $C_{1-4}$ alkyl halide or a tri-$C_{1-4}$-alkylorthoformate, and halogenation of the resulting enone of formula (W) under known conditions.

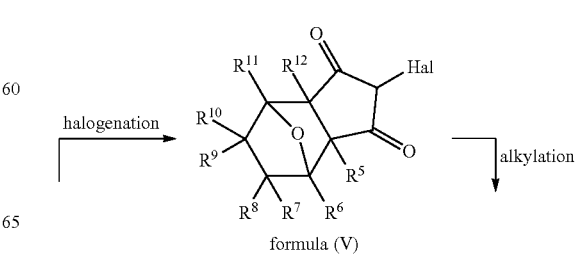

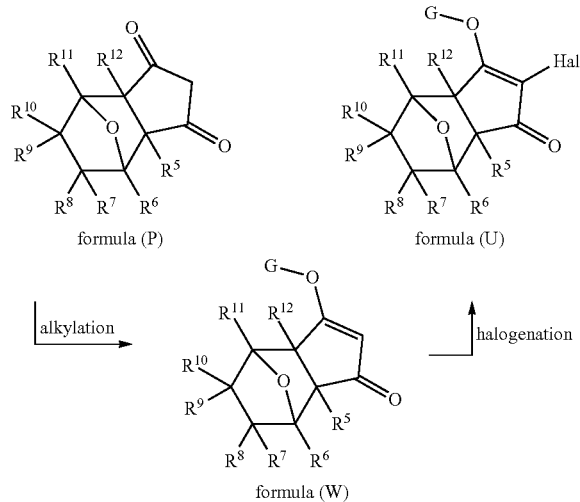

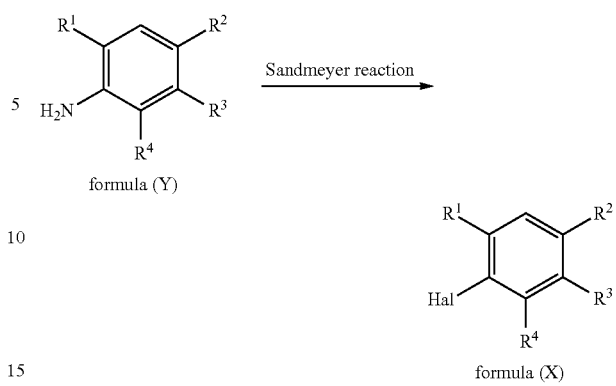

A compound of formula (O) may be prepared from an aryl halide of formula (X), wherein Hal is bromine or iodine, by known methods (see, for example, W. Thompson and J. Gaudino, J. Org. Chem., (1984), 49, 5237 and R. Hawkins et al., J. Am. Chem. Soc., (1960), 82, 3053). For example, an aryl halide of formula (X) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkyl borate (preferably trimethylborate) to give an aryl dialkylboronate which may be hydrolysed to provide a boronic acid of formula (O) under acidic conditions.

Additional compounds of formula (A) may be prepared by reacting a compound of formula (P), or a compound of formula (R) with an organolead reagent of formula (Z) under conditions described, for example, by J. Pinhey, Pure and Appl. Chem., (1996), 68 (4), 819 and by M. Moloney et al., Tetrahedron Lett., (2002), 43, 3407.

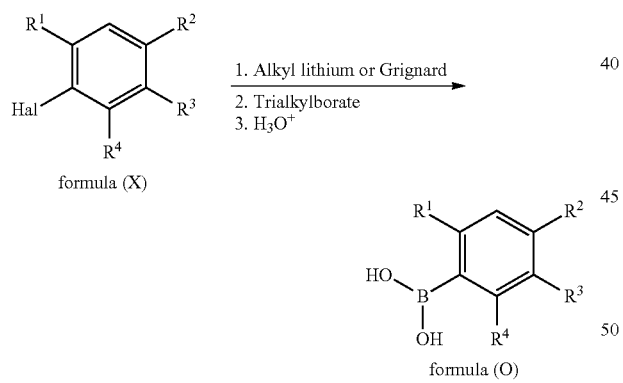

Alternatively a compound of formula (X) may be reacted with a cyclic boronate ester derived from a 1,2- or a 1,3-alkanediol such as pinacol, 2,2-dimethyl-1,3-propanediol and 2-methyl-2,4-pentanediol) under known conditions (see, for example, N. Miyaura et al., J. Org. Chem., (1995), 60, 7508, and W. Zhu and D. Ma, Org. Lett., (2006), 8 (2), 261), and the resulting boronate ester may be hydrolysed under acidic conditions to give a boronic acid of formula (O). An aryl halide of formula (X) may be prepared from an aniline of formula (Y) by known methods, for example the Sandmeyer reaction, via the corresponding diazonium salts. Anilines of formula (Y) are known compounds, or may be made from known compounds, by known methods.

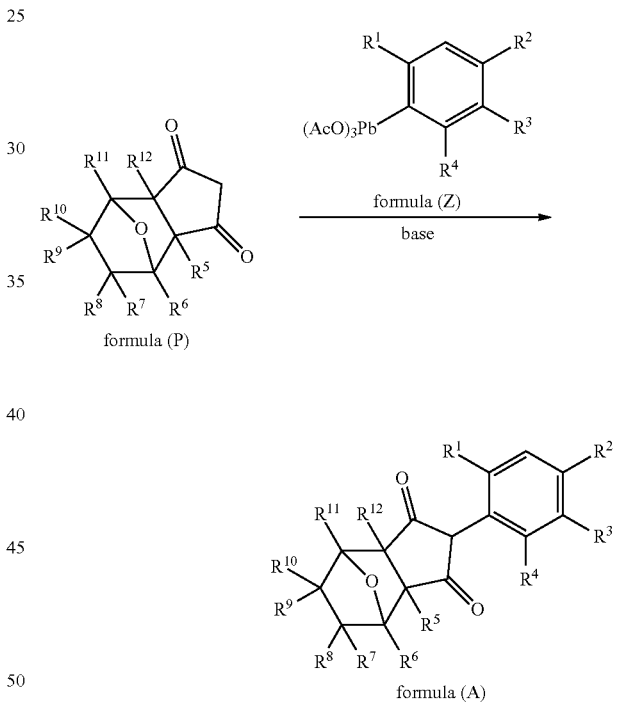

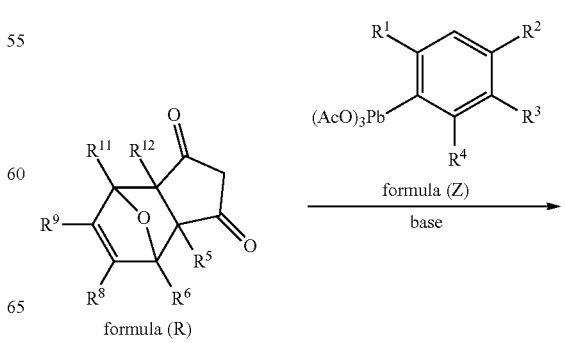

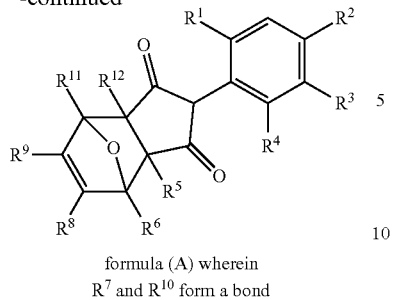

formula (A) wherein
$R^7$ and $R^{10}$ form a bond

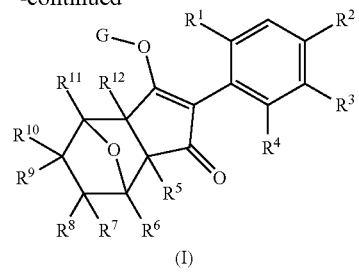

(I)

The organolead reagent of formula (Z) may be prepared from a boronic acid of formula (O), a stannane of formula (AA), wherein R is $C_1$-$C_4$ alkyl or by direct plumbation of a compound of formula (AB) with lead tetraacetate according to known procedures.

For example, compounds of formula (AC) are alkenes, and as such undergo further reactions typical of alkenes to give compounds of formula I according to known procedures. Examples of such reactions include, but are not restricted to, reduction, halogenation, epoxidation, cyclopropanation, dihydroxylation, hydroarylation, hydrovinylation and hydra-

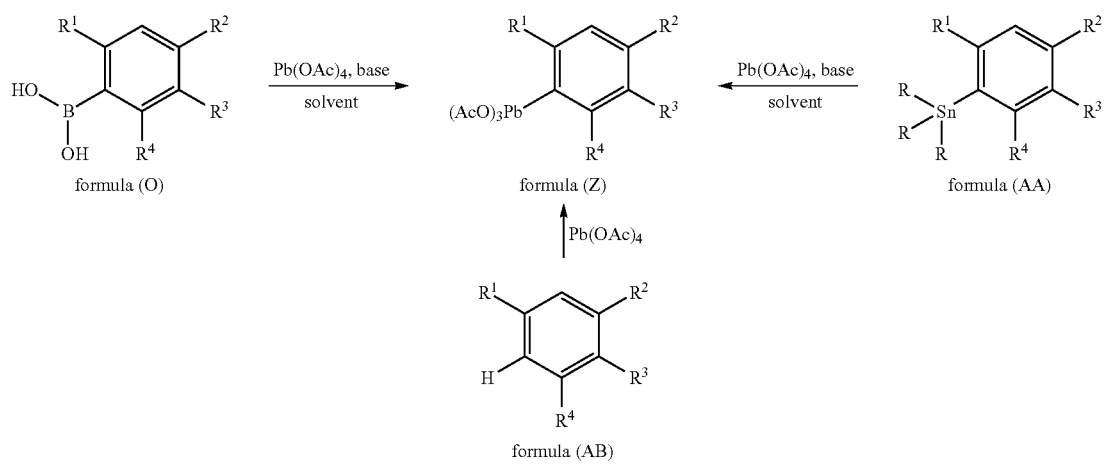

Further compounds of formula (A) may be prepared by reacting a compound of formula (P) or a compound of formula (R) with suitable triarylbismuth compound under conditions described, for example, by A. Yu. Fedorov et al., Russ. Chem. Bull. Int. Ed., (2005), 54 (11), 2602, and by P. Koech and M. Krische, J. Am. Chem. Soc., (2004), 126 (17), 5350 and references therein.

In a further approach, a compound of formula I may be prepared from a compound of formula (AC) by suitable derivatisation under standard conditions.

tion. Compounds of formula (AC) wherein $R^8$ or $R^9$ is bromine or iodine are vinyl halides, and undergo known reactions of vinyl halides such as Suzuki-Miyaura, Sonogashira, Stille and related reactions. Certain other compounds of formula (AC), wherein $R^8$ or $R^9$ is $C_1$-$C_6$alkoxy, are enol ethers, and these may be hydrolysed to the corresponding ketone using standard procedures. In turn, the ketone produced may be further transformed, for example by ketalisation, oximation, reduction and the like under known conditions to give additional compounds of formula I. Similarly, compounds of formula (AC) wherein $R^8$ or $R^9$ is $C_1$-$C_6$amino or di-$C_1$-$C_6$amino are enamines, and these also may be hydrolysed to the corresponding ketone using standard procedures.

A compound of formula (AC), wherein G is $C_1$-$C_4$ alkyl, may be prepared from a compound of formula (AD), wherein G is $C_1$-$C_4$ alkyl and X is halogen or other suitable leaving group (such as an alkyl or arylsulfonate, or an arylselenoxide), by reaction with a compound of formula (I-1), optionally in a suitable solvent, and optionally in the presence of a suitable base.

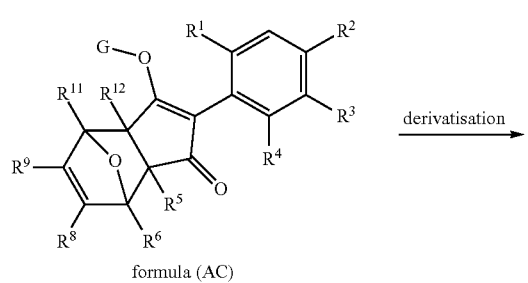

formula (AC)

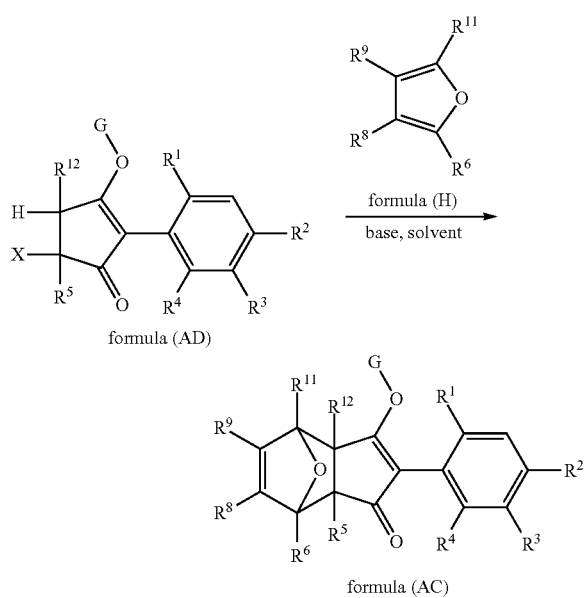

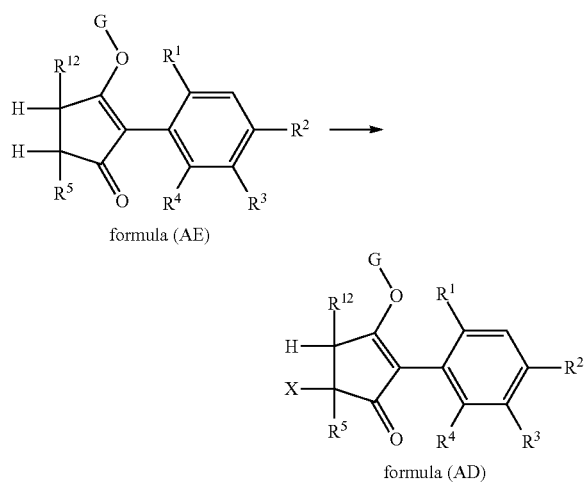

Suitable solvents include toluene, dichloromethane and chloroform and suitable bases include organic bases such as triethylamine, Hunig's base and 1,8-diazabicyclo[5.4.0]undec-7-ene. Preferably the solvent is toluene and the base is 1,8-diazabicyclo[5.4.0]undec-7-ene.

A compound of formula (AD) may be prepared from a compound of formula (AE), under known conditions.

For example, a compound of formula (AD) wherein X is chlorine may be prepared by reacting a compound of formula (AE) with copper(II) chloride and lithium chloride according to the procedure of E. Kosower et al., J. Org. Chem., (1963), 28, 630.

Compounds of formula (AE) are known compounds or may be made from known compounds by known methods (see, for example, Y. Song, B. Kim and J-N Heo, Tetrahedron Lett., (2005), 46, 5977). Alternatively, a compound of formula (AE) wherein G is $C_1$-$C_4$alkyl may be prepared from a compound of formula (AE), wherein G is hydrogen, for example by reaction with a $C_{1-4}$ alkyl halide or a tri-$C_{1-4}$-alkylorthoformate. Compounds of formula (AE), wherein G is hydrogen, are known, or may be prepared from known compounds by known methods (see, for example, T. Wheeler, U.S. Pat. No. 4,338,122, U.S. Pat. No. 4,283,348, J. T. Kuethe et al., J. Org. Chem., (2002), 67, 5993, S. Buchwald et al., J. Am. Chem. Soc., (2003), 125, 11818).

Alternatively, a compound of formula (AE), wherein G is $C_{1-4}$alkyl, may be prepared by reacting a compound of formula (AF), wherein G is $C_{1-4}$alkyl and Z is a halogen, preferably bromine or iodine, with a boronic acid of formula (O) in the presence of a suitable metal catalyst, a suitable base, and optionally a suitable ligand, in a suitable solvent.

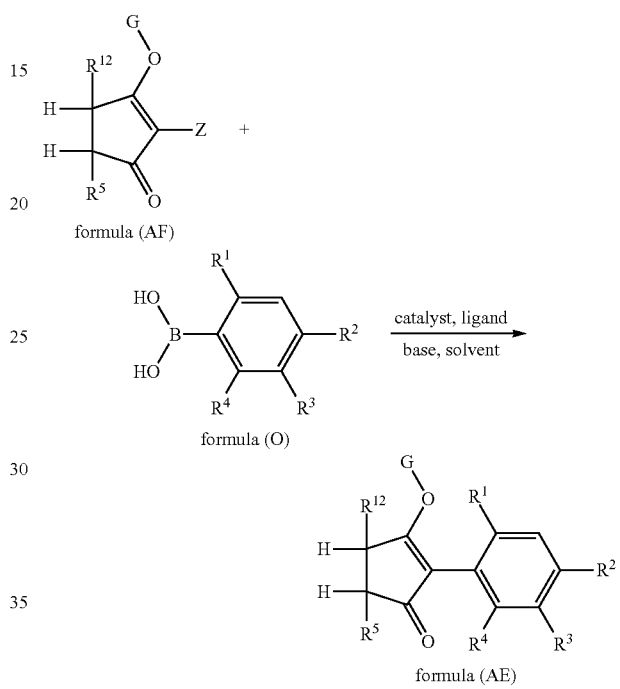

Suitable solvents include toluene and n-butanol, suitable bases include inorganic bases such as potassium phosphate, a suitable metal catalyst is a palladium catalyst, for example in the form of palladium(II)acetate, and suitable ligands include substituted phosphines, for example 2-dicyclohexylphosphino-2',6'-dimethoxybiphenyl.

Compounds of formula (AF) are known compounds, or may be prepared by methods known in the literature. For example a compound of formula (AF) wherein G is $C_{1-4}$alkyl and Z is a bromine atom may be prepared by reacting a compound of formula (AG), wherein G is $C_{1-4}$alkyl, with a suitable brominating agent, such as N-bromosuccinimide, in a suitable solvent, such as 1,2-dichloroethane, as described by R. Shepherd and A. White, J. Chem. Soc. Perkin Trans. 1 (1987), 10, 2153.

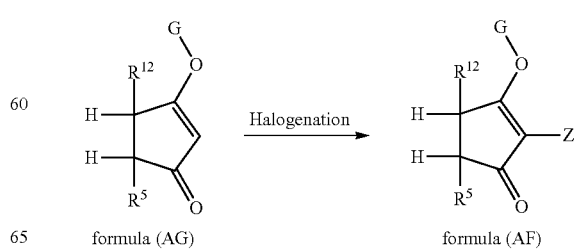

In a similar manner, a compound of formula (A) may be prepared from a compound of formula (AH) by suitable derivatisation under standard conditions.

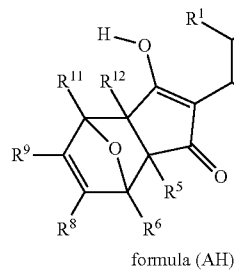

formula (AH)

derivatisation

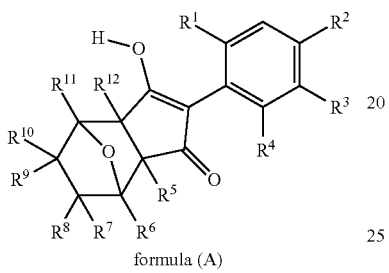

formula (A)

For example, compounds of formula (AH) are alkenes, and as such undergo further reactions typical of alkenes to give compounds of formula (A) according to known procedures. Examples of such reactions include, but are not restricted to, reduction, halogenation, epoxidation, cyclopropanation, dihydroxylation, hydroarylation, hydrovinylation and hydration. Compounds of formula (AH) wherein $R^8$ or $R^9$ is bromine or iodine are vinyl halides, and undergo known reactions of vinyl halides such as Suzuki-Miyaura, Sonogashira, Stille and related reactions. Certain other compounds of formula (AH), wherein $R^8$ or $R^9$ is $C_1$-$C_6$alkoxy, are enol ethers, and these may be hydrolysed to the corresponding ketone using standard procedures. In turn, the ketone produced may be further transformed, for example by ketalisation, oximation, reduction and the like under known conditions to give additional compounds of formula (A). Similarly, compounds of formula (AH) wherein $R^8$ or $R^9$ is $C_1$-$C_6$amino or di-$C_1$-$C_6$amino are enamines, and these also may be hydrolysed to the corresponding ketone using standard procedures.

A compound of formula (AH) may be prepared from a compound of formula (AI) by reaction with a compound of formula (H), optionally in a suitable solvent, and optionally in the presence of a suitable catalyst. The compounds of formula (AI) have been particularly designed as intermediates in the synthesis of the compounds of the formula I.

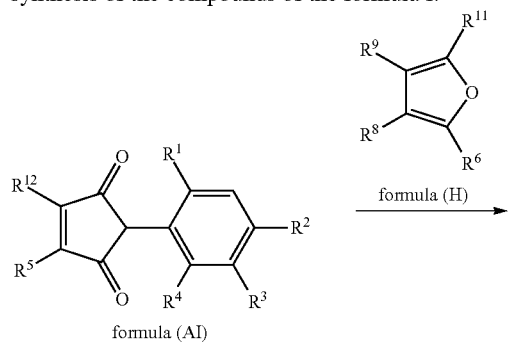

formula (AI)

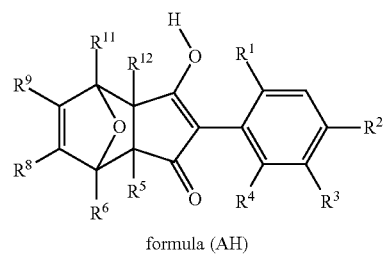

formula (H)

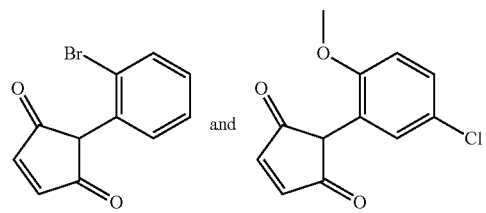 [SMILES: O=C1C=CC(=O)C1c1ccccc1Br ; COc1ccc(Cl)cc1C1C(=O)C=CC1=O]

formula (AH)

Compounds of the formula (AI) having the specific formulae and are known under the CAS registry numbers 299968-82-4 and 528833-96-7, respectively.

Preferably the catalyst is a Lewis acid catalyst such as aluminium chloride, bismuth (III) chloride, bismuth (III) trifluoromethanesulfonate, boron trifluoride, cerium (III) chloride, copper (I) trifluoromethanesulfonate, diethylaluminium chloride, hafnium (IV) chloride, iron (III) chloride, lithium perchlorate, lithium trifluoromethanesulfonate, magnesium bromide, magnesium iodide, scandium (III) trifluoromethanesulfonate, tin (IV) chloride, titanium (IV) chloride, titanium (IV) isopropoxide, trimethyl aluminium, N-trimethylsilyl-bis(trifluoromethanesulfonyl)imide, trimethylsilyl trifluoromethane-sulfonate, ytterbium (III) trifluoromethane-sulfonate, zinc iodide and zirconium (IV) chloride. Magnesium iodide is particularly preferred. Suitable solvents include those which are known to be effective solvents for conducting Diels-Alder reactions, among them, for example, chloroform, dichloromethane, diethyl ether, ethanol, methanol, perfluorinated alkanes, such as perfluorohexane, toluene, water, and ionic liquids such as 1-butyl-3-methylimidazolium tetrafluoroborate and 1-butyl-3-methylimidazolium hexafluorophosphate. Dichloromethane is particularly preferred as a solvent.

A compound of formula (AI), may be prepared by oxidising a compound of formula (AJ) in a suitable solvent such as toluene, acetone, chloroform, dichloromethane or 1,4-dioxane. A wide range of oxidants are suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1,-tris(acetyloxy)-1,1-dihydro-1,2-benziodoxol-3-(1H)-one (Dess-Martin periodinane), Suitable procedures are described, for example, by K. Saito and H. Yamachika, U.S. Pat. No. 4,371,711. and by G. Piancatelli et al., Tetrahedron (1978), 34, 2775. The use of chromium trioxide in a mixture of sulfuric acid and acetone (Jones reagent) is preferred.

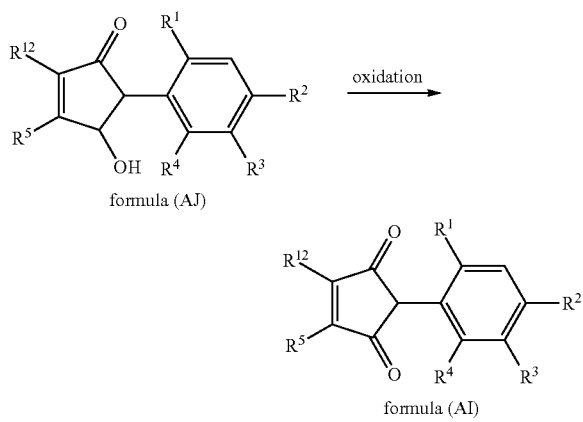

formula (AJ)

formula (AI)

The compounds of the formula AI have been particularly designed as intermediates for the synthesis of the compounds of the formula I.

Particularly useful compounds of the formula AI are those, wherein $R^5$ and $R^{12}$ are hydrogen.

In another group of useful compounds of the formula I, $R^1$, $R^2$ and $R^4$ are independently of each other methyl or ethyl.

In another group of useful compounds of the formula I, $R^1$, $R^2$ and $R^4$ are independently of each other methyl or ethyl, and $R^3$, $R^5$ and $R^{12}$ are hydrogen.

A compound of formula (AJ) may be prepared from a compound of formula (AK) by treatment with a suitable acid catalyst in the presence of water and optionally in the presence of a suitable solvent, according to known procedures.

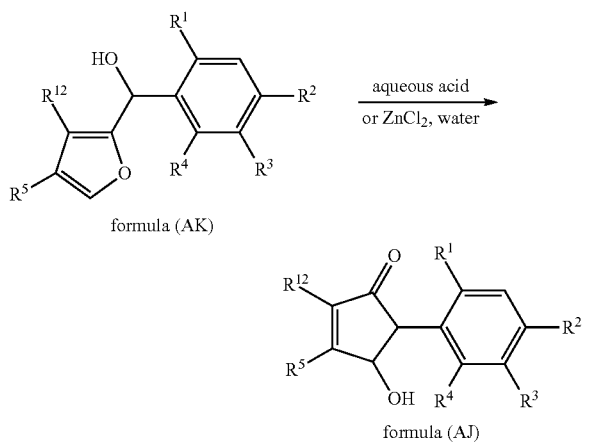

formula (AK)

formula (AJ)

For example, a compound of formula (AK) may be converted to a compound of formula (AJ) in the presence of an aqueous solution of an acid such as phosphoric acid or polyphosphoric acid as described, for example by K. Saito and H. Yamachika, U.S. Pat. No. 4,371,711. Alternatively a compound of formula (AJ) may be prepared from a compound of formula (AK) by rearrangement in the presence of a Lewis acid catalyst such as zinc chloride according to the procedure of G. Piancatelli et al., Tetrahedron, (1978), 34, 2775.

A compound of formula (AK) may be prepared by the reduction of a compound of formula (AL) by known conditions (see, for example R Silvestri et al., J. Med. Chem., 2005, 48, 4378-4388).

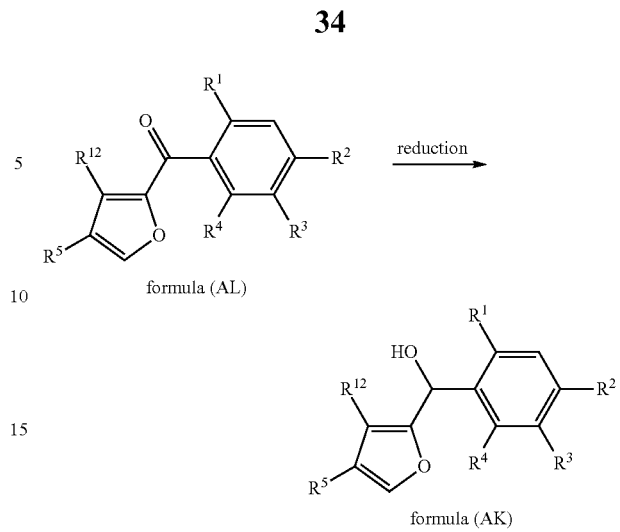

formula (AL)

formula (AK)

Compounds of formula (AL) are known, or may be made by known methods from known compounds (see, for example, L. Liebeskind et al., Org. Lett., (2003), 5 (17), 3033-3035, H. Firouzabadi, N. Iranpoor and F. Nowrouzi, Tetrahedron, (2004), 60,10843, R. Silvestri et al., J. Med. Chem., (2005), 48, 4378 and references therein).

Alternatively a compound of formula (AK) may be prepared by the addition of a suitable organometallic reagent such as an arylmagnesium halide of formula (AM) wherein Hal is a halide such as chloride, bromide or iodide, or an aryllithium reagent of formula (AN) or a diarylzinc reagent of formula (AO) to a furan-2-carboxaldehyde of formula (AP) according to known procedures (see, for example G. Panda et al., Tetrahedron Lett., (2005), 46, 3097).

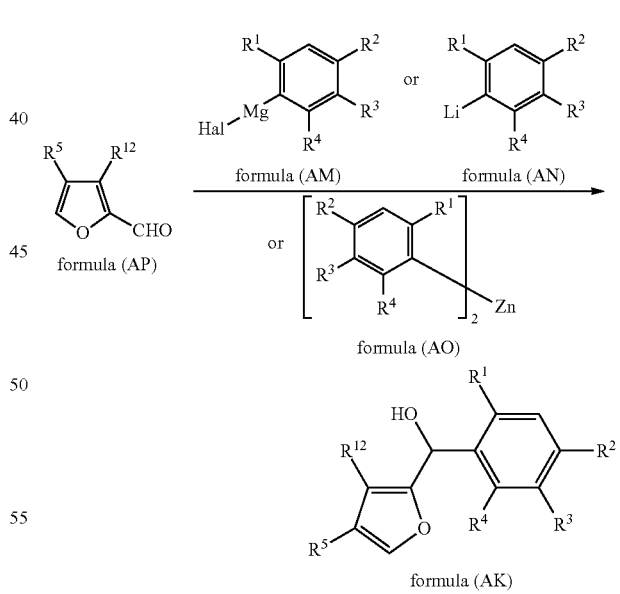

formula (AP)

formula (AM)

formula (AN)

formula (AO)

formula (AK)

Additional compounds of formula (AK) may be prepared from compounds of formula (AR) by reaction with a strong base, for a example an alkyl lithium reagent such as n-butyllithium, optionally in the presence of an additive such as tetramethylethylenediamine, and in a suitable solvent such as diethyl ether or tetrahydrofuran, followed by reaction with a benzaldehyde of formula (AS) as described, for example by I. Gupta and M. Ravikanth, J. Org. Chem., (2004), 69, 6796, A.

M. Echavarren et al., J. Am. Chem. Soc., (2003), 125 (19), 5757, and by T. K. Chandrashekar et al., J. Org. Chem., (2002), 67, 6309-6319.

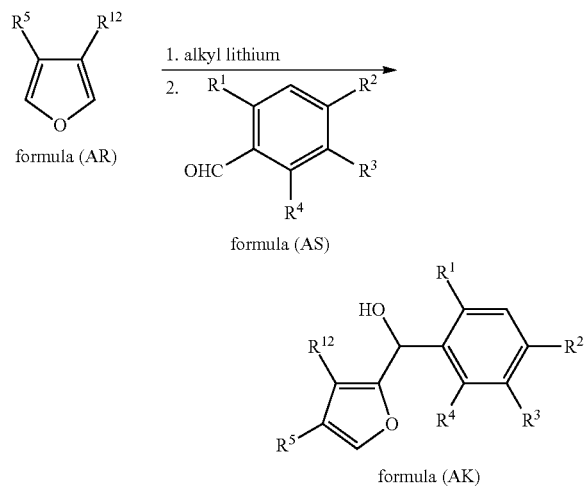

formula (AR)

formula (AS)

formula (AK)

The organometallic reagents of formula (AM), formula (AN) and formula (AO) are known compounds or may be made by known methods from known compounds. Compounds of formula (AP), formula (AR) and formula (AS) are known compounds, or may be prepared from known compounds by known methods.

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, antifoams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). Further oil additives that are preferred according to the invention are SCORE® (Syngenta Crop Protection Canada) and Adigor® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

| Preferred formulations have especially the following compositions: | |
|---|---|
| Emulsifiable concentrates: | |
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |

-continued

| Preferred formulations have especially the following compositions: | |
|---|---|
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

(% = percent by weight):

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) | 99.0% | 93% | 83% | e.g. $CaCO_3$ or $SiO_2$

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) | 98.0% | 92% | 80% | e.g. $CaCO_3$ or $SiO_2$

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, and for non-selective weed control, which comprises treating the useful plants or the area under cultivation or the locus thereof with a compound of formula I.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 146 below. The following mixtures of the compound of formula I are especially important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC; compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1] oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula I may also be in the form of esters or salts, as mentioned e.g. in The Pesticide Manual, 12th Edition (BCPC) 2000.

The compounds of formula I according to the invention can also be used in combination with safeners. Preferably, in these mixtures, the compound of the formula I is one of those compounds listed in Tables 1 to 146 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

It is preferred to apply the other herbicide together with one of the safeners mentioned above.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Example 1

Preparation of (1RS,2SR,6RS,7SR)-4-(2,6-diethyl-4-methylphenyl)-10-oxatricyclo-[5.2.1.0$^{2,6}$]decane-3,5-dione

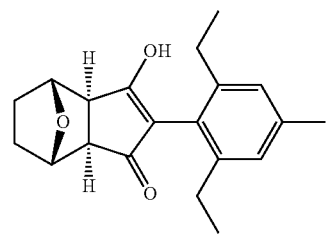 [SMILES: CCc1cc(C)cc(CC)c1C1=C(O)[C@H]2[C@@H](C1=O)[C@@H]1CC[C@H]2O1]

Step 1: Preparation of (1RS,2SR,6RS,7SR)-10-oxatricyclo[5.2.1.0$^{2,6}$]dec-8-ene-3,5-dione

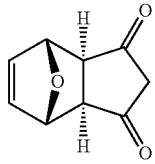

Furan (13.9 ml, 0.19 mol) is added to cyclopentene-1,4-dione (18.4 g, 0.19 mol) and the reaction mixture is stirred at room temperature for 5 days. The mixture is diluted with methanol and (1RS,2SR,6RS,7SR)-10-oxatricyclo[5.2.1.0$^{2,6}$]dec-8-ene-3,5-dione is collected by filtration, and used without further purification in the next step.

Step 2: Preparation of (1RS,2SR,6RS,7SR)-10-oxatricyclo[5.2.1.0$^{2,6}$]decane-3,5-dione

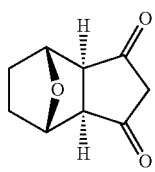

(1RS,2SR,6RS,7SR)-10-oxatricyclo[5.2.1.0$^{2,6}$]dec-8-ene-3,5-dione (2.1 g, 12.8 mmol), prepared in Step 1, is dissolved in warm methanol (180 ml) and the mixture is allowed to cool to room temperature. The mixture is then hydrogenated in the presence of 5% palladium on carbon (approx. 50 mg) at 3.5 bar for 4 hours. The catalyst is removed by filtration through diatomaceous earth and the filtrate is concentrated under reduced pressure to afford (1RS,2SR,6RS,7SR)-10-oxatricyclo[5.2.1.0$^{2,6}$]decane-3,5-dione.

Step 3: Preparation of (1RS,2SR,6RS,7SR)-4-(2,6-diethyl-4-methylphenyl)-10-oxatricyclo-[5.2.1.0$^{2,6}$]decane-3,5-dione

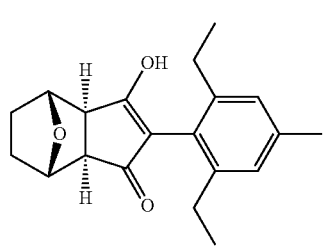 [SMILES: CCc1cc(C)cc(CC)c1C1=C(O)[C@H]2[C@@H](C1=O)[C@@H]1CC[C@H]2O1]

Iodobenzene diacetate (10.3 g, 32.0 mol) and sodium carbonate (3.38 g, 32.0 mmol) are suspended in water (100 ml) and the resultant yellow suspension is stirred at room temperature for 30 minutes. Meanwhile, (1RS,2SR,6RS,7SR)-10-oxatricyclo[5.2.1.0$^{2,6}$]decane-3,5-dione (5.3 g, 32.0 mol) is added to a solution of sodium carbonate (3.38 g, 32.0 mol) in water (50 ml) and ethanol (50 ml) and the mixture is stirred at room temperature to produce an orange solution. The two mixtures are combined and stirred for 3 hours at room temperature, then the mixture is poured into water and extracted with dichloromethane. The organic extracts are combined, dried over anhydrous magnesium sulfate, filtered and the filtrate evaporated under reduced pressure to give an iodonium ylide, used without further purification in the next step.

The iodonium ylide (3 g, 8.15 mmol), prepared above, is added to a solution of 2,6-diethyl-4-methylphenylboronic acid (1.57 g, 8.15 mmol), tetrabutylammonium bromide (2.63 g, 8.15 mmol), lithium hydroxide monohydrate (1.03 g, 24.5 mmol) and palladium (II)acetate (92 mg, 0.41 mmol) in 1,2-dimethoxyethane (80 ml) and water (20 ml) and the reaction mixture is heated at 50° C. for 5 hours under an atmosphere of nitrogen. The reaction mixture is cooled to room temperature and partitioned between dilute aqueous hydrochloric acid and ethyl acetate. The organic phase is then extracted into 0.5 M aqueous potassium carbonate solution and the organic phase discarded. The aqueous phase is acidified with concentrated hydrochloric acid and extracted with ethyl acetate. The organic extract is dried over anhydrous magnesium sulfate, filtered and the filtrate concentrated under reduced pressure. The residue is purified by column chromatography on silica gel to afford (1RS,2SR,6RS,7SR)-4-(2,6-diethyl-4-methylphenyl)-10-oxatricyclo[5.2.1.0$^{2,6}$]decane-3,5-dione.

$^1$H NMR (400 MHz, CDCl$_3$) $\delta_H$ 6.88-6.87 (2H, m), 4.55-4.54 (2H, m), 2.62 (2H, s), 2.36-2.27 (7H, m), 1.69-1.67 (2H, m), 1.40-1.39 (2H, m), 1.03 (6H, q).

Example 2

Preparation of (1RS, 2RS,6SR,7SR)-4-(2,6-diethyl-4-methylphenyl)-5-methoxy-10-oxa-tricyclo[5.2.1.0$^{2,6}$]deca-4,8-dien-3-one

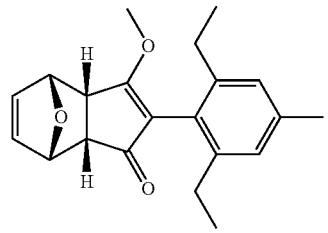 [SMILES: CCc1cc(C)cc(CC)c1C1=C(OC)[C@@H]2[C@H](C1=O)[C@@H]1C=C[C@H]2O1]

Step 1: Preparation of 2-bromo-3-methoxycyclopent-2-enone

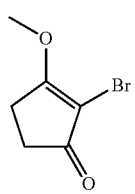

N-Bromosuccinimide (24.92 g, 0.140 mol) is added, portionwise, over 1 hour to a stirred solution of 3-methoxycyclopent-2-enone (14.95 g, 0.133 mol) in 1,2-dichloroethane (300 ml) at 0° C. in an amber flask. The reaction mixture is stirred at 0° C. for a further 90 minutes and then any remaining solid is removed by filtration. The filtrate is evaporated to dryness under reduced pressure, the resultant solid is dissolved in warm toluene (600 ml) and washed quickly with ice-cold water (2×100 ml). The organic phase is dried over anhydrous magnesium sulfate, filtered and the filtrate evaporated under reduced pressure until approximately 150 ml remains. The residue is cooled with an ice bath and left for 30 minutes. The resultant solid is removed by filtration, washed with hexane (50 ml) and air-dried to give 2-bromo-3-methoxycyclopent-2-enone.

Step 2: Preparation of 2-(2,6-diethyl-4-methylphenyl)-3-methoxycyclopent-2-enone

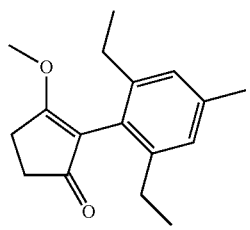

To a stirred suspension of 2-bromo-3-methoxycyclopent-2-enone (17.5 g, 91.6 mmol), 2,6-diethyl-4-methylphenyl boronic acid (26.4 g, 137 mmol) and freshly powdered potassium phosphate (38.9 g, 183 mmol) in anhydrous, degassed toluene (450 ml) under a nitrogen atmosphere are added palladium (II)acetate (0.411 g, 1.83 mmol) and 2-dicyclohexylphosphino-2',6'-dimethoxybiphenyl (1.51 g, 3.67 mmol). The reaction mixture is heated at 90° C. for 6.5 hours and then allowed to cool to room temperature overnight. The reaction is diluted with water (400 ml) and extracted with ethyl acetate (3×150 ml). The combined organic extracts are washed with brine (50 ml), dried over anhydrous magnesium sulfate, filtered and the filtrate is evaporated to dryness under reduced pressure to give a brown oil. The crude product is purified by column chromatography on silica gel to give 2-(2,6-diethyl-4-methylphenyl)-3-methoxycyclopent-2-enone.

Step 3: Preparation of 5-chloro-2-(2,6-diethyl-4-methylphenyl)-3-methoxycyclopent-2-enone

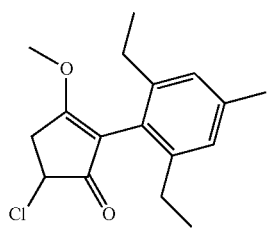 [SMILES: CCc1cc(C)cc(CC)c1C1=C(OC)CC(Cl)C1=O]

To a stirred solution of 2-(2,6-diethyl-4-methylphenyl)-3-methoxycyclopent-2-enone (0.715 g, 2.77 mmol) in 1,4-dioxane (45 ml), and under an atmosphere of nitrogen, are added copper (II) chloride (0.743 g, 5.53 mmol) and lithium chloride (0.176 g, 4.15 mmol). The reaction is heated at reflux for 7 hours and allowed to cool to room temperature overnight. The remaining solid is removed by filtration and washed with ethyl acetate (50 ml). The filtrate is washed with water (2×25 ml) and the aqueous washings re-extracted with ethyl acetate (1.5 ml). The combined organic phases are washed with brine (15 ml), dried over anhydrous magnesium sulfate, filtered and the filtrate is evaporated under reduced pressure to give a brown oil. The crude product is purified by column chromatography on silica gel to give 5-chloro-2-(2,6-diethyl-4-methylphenyl)-3-methoxycyclopent-2-enone.

Step 4: Preparation of (1RS,2RS,6SR,7SR)-4-(2,6-diethyl-4-methylphenyl)-5-methoxy-10-oxa-tricyclo[5.2.1.0$^{2,6}$]deca-4,8-dien-3-one

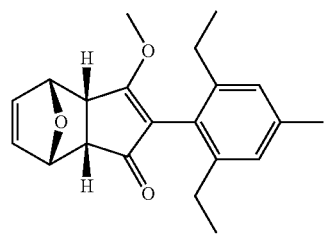 [SMILES: CCc1cc(C)cc(CC)c1C1=C(OC)[C@@H]2[C@H](C1=O)[C@@H]1C=C[C@H]2O1]

To a stirred solution of 5-chloro-2-(2,6-diethyl-4-methylphenyl)-3-methoxycyclopent-2-enone (0.530 g, 1.81 mmol) in furan (40 ml) at room temperature is added by syringe pump over two hours a solution of 1,8-diazabicyclo[5.4.0]undec-7-ene (0.540 ml, 3.62 mmol) in furan (10 ml). The reaction is stirred at room temperature for a further 30 minutes and then evaporated to dryness under reduced pressure. The residue is diluted with water (50 ml), 2 M aqueous hydrochloric acid (25 ml) is added and the mixture is extracted with ethyl acetate (3×50 ml). The combined organic extracts are washed with brine (20 ml), dried over anhydrous magnesium sulfate, filtered and the filtrate is evaporated to dryness under reduced pressure. The residue is purified by column chromatography on silica gel to give (1RS,2RS,6SR,7SR)-4-(2,6-diethyl-4-methylphenyl)-5-methoxy-10-oxa-tricyclo[5.2.1.0$^{2,6}$]deca-4,8-dien-3-one.

$^1$H NMR (400 MHz, CDCl$_3$) $\delta_H$ 6.90 (2H, s), 6.45 (1H, dd), 6.35 (1H, dd), 5.30 (1H, d), 5.25 (1H, d), 3.65 (3H, s), 3.65 (1H, dd), 3.45 (1H, dd), 2.35 (4H, m), 2.30 (3H, s), 1.10 (6H, m).

Note: A quantity of (1RS,2SR,6RS,7SR)-4-(2,6-diethyl-4-methylphenyl)-5-methoxy-10-oxatricyclo[5.2.1.0$^{2,6}$]deca-4,8-dien-3-one is also formed during the course of this reaction.

Example 3

Preparation of (1RS,2RS,6SS,7SR)-4-(2,6-diethyl-4-methylphenyl)-5-methoxy-10-oxa-tricyclo[5.2.1.0$^{2,6}$]dec-4-en-3-one

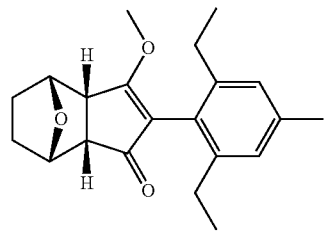 [SMILES: CCc1cc(C)cc(CC)c1C1=C(OC)[C@@H]2[C@H](C1=O)[C@@H]1CC[C@H]2O1]

To a solution of (1RS,2RS,6SR,7SR)-4-(2,6-diethyl-4-methylphenyl)-5-methoxy-10-oxa-tricyclo[5.2.1.0$^{2,6}$]deca-4,8-dien-3-one (0.052 g, 0.16 mmol) in methanol (10 ml) is added 5% palladium on carbon (10 mg). The reaction is stirred under an atmosphere of hydrogen for 90 minutes. The reaction is filtered through diatomaceous earth and the filter pad is washed with ethyl acetate (10 ml). The solvent is removed under reduced pressure to yield (1RS,2RS,6-SR,7SR)-4-(2,6-diethyl-4-methylphenyl)-5-methoxy-10-oxa-tricyclo[5.2.1.0$^{2,6}$]dec-4-en-3-one.

$^1$H NMR (400 MHz, CDCl$_3$) $\delta_H$ 6.90 (2H, m), 4.85 (2H, m), 3.70 (3H, s), 3.60 (1H, m), 3.35 (1H, dd), 2.50 (2H, m), 2.35 (2H, m), 2.30 (3H, s), 1.90-1.75 (4H, m), 1.20 (3H, t), 1.10 (3H, t).

Example 4

Preparation of (1RS,2RS,6SS,7SR)-4-(2,6-diethyl-4-methylphenyl)-10-oxatricyclo-[5.2.1.0$^{2,6}$]decane-3,5-dione

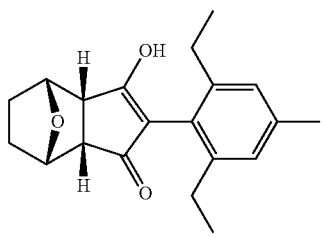 [SMILES: CCc1cc(C)cc(CC)c1C1=C(O)[C@@H]2[C@H](C1=O)[C@@H]1CC[C@H]2O1]

To a solution of (1RS,2RS,6SR,7SR)-4-(2,6-diethyl-4-methylphenyl)-5-methoxy-10-oxa-tricyclo[5.2.1.0$^{2,6}$]dec-4-en-3-one (0.049 g, 0.15 mmol) in THF (1 ml) in a 5 ml microwave vial is added 2 M aqueous hydrochloric acid (4 ml). The reaction mixture is at 140° C. under microwave irradiation for 50 minutes. The reaction mixture is cooled to room temperature, diluted with 2 M aqueous potassium carbonate solution (20 ml) and washed with diethyl ether (2×5 ml). The pH of the aqueous phase is adjusted to approx. 2 by addition of 5 M aqueous hydrochloric acid and then extracted with ethyl acetate (3×10 ml). The combined organic extracts are washed with brine (10 ml), dried over anhydrous magnesium sulfate, filtered and the filtrate is evaporated to dryness under reduced pressure to give a yellow oil. The crude product is purified by column chromatography on silica gel to give (1RS,2RS,6SS,7SR)-4-(2,6-diethyl-4-methylphenyl)-10-oxatricyclo-[5.2.1.0$^{2,6}$]decane-3,5-dione.

$^1$H NMR (400 MHz, CDCl$_3$) $\delta_H$ 6.95 (2H, s), 4.75 (2H, br), 3.40 (2H, br), 2.45 (2H, q), 2.35 (2H, q), 2.30 (3H, s), 1.80 (4H, m), 1.15 (3H, t), 1.05 (3H, t).

Example 5

Preparation of (1RS,2SR,6RS,7SR)-4-(2,6-diethyl-4-methylphenyl)-5-methoxy-10-oxatricyclo[5.2.1.0$^{2,6}$]dec-4-en-3-one

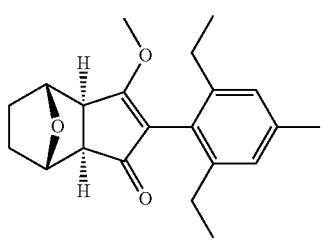 [SMILES: CCc1cc(C)cc(CC)c1C1=C(OC)[C@H]2[C@@H](C1=O)[C@@H]1CC[C@H]2O1]

Step 1: Preparation of (1RS,2SR,6RS,7SR)-5-methoxy-10-oxatricyclo[5.2.1.0$^{2,6}$]dec-4-en-3-one

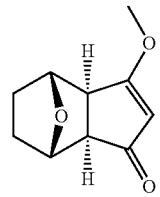

Iodine (0.10 g, 0.38 mmol) is added to a solution of (1RS,2SR,6RS,7SR)-10-oxa-tricyclo[5.2.1.0$^{2,6}$]decane-3,5-dione (2.1 g, 12.65 mmol) in methanol (50 ml) and the reaction mixture is stirred for 2 hours at room temperature. The solvent is then removed under reduced pressure, dichloromethane is added and the organic layer is washed with saturated aqueous sodium thiosulfate solution, water and brine. The organic layer is dried over anhydrous magnesium sulfate, filtered and the filtrate is evaporated under reduced pressure to give (1RS,2SR,6RS,7SR)-5-methoxy-10-oxatricyclo[5.2.1.0$^{2,6}$]dec-4-en-3-one and used without further purification in the next step.

Step 2: Preparation of (1RS,2SR,6RS,7SR)-4-bromo-5-methoxy-10-oxatricyclo[5.2.1.0$^{2,6}$]dec-4-en-3-one

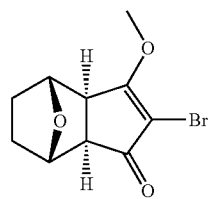

A solution of bromine (0.14 ml, 2.8 mmol) in dichloromethane (5 ml) is added dropwise to a solution of the enol ether (0.48 g, 2.6 mmol) prepared in step 1 in dichloromethane (40 ml) at 0° C. and the reaction mixture is stirred for 1 hour. Triethylamine (0.64 ml, 4.6 mmol) is then added and the reaction mixture is allowed to warm to room temperature and then stirred for 3 hours. The reaction mixture is washed with 2M aqueous hydrochloric acid and brine, dried over anhydrous magnesium sulfate, filtered and the filtrate evaporated under reduced pressure. The residue is purified by column chromatography on silica gel to give (1RS,2SR,6RS,7SR)-4-bromo-5-methoxy-10-oxatricyclo[5.2.1.0$^{2,6}$]dec-4-en-3-one.

Step 3: Preparation of (1RS,2SR,6RS,7SR)-4-(2,6-diethyl-4-methylphenyl)-5-methoxy-10-oxatricyclo[5.2.1.0$^{2,6}$]dec-4-en-3-one

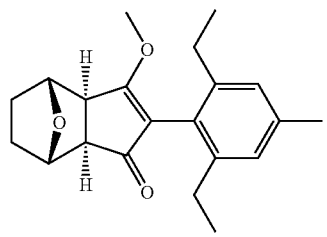 [SMILES: CCc1cc(C)cc(CC)c1C1=C(OC)[C@H]2[C@@H](C1=O)[C@@H]1CC[C@H]2O1]

A mixture of (1RS, 2SR,6RS,7SR)-4-bromo-5-methoxy-10-oxatricyclo[5.2.1.0$^{2,6}$]dec-4-en-3-one (0.315 g, 1.2 mmol), 2,6-diethyl-4-methylphenylboronic acid (0.35 g, 1.8 mmol), 2-dicyclohexylphosphino-2',6'-dimethoxybiphenyl (20 mg, 0.048 mmol), palladium (II)acetate (5.5 mg, 0.024 mmol) and potassium phosphate (0.51 g, 2.4 mmol) are heated in degassed toluene at 95° C. for 24 hours. The reaction mixture is partitioned between dichloromethane and water, and the organic phase is dried over anhydrous magnesium sulfate, filtered and the filtrate is evaporated under reduced pressure. The residue is purified by column chromatography on silica gel to give (1RS,2SR,6RS,7SR)-4-(2,6-diethyl-4-methylphenyl)-5-methoxy-10-oxatricyclo[5.2.1.0$^{2,6}$]dec-4-en-3-one.

$^1$H NMR (400 MHz, CDCl$_3$) δ$_H$ 6.90 (1H, s), 6.80 (1H, s), 4.73 (1H, d), 4.66 (1H, d), 3.58 (3H, s), 2.91 (1H, d), 2.66 (1H, d), 2.50-2.36 (4H, m), 2.30 (3H, s), 1.88-1.81 (2H, m), 1.62-1.56 (2H, m), 1.12-1.09 (6H, m).

Example 6

Preparation of (1RS,2SR,6RS,7SR)-4-(2,4,6-trimethylphenyl)-10-oxatricyclo[5.2.1.0$^{2,6}$]dec-8-en-3,5-dione

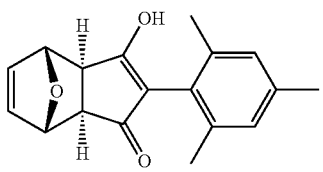 [SMILES: Cc1cc(C)c(C2=C(O)[C@H]3[C@@H](C2=O)[C@@H]2C=C[C@H]3O2)c(C)c1]

Step 1: Preparation of (2,4,6-trimethylphenyl)furan-2-ylmethanol

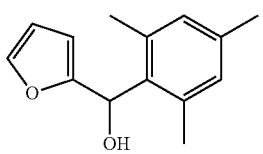 [SMILES: Cc1cc(C)c(C(O)c2ccco2)c(C)c1]

A solution of 2,4,6-trimethyl-1-bromobenzene (30.9 g, 155 mmol) in tetrahydrofuran (100 ml) is added slowly to magnesium turnings (3.77 g, 155 mmol), until the magnesium is just covered. A small quantity of iodine is added and the mixture is allowed to stand at room temperature for 25 minutes and then heated and stirred until the brown colour is lost. The remainder of the aryl bromide solution is added dropwise over a 20 minute period, with occasional heating to maintain the formation of the Grignard reagent solution. The reaction is stirred at room temperature for 1 hour. A solution of furfural (12.8 ml, 155 mmol) in tetrahydrofuran (70 ml) is added dropwise, and once the addition is complete, the reaction is stirred at room temperature for 2 hours. The reaction is quenched by cautious addition of excess saturated ammonium chloride solution, then extracted into ethyl acetate, washed with brine, dried over anhydrous magnesium sulfate, filtered and concentrated under reduced pressure. Purification by column chromatography on silica gel affords (2,4,6-trimethylphenyl)furan-2-ylmethanol.

Step 2: Preparation of 5-(2,4,6-trimethylphenyl)-4-hydroxycyclopent-2-enone

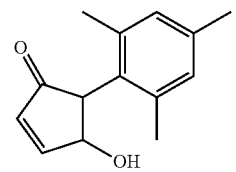 [SMILES: Cc1cc(C)c(C2C(=O)C=CC2O)c(C)c1]

A solution of (2,4,6-trimethylphenyl)furan-2-ylmethanol (27.8 g, 129 mmol) in acetone (730 ml) and water (100 ml) is heated to 55° C. and polyphosphoric acid (2 g) is added. The mixture is stirred at 55° C. for 7 hours, then cooled to room temperature overnight. The reaction mixture is concentrated under reduced pressure to remove most of the acetone then ethyl acetate (500 ml) is added, and the reaction mixture is partitioned. The aqueous phase is extracted into ethyl acetate and the organic solutions are combined, washed with saturated aqueous sodium bicarbonate solution and brine, dried over anhydrous magnesium sulfate, filtered and the filtrate is concentrated under reduced pressure. The residue is purified by column chromatography on silica gel to give 5-(2,4,6-trimethylphenyl)-4-hydroxycyclopent-2-enone.

Step 3: Preparation of 2-(2,4,6-trimethylphenyl)cyclopent-4-ene-1,3-dione

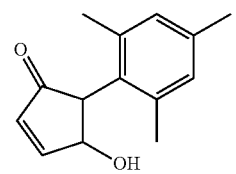 [SMILES: Cc1cc(C)c(C2C(=O)C=CC2O)c(C)c1]

Jones' reagent (138 ml of 1.67 M solution, 230 mmol) is added dropwise over 40 minutes to a cooled (ice-bath) solution of 5-(2,4,6-trimethylphenyl)-4-hydroxycyclopent-2-enone (49.66 g, 230 mmol) in acetone (600 ml). The mixture is stirred for 1 hour. Isopropanol (100 ml) is added and the mixture is stirred at room temperature for 2 hours. The mixture is diluted with ethyl acetate and washed with brine, dried over anhydrous magnesium sulfate, filtered and the filtrate is evaporated under reduced pressure to give 2-(2,4,6-trimethylphenyl)cyclopent-4-ene-1,3-dione.

Step 4: Preparation of (1RS,2SR,6RS,7SR)-4-(2,4,6-trimethylphenyl)-10-oxatricyclo-[5.2.1.0$^{2,6}$]dec-8-en-3,5-dione

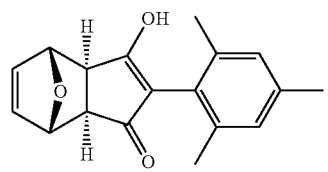 [SMILES: Cc1cc(C)c(C2=C(O)[C@H]3[C@@H](C2=O)[C@@H]2C=C[C@H]3O2)c(C)c1]

Furan (214 ml, 3.15 mol) and magnesium iodide (7.0 g, 0.025 mol) are added to 2-(2,4,6-trimethylphenyl)cyclopent-4-ene-1,3-dione (27.0 g, 0.126 mol) and the mixture is stirred at room temperature for 4 days. The reaction mixture is concentrated under reduced pressure and the residue is purified by column chromatography on silica gel to give (1RS,2SR,6RS,7SR)-4-(2,4,6-trimethylphenyl)-10-oxatricyclo[5.2.1.0$^{2,6}$]dec-8-en-3,5-dione.

$^1$H NMR (400 MHz, CDCl$_3$) $\delta_H$ 6.86 (2H, s), 6.47 (2H, s), 5.01 (2H, s), 2.74 (2H, s), 2.23 (3H, s), 2.08 (3H, s), 2.06 (3H, s).

Example 7

Preparation of (1RS,2SR,6RS,7SR)-4-(2,4,6-trimethylphenyl)-10-oxatricyclo[5.2.1.0$^{2,6}$]decane-3,5-dione

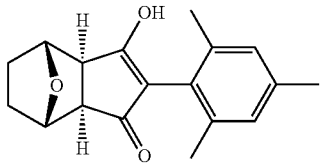 [SMILES: Cc1cc(C)c(C2=C(O)[C@H]3[C@@H](C2=O)[C@@H]2CC[C@H]3O2)c(C)c1]

A solution of (1RS,2SR,6RS,7SR)-4-(2,4,6-trimethylphenyl)-10-oxatricyclo[5.2.1.0$^{2,6}$]dec-8-en-3,5-dione (205 mg, 0.66 mmol) in methanol (250 ml) is hydrogenated at 2 bar over 5% palladium on carbon (approximately 20 mgs) for 1 hour at room temperature. The catalyst is removed by filtration through diatomaceous earth and the solvent is evaporated under reduced pressure. Trituration with diethyl ether gives (1RS,2SR,6RS,7SR)-4-(2,4,6-trimethylphenyl)-10-oxatricyclo[5.2.1.0$^{2,6}$]decane-3,5-dione.

$^1$H NMR (400 MHz, d$_4$-MeOH) $\delta_H$ 6.88 (2H, s), 4.61 (2H, s), 2.87 (2H, s), 2.27 (3H, s), 2.06 (6H, s), 1.84-1.82 (2H, m), 1.71-1.66 (2H, m).

Example 8

Preparation of (1RS,2SR,6RS,7RS)-4-(2,4,6-trimethylphenyl)-8-trimethylsilylethynyl-10-oxatricyclo[5.2.1.0$^{2,6}$]decane-3,5-dione

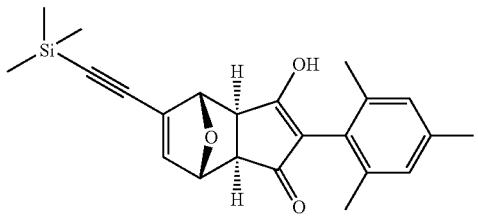

3-(Trimethylsilylethynyl)furan (10.0 g, 61 mmol) and magnesium iodide (1.11 g, 4 mmol) are added to 2-(2,4,6-trimethylphenyl)cyclopent-4-ene-1,3-dione (4.34 g, 20 mmol) and the mixture is stirred at room temperature for 3 days. The reaction mixture is concentrated under reduced pressure and the residue is purified by column chromatography on silica gel to give (1RS,2SR,6RS,7RS)-4-(2,4,6-trimethylphenyl)-8-trimethylsilylethynyl-10-oxatricyclo-[5.2.1.0$^{2,6}$]decane-3,5-dione.

$^1$H NMR (400 MHz, CDCl$_3$) $\delta_H$ 6.65 (2H, s), 6.26 (1H, s), 4.75 (1H, s), 4.67 (1H, s), 2.62 (1H, d), 2.52 (1H, d), 2.03 (3H, s), 1.84 (3H, s), 1.80 (3H, s), 0.00 (9H, s).

Example 9

Preparation of (1RS,2SR,6RS,7RS)-8-ethynyl-4-(2,4,6-trimethylphenyl)-10-oxatricyclo-[5.2.1.0$^{2,6}$]decane-3,5-dione

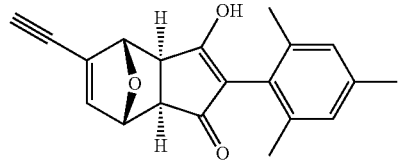 [SMILES: C#CC1=C[C@@H]2O[C@H]1[C@H]1C(O)=C(c3c(C)cc(C)cc3C)C(=O)[C@H]12]

Potassium carbonate (2.58 g, 19 mmol) is added to a stirred solution of (1RS,2SR,6RS,7RS)-4-(2,4,6-trimethylphenyl)-8-trimethylsilylethynyl-10-oxatricyclo-[5.2.1.0$^{2,6}$]decane-3,5-dione (6.43 g, 17 mmol) in methanol (100 ml). The reaction mixture is stirred at room temperature for 2 hours and 30 minutes, then dilute aqueous hydrochloric acid is added and the mixture is extracted with ethyl acetate. The organic extracts are combined, dried over anhydrous magnesium sulfate, filtered and the filtrate is evaporated under reduced pressure to give (1RS,2SR,6RS,7RS)-8-ethynyl-4-(2,4,6-trimethylphenyl)-10-oxatricyclo-[5.2.1.0$^{2,6}$]decane-3,5-dione.

$^1$H NMR (400 MHz, d$_4$-MeOH) $\delta_H$ 6.85 (2H, s), 6.72 (1H, d), 5.03 (1H, d), 3.96 (1H, s), 2.92-2.88 (2H, m), 2.24 (3H, s), 2.06 (3H, s), 2.01 (3H, s).

Example 10

Preparation of (1RS,2SR,6RS,7SR,8RS)-8-ethyl-4-(2,4,6-trimethylphenyl)-10-oxatricyclo-[5.2.1.0$^{2,6}$]decane-3,5-dione and (1RS,2SR,6RS,7SR,8SR)-8-ethyl-4-(2,4,6-trimethylphenyl)-10-oxatricyclo[5.2.1.0$^{2,6}$]decane-3,5-dione

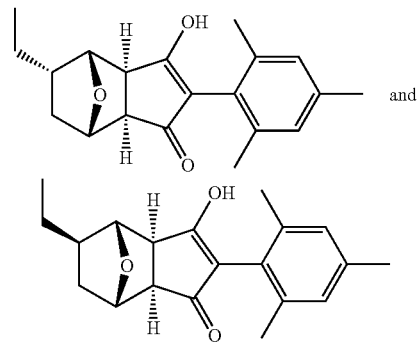

A solution of (1RS,2SR,6RS,7RS)-8-ethynyl-4-(2,4,6-trimethylphenyl)-10-oxatricyclo-[5.2.1.0$^{2,6}$]decane-3,5-dione (1.0 g, 3.3 mmol) in methanol (100 ml) and dichloromethane (100 ml) is hydrogenated at 3.5 bar over 5% palladium on carbon (approximately 50 mg) until the reaction is judged to be complete by mass spectrometry. The catalyst is removed by filtration through diatomaceous earth and the solvent is evaporated under reduced pressure. Purification by column chromatography on silica gel gives an approximately 1:1 mixture of (1RS,2SR,6RS,7SR,8RS)-8-ethyl-4-(2,4,6-trimethylphenyl)-10-oxatricyclo-[5.2.1.0$^{2,6}$]decane-3,5-dione and (1RS,2SR,6RS,7SR,8SR)-8-ethyl-4-(2,4,6-trimethylphenyl)-10-oxatricyclo-[5.2.1.0$^{2,6}$]decane-3,5-dione.

(1RS,2SR,6RS,7SR,8RS)-8-ethyl-4-(2,4,6-trimethylphenyl)-10-oxatricyclo-[5.2.1.0$^{2,6}$]decane-3,5-dione: $^1$H NMR (400 MHz, CDCl$_3$) $\delta_H$ 6.82 (2H, s), 4.44 (1H, d), 4.24 (1H, s), 2.45-2.40 (2H, m), 2.22 (3H, s), 2.02 (6H, s), 1.58-1.52 (2H, m), 1.38-1.33 (1H, m), 1.25-1.16 (2H, m), 0.85-0.82 (3H, m).

(1RS,2SR,6RS,7SR,8SR)-8-ethyl-4-(2,4,6-trimethylphenyl)-10-oxatricyclo-[5.2.1.0$^{2,6}$]decane-3,5-dione: $^1$H NMR (400 MHz, CDCl$_3$) $\delta_H$ 6.85 (2H, s), 4.51 (1H, d), 4.43 (1H, d), 3.07 (1H, d), 2.82-2.81 (1H, m), 2.24 (3H, s), 2.10-2.05 (2H, m), 2.04 (6H, s), 1.87-1.79 (1H, m), 1.53-1.46 (2H, m), 1.00 (3H, t).

Example 11

Preparation of (1RS,2SR,6RS,7SR)-4-(5-bromo-2-ethylphenyl)-1,7-dimethyl-10-oxatricyclo[5.2.1.0$^{2,6}$]dec-8-en-3,5-dione

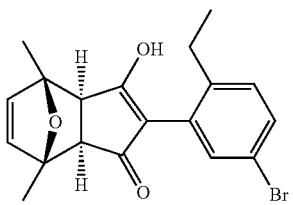 [SMILES: CCc1ccc(Br)cc1C1=C(O)[C@H]2[C@@H](C1=O)[C@]1(C)C=C[C@@]2(C)O1]

Step 1: Preparation of (5-bromo-2-ethylphenyl)furan-2-ylmethanol

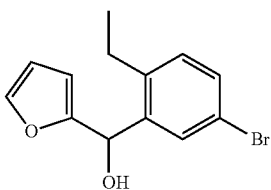 [SMILES: CCc1ccc(Br)cc1C(O)c1ccco1]

4-Bromo-2-iodoethyl benzene (50.0 g, 0.161 mol) is dissolved in anhydrous tetrahydrofuran (250 ml) and cooled to −70° C. under an atmosphere of nitrogen. Isopropylmagnesium chloride (2 M solution in THF, 100 ml, 0.200 mmol) is added dropwise with vigorous stirring over 40 minutes, maintaining the internal temp below −60° C. by external cooling. When the addition is complete, the reaction is stirred at −70° C. for 20 minutes then allowed to warm to room temperature over 1 hour and 20 minutes. The reaction mixture is then cooled to −70° C. and a solution of 2-furaldehyde (16 ml, 18.6 g, 190 mmol) in tetrahydrofuran (50 ml) is added dropwise over 40 minutes. On completion of the addition, the reaction is allowed to warm to room temperature and stirred at room temperature for 3 hours. Saturated aqueous ammonium chloride solution (~500 ml) is added and the mixture is extracted into ethyl acetate. The organic solutions are combined, washed with brine, dried over anhydrous magnesium sulfate and concentrated under reduced pressure. The residue is further purified by column chromatography on silica gel to give (5-bromo-2-ethylphenyl)-furan-2-ylmethanol.

Step 2: Preparation of 5-(5-bromo-2-ethylphenyl)-4-hydroxycyclopent-2-enone

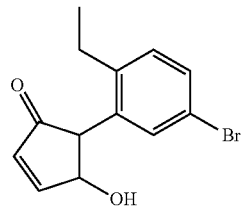 [SMILES: CCc1ccc(Br)cc1C1C(=O)C=CC1O]

A solution of (5-bromo-2-ethylphenyl)furan-2-ylmethanol (40.73 g, 0.145 mol) in acetone (1150 ml) and water (170 ml) is heated to 55° C. and 30 drops of polyphosphoric acid are added. The mixture is stirred at 55° C. for 44 hours, then cooled to room temperature. The reaction mixture is concentrated under reduced pressure to remove most of the acetone then ethyl acetate (500 ml) is added, and the reaction mixture is partitioned. The aqueous phase is extracted into ethyl acetate and the organic solutions are combined, washed with saturated aqueous sodium bicarbonate solution and brine, dried over anhydrous magnesium sulfate, filtered and the filtrate is concentrated under reduced pressure. The residue is purified by column chromatography on silica gel to give 5-(5-bromo-2-ethylphenyl)-4-hydroxycyclopent-2-enone.

Step 3: Preparation of 2-(5-bromo-2-ethylphenyl)cyclopent-4-ene-1,3-dione

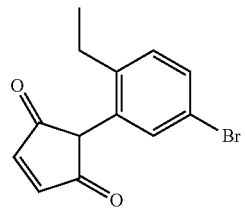 [SMILES: CCc1ccc(Br)cc1C1C(=O)C=CC1=O]

Jones' reagent (75 ml of 1.67 M solution, 125 mmol) is added dropwise over 30 minutes to a cooled (ice-bath) solution of 5-(5-bromo-4-ethylphenyl)-4-hydroxycyclopent-2-enone (33 g, 117 mmol) in acetone (400 ml). The mixture is stirred for 20 minutes, then the cooling bath is removed and the mixture is stirred for 1 hour at room temperature. Isopropanol (150 ml) is added to the yellow slurry and the mixture is stirred at room temperature for 2 hours. The mixture is diluted with ethyl acetate and washed with brine, dried over anhydrous magnesium sulfate, filtered and the filtrate is evaporated under reduced pressure to give 2-(5-bromo-2-ethylphenyl)cyclopent-4-ene-1,3-dione.

Step 4: Preparation of (1RS,2SR,6RS,7SR)-4-(5-bromo-2-ethylphenyl)-1,7-dimethyl-10-oxatricyclo[5.2.1.0$^{2,6}$]dec-8-en-3,5-dione

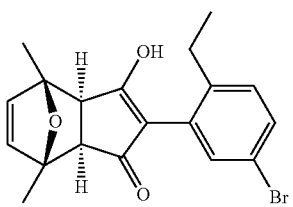 [SMILES: CCc1ccc(Br)cc1C1=C(O)[C@H]2[C@@H](C1=O)[C@]1(C)C=C[C@@]2(C)O1]

2,5-Dimethylfuran (2.3 ml, 21.6 mmol) and magnesium iodide (0.40 g, 1.4 mmol) are added to a solution of 2-(5-bromo-2-ethylphenyl)cyclopent-4-ene-1,3-dione (2.0 g, 7.2 mmol) in dichloromethane (10 ml) and the mixture is stirred at room temperature for 3 days. The reaction mixture is concentrated under reduced pressure and the residue is purified by column chromatography on silica gel to give (1RS,2SR,6RS,7SR)-4-(5-bromo-2-ethylphenyl)-1,7-dimethyl-10-oxatricyclo[5.2.1.0$^{2,6}$]dec-8-en-3,5-dione.

$^1$H NMR (400 MHz, d$_4$-MeOH) δ$_H$ 7.39 (1H, dd), 7.18 (1H, d), 7.16 (1H, d), 6.35 (2H, s), 2.79 (2H, s), 2.46 (2H, q), 1.61 (6H, s), 1.07 (3H, t).

Example 12

Preparation of (1RS,2SR,6RS,7SR)-4-(5-bromo-2-ethylphenyl)-1,7-dimethyl-10-oxatricyclo[5.2.1.0$^{2,6}$]decane-3,5-dione

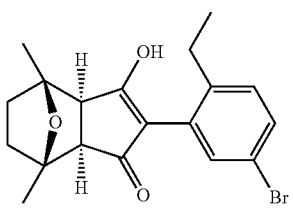 [SMILES: CCc1ccc(Br)cc1C1=C(O)[C@H]2[C@@H](C1=O)[C@]1(C)CC[C@@]2(C)O1]

A solution of (1RS,2SR,6RS,7SR)-4-(5-bromo-2-ethylphenyl)-1,7-dimethyl-10-oxatricyclo[5.2.1.0$^{2,6}$]dec-8-en-3,5-dione (1.63 g, 4.3 mmol) in methanol (200 ml) is hydrogenated at 3.5 bar over 5% palladium on carbon for 1 hour and 30 minutes at room temperature. The catalyst is removed by filtration through diatomaceous earth and the solvent is evaporated under reduced pressure. Trituration with diethyl ether gives (1RS,2SR,6RS,7SR)-4-(5-bromo-2-ethylphenyl)-1,7-dimethyl-10-oxatricyclo[5.2.1.0$^{2,6}$]decane-3,5-dione.

$^1$H NMR (400 MHz, d$_4$-MeOH) δ$_H$ 7.36 (1H, dd), 7.17 (1H, d), 7.15 (1H, d), 2.81 (2H, s), 2.48-2.43 (2H, m), 1.84-1.79 (2H, m), 1.69-1.65 (2H, m), 1.51 (6H, s), 1.08 (3H, t).

Example 13

Preparation of (1RS,2SR,6RS,7SR)-4-(5-bromo-2-ethylphenyl)-10-oxatricyclo[5.2.1.0$^{2,6}$]dec-8-en-3,5-dione

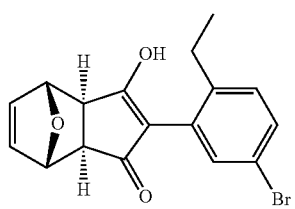 [SMILES: CCc1ccc(Br)cc1C1=C(O)[C@H]2[C@@H](C1=O)[C@@H]1C=C[C@H]2O1]

Furan (4.0 ml, 55.0 mmol) and magnesium iodide (1.00 g, 3.6 mmol) are added to a solution of 2-(5-bromo-2-ethylphenyl)cyclopent-4-ene-1,3-dione (5.0 g, 17.9 mmol) in dichloromethane (20 ml) and the mixture is stirred at room temperature for 3 days. A further quantity of furan (1.3 ml, 17.8 mmol) is added and stirring continued for 18 hours, and then a further quantity of furan (1.3 ml, 17.8 mmol) is added and the mixture is stirred for 48 hours, and then allowed to stand at room temperature for 5 days. The reaction mixture is dissolved in methanol and concentrated under reduced pressure. The residue is purified by column chromatography on silica gel to give (1RS,2SR,6RS,7SR)-4-(5-bromo-2-ethylphenyl)-10-oxatricyclo[5.2.1.0$^{2,6}$]dec-8-en-3,5-dione.

$^1$H NMR (400 MHz, d$_4$-MeOH) δ$_H$ 7.37 (1H, dd), 7.17 (1H, d), 7.14 (1H, d), 6.54 (2H, s), 4.96 (2H, s), 2.79 (2H, s), 2.44 (2H, q), 1.06 (3H, t)

Example 14

Preparation of (1RS, 2SR,6RS,7SR)-4-(5-bromo-2-ethylphenyl)-10-oxatricyclo[5.2.1.0$^{2,6}$]decane-3,5-dione

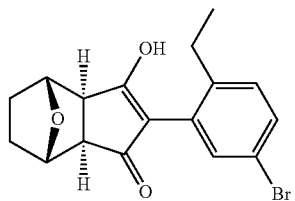 [SMILES: CCc1ccc(Br)cc1C1=C(O)[C@H]2[C@@H](C1=O)[C@@H]1CC[C@H]2O1]

A solution of (1RS, 2SR,6RS,7SR)-4-(5-bromo-2-ethylphenyl)-10-oxatricyclo[5.2.1.0$^{2,6}$]-dec-8-en-3,5-dione (3.00 g, 8.6 mmol) in methanol (250 ml) is hydrogenated at 3.5 bar over 5% palladium on carbon for 2 hours at room temperature. The catalyst is removed by filtration through diatomaceous earth and the solvent is evaporated under reduced pressure to give (1RS,2SR,6RS,7SR)-4-(5-bromo-2-ethylphenyl)-10-oxatricyclo-[5.2.1.0$^{2,6}$]decane-3,5-dione.

$^1$H NMR (400 MHz, d$_4$-MeOH) δ$_H$ 7.34 (1H, dd), 7.15 (2H, d), 4.59 (2H, s), 2.78 (2H, s), 2.43 (2H, q), 1.81-1.78 (2H, m), 1.66-1.61 (2H, m), 1.06 (3H, t).

Example 15

Preparation of (1RS,2RS,6SR,7SR)-8-bromo-4-(2,4,6-trimethylphenyl)-10-oxatricyclo-[5.2.1.0$^{2,6}$]dec-8-en-3,5-dione

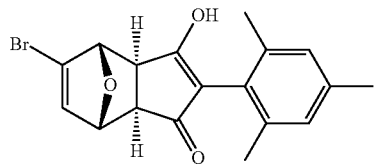 [SMILES: Cc1cc(C)c(C2=C(O)[C@H]3[C@@H](C2=O)[C@@H]2C=C(Br)[C@H]3O2)c(C)c1]

3-Bromofuran (5.2 g, 56 mmol) and magnesium iodide (1.5 g, 5.6 mmol) are added to 2-(2,4,6-trimethylphenyl)cyclopent-4-ene-1,3-dione (4.0 g, 18.7 mmol) and the mixture is stirred at room temperature for 2 days; small quantities of dichloromethane are added when required to aid stirring. The reaction mixture is allowed to stand at room temperature for 17 hours, then concentrated under reduced pressure. The residue is purified by column chromatography on silica gel to give (1RS, 2RS,6SR,7SR)-8-bromo-4-(2,4,6-trimethylphenyl)-10-oxatricyclo-[5.2.1.0$^{2,6}$]dec-8-en-3,5-dione.

$^1$H NMR (400 MHz, CDCl$_3$) δ$_H$ 6.87 (2H, s), 6.40 (1H, d), 4.95 (1H, s), 4.82 (1H, s), 2.90 (1H, d), 2.81 (1H, d), 2.25 (3H, s), 2.07 (3H, s), 2.03 (3H, s).

Example 16

Preparation of (1RS,2SR,6RS,7RS)-8-(4-fluorophenyl)-4-(2,4,6-trimethylphenyl)-10-oxatricyclo[5.2.1.0$^{2,6}$]dec-8-en-3,5-dione

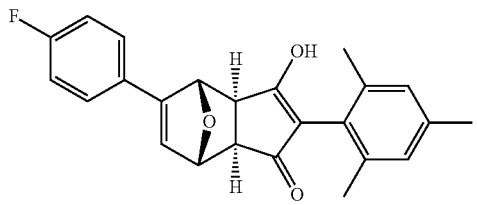 [SMILES: Cc1cc(C)c(C2=C(O)[C@H]3[C@@H](C2=O)[C@@H]2C=C(c4ccc(F)cc4)[C@H]3O2)c(C)c1]

A mixture of (1RS,2RS,6SR,7SR)-8-bromo-4-(2,4,6-trimethylphenyl)-10-oxatricyclo-[5.2.1.0$^{2,6}$]dec-8-en-3,5-dione (300 mg, 0.82 mmol), 4-fluorophenylboronic acid (171 mg, 1.22 mmol), sodium 2'-dicyclohexylphosphino-2,6-dimethoxy-1,1-biphenyl-3-sulfonate hydrate (17 mg, 0.03 mmol), potassium phosphate (522 mg, 2.5 mmol) and palladium acetate (4 mg, 0.02 mmol) in water (8 ml) are heated for 150° C. for 25 minutes under microwave irradiation. The mixture is cooled to room temperature and dilute aqueous hydrochloric acid is added. The mixture is filtered and the filtrate is extracted with ethyl acetate. The organic extracts are combined, dried over anhydrous magnesium sulfate, filtered and the filtrate is concentrated under reduced pressure. Purification by column chromatography on silica gel gives (1RS, 2SR,6RS,7RS)-8-(4-fluorophenyl)-4-(2,4,6-trimethylphenyl)-10-oxatricyclo[5.2.1.0$^{2,6}$]dec-8-en-3,5-dione.

$^1$H NMR (400 MHz, CDCl$_3$) δ$_H$ 7.35-7.32 (2H, m), 6.86 (1H, s), 6.85 (1H, s), 6.82-6.77 (2H, m), 6.37 (1H, d), 5.31 (1H, s), 5.03 (1H, d), 2.82-2.78 (2H, m), 2.25 (3H, s), 2.07 (3H, s), 2.05 (3H, s).

Example 17

Preparation of (1RS,2SR,6RS,7SR,8SR)-8-(4-fluorophenyl)-4-(2,4,6-trimethylphenyl)-10-oxatricyclo[5.2.1.0$^{2,6}$]decane-3,5-dione

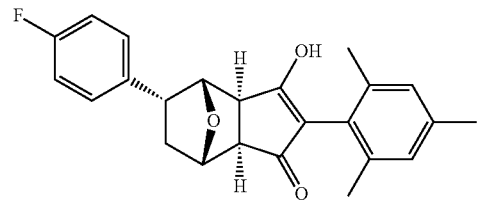 [SMILES: Cc1cc(C)c(C2=C(O)[C@@H]3[C@@H]4O[C@@H](C[C@@H]4c4ccc(F)cc4)[C@@H]3C2=O)c(C)c1]

A suspension of (1RS,2SR,6RS,7RS)-8-(4-fluorophenyl)-4-(2,4,6-trimethylphenyl)-10-oxatricyclo[5.2.1.0$^{2,6}$]dec-8-en-3,5-dione (99 mg, 0.26 mmol) in methanol (20 ml) is hydrogenated at 3 bar over 5% palladium on carbon for 5 hours at room temperature. The catalyst is removed by filtration through diatomaceous earth and the solvent is evaporated under reduced pressure to give (1RS,2SR,6RS,7SR,8SR)-8-(4-fluorophenyl)-4-(2,4,6-trimethylphenyl)-10-oxatricyclo[5.2.1.0$^{2,6}$]decane-3,5-dione.

$^1$H NMR (400 MHz, CDCl$_3$) δ$_H$ 7.39 (2H, dd), 7.11 (2H, t), 6.86 (1H, s), 6.85 (1H, s), 4.73 (1H, d), 4.68 (1H, s), 3.63-3.58 (1H, m), 2.94 (1H, d), 2.75 (1H, d), 2.38-2.30 (1H, m), 2.25 (3H, s), 2.08 (3H, s), 2.03 (3H, s), 1.92 (1H, dd).

Example 18

Preparation of (1RS,2SR,6RS,7SR,8RS)-8-(3-fluorophenyl)-4-(2,4,6-trimethylphenyl)-10-oxatricyclo[5.2.1.0$^{2,6}$]decane-3,5-dione

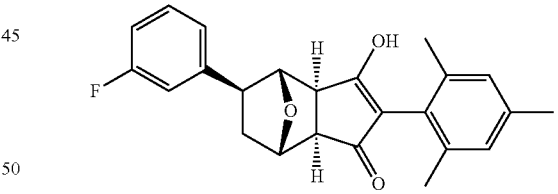

Bis(triphenylphosphine)palladium diacetate (20 mg, 0.024 mmol), 1-fluoro-3-iodo-benzene (104 mg, 0.47 mmol) and piperidine (0.16 ml, 1.6 mmol) are added to a solution of (1RS,2SR,6RS,7SR)-4-(2,4,6-trimethylphenyl)-10-oxatricyclo[5.2.1.0$^{2,6}$]dec-8-en-3,5-dione (0.20 g, 0.71 mmol) in dry N,N-dimethylformamide (2 ml). Formic acid (0.06 ml, 1.6 mmol) is added and the reaction mixture is heated at 50° C. for 2 hours. The reaction mixture is cooled to room temperature, water (1 ml) and dichloromethane (1 ml) are added, and the mixture is stirred for 1 hour. The two phases are separated, the organic phase collected and the solvent is evaporated. The residue is purified by preparative reverse-phase HPLC to give (1RS,2SR,6RS,7SR,8RS)-8-(3-fluorophenyl)-4-(2,4,6-trimethylphenyl)-10-oxatricyclo-[5.2.1.0$^{2,6}$]decane-3,5-dione.

¹H NMR (400 MHz, CDCl₃) δ$_H$ 7.75-7.66 (1H, m), 7.25-7.21 (1H, m), 7.06-7.02 (2H, m), 6.88 (1H, s), 6.87 (1H, s), 4.83 (1H, br. s), 4.59 (1H, s), 3.00-2.98 (1H, m), 2.83-2.70 (2H, br. s), 2.25 (3H, s), 2.20-2.16 (1H, m), 2.09 (3H, s), 2.08 (3H, s), 1.92-1.89 (1H, m).

Example 19

Preparation of (1RS,2SR,6RS,7SR,8RS)-8-[2,6-bis(trifluoromethyl)pyridin-4-yl]-4-(2,4,6-trimethylphenyl)-10-oxatricyclo[5.2.1.0$^{2,6}$]decane-3,5-dione

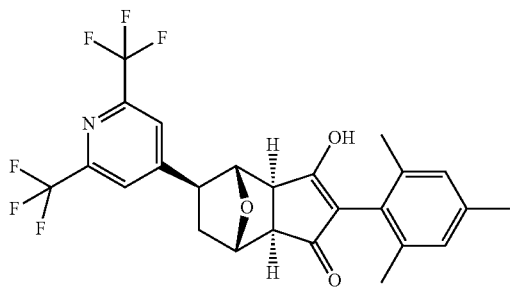 [SMILES: Cc1cc(C)c(C2=C(O)[C@@H]3[C@@H]4O[C@@H](C[C@H]4c4cc(C(F)(F)F)nc(C(F)(F)F)c4)[C@@H]3C2=O)c(C)c1]

A mixture of (1RS,2SR,6RS,7SR)-4-(2,4,6-trimethylphenyl)-10-oxatricyclo-[5.2.1.0$^{2,6}$]dec-8-en-3,5-dione (400 mg, 1.4 mmol), 2,6-bis(trifluoromethyl)-4-chloropyridine (531 mg, 1.4 mmol), palladium acetate (16 mg, 0.07 mmol), 2'-dicyclohexylphosphino-2,6-dimethoxy-1,1'-biphenyl (67 mg, 0.14 mmol), potassium formate (353 mg, 4.2 mmol), tetrabutylammonium chloride (389 mg, 1.4 mmol) and copper iodide (53 mg, 0.28 mmol) in dry N,N-dimethylformamide (6 ml) are heated, at 150° C. for 30 minutes under microwave irradiation. Purification by preparative reverse-phase HPLC gives (1RS,2SR,6RS,7SR,8RS)-8-[2,6-bis(trifluoromethyl)pyridin-4-yl]-4-(2,4,6-trimethylphenyl)-10-oxatricyclo[5.2.1.0$^{2,6}$]decane-3,5-dione.

¹H NMR (400 MHz d₄-MeOH) δ$_H$ 7.81 (1H, s), 7.26 (1H, s), 6.92 (1H, s), 6.90 (1H, s), 4.91 (1H, d), 4.64 (1H, s), 3.19-3.17 (1H, m), 2.99-2.95 (2H, m), 2.32-2.27 (1H, m), 2.26 (3H, s), 2.09 (3H, s), 2.07 (3H, s), 1.93-1.90 (1H, m).

Example 20

Preparation of (1RS,2SR,6RS,7SR, 8RS)-4-(2,4,6-trimethylphenyl)-8-vinyl-10-oxatricyclo[5.2.1.0$^{2,6}$]decane-3,5-dione

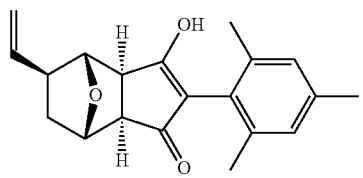 [SMILES: C=C[C@@H]1C[C@@H]2O[C@H]1[C@H]1C(O)=C(c3c(C)cc(C)cc3C)C(=O)[C@H]12]

A mixture of (1RS,2SR,6RS,7SR)-4-(2,4,6-trimethylphenyl)-10-oxatricyclo[5.2.1.0$^{2,6}$]dec-8-en-3,5-dione (510 mg, 1.8 mmol), vinyl iodide (280 mg, 1.8 mmol), palladium acetate (20 mg, 0.09 mmol), sodium formate (454 mg, 5.4 mmol) and tetrabuylammonium chloride (500 mg, 1.8 mmol) in dry N,N-dimethylformamide (15 ml) are heated at 150° C. for 20 minutes under microwave irradiation. The mixture is cooled to room temperature and partitioned between water and ethyl acetate. The organic extracts are combined, dried over anhydrous magnesium sulfate, filtered and the filtrate is evaporated under reduced pressure. The residue is purified by column chromatography on silica gel to give (1RS,2SR,6RS,7SR,8RS)-4-(2,4,6-trimethylphenyl)-8-vinyl-10-oxatricyclo[5.2.1.0$^{2,6}$]decane-3,5-dione.

¹H NMR (400 MHz, CDCl₃) δ$_H$ 6.90-6.89 (2H, m), 5.80-5.71 (1H, m), 5.05-4.97 (2H, m), 4.68 (1H, d), 4.44 (1H, s), 2.81-2.76 (2H, m), 2.51-2.46 (1H, m), 2.26 (3H, s), 2.07 (3H, s), 2.06 (3H, s), 1.89-1.84 (1H, m), 1.67-1.62 (1H, m).

Example 21

Preparation of methyl [(1RS,2SR,6RS,7SR. 8RS)-3,5-dioxo-4-(2,4,6-trimethylphenyl)-10-oxatricyclo[5.2.1.0$^{2,6}$]dec-8-yl]acrylate

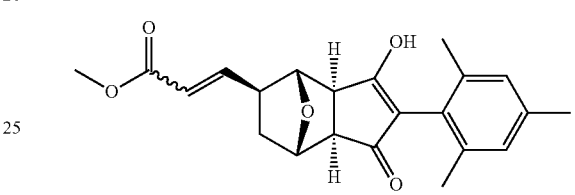

Benzylidene[1,3-bis(2,4,6-trimethylphenyl)-2-imidazolidinylidene]dichloro(tricyclohexyl-phosphine)ruthenium (14 mg, 0.016 mmol) is added to a suspension of (1RS,2SR,6RS,7SR,8RS)-4-(2,4,6-trimethylphenyl)-8-vinyl-10-oxatricyclo[5.2.1.0$^{2,6}$]decane-3,5-dione (100 mg, 0.32 mmol) and methyl acrylate (0.03 ml, 0.35 mmol) in dichloromethane (1 ml) and the mixture is stirred at reflux for 2 hours. The reaction mixture is cooled to room temperature, the solvent evaporated under reduced pressure and the residue is purified by column chromatography on silica gel to give methyl [1RS,2SR,6RS,7SR,8RS)-3,5-dioxo-4-(2,4,6-trimethylphenyl)-10-oxatricyclo-[5.2.1.0$^{2,6}$]dec-8-yl]acrylate. Proton NMR indicates the product comprises a mixture of E- and Z-isomers.

E-Isomer: ¹H NMR (400 MHz, CDCl₃) δ$_H$ 6.80 (2H, s), 6.74 (1H, dd), 5.91 (1H, d), 4.58 (1H, d), 4.30 (1H, s), 3.33 (3H, s), 2.85-2.77 (3H, m), 2.21 (3H, s), 1.97 (3H, s), 194 (3H, s), 1.94-1.91 (1H, m), 1.59-1.54 (1H, m).

Example 22

Preparation of (1RS,2SR,6SR,7SR)-1-hydroxymethyl-4-(2,4,6-trimethylphenyl)-10-oxatricyclo[5.2.1.0$^{2,6}$]dec-8-ene-3,5-dione

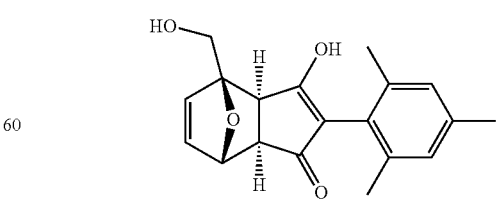

Furfuryl alcohol (4 ml, 46.7 mmol) is added to 2-(2,4,6-trimethylphenyl)cyclopent-4-ene-1,3-dione (2.0 g, 9.3 mmol) and MgI₂ (520 mg, 1.86 mmol) and the reaction is stirred for 17 hours. The reaction mixture is adsorbed onto silica gel and purified by column chromatography on silica gel to give (1RS,2SR,6RS,7SR)-1-hydroxymethyl-4-(2,4,6-trimethylphenyl)-10-oxatricyclo-[5.2.1.0$^{2,6}$]dec-8-ene-3,5-dione.

$^1$H NMR (400 MHz, CDCl$_3$) δ$_H$ 6.87 (2H, s), 6.49 (1H, d), 6.44 (1H, d), 4.96 (1H, d), 3.98 (1H, d), 3.85 (1H, d), 2.82-2.78 (2H, m), 2.24 (3H, s), 2.08 (3H, s), 2.05 (3H, s).

Example 23

Preparation of tert-butyl carbamic acid [(1RS,2SR,6RS,7SR)-3,5-dioxo-4-(2,4,6-trimethylphenyl)-10-oxatricyclo[5.2.1.0$^{2,6}$]dec-8-en-1-yl]methyl ester

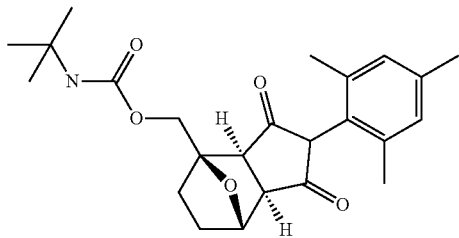 [SMILES: Cc1cc(C)c(C2C(=O)[C@H]3[C@@H]4CC[C@@](COC(=O)NC(C)(C)C)(O4)[C@H]3C2=O)c(C)c1]

Step 1: Preparation of (1RS,2SR,6SR,7SR)-5-benzyloxy-7-hydroxymethyl-4-(2,4,6-trimethylphenyl)-10-oxatricyclo[5.2.1.0$^{2,6}$]deca-4,8-dien-3-one and (1RS,2SR,6RS,7SR)-5-benzyloxy-1-hydroxymethyl-4-(2,4,6-trimethylphenyl)-10-oxatricyclo[5.2.1.0$^{2,6}$]deca-4,8-dien-3-one

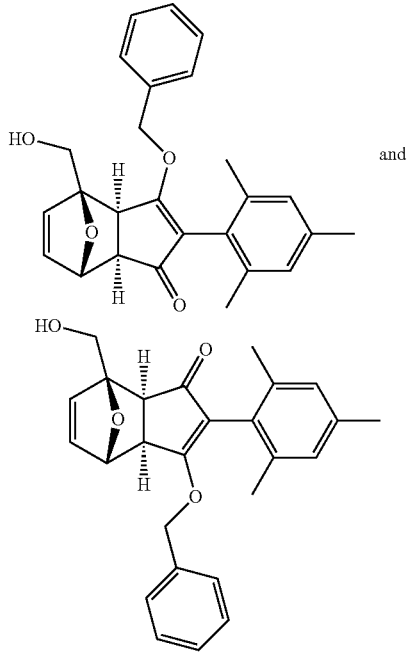

Benzyl bromide (0.72 ml, 6.1 mmol) is added to a mixture of potassium carbonate (840 mg, 6.1 mmol) and (1RS,2SR,6RS,7SR)-1-hydroxymethyl-4-(2,4,6-trimethylphenyl)-10-oxatricyclo-[5.2.1.0$^{2,6}$]dec-8-ene-3,5-dione (1.80 g, 5.8 mmol) in acetone (80 ml), and the reaction mixture is heated at reflux for 4 hours. The reaction mixture is cooled to room temperature, diluted with water and extracted with ethyl acetate. The organic extracts are combined, dried over anhydrous magnesium sulfate, filtered and the filtrate is concentrated under reduced pressure. The residue is purified by column chromatography on silica gel to give a mixture of (1RS,2SR,6SR,7SR)-5-benzyloxy-7-hydroxymethyl-4-(2,4,6-trimethylphenyl)-10-oxatricyclo[5.2.1.0$^{2,6}$]deca-4,8-dien-3-one and (1RS,2SR,6RS,7SR)-5-benzyloxy-1-hydroxymethyl-4-(2,4,6-trimethylphenyl)-10-oxatricyclo[5.2.1.0$^{2,6}$]deca-4,8-dien-3-one.

Step 2: Preparation of tert-butyl carbamic acid [(1RS,2RS,6RS,7SR)-3-benzyloxy-5-oxo-4-(2,4,6-trimethylphenyl)-10-oxatricyclo[5.2.1.0$^{2,6}$]deca-4,8-dien-1-yl]methyl ester and tert-butyl carbamic acid [(1RS,2SR,6RS,7SR)-5-benzyloxy-3-oxo-4-(2,4,6-trimethylphenyl)-10-oxatricyclo[5.2.1.0$^{2,6}$]deca-4,8-dien-1-yl]methyl ester

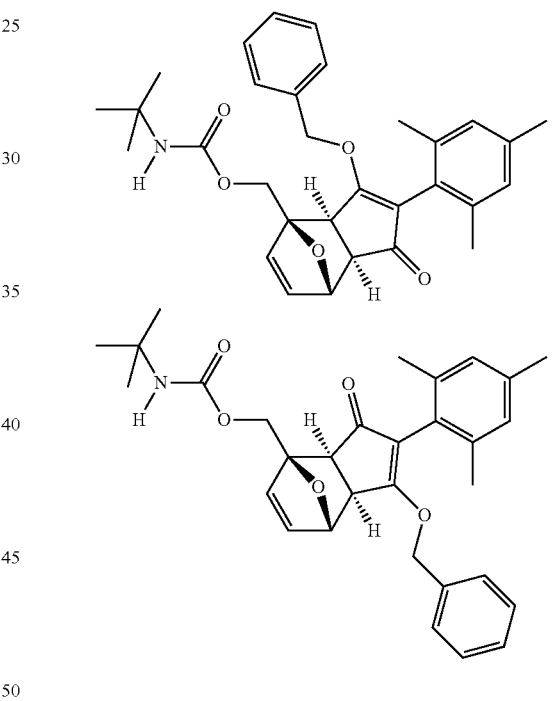

Sodium hydride (60 mg, 1.97 mmol) is added to a cooled (0° C.) mixture of (1RS,2SR,6SR,7SR)-5-benzyloxy-7-hydroxymethyl-4-(2,4,6-trimethylphenyl)-10-oxatricyclo [5.2.1.0$^{2,6}$]deca-4,8-dien-3-one and (1RS,2SR,6RS,7SR)-5-benzyloxy-1-hydroxymethyl-4-(2,4,6-trimethylphenyl)-10-oxatricyclo[5.2.1.0$^{2,6}$]deca-4,8-dien-3-one (265 mg, 0.66 mmol) in tetrahydrofuran (10 ml). The mixture is stirred for a few minutes and then tert-butyl isocyanate (0.15 ml, 1.32 mmol) is added. The reaction is allowed warm to room temperature and stirred for 17 hours. The mixture is partitioned between water and ethyl acetate, and the organic solutions are combined, dried over anhydrous magnesium sulfate, filtered and the filtrate is evaporated. The residue is purified by column chromatography on silica gel to give a mixture of tert-butyl carbamic acid [(1RS,2RS,6RS,7SR)-3-benzyloxy-5-oxo-4-(2,4,6-trimethylphenyl)-10-oxatricyclo-[5.2.1.0$^{2,6}$]deca-4,8-dien-1-yl]methyl ester and tert-butyl carbamic acid

[(1RS,2SR,6RS,7SR)-5-benzyloxy-3-oxo-4-(2,4,6-trimethylphenyl)-10-oxatricyclo-[5.2.1.0$^{2,6}$]deca-4,8-dien-1-yl]methyl ester.

Step 3: Preparation of tert-butyl carbamic acid [(1RS,2SR,6RS,7SR)-3,5-dioxo-4-(2,4,6-trimethylphenyl)-10-oxatricyclo[5.2.1.0$^{2,6}$]dec-8-en-1-yl] methyl ester

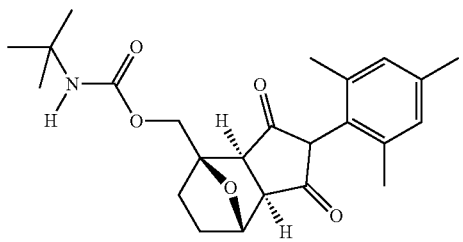 [SMILES: Cc1cc(C)c(C2C(=O)[C@H]3[C@@H]4CC[C@@](COC(=O)NC(C)(C)C)(O4)[C@H]3C2=O)c(C)c1]

A suspension of a mixture of [(1RS,2RS,6RS,7SR)-3-benzyloxy-5-oxo-4-(2,4,6-trimethylphenyl)-10-oxatricyclo-[5.2.1.0$^{2,6}$]deca-4,8-dien-1-yl]methyl ester and tert-butyl carbamic acid [(1RS, 2SR,6RS,7SR)-5-benzyloxy-3-oxo-4-(2,4,6-trimethylphenyl)-10-oxatricyclo-[5.2.1.0$^{2,6}$]deca-4,8-dien-1-yl]methyl ester (147 mg, 0.29 mmol) in methanol (20 ml) is hydrogenated at 3 bar over 5% palladium on carbon for 5 hours. The catalyst is removed by filtration and the filtrate is concentrated under reduced pressure to give tert-butyl carbamic acid [(1RS,2SR,6RS,7SR)-3,5-dioxo-4-(2,4,6-trimethylphenyl)-10-oxatricyclo[5.2.1.0$^{2,6}$]dec-8-en-1-yl]methyl.

$^1$H NMR (400 MHz, CDCl$_3$) $\delta_H$ 6.83 (2H, s), 5.02 (1H, s), 4.72 (1H, d), 4.65 (1H, d), 4.12 (1H, d), 2.83 (1H, d), 2.70 (1H, d), 2.23 (3H, s), 2.07 (3H, s), 2.06 (3H, s), 1.86-1.80 (2H, m), 1.57-1.45 (2H, m), 1.29 (9H, s).

Example 24

Preparation of (1RS,2SR,6RS,7SR)-4-(4-bromo-2-ethylphenyl)-10-oxatricyclo-[5.2.1.0$^{2,6}$]decane-3,5-dione

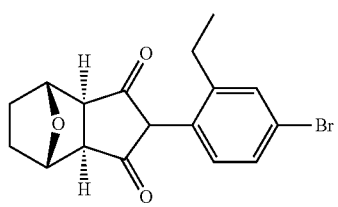 [SMILES: CCc1cc(Br)ccc1C1C(=O)[C@@H]2[C@H](C1=O)[C@H]1CC[C@@H]2O1]

Step 1: Preparation of 4-bromo-2-ethylphenyllead triacetate

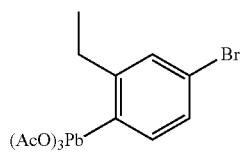

Dry chloroform (30 ml) is added to a mixture of lead tetraacetate (8.52 g, 19.3 mmol) and mercuric diacetate (0.28 g, 0.875 mmol) under an atmosphere of nitrogen, and the reaction mixture is stirred and heated to 40° C. 4-Bromo-2-ethylphenylboronic acid (4.0 g, 17.5 mmol) is added in one portion and the mixture is stirred at 40° C. for 4 hours. The reaction mixture is cooled to 0° C., and potassium carbonate (2.66 g, 19.3 mmol) is added portionwise. The mixture is stirred for 5 minutes, then filtered through a small plug of diatomaceous earth, washing with chloroform. The filtrate concentrated under reduced pressure to give 4-bromo-2-ethylphenyllead triacetate.

Step 2: Preparation of (1RS,2SR,6RS,7SR)-4-(4-bromo-2-ethylphenyl)-10-oxatricyclo-[5.2.1.0$^{2,6}$] decane-3,5-dione

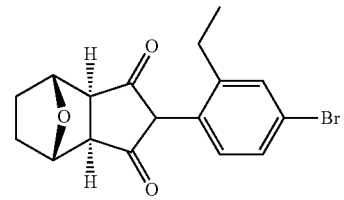 [SMILES: CCc1cc(Br)ccc1C1C(=O)[C@@H]2[C@H](C1=O)[C@H]1CC[C@@H]2O1]

4-Dimethylaminopyridine (3.67 g, 30.0 mmol) and toluene (10 ml) are added to a solution of (1RS,2SR,6RS,7SR)-10-oxatricyclo[5.2.1.0$^{2,6}$]decane-3,5-dione (1.0 g, 6.0 mmol) in chloroform (40 ml) and the reaction mixture is heated to 80° C. 4-Bromo-2-ethylphenyllead triacetate (5.13 g, 9.04 mmol) is added portionwise over 20 minutes, and once the addition is complete the reaction mixture is stirred at 80° C. for a further 4 hours. The mixture is cooled to room temperature, 2 M aqueous hydrochloric acid (40 ml) is added, and the mixture is stirred vigorously for 15 minutes, then filtered through a small plug of diatomaceous earth, washing with 40 ml dichloromethane. The organic phase is separated, and the aqueous phase is extracted with dichloromethane (2×20 ml). The organic solutions are combined, dried over anhydrous magnesium sulfate, filtered and the filtrate is concentrated under reduced pressure. The residue is purified by column chromatography on silica gel to give (1RS,2SR,6RS,7SR)-4-(4-bromo-2-ethylphenyl)-10-oxatricyclo-[5.2.1.0$^{2,6}$]decane-3,5-dione.

$^1$H NMR (400 MHz, CDCl$_3$) $\delta_H$ 7.39 (1H, dd), 7.27-7.33 (1H, m), 6.97 (1H, dd), 4.68 (2H, m), 2.74 (2H, br. s), 2.48 (2H, q), 1.78-1.87 (2H, m), 1.56 (2H, m), 1.11 (3H, t).

Additional compounds in Table T1 below were prepared by similar methods using appropriate starting materials. It should be noted that certain compounds of the invention exist as a mixture of isomers noted above, under the conditions used to obtain the $^1$H NMR data. Where this has occurred, the characterising data are reported for all isomers present at ambient temperature in the specified solvent. Unless otherwise stated, proton NMR spectra were recorded at ambient temperature. Compounds characterised by HPLC-MS were analysed using one of two methods described below.

Method A

Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.0 | 100 | 1.300 |
| 2.80 | 0.00 | 100 | 1.300 |
| 2.90 | 95.0 | 5 | 1.300 |

Solvent A: H₂O with 0.05% TFA
Solvent B: CH₃CN with 0.05% TFA

Method B

Compounds characterised by HPLC-MS were analysed using a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 100 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: H₂O containing 0.1% HCOOH
Solvent B: CH₃CN containing 0.1% HCOOH

The characteristic values obtained for each compound were the retention time (rt, recorded in minutes) and the molecular ion (typically the cation MH⁺), as listed in Table T1.

TABLE T1

| Compound Number | Structure | $^1$H nmr (CDCl$_3$ unless stated) or other physical data |
|---|---|---|
| T1 | 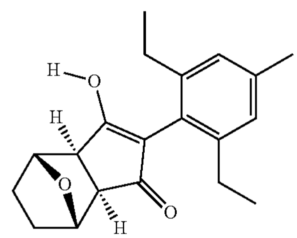 [SMILES: CCc1cc(C)cc(CC)c1C1=C(O)[C@H]2[C@@H](C1=O)[C@@H]1CC[C@H]2O1] | $\delta_H$ 6.88-6.87 (2H, m), 4.55-4.54 (2H, m), 2.62 (2H, s), 2.36-2.27 (7H, m), 1.69-1.67 (2H, m), 1.40-1.39 (2H, m), 1.03 (6H, q). |
| T2 | 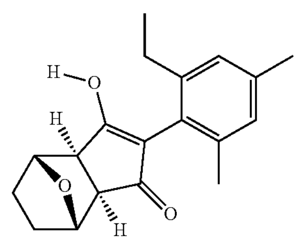 [SMILES: CCc1cc(C)cc(C)c1C1=C(O)[C@H]2[C@@H](C1=O)[C@@H]1CC[C@H]2O1] | $\delta_H$ 6.88 (2H, m), 4.58 (2H, s), 2.65 (2H, m), 2.38-2.32 (2H, m), 2.26 (3H, s), 2.02 (3H, s), 1.76-1.71 (2H, m), 1.45 (2H, m), 1.04 (3H, q). |
| T3 | 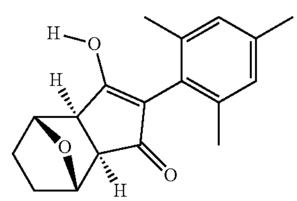 [SMILES: Cc1cc(C)c(C2=C(O)[C@H]3[C@@H](C2=O)[C@@H]2CC[C@H]3O2)c(C)c1] | $\delta_H$ 6.86 (1H, s), 6.85 (1H, s), 4.68-4.67 (2H, m), 2.74 (2H, s), 2.24 (3H, s), 2.10 (3H, s), 2.08 (3H, s), 1.83-1.80 (2H, m), 1.56-1.54 (2H, m). |
| T4 | 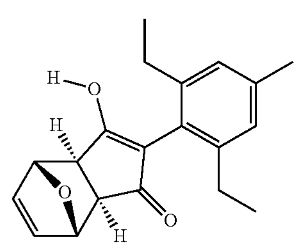 [SMILES: CCc1cc(C)cc(CC)c1C1=C(O)[C@H]2[C@@H](C1=O)[C@@H]1C=C[C@H]2O1] | $\delta_H$ 6.94 (2H, s), 6.44 (2H, s), 5.04 (2H, s), 2.81-2.73 (2H, m), 2.41-2.35 (4H, m), 2.30 (3H, s), 1.10-1.02 (6H, m). |

TABLE T1-continued

| Compound Number | Structure | $^1$H nmr (CDCl$_3$ unless stated) or other physical data |
|---|---|---|
| T5 | 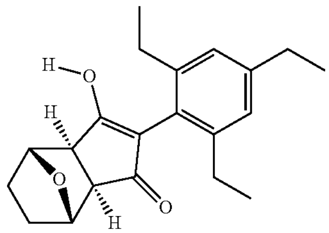 [SMILES: CCc1cc(CC)c(C2=C(O)[C@H]3[C@@H](C2=O)[C@@H]2CC[C@H]3O2)c(CC)c1] | δ$_H$ 6.94 (1H, s), 6.93 (1H, s), 4.64-4.63 (2H, m), 2.73 (2H, s), 2.59 (2H, q), 2.41-2.31 (4H, m), 1.77 (2H, m), 1.48 (2H, m), 1.22 (3H, t), 1.06 (6H, m). |
| T6 | 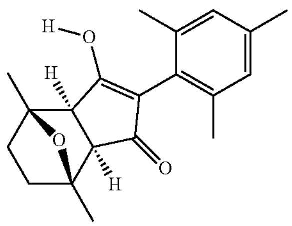 [SMILES: Cc1cc(C)c(C2=C(O)[C@H]3[C@@H](C2=O)[C@]2(C)CC[C@@]3(C)O2)c(C)c1] | δ$_H$ 6.98 (1H, s), 6.97 (1H, s), 2.64-2.59 (2H, brs), 2.25 (3H, s), 2.03 (6H, s), 1.66 (4H, s), 1.50 (6H br s). |
| T7 | 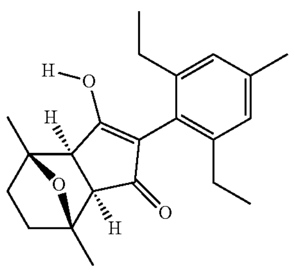 [SMILES: CCc1cc(C)cc(CC)c1C1=C(O)[C@H]2[C@@H](C1=O)[C@]1(C)CC[C@@]2(C)O1] | δ$_H$ 6.95 (1H, s), 6.47 (1H, br s), 3.00 (1H, d), 2.68-2.66 (1H, m), 2.44-2.31 (7H, m), 1.77-1.71 (4H, m), 1.58 (3H, s), 1.55 (3H, s), 1.08 (6H, q). |
| T8 | 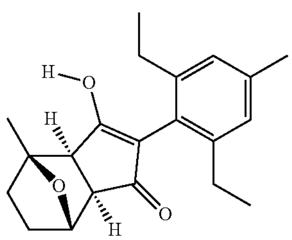 [SMILES: CCc1cc(C)cc(CC)c1C1=C(O)[C@H]2[C@@H](C1=O)[C@@H]1CC[C@@]2(C)O1] | δ$_H$ 6.95 (s), 4.69 (d), 4.64 (d), 3.05 (d), 2.91 (d), 2.81 (d), 2.59 (d), 2.44-2.32 (m), 2.31 (s), 2.00-1.93 (m), 1.67-1.62 (m), 1.61 (s), 1.58 (s), 1.10-1.05 (m). |
| T9 | 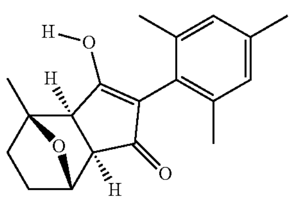 [SMILES: Cc1cc(C)c(C2=C(O)[C@H]3[C@@H](C2=O)[C@@H]2CC[C@@]3(C)O2)c(C)c1] | δ$_H$ 6.92 (2H, s), 6.47 (1H, s), 6.32 (0.5H, s), 6.28 (0.5H, s), 5.14 (0.5H, s), 4.97 (0.5H, br s), 3.06 (0.5H, br s), 2.86 (0.5H, s), 2.80(0.5H br s), 2.50 (0.5H, br s), 2.28 (3H, s), 2.12 (6H, s), 1.70 (3H, br s). |
| T10 | 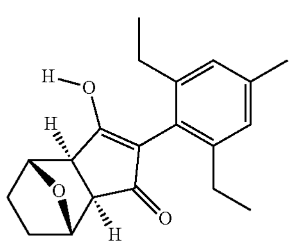 [SMILES: CCc1cc(C)cc(CC)c1C1=C(O)[C@H]2[C@@H](C1=O)[C@@H]1CC[C@H]2O1] | δ$_H$ 6.95 (2H, s), 4.75 (2H, br), 3.40 (2H, br), 2.45 (2H, q), 2.35 (2H, q), 2.30 (3H, s), 1.80 (4H, m), 1.15 (3H, t), 1.05 (3H, t). |

TABLE T1-continued

| Compound Number | Structure | $^1$H nmr (CDCl$_3$ unless stated) or other physical data |
|---|---|---|
| T11 | 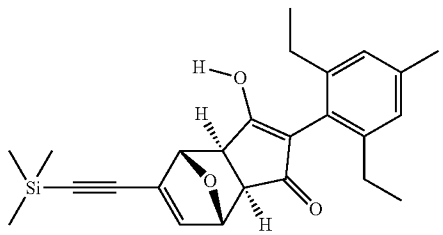 | $\delta_H$ 6.70 (2H, s), 6.24 (1H, s), 4.79 (1H, s), 4.73 (1H, s), 2.67 (1H, br s), 2.56 (1H, d), 2.17-2.08 (7H, m), 0.87-0.77 (6H, m), 0.00 (9H, s). |
| T12 | 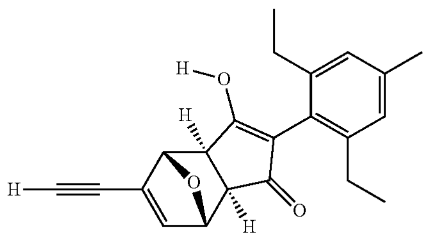 [SMILES: C#CC1=C[C@@H]2O[C@H]1[C@H]1C(O)=C(c3c(CC)cc(C)cc3CC)C(=O)[C@H]12] | $\delta_H$ 6.94 (2H, s), 6.66 (0.5H, s), 6.62 (0.5H, s), 5.14-5.02 (2H, m), 3.42 (1H, s), 3.10 (0.5H, s), 3.00 (0.5H, s), 2.86 (0.5H, s), 2.77 (0.5 H, s), 2.38-2.31 (7H, m), 1.10-1.01 (6H, m). |
| T13 | 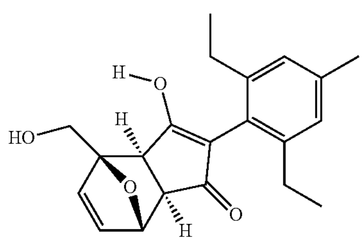 [SMILES: CCc1cc(C)cc(CC)c1C1=C(O)[C@H]2[C@@H](C1=O)[C@@H]1C=C[C@@]2(CO)O1] | $\delta_H$ 6.95 (2H, s), 6.60 (1H, s), 6.53-6.51 (1H, m), 5.07 (1H, s), 4.14-4.00 (2H, m), 3.10-2.90 (br m, 2H), 2.42-2.28 (7H, m), 1.11-1.04 (6H, m). |
| T14 | 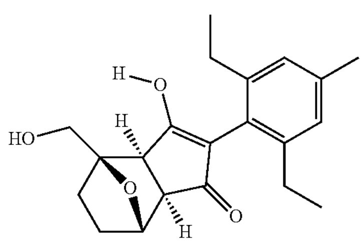 [SMILES: CCc1cc(C)cc(CC)c1C1=C(O)[C@H]2[C@@H](C1=O)[C@@H]1CC[C@@]2(CO)O1] | $\delta_H$ 6.88 (2H, s), 4.57 (1H, d), 3.86 (1H, d), 3.73 (1H, d), 3.23 (1H, s), 2.35-2.27 (7H, m), 1.86-1.53 (4H, m), 1.06-1.00 (6H, m). |
| T15 | 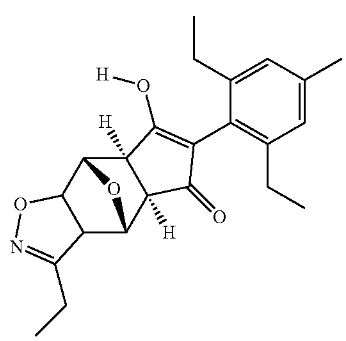 [SMILES: CCC1=NOC2C1[C@@H]1O[C@H]2[C@H]2C(O)=C(c3c(CC)cc(C)cc3CC)C(=O)[C@H]21] | $\delta_H$ 6.94 (1H, s), 6.93 (1H, s), 4.86 (1H, s), 4.79 (1H, d), 4.76 (1H, s), 3.50 (1H, d), 2.96 (1H, s), 2.78 (1H, s), 2.50-2.25 (9H, m), 1.24-1.18 (3H, m), 1.09-1.02 (6H, m). |

TABLE T1-continued

| Compound Number | Structure | ¹H nmr (CDCl₃ unless stated) or other physical data |
|---|---|---|
| T16 | 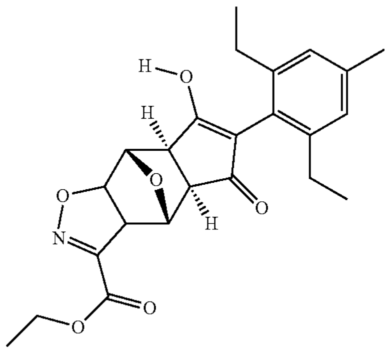 [SMILES: CCOC(=O)C1=NOC2C1[C@@H]1O[C@H]2[C@H]2C(O)=C(c3c(CC)cc(C)cc3CC)C(=O)[C@H]21] | $\delta_H$ 6.92 (2H, s), 5.00 (1H, d), 4.96 (1H, s), 4.93 (1H, s), 4.37-4.32 (2H, m), 3.78 (1H, d), 2.96 (1H, s), 2.61 (1H, s), 2.34-2.30 (7H, m), 1.39-1.35 (3H, m), 1.07-1.00 (6H, m). |
| T17 | 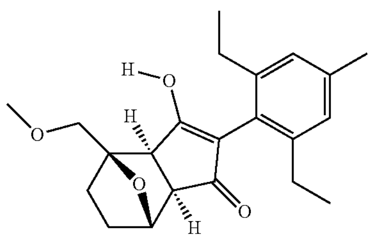 | $\delta_H$ 8.40 (1H, s), 6.93 (1H, s), 6.92 (1H, s), 4.78 (1H, d), 4.01 (1H, d), 3.75 (1H, d), 3.52 (3H, s), 3.11 (1H, d), 2.81 (1H, d), 2.44-2.31 (4H, m), 2.30 (3H, s), 2.00-1.93 (2H, m), 1.75-1.70 (2H, m), 1.09-1.05 (6H, m). |
| T18 | 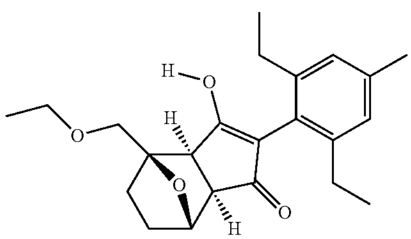 [SMILES: CCOC[C@]12CC[C@H](O1)[C@@H]1C(=O)C(c3c(CC)cc(C)cc3CC)=C(O)[C@@H]12] | $\delta_H$ 6.88 (1H, s), 6.87 (1H, s), 4.66 (1H, d), 3.94 (1H, d), 3.77 (1H, d), 3.65-3.52 (2H, m), 2.88 (1H, s), 2.80 (1H, d), 2.39-2.26 ((7H, m), 1.94-1.90 (2H, m), 1.65-1.60 (4H, m), 1.20 (3H, t), 1.05-1.00 (6H, m). |
| T19 | 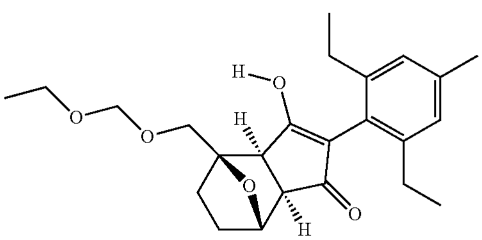 [SMILES: CCOCOC[C@]12CC[C@H](O1)[C@@H]1C(=O)C(c3c(CC)cc(C)cc3CC)=C(O)[C@@H]12] | $\delta_H$ 6.92 (1H, s), 6.91 (1H, s), 4.75 (2H, s), 4.69 (1H, s), 4.04-3.96 (2H, m), 3.64-3.61 (2H, m), 2.94 (1H, br s), 2.81 (1H, d), 2.42-2.30 (4H, m), 2.30 (3H, s), 2.00-1.86 (2H, m), 1.69-1.54 (2H, m), 1.22-1.19 (3H, m), 1.08-1.04 (8H, m). |
| T20 | 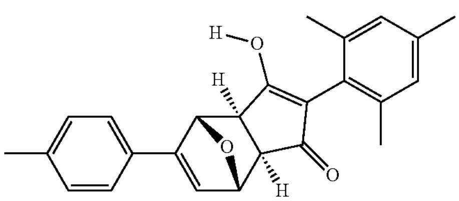 | $\delta_H$ 7.29-7.26 (2H, m), 7.05 (2H, d), 6.85 (1H, s), 6.84 (1H, s), 6.39 (1H, d), 5.32 (1H, s), 5.02 (1H, d), 2.79-2.75 (2H, m), 2.33 (3H, s), 3.23 (3H, s), 2.07 (3H, s), 2.04 (3H, s). |
| T21 | 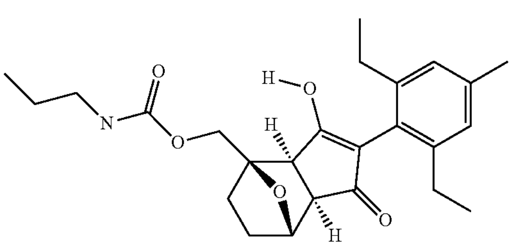 [SMILES: CCCNC(=O)OC[C@]12CC[C@H](O1)[C@@H]1C(=O)C(c3c(CC)cc(C)cc3CC)=C(O)[C@@H]12] | $\delta_H$ 6.87 (2H, s), 5.44 (1H, v. br s), 4.71-4.64 (2H, m), 4.26-4.23 (1H, m), 3.11-3.06 (2H, m), 2.90 (1H, br s), 2.81 (1H, d), 2.38-2.27(4H, m), 2.25 (3H, s), 1.93-1.82 (2H, m), 1.66-1.52 (2H, m), 1.50-1.43 (2H, m), 1.01 (6H, t), 0.87 (3H, t). |

TABLE T1-continued

| Compound Number | Structure | ¹H nmr (CDCl₃ unless stated) or other physical data |
|---|---|---|
| T22 | 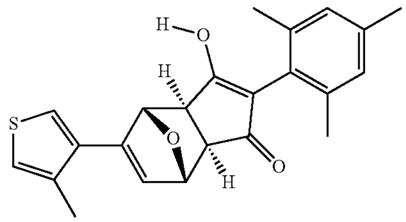 [SMILES: Cc1cc(C)c(C2=C(O)[C@H]3[C@@H](C2=O)[C@@H]2C=C(c4cscc4C)[C@H]3O2)c(C)c1] | $\delta_H$ 7.21 (1H, d), 6.93 (1H, dd), 6.84 (2H, s), 6.30 (1H, s), 5.24 (1H, s), 5.04 (1H, s), 2.82-2.81 (1H, m), 2.78-2.77 (1H, m), 2.28 (3H, s with fine splitting) 2.22 (3H, s), 2.07 (3H, s), 2.04 (3H, s). |
| T23 | 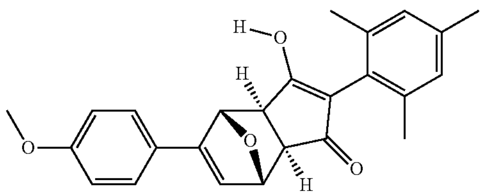 | $\delta_H$ 7.33 (2H, d), 6.86-6.81 (4H, m), 6.35 (1H, s), 5.32 (1H, s), 5.04 (1H, s), 3.80 (3H, s), 2.83-2.82 (1H, m), 2.77 (1H, br s), 2.24 (3H, s), 2.07 (3H, s), 2.05 (3H, s). |
| T24 | 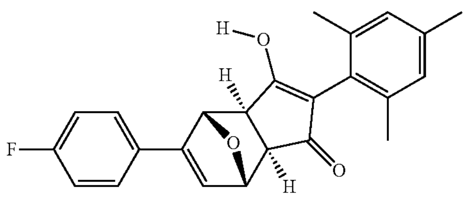 [SMILES: Cc1cc(C)c(C2=C(O)[C@H]3[C@@H](C2=O)[C@@H]2C=C(c4ccc(F)cc4)[C@H]3O2)c(C)c1] | $\delta_H$ 7.35-7.32 (2H, m), 6.86 (1H, s), 6.85 (1H, s), 6.82-6.77 (2H, m), 6.37 (1H, d), 5.31 (1H, s), 5.03 (1H, d), 2.82-2.78 (2H, m), 2.25 (3H, s), 2.07 (3H, s), 2.05 (3H, s). |
| T25 | 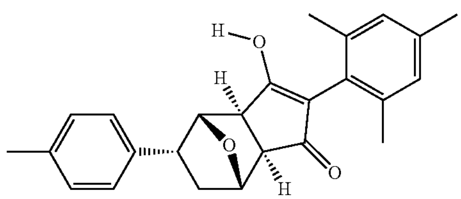 | $\delta_H$ 7.25-7.17 (4H, m), 6.86 (1H, s), 6.84 (1H, s), 4.73 (1H, d), 4.68 (1H, d), 3.61-3.56 (1H, m), 2.90 (1H, d), 2.80 (1H, d), 2.35-2.20 (4H, m). 2.24 (3H, s), 2.07 (3H, s), 2.02 (3H, s), 1.92 (1H, dd). |
| T26 | 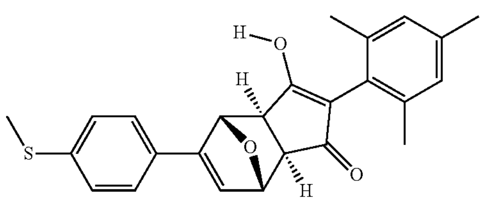 | $\delta_H$ 7.38-7.36 (2H, m), 7.22-7.20 (2H, m), 6.86 (2H, s), 6.58 (1H, d), 5.38 (1H, d), 5.11 (1H, s), 2.90 (1H, m), 2.84 (1H, m), 2.47 (3H, s), 2.24 (3H, s), 2.08 (6H, s). |
| T27 | 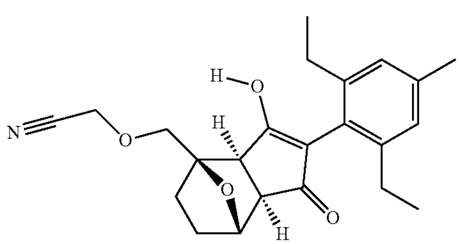 [SMILES: CCc1cc(C)cc(CC)c1C1=C(O)[C@H]2[C@@H](C1=O)[C@@H]1CC[C@@]2(COCC#N)O1] | $\delta_H$ 6.92 (2H, s), 4.62 (1H, d), 4.29-4.27 (1H, m), 4.10-4.03 (2H, m), 3.93-3.90 (1H, m), 2.84 (1H, d), 2.77 (1H, d), 2.38-2.29 (4H, m), 2.30 (3H, s), 1.96-1.88 (2H, m), 1.59-1.51 (2H, m), 1.07-1.03 (6H, m). |
| T28 | 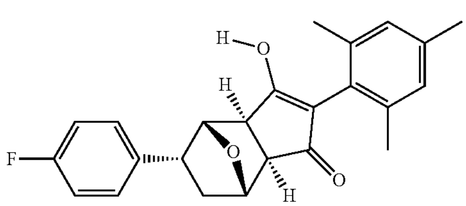 [SMILES: Cc1cc(C)c(C2=C(O)[C@@H]3[C@@H]4O[C@@H](C[C@@H]4c4ccc(F)cc4)[C@@H]3C2=O)c(C)c1] | $\delta_H$ 7.39 (2H, dd), 7.11 (2H, t), 6.86 (1H, s), 6.85 (1H, s), 4.73 (1H, d), 4.68 (1H, d), 3.63-3.58 (1H, m), 2.94 (1H, d), 2.75 (1H, d), 2.38-2.30 (1H, m), 2.25 (3H, s), 2.08 (3H, s), 2.03 (3H, s), 1.92 (1H, dd). |

TABLE T1-continued

| Compound Number | Structure | $^1$H nmr (CDCl$_3$ unless stated) or other physical data |
|---|---|---|
| T29 | 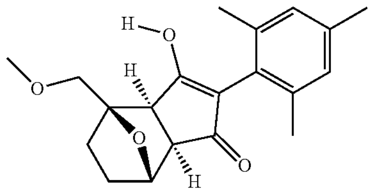 | δ$_H$ 6.82 (2H, s), 4.54 (1H, d), 3.85 (1H, d), 3.67 (1H, d), 3.30 (3H, s), 2.90 (1H, d), 2.78 (1H, d), 2.20 (3H, s), 2.03 (3H, s), 1.99 (3H, s), 1.93 (1H, dd), 1.87-1.81 (1H, m), 1.70-1.63 (1H, m), 1.58-1.54 (1H, m). |
| T30 | 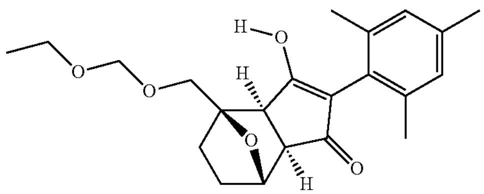 [SMILES: CCOCOC[C@]12CC[C@H](O1)[C@@H]1C(=O)C(c3c(C)cc(C)cc3C)=C(O)[C@@H]12] | δ$_H$ 6.87 (1H, s), 6.86 (1H, s), 4.87-4.81 (1H, m), 4.67-4.65 (1H, m), 4.08-3.93 (2H, m), 3.66-3.58 (2H, m), 2.89-2.84 (1H, m), 2.76-2.73 (1H, m), 2.25 (3H, s), 2.09 (3H, s), 2.06 (3H, s), 1.95-1.84 (2H, m), 1.71-1.59 (2H, m), 1.26-1.17 (3H, m). |
| T31 | 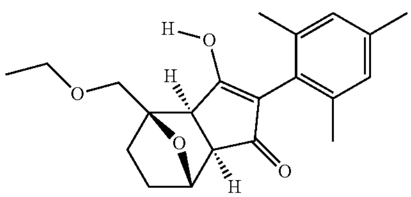 [SMILES: CCOC[C@]12CC[C@H](O1)[C@@H]1C(=O)C(c3c(C)cc(C)cc3C)=C(O)[C@@H]12] | δ$_H$ 6.88 (1H, s), 6.87 (1H, s), 4.67 (1H, t), 3.97 (1H, d), 3.81 (1H, d), 3.70-3.62 (1H, m), 3.60-3.54 (1H, m), 2.87-2.82 (2H, m), 2.25 (3H, s), 2.10 (3H, s), 2.06 (3H, s), 1.99-1.94 (2H, m), 1.69-1.64 (2H, m), 1.23 (3H, t). |
| T32 | 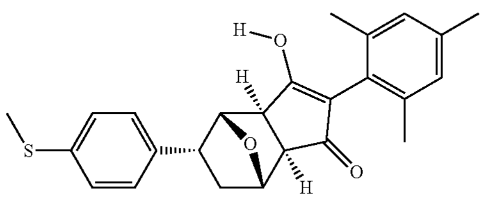 | δ$_H$ 7.20-7.18 (2H, m), 7.12-7.10 (2H, m), 6.88 (1H, s), 6.85 (1H, s), 4.71 (2H, t), 3.55-3.50 (1H, m), 2.77 (1H, d), 2.73 (1H, d), 2.48 (3H, s), 2.32-2.25 (1H, m), 2.23 (3H, s), 2.07 (3H, s), 2.01 (3H, s), 1.72 (1H, dd). |
| T33 | 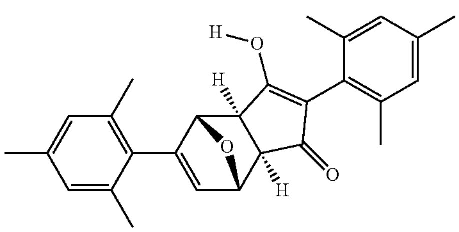 | δ$_H$ 6.93 (2H, s), 6.88 (2H, s), 6.36 (1H, d), 5.13 (1H, d), 5.01 (1H, s), 3.13 (1H, d), 2.96 (1H, d), 2.29 (12H, s), 2.11 (3H, s), 2.09 (3H, s). |
| T34 | 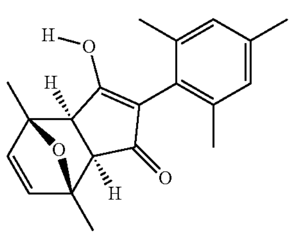 [SMILES: Cc1cc(C)c(C2=C(O)[C@H]3[C@@H](C2=O)[C@]2(C)C=C[C@@]3(C)O2)c(C)c1] | δ$_H$ 2.82 (2H, s), 6.19 (2H, s), 2.51 (2H, br s), 2.22 (3H, s), 2.05 (3H, s), 2.04 (3H, s), 1.57 (6H, s). |
| T35 | 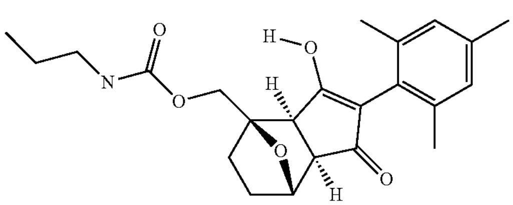 [SMILES: CCCNC(=O)OC[C@]12CC[C@H](O1)[C@@H]1C(=O)C(c3c(C)cc(C)cc3C)=C(O)[C@@H]12] | δ$_H$ 6.88 (1H, s), 6.87 (1H, s), 4.73-4.69 (2H, m), 4.29 (1H, d), 3.14-3.09 (2H, m), 2.93 (1H, d), 2.85 (1H, d), 2.25 (3H, s), 2.09 (3H, s), 2.06 (3H, s), 1.97-1.86 (2H, m), 1.71-1.59 (2H, m), 1.54-1.47 (2H, m), 0.91 (3H, t). |

| Compound Number | Structure | ¹H nmr (CDCl₃ unless stated) or other physical data |
|---|---|---|
| T36 | 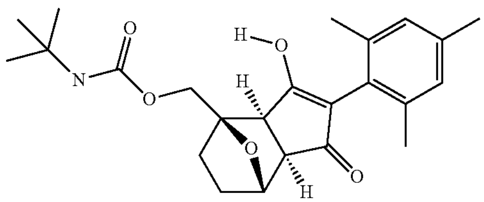 [SMILES: Cc1cc(C)c(C2=C(O)[C@H]3[C@@H](C2=O)[C@@H]2CC[C@@]3(COC(=O)NC(C)(C)C)O2)c(C)c1] | $\delta_H$ 6.83 (2H, s), 5.02 (1H, s), 4.72 (1H, d), 4.65 (1H, d), 4.12 (1H, d), 2.83 (1H, d), 2.70 (1H, d), 2.23 (3H, s), 2.07 (3H, s), 2.06 (3H, s), 1.86-1.80 (2H, m), 1.57-1.45 (2H, m), 1.29 (9H, s). |
| T37 | 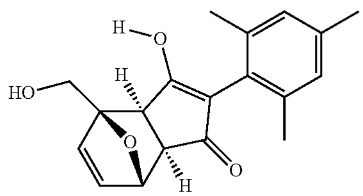 [SMILES: Cc1cc(C)c(C2=C(O)[C@H]3[C@@H](C2=O)[C@@H]2C=C[C@@]3(CO)O2)c(C)c1] | LC-MS (Method A) ES⁺: MH⁺ = 313; rt = 1.07 mins |
| T38 | 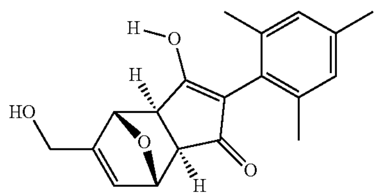 [SMILES: Cc1cc(C)c(C2=C(O)[C@H]3[C@@H](C2=O)[C@@H]2C=C(CO)[C@H]3O2)c(C)c1] | LC-MS (Method A) ES⁺: MH⁺ = 313; rt = 1.07 mins |
| T39 | 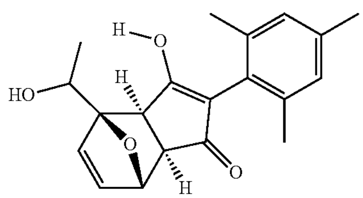 [SMILES: Cc1cc(C)c(C2=C(O)[C@H]3[C@@H](C2=O)[C@@H]2C=C[C@@]3(C(C)O)O2)c(C)c1] | LC-MS (Method A) ES⁺: MH⁺ = 327; rt = 1.23 mins |
| T40 | 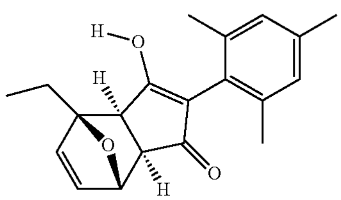 [SMILES: CC[C@]12C=C[C@H](O1)[C@@H]1C(=O)C(c3c(C)cc(C)cc3C)=C(O)[C@@H]12] | LC-MS (Method A) ES⁺: MH⁺ = 311; rt = 1.34 mins |
| T41 | 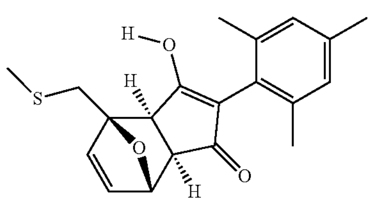 | LC-MS (Method A) ES⁺: MH⁺ = 343; rt = 1.35 mins |
| T42 | 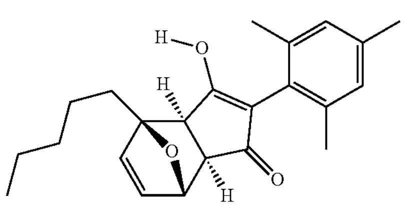 [SMILES: CCCCC[C@]12C=C[C@H](O1)[C@@H]1C(=O)C(c3c(C)cc(C)cc3C)=C(O)[C@@H]12] | LC-MS (Method A) ES⁺: MH⁺ = 353; rt = 1.79 mins |

TABLE T1-continued

| Compound Number | Structure | $^1$H nmr (CDCl$_3$ unless stated) or other physical data |
|---|---|---|
| T43 | 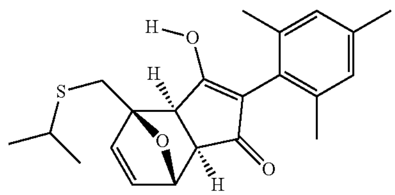 [SMILES: Cc1cc(C)c(C2=C(O)[C@H]3[C@@H](C2=O)[C@@H]2C=C[C@@]3(CSC(C)C)O2)c(C)c1] | LC-MS (Method A) ES$^+$: MH$^+$ = 371; rt = 1.50 mins |
| T44 | 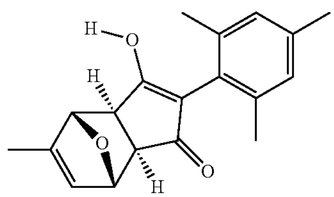 | LC-MS (Method A) ES$^+$: MH$^+$ = 297; rt = 1.25 mins |
| T45 | 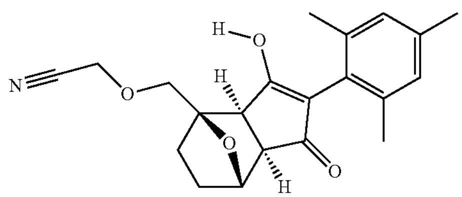 [SMILES: Cc1cc(C)c(C2=C(O)[C@H]3[C@@H](C2=O)[C@@H]2CC[C@@]3(COCC#N)O2)c(C)c1] | $\delta_H$ 6.86 (2H, s), 4.61-4.58 (2H, m), 4.43 (1H, d), 4.07 (1H, d), 3.95 (1H, d), 2.98-2.85 (2H, m), 2.24 (3H, s), 2.08 (3H, s), 2.06 (3H, s), 1.91-1.87 (2H, m), 1.76-1.70 (1H, m), 1.65-1.59 (1H, m). |
| T46 | 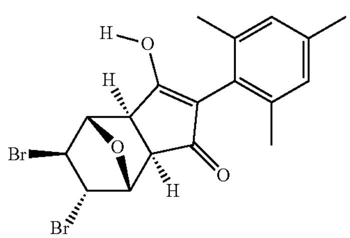 [SMILES: Cc1cc(C)c(C2=C(O)[C@@H]3[C@@H]4O[C@@H]([C@H](Br)[C@H]4Br)[C@@H]3C2=O)c(C)c1] | $\delta_H$ 6.93 (2H, s), 4.75 (1H, d), 4.72 (1H, s), 4.38 (1H, dd), 3.93 (1H, d), 3.68 (1H, d), 2.90 (1H, d), 2.38-2.31 (7H, m), 1.08-1.01 (6H, m). |
| T47 | 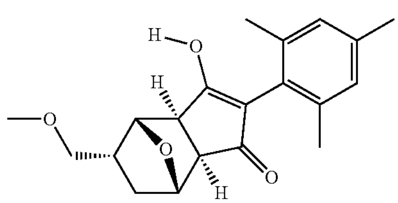 | $\delta_H$ 6.82 (2H, s), 4.50-4.45 (2H, m), 3.36-3.34 (1H, m), 3.26-3.24 (4H, m), 2.92 (1H, d), 2.47 (1H, d), 2.41-2.36 (1H, m), 2.23 (3H, s), 2.02 (6H, s), 1.95-1.88 (1H, m), 1.00 (1H, dd). |
| T48 | 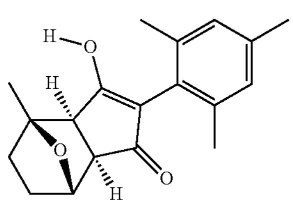 [SMILES: Cc1cc(C)c(C2=C(O)[C@H]3[C@@H](C2=O)[C@@H]2CC[C@@]3(C)O2)c(C)c1] | $\delta_H$ 6.84-6.83 (2H, m), 4.47 (1H, d), 2.63 (1H, d), 2.41 (1H, d), 2.23 (3H, s), 2.04 (3H, s), 2.01 (3H, s), 1.86-1.83 (1H, m), 1.55-1.46 (3H, m), 1.48 (3H, s). |
| T49 | 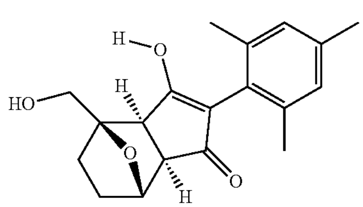 [SMILES: Cc1cc(C)c(C2=C(O)[C@H]3[C@@H](C2=O)[C@@H]2CC[C@@]3(CO)O2)c(C)c1] | $\delta_H$ 6.85 (2H, s), 4.55 (1H, d), 3.84 (1H, d), 3.75 (1H, d), 2.76-2.70 (2H, m), 2.23 (3H, s), 2.03 (6H, s). |

TABLE T1-continued

| Compound Number | Structure | $^1$H nmr (CDCl$_3$ unless stated) or other physical data |
|---|---|---|
| T50 | 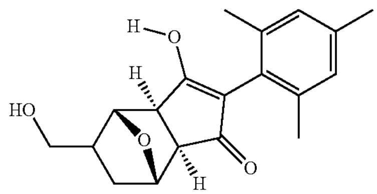 [SMILES: Cc1cc(C)c(C2=C(O)[C@H]3[C@@H](C2=O)[C@@H]2CC(CO)[C@H]3O2)c(C)c1] | $\delta_H$ 6.83-6.82 (2H, m), 4.48-4.45 (2H, m), 3.35-3.34 (1H, m), 3.26-3.24 (1H, m), 2.93 (1H, d), 2.48 (1H, d), 2.23 (3H, s), 2.02 (6H, s), 2.42-2.36 (1H, m), 1.94-1.88 (1H, m), 1.01 (1H, dd). |
| T51 | 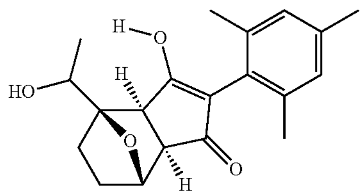 [SMILES: Cc1cc(C)c(C2=C(O)[C@H]3[C@@H](C2=O)[C@@H]2CC[C@@]3(C(C)O)O2)c(C)c1] | $\delta_H$ 6.85 (2H, s), 4.55 (1H, d), 4.03 (1H, q), 2.76 (1H, d), 2.72 (1H, d), 2.23 (3H, s), 2.04 (3H, s), 2.03 (3H, s), 1.84-1.70 (2H, m), 1.58-1.41 (2H, m), 1.24 (3H, d). |
| T52 | 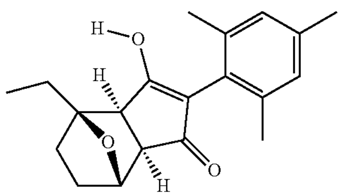 [SMILES: CC[C@]12CC[C@H](O1)[C@@H]1C(=O)C(c3c(C)cc(C)cc3C)=C(O)[C@@H]12] | $\delta_H$ 6.82 (1H, s), 6.81 (1H, s), 4.42 (1H, d), 2.53-2.48 (2H, m), 2.22 (3H, s), 2.00 (3H, s), 1.98 (3H, s), 1.93-1.86 (1H, m), 1.77-1.70 (2H, m), 1.54-1.41 (3H, m), 1.03 (3H, t). |
| T53 | 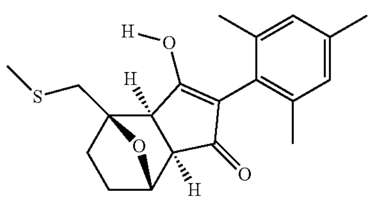 | $\delta_H$ 6.83 (2H, s), 4.49 (1H, d), 3.00-2.92 (2H, m), 2.62-2.58 (2H, m), 2.23 (3H, s), 2.14 (3H, s), 2.02 (3H, s), 2.00 (3H, s), 2.00-1.85 (2H, m), 1.52-1.47 (2H, m). |
| T54 | 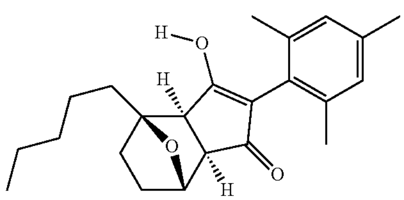 [SMILES: CCCCC[C@]12CC[C@H](O1)[C@@H]1C(=O)C(c3c(C)cc(C)cc3C)=C(O)[C@@H]12] | $\delta_H$ 6.84 (1H, s), 6.83 (1H, s), 4.45 (1H, d), 2.60-2.56 (2H, m), 2.23 (3H, s), 2.04 (3H, s), 2.00 (3H, s), 1.93-1.88 (1H, m), 1.80-1.76 (1H, m), 1.69-1.46 (4H, m), 1.35-1.26 (6H, m), 0.88-0.85 (3H, m). |
| T55 | 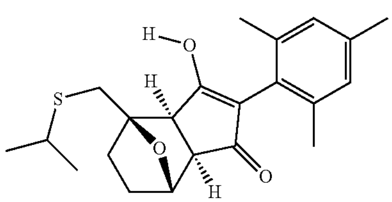 [SMILES: Cc1cc(C)c(C2=C(O)[C@H]3[C@@H](C2=O)[C@@H]2CC[C@@]3(CSC(C)C)O2)c(C)c1] | $\delta_H$ 6.86 (2H, m), 3.11-3.00 (4H, m), 2.72 (1H, d), 2.25 (3H, s), 2.09 (3H, s), 2.05 (3H, s), 1.98-1.89 (1H, m), 1.79-1.56 (3H, m), 1.33-1.25 (6H, m). |
| T56 | 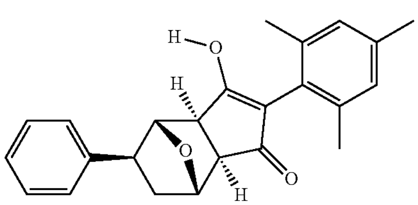 | $\delta_H$ 7.28-7.17 (5H, m), 6.89 (1H, s), 6.88 (1H, s), 4.72 (1H, d), 4.53 (1H, s), 2.89 (1H, dd), 3.02 (1H, d), 2.96 (1H, d), 2.32-2.30 (1H, m), 2.27 (3H, s), 2.07 (6H, s), 1.90-1.85 (1H, m). |

TABLE T1-continued

| Compound Number | Structure | $^1$H nmr (CDCl$_3$ unless stated) or other physical data |
|---|---|---|
| T57 | 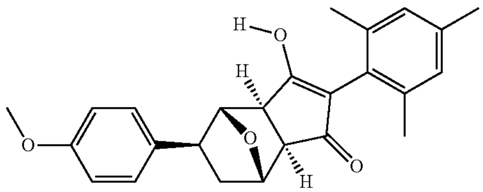 | $\delta_H$ 7.26-7.23 (2H, m), 6.88-6.85 (4H, m), 4.74 (1H, d), 4.40 (1H, s), 3.79 (3H, s), 3.10 (1H, dd), 3.02 (1H, d, 2.96 (1H, d), 2.32-2.30 (1H, m), 2.27 (3H, s), 2.07 (6H, s), 1.90-1.85 (1H, m). |
| T58 | 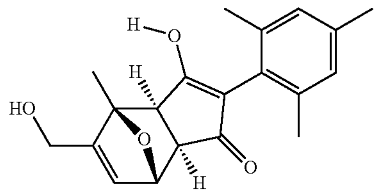 [SMILES: Cc1cc(C)c(C2=C(O)[C@H]3[C@@H](C2=O)[C@@H]2C=C(CO)[C@@]3(C)O2)c(C)c1] | LC-MS (Method A) ES$^+$: MH$^+$ = 327; rt = 1.10 mins |
| T59 | 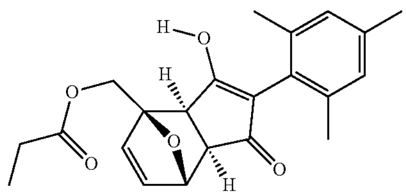 [SMILES: CCC(=O)OC[C@]12C=C[C@H](O1)[C@@H]1C(=O)C(c3c(C)cc(C)cc3C)=C(O)[C@@H]12] | LC-MS (Method A) ES$^+$: MH$^+$ = 369; rt = 1.33 mins |
| T60 | 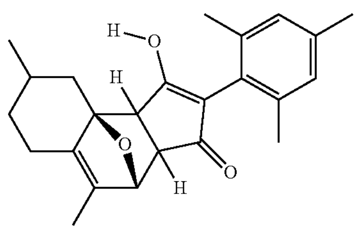 [SMILES: CC1=C2CCC(C)C[C@@]23O[C@@H]1C1C(=O)C(c2c(C)cc(C)cc2C)=C(O)C13] | LC-MS (Method A) ES$^+$: MH$^+$ = 365; rt = 1.77 mins |
| T61 | 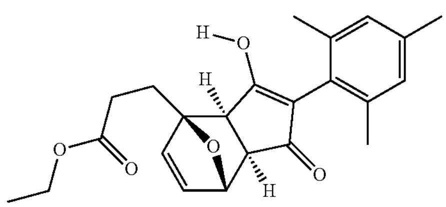 [SMILES: CCOC(=O)CC[C@]12C=C[C@H](O1)[C@@H]1C(=O)C(c3c(C)cc(C)cc3C)=C(O)[C@@H]12] | LC-MS (Method A) ES$^+$: MH$^+$ = 383; rt = 1.36 mins |
| T62 | 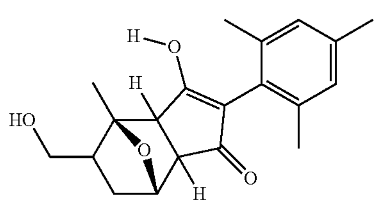 [SMILES: Cc1cc(C)c(C2=C(O)C3C(C2=O)[C@@H]2CC(CO)[C@@]3(C)O2)c(C)c1] | $\delta_H$ 6.86 (2H, s), 4.48 (1H, d), 3.68-3.48 (2H, m), 2.81-2.74 (1H, m), 2.67 (1H, d), 2.23 (3H, s), 2.07 (3H, s), 2.04 (3H, s), 1.54 (3H, s), 1.27-1.26 (1H, m), 1.04-1.01 (2H, m). |
| T63 | 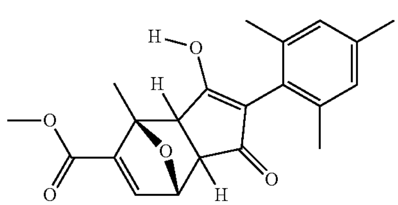 | LC-MS (Method A) ES$^+$: MH$^+$ = 355; rt = 1.36 mins |

TABLE T1-continued

| Compound Number | Structure | $^1$H nmr (CDCl$_3$ unless stated) or other physical data |
|---|---|---|
| T64 | 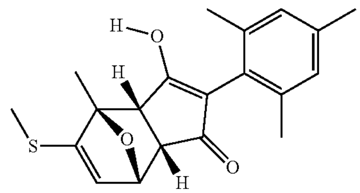 | LC-MS (Method A) ES$^+$: MH$^+$ = 343; rt = 1.37 mins |
| T65 | 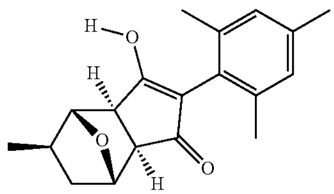 | d$_4$-MeOH δ$_H$ = 6.85 (2H, m), 4.51 (1H, d), 4.37 (1H, d), 3.14 (1H, d), 2.84 (1H, d), 2.28-2.24 (1H, m), 2.24 (3H, s), 2.13 (1H, dd), 2.04 (3H, s), 2.03 (3H, s), 1.13 (3H, d), 1.11-1.06 (1H, m). |
| T66 | 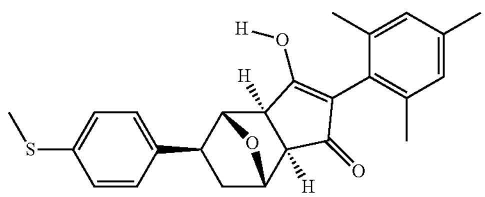 | δ$_H$ 7.26-7.18 (4H, m), 6.85 (2H, s), 4.72 (1H, d), 4.40 (1H, s), 3.09 (1H, dd), 3.00 (1H, d), 2.94 (1H, d), 2.44 (3H, s), 2.29-2.24 (1H, m), 2.24 (3H, s), 2.05 (6H, s), 1.88-1.82 (1H, m). |
| T67 | 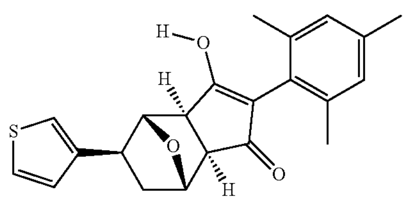 [SMILES: Cc1cc(C)c(C2=C(O)[C@@H]3[C@@H]4O[C@@H](C[C@H]4c4ccsc4)[C@@H]3C2=O)c(C)c1] | δ$_H$ 7.24-7.21 (1H, m), 6.94-6.93 (2H, m), 6.88 (2H, s), 4.75 (1H, d), 4.45 (1H, s), 3.52 (1H, dd), 3.05 (1H, d), 2.96 (1H, d), 2.35-2.29 (1H, m), 2.27 (3H, s), 2.08 (6H, s), 2.01-1.95 (1H, m). |
| T68 | Isomer A<br><br>Isomer B | Approximately 3:2 Mixture of Isomer A:Isomer B Isomer A: δ$_H$ 6.86 (1H, s), 6.85 (1H, s), 4.55 (1H, d), 4.53 (1H, d), 3.50-3.42 (3H, m), 3.36-3.33 (1H, m), 3.02 (1H, d), 2.49-2.43 (2H, m), 2.25 (3H, s), 2.05 (6H, s), 2.01-1.94 (1H, m), 1.19 (3H, t), 1.06 (1H, dd). |
| T69 | 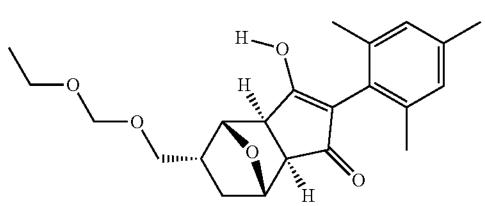 [SMILES: CCOCOC[C@H]1C[C@@H]2O[C@H]1[C@H]1C(O)=C(c3c(C)cc(C)cc3C)C(=O)[C@H]12] | δ$_H$ 6.85 (2H, s), 4.69(2H, s), 4.56-4.54 (2H, m), 3.76-3.55 (5H, m), 3.12 (1H, d), 2.83 (1H, d), 2.55-2.45 (1H, m), 2.24 (3H, s), 2.04 (3H, s), 1.24-1.15 (4H, m). |

TABLE T1-continued

| Compound Number | Structure | ¹H nmr (CDCl₃ unless stated) or other physical data |
|---|---|---|
| T70 | 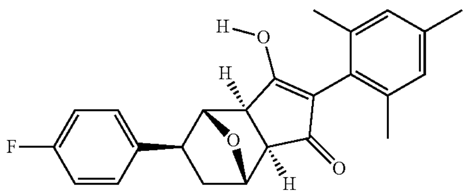 [SMILES: Cc1cc(C)c(C2=C(O)[C@@H]3[C@@H]4O[C@@H](C[C@H]4c4ccc(F)cc4)[C@@H]3C2=O)c(C)c1] | $\delta_H$ 7.34-7.31 (2H, m), 7.00 (2H, t), 6.85 (2H, s), 4.73 (1H, d), 4.39 (1H, s), 3.13 (1H, dd), 3.01 (1H, d), 2.95 (1H, d), 2.30-2.27 (1H, m), 2.24 (3H, s), 2.05 (6H, s), 1.87-1.81 (1H, m). |
| T71 | 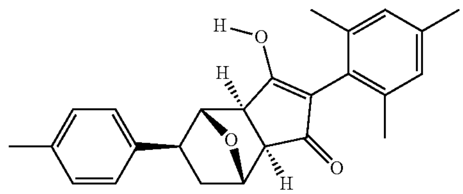 | $\delta_H$ 7.21 (2H, d), 7.11 (2H, d), 6.88 (2H, s), 4.74 (1H, d), 4.42 (1H, s), 3.09 (1H, dd), 3.02 (1H, d), 2.96 (1H, d), 2.32 (3H, s), 2.29-2.24 (1H, m), 2.27 (3H, s), 2.08 (6H, s), 1.91-1.85 (1H, m). |
| T72 | 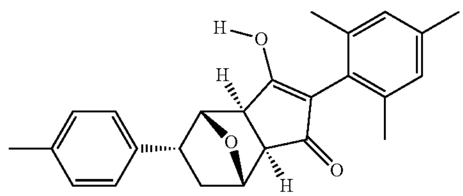 | $\delta_H$ 7.25-7.18 (4H, m), 6.86 (1H, s), 6.84 (1H, s), 4.73 (1H, d), 4.68 (1H, d), 3.61-3.56 (1H, m), 2.90 (1H, d), 2.80 (1H, d), 2.35 (3H, s), 2.32-2.28 (1H, m), 2.24 (3H, s), 2.07 (3H, s), 2.02 (3H, s), 1.92 (1H, dd). |
| T73 | 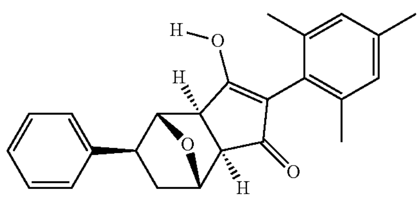 | $\delta_H$ 7.29-7.27 (3H, m), 7.22-7.19 (2H, m), 6.89 (1H, s), 6.88 (1H, s), 4.85 (1H, d), 4.61 (1H, s), 3.01 (1H, dd), 2.26 (3H, s), 2.19 (1H, dd), 2.10 (3H, s), 2.09 (3H, s), 2.00-1.96 (1H, m). |
| T74 | 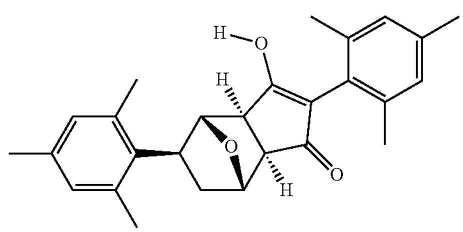 | $\delta_H$ 6.90 (1H, s), 6.88 (1H, s), 6.86-6.82 (2H, m), 4.82-4.77 (2H, m), 3.12-3.05 (2H, m), 2.28-2.86 (1H, m), 2.41-2.39 (1H, m), 2.26 (3H, s), 2.23 (3H, s), 2.11 (6H, s), 2.08 (3H, s), 2.01-1.97 (1H, m). |
| T75 | 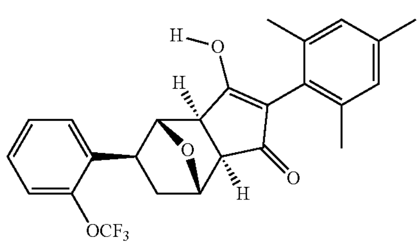 [SMILES: Cc1cc(C)c(C2=C(O)[C@@H]3[C@@H]4O[C@@H](C[C@H]4c4ccccc4OC(F)(F)F)[C@@H]3C2=O)c(C)c1] | $\delta_H$ 7.79-7.76 (1H, m), 7.59-7.56 (1H, m), 7.28-7.20 (2H, m), 6.90 (1H, s), 6.89 (1H, s), 4.88-4.86 (1H, m), 4.67 (1H, s), 3.47-3.42 (1H, m), 3.14-3.00 (2H, m), 2.26 (3H, s), 2.25-2.21 (1H, m), 2.11 (3H, s), 2.09 (3H, s), 1.88-1.84 (1H, m). |
| T76 | 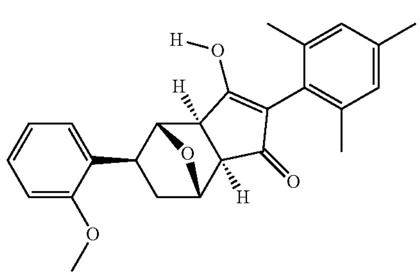 [SMILES: COc1ccccc1[C@@H]1C[C@@H]2O[C@H]1[C@H]1C(O)=C(c3c(C)cc(C)cc3C)C(=O)[C@H]12] | $\delta_H$ 7.39-7.35 (1H, m), 7.19-7.16 (1H, m), 6.93-6.83 (4H, m), 4.82 (1H, brs), 4.62 (1H, s), 3.48 (3H, s), 3.54 (1H, dd), 3.13-3.02 (2H, brm), 2.26 (3H, s), 2.17-2.13 (1H, m), 2.10 (3H, s), 2.09 (3H, s), 1.90-1.84 (1H, m). |

TABLE T1-continued

| Compound Number | Structure | ¹H nmr (CDCl₃ unless stated) or other physical data |
|---|---|---|
| T77 | 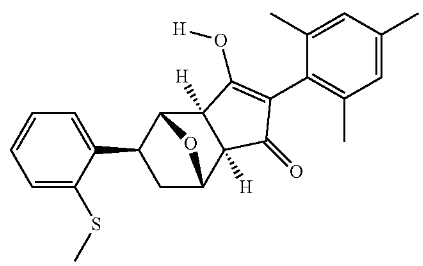 [SMILES: CSc1ccccc1[C@@H]1C[C@@H]2O[C@H]1[C@H]1C(O)=C(c3c(C)cc(C)cc3C)C(=O)[C@H]12] | $\delta_H$ 7.42 (1H, d), 7.21-7.12 (3H, m), 6.88 (1H, s), 6.87 (1H, s), 4.82 (1H, s), 4.82 (1H, d), 4.68 (1H, s), 3.51 (1H, dd), 2.47 (3H, s), 2.25 (3H, s), 2.23-2.20 (1H, m), 2.10 (3H, s), 2.08 (3H, s), 1.85-1.81 (1H, m). |
| T78 | 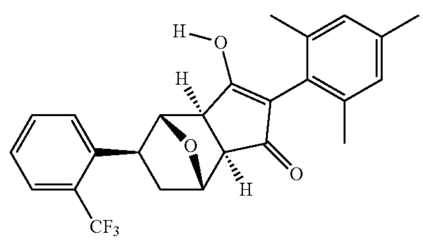 [SMILES: Cc1cc(C)c(C2=C(O)[C@@H]3[C@@H]4O[C@@H](C[C@H]4c4ccccc4C(F)(F)F)[C@@H]3C2=O)c(C)c1] | $\delta_H$ 7.73-7.70 (2H, m), 7.59 (1H, d), 7.52-7.50 (1H, m), 7.31-7.28 (1H, m), 6.89 (1H, s), 6.88 (1H, s), 4.86 (1H, br S), 4.64 (1H, s), 3.42 (1H, br S), 3.13-3.05 (2H, m), 2.26 (3H, s), 2.66-2.24 (1H, m), 2.11 (3H, s), 2.08 (3H, s), 1.92-1.88 (1H, m). |
| T79 | 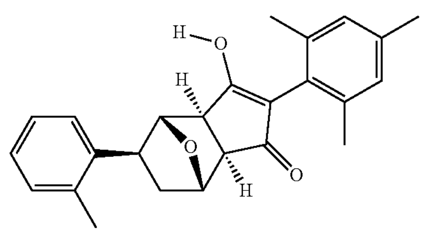 [SMILES: Cc1cc(C)c(C2=C(O)[C@@H]3[C@@H]4O[C@@H](C[C@H]4c4ccccc4C)[C@@H]3C2=O)c(C)c1] | $\delta_H$ 7.42-7.39 (1H, m), 7.18-7.11 (3H, m), 6.91 (1H, s), 6.90 (1H, s), 4.87-4.85 (1H, m), 4.74 (1H, s), 3.24-3.22 (1H, m), 3.13-3.07 (2H, m), 2.36 (3H, s), 2.34 (3H, s), 2.24-2.22 (1H, m), 2.19 (3H, s), 2.09 (3H, s), 1.88-186 (1H, m). |
| T80 | 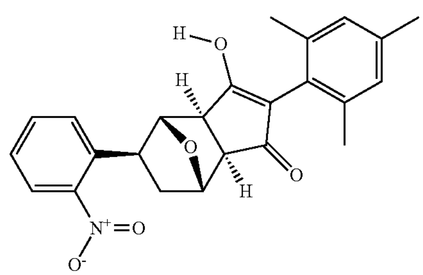 [SMILES: Cc1cc(C)c(C2=C(O)[C@@H]3[C@@H]4O[C@@H](C[C@H]4c4ccccc4[N+](=O)[O-])[C@@H]3C2=O)c(C)c1] | $\delta_H$ 7.79-7.73 (2H, m), 7.56 (1H, t), 7.35 (1H, t), 6.90 (1H, s), 6.89 (1H, s), 4.87 (1H, br s), 4.71 (1H, s), 3.47 (1H, br. s), 3.13-3.06 (2H, m), 2.42-2.30 (1H, m), 2.26 (3H, s), 2.11 (3H, s), 2.09 (3H, s), 1.98-1.97 (1H, m). |
| T81 | 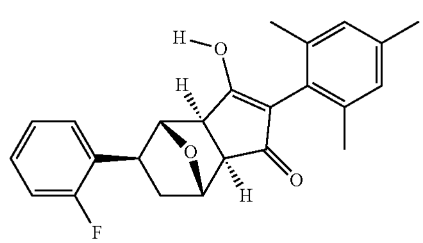 [SMILES: Cc1cc(C)c(C2=C(O)[C@@H]3[C@@H]4O[C@@H](C[C@H]4c4ccccc4F)[C@@H]3C2=O)c(C)c1] | $\delta_H$ 7.45-7.43 (1H, m), 7.18-7.16 (1H, m), 7.11-7.08 (1H, m), 7.02-6.98 (1H, m), 6.89 (1H, s), 6.88 (1H, s), 4.85 (1H, d), 4.65 (1H, s), 3.44 (1H, br. s), 3.15-3.00 (2H, br. s), 2.26 (3H, s), 2.22-2.17 (1H, m), 2.10 (3H, s), 2.09 (3H, s), 1.92-1.88 (1H, s) |
| T82 | 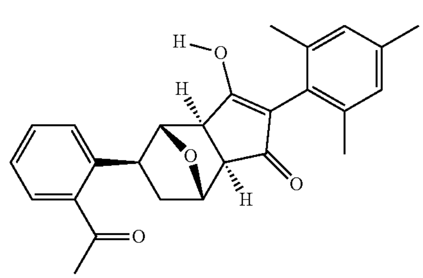 [SMILES: CC(=O)c1ccccc1[C@@H]1C[C@@H]2O[C@H]1[C@H]1C(O)=C(c3c(C)cc(C)cc3C)C(=O)[C@H]12] | $\delta_H$ 7.47-7.96 (2H, m), 7.14-7.11 (2H, m), 6.90 (2H, s), 4.88 (1H, s), 4.57 (1H, s), 3.21 (1H, s), 2.94-2.74 (2H, br. s), 2.62, (3H, s), 2.26 (3H, s), 2.25-2.23 (1H, m), 2.11 (3H, s), 2.10 (3H, s), 2.01-1.93 (1H, m). |

TABLE T1-continued

| Compound Number | Structure | ¹H nmr (CDCl₃ unless stated) or other physical data |
|---|---|---|
| T83 | 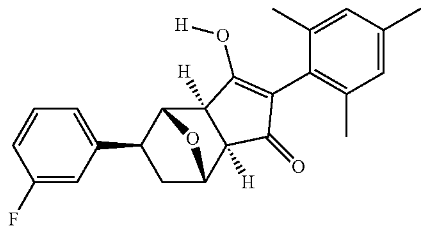 [SMILES: Cc1cc(C)c(C2=C(O)[C@@H]3[C@@H]4O[C@@H](C[C@H]4c4cccc(F)c4)[C@@H]3C2=O)c(C)c1] | δ$_H$ 7.75-7.66 (1H, m), 7.25-7.21 (1H, m), 7.06-7.02 (2H, m), 6.88 (1H, s), 6.87 (1H, s), 4.83 (1H, br. s), 4.59 (1H, s), 3.00-2.98 (1H, m), 2.83-2.70 (2H, br. s), 2.25 (3H, s), 2.20-2.16 (1H, m), 2.09 (3H, s), 2.08 (3H, s), 1.92-1.89 (1H, m). |
| T84 | 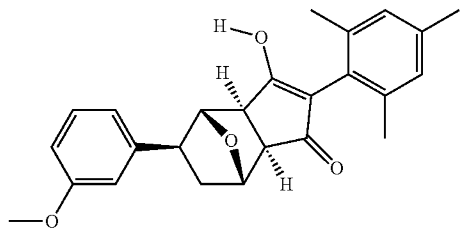 | δ$_H$ 7.79-7.77 (1H, m), 7.21-7.18 (1H, m), 6.89-6.86 (3H, m), 6.76-6.74 (1H, m), 4.83 (1H, d), 4.62 (1H, s), 3.80 (3H, s), 2.99 (1H, dd), 2.80-2.70 (2H, br. s), 2.26 (3H, s), 2.18 (1H, dd), 2.10 (3H, s), 2.09 (3H, s), 1.97-1.95 (1H, m). |
| T85 | 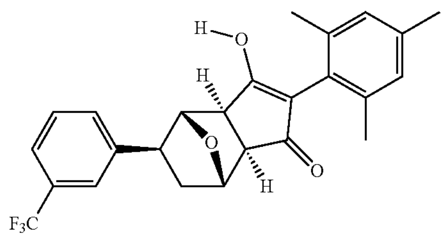 | δ$_H$ 7.54-7.46 (3H, m), 7.41-7.38 (1H, m), 6.87 (1H, s), 6.88 (1H, s), 4.85 (1H, d), 4.60 (1H, s), 3.06 (1H, dd), 2.25 (3H, s), 2.21 (1H, dd), 2.10 (3H, s), 2.08 (3H, s), 1.93-1.90 (1H, m). |
| T86 | 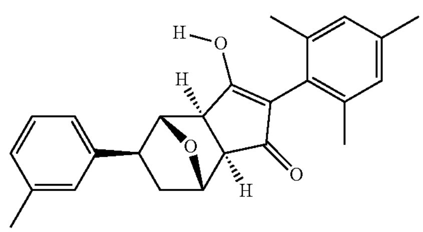 [SMILES: Cc1cccc([C@@H]2C[C@@H]3O[C@H]2[C@H]2C(O)=C(c4c(C)cc(C)cc4C)C(=O)[C@H]23)c1] | δ$_H$ 7.19-7.08 (3H, m), 7.03-7.07 (1H, m), 6.89 (1H, s), 6.88 (1H, s), 4.84 (1H, d), 4.60 (1H, s), 2.98 (1H, dd), 2.33 (3H, s), 2.26 (3H, s), 2.17 (1H, dd), 2.10 (3H, s), 2.08 (3H, s), 1.97-1.95 (1H, br. m). |
| T87 | 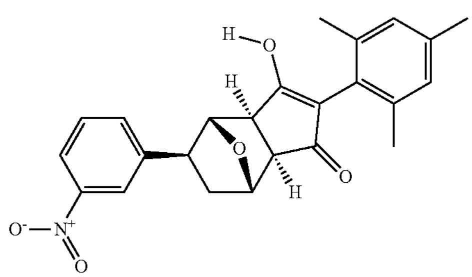 [SMILES: Cc1cc(C)c(C2=C(O)[C@@H]3[C@@H]4O[C@@H](C[C@H]4c4cccc([N+](=O)[O-])c4)[C@@H]3C2=O)c(C)c1] | δ$_H$ 8.09-8.07 (1H, m), 7.68-7.67 (2H, m), 7.46 (1H, t), 6.89 (1H, s), 6.88 (1H, s), 4.89 (1H, d), 4.62 (1H, s), 3.13 (1H, dd), 2.28-2.24 (1H, m), 2.25 (3H, s), 2.10 (3H, s), 2.08 (3H, s), 1.95-1.95 (1H, m). |
| T88 | 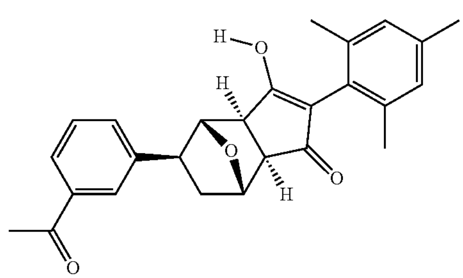 [SMILES: CC(=O)c1cccc([C@@H]2C[C@@H]3O[C@H]2[C@H]2C(O)=C(c4c(C)cc(C)cc4C)C(=O)[C@H]23)c1] | δ$_H$ 7.88-7.86 (1H, m), 7.79 (1H, d), 7.55-7.53 (1H, m), 7.39 (1H, t), 6.88 (1H, s), 6.87 (1H, s), 4.87 (1H, d), 4.61 (1H, s), 3.09 (1H, dd), 2.60 (3H, s), 2.25 (3H, s), 2.23-2.20 (1H, m), 2.10 (3H, s), 2.08 (3H, s), 1.96-1.94 (1H, m). |

TABLE T1-continued

| Compound Number | Structure | ¹H nmr (CDCl$_3$ unless stated) or other physical data |
|---|---|---|
| T89 | 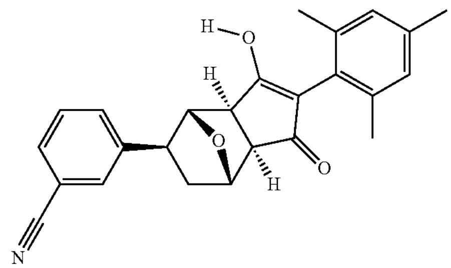 [SMILES: Cc1cc(C)c(C2=C(O)[C@@H]3[C@@H]4O[C@@H](C[C@H]4c4cccc(C#N)c4)[C@@H]3C2=O)c(C)c1] | $\delta_H$ 7.62-7.60 (1H, m), 7.56-7.50 (2H, m), 7.39 (1H, t), 6.90 (1H, s), 6.88 (1H, s), 4.88 (1H, br. s), 4.59 (1H, s), 3.05-3.03 (1H, m), 2.26 (3H, s), 2.24-2.20 (1H, m), 2.10 (3H, s), 2.08 (3H, s), 1.92-1.89 (1H, m). |
| T90 | 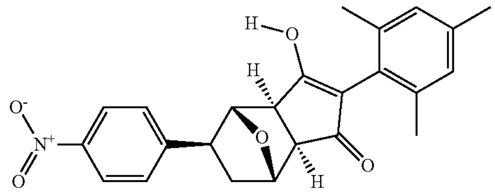 [SMILES: Cc1cc(C)c(C2=C(O)[C@@H]3[C@@H]4O[C@@H](C[C@H]4c4ccc([N+](=O)[O-])cc4)[C@@H]3C2=O)c(C)c1] | $\delta_H$ 8.14 (2H, d), 7.47 (2H, d), 6.89 (1H, s), 6.87 (1H, s), 4.89 (1H, d), 4.63 (1H, s), 3.12 (1H, dd), 2.27-2.23 (1H, m), 2.26 (3H, s), 2.10 (3H, s), 2.08 (3H, s), 1.95-1.91 (1H, m). |
| T91 | 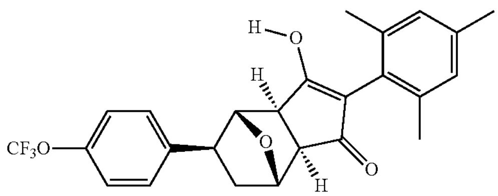 | $\delta_H$ 7.35-7.31 (2H, m), 7.15-7.12 (2H, m), 6.91 (1H, s), 6.90 (1H, s), 4.87 (1H, br. s), 4.61 (1H, s), 3.07-3.05 (1H, m), 2.27 (3H, s), 2.22-2.20 (1H, m), 2.10 (3H, s), 2.09 (3H, s), 1.93-1.91 (1H, m). |
| T92 | 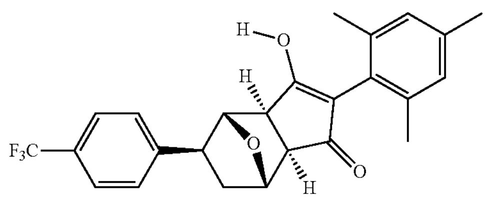 [SMILES: Cc1cc(C)c(C2=C(O)[C@@H]3[C@@H]4O[C@@H](C[C@H]4c4ccc(C(F)(F)F)cc4)[C@@H]3C2=O)c(C)c1] | $\delta_H$ 7.54 (2H, d), 7.43-7.41 (2H, m), 6.89 (1H, s), 6.88 (1H, s), 4.87 (1H, d), 4.61 (1H, s), 3.07 (1H, dd), 2.26 (3H, s), 2.23 (1H, dd), 2.10 (3H, s), 2.08 (3H, s), 1.95-1.91 (1H, m). |
| T93 | 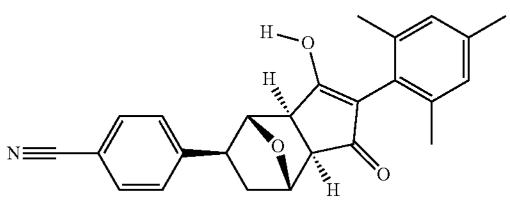 [SMILES: Cc1cc(C)c(C2=C(O)[C@@H]3[C@@H]4O[C@@H](C[C@H]4c4ccc(C#N)cc4)[C@@H]3C2=O)c(C)c1] | $\delta_H$ 7.57 (2H, d), 7.41 (2H, d), 6.88 (1H, s), 6.87 (1H, s), 4.86 (1H, d), 4.60 (1H, s), 3.05 (1h, dd), 2.25 (3H, s), 2.23-2.20 (1H, m), 2.09 (3H, s), 2.08 (3H, s), 1.95-1.91 (1H, m). |
| T94 | 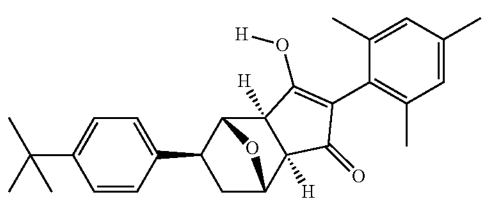 [SMILES: Cc1cc(C)c(C2=C(O)[C@@H]3[C@@H]4O[C@@H](C[C@H]4c4ccc(C(C)(C)C)cc4)[C@@H]3C2=O)c(C)c1] | $\delta_H$ 7.31-7.29 (2H, m), 7.24-7.22 (2H, m), 6.89 (1H, s), 6.88 (1H, s), 4.85 (1H, d), 4.59 (1H, s), 3.00 (1H, dd), 2.26 (3H, s), 2.17 (1H, dd), 2.10 (3H, s), 2.09 (3H, s), 1.99-1.96 (1H, m), 1.30 (9H, s). |
| T95 | 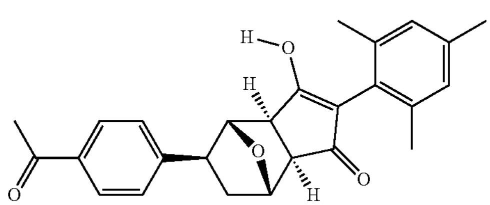 [SMILES: CC(=O)c1ccc([C@@H]2C[C@@H]3O[C@H]2[C@H]2C(O)=C(c4c(C)cc(C)cc4C)C(=O)[C@H]23)cc1] | $\delta_H$ 7.88 (2H, d), 7.41-7.38 (2H, m), 6.90 (1H, s), 6.88 (1H, s), 4.88 (1H, br. s), 4.63 (1H, s), 3.08 (1H, br. s), 2.58 (3H, s), 2.26 (3H, s), 2.23-2.21 (1H, m), 2.11 (3H, s), 2.09 (3H, s), 1.95-1.93 (1H, m). |

TABLE T1-continued

| Compound Number | Structure | $^1$H nmr (CDCl$_3$ unless stated) or other physical data |
|---|---|---|
| T96 | 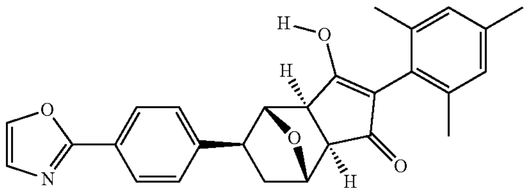 [SMILES: Cc1cc(C)c(C2=C(O)[C@@H]3[C@@H]4O[C@@H](C[C@H]4c4ccc(-c5ncco5)cc4)[C@@H]3C2=O)c(C)c1] | LC-MS (Method A) ES$^+$: MH$^+$ = 428; rt = 1.52 mins |
| T97 | 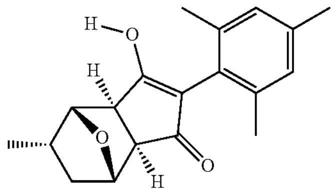 | δ$_H$ 6.85 (2H, s), 4.50 (1H, d), 4.37 (1H, d), 3.31-3.29 (1H, m), 3.12 (1H, d), 2.81 (1H, d), 2.24 (3H, s), 2.14-2.07 (1H, m), 2.05 (3H, s), 2.03 (3H, s), 1.12 (3H, d), 1.07 (1H, dd). |
| T98 | 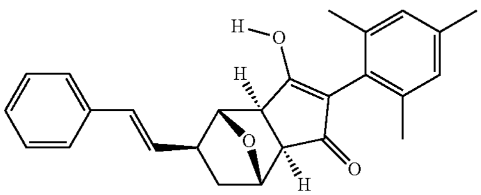 [SMILES: Cc1cc(C)c(C2=C(O)[C@@H]3[C@@H]4O[C@@H](C[C@H]4/C=C/c4ccccc4)[C@@H]3C2=O)c(C)c1] | δ$_H$ 7.33-7.18 (5H, m), 6.84-6.81 (2H, m), 6.35 (1H, d), 6.08 (1H, dd), 4.63 (1H, d), 4.42 (1H, s), 2.68-2.63 (2H, m), 2.55-2.48 (1H, m), 2.22 (3H, s), 2.04 (3H, s), 2.02 (3H, s), 1.85-1.80 (1H, m), 1.64-1.60 (1H, m). |
| T99 | 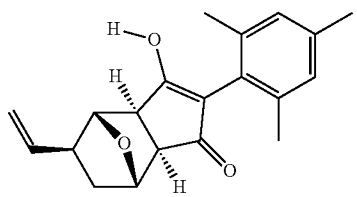 [SMILES: C=C[C@@H]1C[C@@H]2O[C@H]1[C@H]1C(O)=C(c3c(C)cc(C)cc3C)C(=O)[C@H]12] | δ$_H$ 6.90-6.89 (2H, m), 5.80-5.71 (1H, m), 5.05-4.97 (2H, m), 4.68 (1H, d), 4.44 (1H, s), 2.81-2.76 (2H, m), 2.51-2.46 (1H, m), 2.26 (3H, s), 2.07 (3H, s), 2.06 (3H, s), 1.89-1.84 (1H, m), 1.67-1.62 (1H, m). |
| T100 | 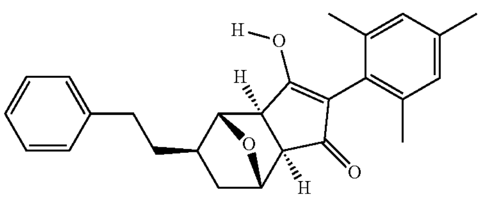 [SMILES: Cc1cc(C)c(C2=C(O)[C@@H]3[C@@H]4O[C@@H](C[C@H]4CCc4ccccc4)[C@@H]3C2=O)c(C)c1] | δ$_H$ 7.27-7.12 (6H, m), 6.83 (2H, br. s), 4.55 (1H, d), 4.33 (1H, s), 2.75-2.71 (2H, m), 2.64 (2H, t), 2.23 (3H, s), 2.04 (6H, s), 1.74-1.68 (3H, m), 1.57-1.50 (1H, m), 1.44-1.41 (1H, m). |
| T101 | 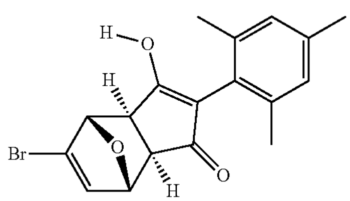 [SMILES: Cc1cc(C)c(C2=C(O)[C@H]3[C@@H](C2=O)[C@@H]2C=C(Br)[C@H]3O2)c(C)c1] | δ$_H$ 6.87 (2H, s), 6.40 (1H, d), 4.95 (1H, s), 4.82 (1H, s), 2.90 (1h, d), 2.81 (1H, d), 2.25 (3H, s), 2.07 (3H, s), 2.03 (3H, s). |
| T102 | 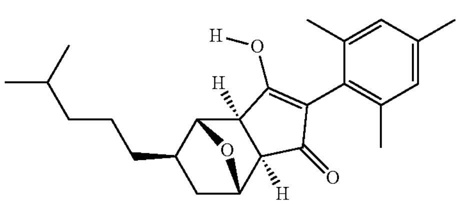 [SMILES: Cc1cc(C)c(C2=C(O)[C@@H]3[C@@H]4O[C@@H](C[C@H]4CCCC(C)C)[C@@H]3C2=O)c(C)c1] | δ$_H$ 6.82 (2H, s), 4.47 (1H, d), 4.25 (1H, s), 2.50-2.46 (2H, m), 2.22 (3H, s), 2.02 (3H, s), 2.01 (3H, s), 1.69-1.50 (4H, m), 1.34-1.12 (6H, m), 0.88-0.86 (6H, m). |

TABLE T1-continued

| Compound Number | Structure | ¹H nmr (CDCl₃ unless stated) or other physical data |
|---|---|---|
| T103 | 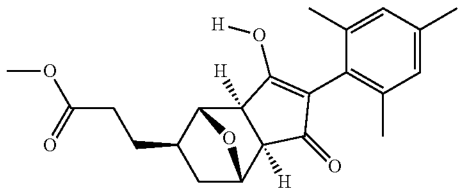 | $\delta_H$ 6.81 (2H, s), 4.47 (1H, d), 4.24 (1H, s), 3.64 (3H, s), 2.52-2.47 (2H, m), 2.28-2.20 (5H, m), 2.00 (6H, s), 1.70-1.48 (H, m), 1.27-1.24 (1H, m). |
| T104 | 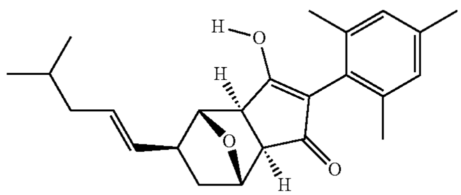 [SMILES: Cc1cc(C)c(C2=C(O)[C@@H]3[C@@H]4O[C@@H](C[C@H]4/C=C/CC(C)C)[C@@H]3C2=O)c(C)c1] | Aproximately 85:15 mixture of E- and Z-isomers. E-isomer: $\delta_H$ 6.84 (2H, s), 5.42-5.26 (2H, m), 4.53 (1H, d), 4.29 (1H, s), 2.58 (1H, m), 2.37-2.29 (1H, m), 2.23 (3H, s), 2.02 (3H, s), 2.01 (3H, s), 1.86-1.83 (2H, m), 1.75-1.70 (1H, m), 1.63-1.47 (3H, m), 0.89-0.86 (6H, m). |
| T105 | 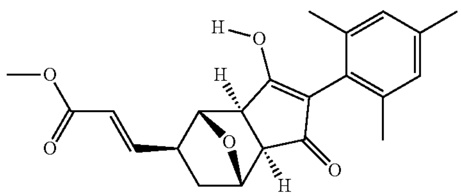 | Approximately 3:2 mixture of E- and Z-isomers. E-isomer $\delta_H$ 6.80 (2H, s), 6.74 (1H, dd), 5.91 (1H, d), 4.58 (1H, d), 4.30 (1H, s), 3.33 (3H, s), 2.85-2.77 (3H, m), 2.21 (3H, s), 1.97 (3H, s), 194 (3H, s), 1.94-1.91 (1H, m), 1.59-1.54 (1H, m). |
| T106 | 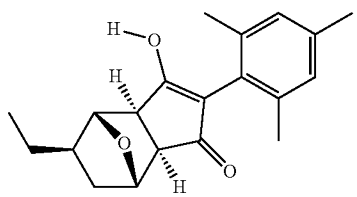 [SMILES: CC[C@@H]1C[C@@H]2O[C@H]1[C@H]1C(O)=C(c3c(C)cc(C)cc3C)C(=O)[C@H]12] | $\delta_H$ 6.82 (2H, s), 4.44 (1H, d), 4.24 (1H, s), 2.45-2.40 (2H, m), 2.22 (3H, s), 2.02 (6H, s), 1.58-1.52 (2H, m), 1.38-1.33 (1H, m), 1.25-1.16 (2H, m), 0.85-0.82 (3H, m). |
| T107 | 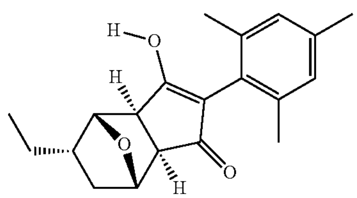 [SMILES: CC[C@H]1C[C@@H]2O[C@H]1[C@H]1C(O)=C(c3c(C)cc(C)cc3C)C(=O)[C@H]12] | $\delta_H$ 6.85 (2H, s), 4.51 (1H, d), 4.43 (1H, d), 3.07 (1H, d), 2.82-2.81 (1H, m), 2.24 (3H, s), 2.10-2.05 (2H, m), 2.04 (6H, s), 1.87-1.79 (1H, m), 1.53-1.46 (2H, m), 1.00 (3H, t). |
| T108 | 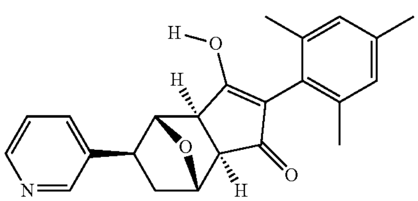 [SMILES: Cc1cc(C)c(C2=C(O)[C@@H]3[C@@H]4O[C@@H](C[C@H]4c4cccnc4)[C@@H]3C2=O)c(C)c1] | $\delta_H$ 8.82 (1H, s), 8.76 (1H, d), 8.03 (1H, dd), 6.82 (2H, s), 4.90 (1H, d), 4.63 (1H, s), 3.55 (1H, dd), 3.16 (1H, d), 3.08 (1H, d), 2.46-2.40 (1H, m), 2.23 (3H, s), 2.08 (6H, s), 2.02-1.96 (1H, m). |
| T109 | 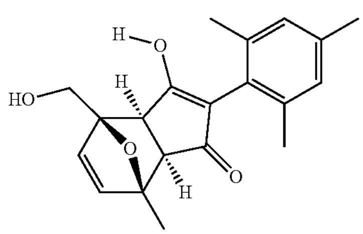 | LC-MS (Method A) ES⁺: MH⁺ = 327; rt = 4.97 mins |

TABLE T1-continued

| Compound Number | Structure | $^1$H nmr (CDCl$_3$ unless stated) or other physical data |
|---|---|---|
| T110 | 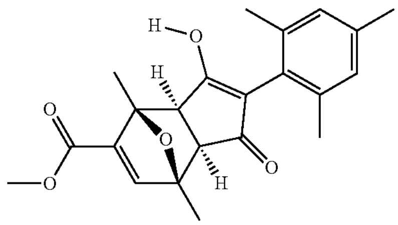 | LC-MS (Method A) ES$^+$: MH$^+$ = 369; rt = 4.98 mins |
| T111 | 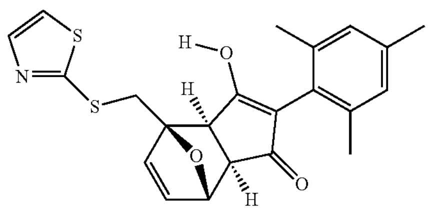 [SMILES: Cc1cc(C)c(C2=C(O)[C@H]3[C@@H](C2=O)[C@@H]2C=C[C@@]3(CSc3nccs3)O2)c(C)c1] | LC-MS (Method A) ES$^+$: MH$^+$ = 412; rt = 5.70 mins |
| T112 | 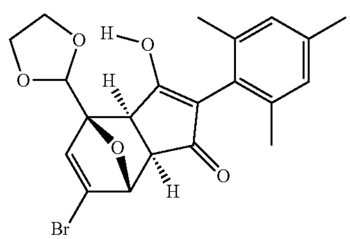 [SMILES: Cc1cc(C)c(C2=C(O)[C@H]3[C@@H](C2=O)[C@H]2O[C@]3(C3OCCO3)C=C2Br)c(C)c1] | LC-MS (Method A) ES$^+$: MH$^+$ = 435; rt = 4.23 mins |
| T113 | 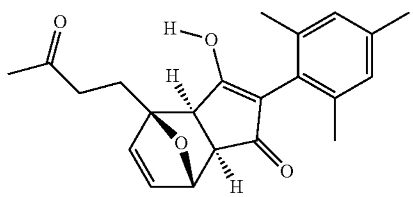 [SMILES: CC(=O)CC[C@]12C=C[C@H](O1)[C@@H]1C(=O)C(c3c(C)cc(C)cc3C)=C(O)[C@@H]12] | LC-MS (Method A) ES$^+$: MH$^+$ = 353; rt = 4.48 mins |
| T114 | 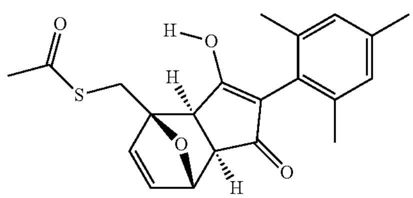 [SMILES: CC(=O)SC[C@]12C=C[C@H](O1)[C@@H]1C(=O)C(c3c(C)cc(C)cc3C)=C(O)[C@@H]12] | LC-MS (Method A) ES$^+$: MH$^+$ = 371; rt = 5.23 mins |
| T115 | 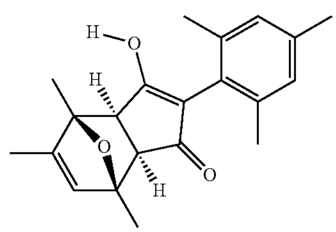 | LC-MS (Method A) ES$^+$: MH$^+$ = 325; rt = 4.22 mins |
| T116 | 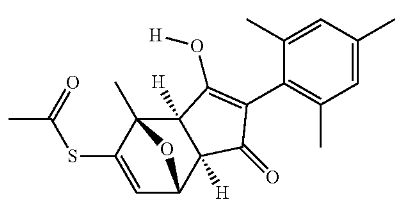 [SMILES: CC(=O)SC1=C[C@@H]2O[C@@]1(C)[C@H]1C(O)=C(c3c(C)cc(C)cc3C)C(=O)[C@@H]21] | LC-MS (Method A) ES$^+$: MH$^+$ = 371; rt = 5.51 mins |

TABLE T1-continued

| Compound Number | Structure | $^1$H nmr (CDCl$_3$ unless stated) or other physical data |
|---|---|---|
| T117 | (structure with CF$_3$CF$_2$, OH, mesityl group) | LC-MS (Method A) ES$^+$: MH$^+$ = 431; rt = 4.98 mins |
| T118 | (structure with n-C$_6$H$_{13}$, mesityl group) | LC-MS (Method A) ES$^+$: MH$^+$ = 381; rt = 7.34 mins |
| T119 | (structure with n-C$_3$H$_7$, mesityl group) | LC-MS (Method A) ES$^+$: MH$^+$ = 339, rt = 6.54 mins |
| T120 | (structure with allyl-CH(OH)-, mesityl group) | LC-MS (Method A) ES$^+$: MH$^+$ = 353; rt = 5.23 mins |
| T121 | (structure with pyrazinyl-S-CH$_2$-, mesityl group) | LC-MS (Method A) ES$^+$: MH$^+$ = 407; rt = 5.04 mins |
| T122 | (structure with HOCH$_2$-, methyl, mesityl group) | LC-MS (Method B) ES$^+$: MH$^+$ = 329; rt = 1.18 mins |
| T123 | (structure with CH$_3$C(O)CH$_2$CH$_2$-, mesityl group) | LC-MS (Method B) ES$^+$: MH$^+$ = 355; rt = 1.32 mins |

TABLE T1-continued

| Compound Number | Structure | ¹H nmr (CDCl₃ unless stated) or other physical data |
|---|---|---|
| T124 | 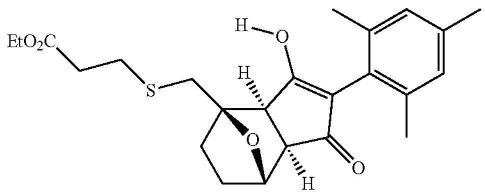 [SMILES: CCOC(=O)CCSC[C@]12CC[C@H](O1)[C@@H]1C(=O)C(c3c(C)cc(C)cc3C)=C(O)[C@@H]12] | LC-MS (Method B) ES⁺: MH⁺ = 43; rt = 1.58 mins |
| T125 | 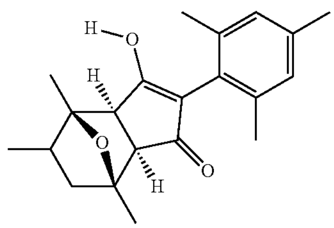 | LC-MS (Method B) ES⁺: MH⁺ = 327; rt = 1.45 mins |
| T126 | 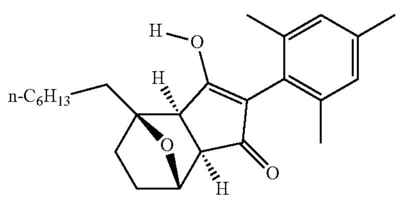 | LC-MS (Method B) ES⁺: MH⁺ = 383; rt = 1.93 mins |
| T127 | 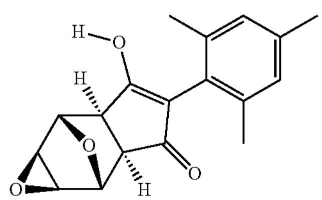 [SMILES: Cc1cc(C)c(C2=C(O)[C@@H]3[C@@H]4O[C@@H]([C@H]5O[C@H]54)[C@@H]3C2=O)c(C)c1] | d₄-MeOH $\delta_H$ 6.84 (2H, s), 4.50 (2H, s), 3.56 (2H, s), 2.88 (2H, s), 2.23 (3H, s), 2.05 (3H, s), 2.02 (3H, s). |
| T128 | 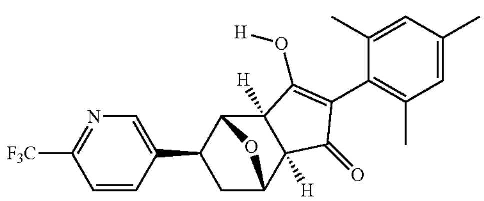 [SMILES: Cc1cc(C)c(C2=C(O)[C@@H]3[C@@H]4O[C@@H](C[C@H]4c4ccc(C(F)(F)F)nc4)[C@@H]3C2=O)c(C)c1] | d₄-MeOH $\delta_H$ 8.68 (1H, d), 8.03 (1H, dd), 7.78 (1H, d), 6.89 (2H, s), 4.83 (1H, d), 4.52 (1H, s), 3.36-3.34 (1H, m), 3.10 (1H, d), 3.03 (1H, d), 2.83 (1H, dd), 2.27 (3H, s), 2.09 (3H, s), 2.08 (3H, s), 1.93-1.88 (1H, m). |
| T129 | 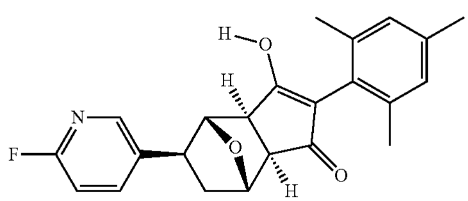 [SMILES: Cc1cc(C)c(C2=C(O)[C@@H]3[C@@H]4O[C@@H](C[C@H]4c4ccc(F)nc4)[C@@H]3C2=O)c(C)c1] | d₄-MeOH $\delta_H$ 8.10 (1H, d), 7.95-7.90 (1H, m), 7.00 (1H, dd), 6.85 (2H, s), 4.77 (1H, d), 4.41 (1H, s), 3.21 (1H, dd), 3.03 (1H, d), 2.96 (1H, d), 2.30 (1H, dd), 2.23 (3H, s), 2.05 (6H, s), 1.85-1.80 (1H, m). |
| T130 | 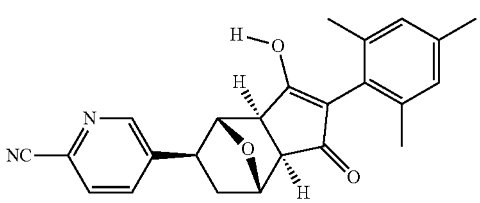 [SMILES: Cc1cc(C)c(C2=C(O)[C@@H]3[C@@H]4O[C@@H](C[C@H]4c4ccc(C#N)nc4)[C@@H]3C2=O)c(C)c1] | d₄-MeOH $\delta_H$ 8.65 (1H, d), 7.97 (1H, dd), 7.81 (1H, d), 6.85 (2H, s), 4.80 (1H, d), 4.48 (1H, s), 3.34-3.31 (1H, m), 3.06 (1H, d), 2.99 (1H, d), 2.35 (1H, dd), 2.24 (3H, s), 2.05 (3H, s), 2.04 (3H, s), 1.91-1.86 (1H, m). |

TABLE T1-continued

| Compound Number | Structure | $^1$H nmr (CDCl$_3$ unless stated) or other physical data |
|---|---|---|
| T131 | 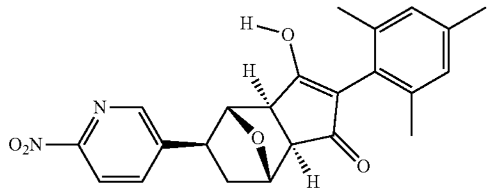 [SMILES: Cc1cc(C)c(C2=C(O)[C@@H]3[C@@H]4O[C@@H](C[C@H]4c4ccc([N+](=O)[O-])nc4)[C@@H]3C2=O)c(C)c1] | d$_4$-MeOH δ$_H$ 8.63 (1H, d), 8.34 (1H, d), 8.22 (1H, dd), 6.92 (2H, s), 4.88 (1H, d), 4.56 (1H, s), 3.48 (1H, dd), 3.14 (1H, d), 3.06 (1H, d), 2.43 (1H, dd), 2.31 (3H, s), 2.12 (3H, s), 2.11 (3H, s), 2.00-1.94 (1H, m). |
| T132 | 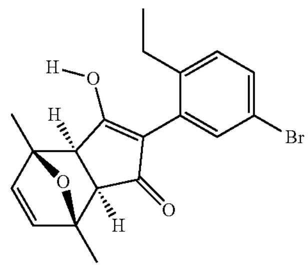 [SMILES: CCc1ccc(Br)cc1C1=C(O)[C@H]2[C@@H](C1=O)[C@]1(C)C=C[C@@]2(C)O1] | d$_4$-MeOH δ$_H$ 7.39 (1H, dd), 7.18 (1H, d), 7.16 (1H, d), 6.35 (2H, s), 2.79 (2H, s), 2.46 (2H, q), 1.61 (6H, s), 1.07 (3H, t) |
| T133 | 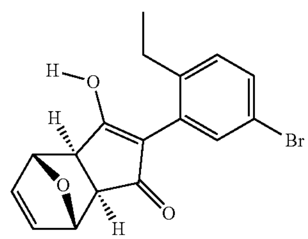 [SMILES: CCc1ccc(Br)cc1C1=C(O)[C@H]2[C@@H](C1=O)[C@@H]1C=C[C@H]2O1] | d$_4$-MeOH δ$_H$ 7.37 (1H, dd), 7.17 (1H, d), 7.14 (1H, d), 6.54 (2H, s), 4.96 (2H, s), 2.79 (2H, s), 2.44 (2H, q), 1.06 (3H, t) |
| T134 | 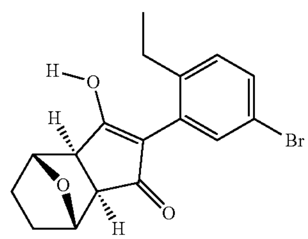 [SMILES: CCc1ccc(Br)cc1C1=C(O)[C@H]2[C@@H](C1=O)[C@@H]1CC[C@H]2O1] | d$_4$-MeOH δ$_H$ 7.34 (1H, dd), 7.15 (2H, d), 4.59 (2H, s), 2.78 (2H, s), 2.43 (2H, q), 1.81-1.78 (2H, m), 1.66-1.61 (2H, m), 1.06 (3H, t) |
| T135 | 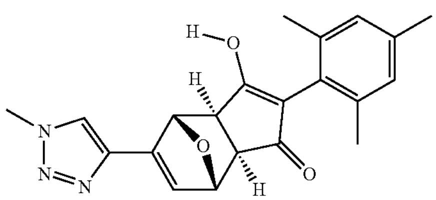 | d$_4$-MeOH δ$_H$ 8.13 (1H, s), 6.80 (2H, s), 6.76 (1H, d), 5.28 (1H, s), 5.06 (1H, d), 4.11 (3H, s), 2.71 (1H, d), 2.60 (1H, d), 2.21 (3H, s), 2.08 (6H, s). |
| T136 | 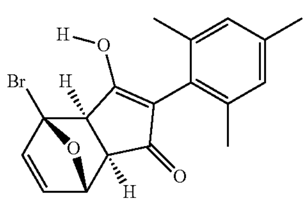 [SMILES: Cc1cc(C)c(C2=C(O)[C@H]3[C@@H](C2=O)[C@@H]2C=C[C@@]3(Br)O2)c(C)c1] | δ$_H$ 6.82 (2H, s), 6.48-6.44 (2H, m), 4.98 (1H, s), 2.93-2.87 (2H, m), 2.19 (3H, s), 2.05 (3H, s), 2.02 (3H, s). |
| T137 | 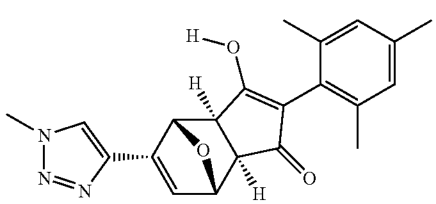 | d$_4$-MeOH δ$_H$ 7.93 (1H, s), 6.82 (1H, s), 6.80 (1H, s), 4.72 (1H, d), 4.71 (1H, d), 4.12 (3H, s), 3.59-3.54 (1H, m), 2.76 (1H, d), 2.66 (1H, d), 2.41-2.32 (1H, m), 2.23 (3H, s), 2.10 (3H, s), 2.06 (3H, s), 2.00-1.95 (1H, m). |

TABLE T1-continued

| Compound Number | Structure | ¹H nmr (CDCl₃ unless stated) or other physical data |
|---|---|---|
| T138 | Isomer A / Isomer B | Approximately 9:1 mixture of Isomer A:Isomer B. Isomer A: d₄-MeOH δ$_H$ 6.83 (2H, s), 4.77 (1H, d,), 4.69 (1H, d), 3.22 (1H, d), 3.16-3.13 (1H, m), 2.85 (1H, d), 2.35-2.29 (1H, m), 2.23 (3H, s), 2.07 (3H, s), 2.03 (3, s), 1.87 (1H, dd). |
| T139 | 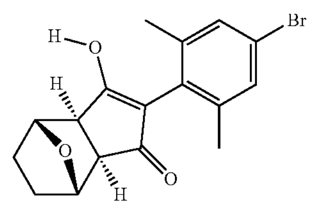 [SMILES: Cc1cc(Br)cc(C)c1C1=C(O)[C@H]2[C@@H](C1=O)[C@@H]1CC[C@H]2O1] | d₆-DMSO δ$_H$ 7.17 (1H, s), 7.18 (1H, s), 6.50 (2H, s), 4.86 (2H, s) 2.7 (2H, br. s), 2.00 (3H, s), 1.95 (3H, s) |
| T140 | 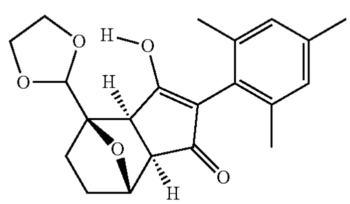 [SMILES: Cc1cc(C)c(C2=C(O)[C@H]3[C@@H](C2=O)[C@@H]2CC[C@@]3(C3OCCO3)O2)c(C)c1] | d₄-MeOH δ$_H$ 6.83 (2H, s), 5.35 (1H, s), 4.64 (1H, d), 4.05-3.93 (4H, m), 2.84-2.80 (2H, m), 2.24 (3H, s), 2.10 (3H, s), 2.08 (3H, s), 1.93-1.85 (2H, m), 1.73-1.68 (1H, m), 1.58-1.54 (1H, m). |
| T141 | 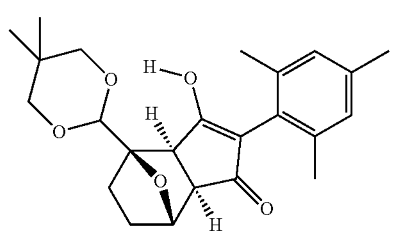 | d₄-MeOH δ$_H$ 6.82 (1H, s), 6.80 (1H, s), 5.04 (1H, s), 4.62 (1H, d), 3.66-3.49 (4H, m), 2.72-2.67 (2H, m), 2.23 (3H, s), 2.12 (3H, s), 2.10 (3H, s), 2.11-2.08 (1H, m), 1.94-1.83 (1H, m), 1.70-1.62 (2H, m), 1.21 (3H, s), 0.74 (3H, s). |
| T142 | 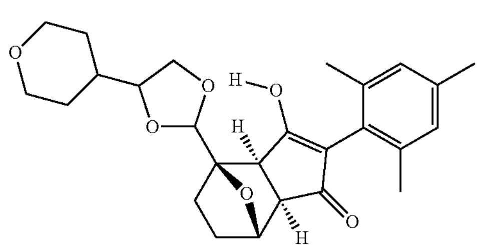 [SMILES: Cc1cc(C)c(C2=C(O)[C@H]3[C@@H](C2=O)[C@@H]2CC[C@@]3(C3OCC(C4CCOCC4)O3)O2)c(C)c1] | LC-MS (Method B) ES⁺: MH⁺ = 439; rt = 1.35 mins |

TABLE T1-continued

| Compound Number | Structure | ¹H nmr (CDCl₃ unless stated) or other physical data |
|---|---|---|
| T143 | 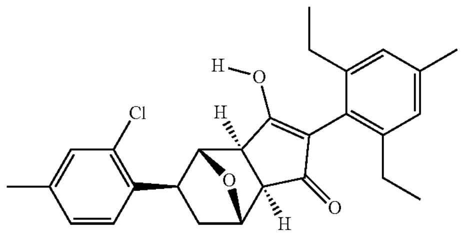 | δ$_H$ 7.32 (1H, d), 7.15 (1H, s), 7.02 (1H, d), 6.91-6.90 (2H, m), 4.75-4.73 (1H, br. m), 4.62 (1H, s), 3.46-3.44 (1H, m), 2.95-2.84 (2H, m), 2.37-2.28 (10H, m), 2.16-2.11 (1H, m), 1.76-1.73 (1H, m), 1.06-1.02 (6H, m). |
| T144 | 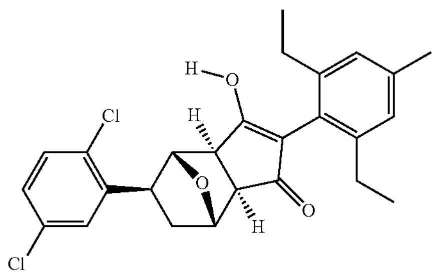 [SMILES: CCc1cc(C)cc(CC)c1C1=C(O)[C@@H]2[C@@H]3O[C@@H](C[C@H]3c3cc(Cl)ccc3Cl)[C@@H]2C1=O] | δ$_H$ 7.48 (1H, s), 7.28 (1H, s), 7.13 (1H, d), 6.96-6.94 (2H, m), 4.86 (1H, s), 4.68 (1H, s), 3.52 (1H, s with fine splitting), 3.11-2.90 (2H, m), 2.40-2.23 (8H, m), 1.83-1.80 (1H, m), 1.10-1.06 (6H, m). |
| T145 | 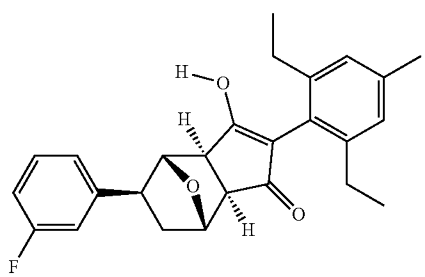 [SMILES: CCc1cc(C)cc(CC)c1C1=C(O)[C@@H]2[C@@H]3O[C@@H](C[C@H]3c3cccc(F)c3)[C@@H]2C1=O] | δ$_H$ 7.26-7.21 (2H, m), 7.05-7.02 (2H, m), 6.94-6.88 (3H, m), 4.81 (1H, s), 4.59 (1H, s), 2.99-2.85 (3H, m), 2.40-2.30 (7H, m), 2.19-2.14 (1H, m), 1.91-1.89 (1H, m), 1.06 (6H, t). |
| T146 | 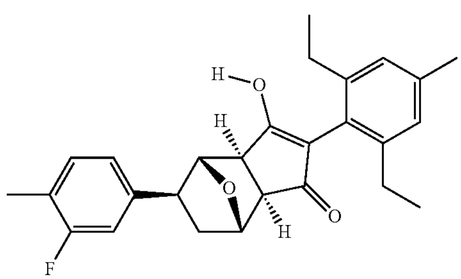 | δ$_H$ 7.08-7.05 (1H, m), 6.97-6.92 (4H, m), 4.80 (1H, br. s), 4.56 (1H, s), 3.10-2.82 (3H, m), 2.38-2.33 (4H, m), 2.30 (3H, s), 2.23 (3H, s), 2.18-2.11 (1H, m), 1.90-1.86 (1H, m), 1.08-1.05 (6H, m). |
| T147 | 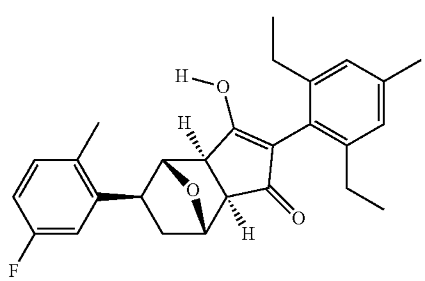 [SMILES: CCc1cc(C)cc(CC)c1C1=C(O)[C@@H]2[C@@H]3O[C@@H](C[C@H]3c3cc(F)ccc3C)[C@@H]2C1=O] | δ$_H$ 7.16-7.13 (1H, m), 7.08-7.05 (1H, m), 6.96 (1H, s), 6.94 (1H, s), 6.81-6.78 (1H, m), 4.86 (1H, br. s), 4.67 (1H, s), 3.18 (1H, br. s), 3.10 (1H, br. s), 2.85 (1H, br. s), 2.40-2.36 4H, m), 2.31 (3H, s), 2.28 (3H, s), 2.23-2.18 (1H, m), 1.81 (1H, br. s), 1.10-1.06 (6H, m). |

TABLE T1-continued

| Compound Number | Structure | $^1$H nmr (CDCl$_3$ unless stated) or other physical data |
|---|---|---|
| T148 | 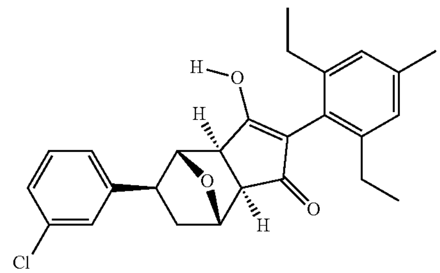 [SMILES: CCc1cc(C)cc(CC)c1C1=C(O)[C@@H]2[C@@H]3O[C@@H](C[C@H]3c3cccc(Cl)c3)[C@@H]2C1=O] | δ$_H$ 7.34-7.31 (1H, m), 7.25-7.15 (3H, m), 6.96 (1H, s), 6.94 (1H, s), 4.87-4.85 (1H, m), 4.65 (1H, s), 3.11-3.08 (1H, m), 3.02-2.98 (1H, m), 2.86-2.80 (1H, m), 2.43-2.33 (4H, m), 2.31 (3H, s), 2.23-2.18 (1H, m), 2.00-1.92 (1H, m), 1.09-1.06 (6H, m). |
| T149 | 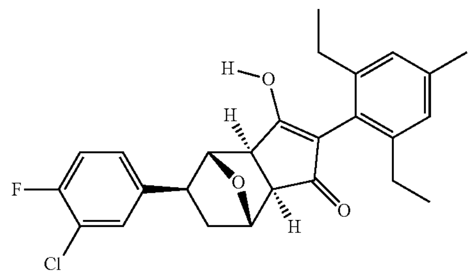 [SMILES: CCc1cc(C)cc(CC)c1C1=C(O)[C@@H]2[C@@H]3O[C@@H](C[C@H]3c3ccc(F)c(Cl)c3)[C@@H]2C1=O] | δ$_H$ 7.36 (1H, d), 7.16-7.13 (1H, m), 7.04 (1H, t), 6.95 (1H, s), 6.94 (1H, s), 4.83 (1H, br. s), 4.56 (1H, s), 2.96-2.83 (3H, m), 2.39-2.35 (4H, m), 2.31 (3H, s), 2.21-2.16 (1H, m), 1.88-1.85 (1H, m), 1.08-1.05 (6H, m). |
| T150 | 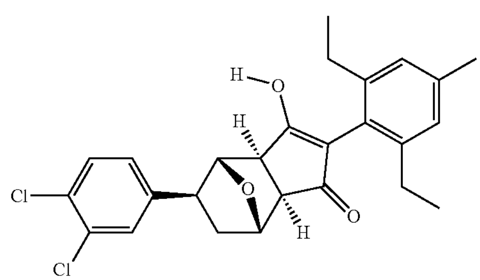 [SMILES: CCc1cc(C)cc(CC)c1C1=C(O)[C@@H]2[C@@H]3O[C@@H](C[C@H]3c3ccc(Cl)c(Cl)c3)[C@@H]2C1=O] | δ$_H$ 7.41-7.39 (1H, m), 7.35-7.33 (1H, m), 7.12-7.10 (1H, m), 6.94 (1H, s), 6.93 (1H, s), 4.82-4.80 (1H, m), 4.56 (1H, s), 2.98-2.80 (3H, m), 2.37-2.33 (4H, m), 2.30 (3H, s), 2.19-2.15 (1H, m), 1.87-1.83 (1H, m), 1.08-1.04 (6H, m). |
| T151 | 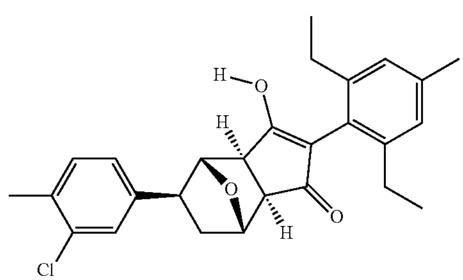 | δ$_H$ 7.28 (1H, br. s), 7.13-7.11 (1H, m), 7.07-7.05 (1H, m), 6.94 (1H, s), 6.92 (1H, s), 4.79-4.78 (1H, m), 4.55 (1H, s), 2.95-2.80 (3H, m), 2.39-2.34 (4H, m), 2.33 (3H, s), 2.30 (3H, s), 2.15-2.10 (1H, m), 1.89-1.84 (1H, m), 1.07-1.04 (6H, m). |
| T152 | 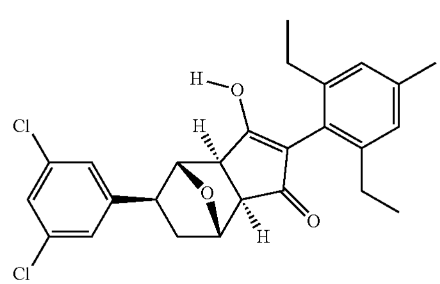 [SMILES: CCc1cc(C)cc(CC)c1C1=C(O)[C@@H]2[C@@H]3O[C@@H](C[C@H]3c3cc(Cl)cc(Cl)c3)[C@@H]2C1=O] | δ$_H$ 7.22-7.18 (3H, m), 6.93 (1H, s), 6.92 (1H, s), 4.79 (1H, s), 4.56 (1H, s), 2.93-2.88 (2H, m), 2.37-2.32 (6H, m), 2.29 (3H, s), 2.13 (1H, br. m), 1.85 (1H, br. m), 1.07-1.04 (6H, m). |

| Compound Number | Structure | ¹H nmr (CDCl₃ unless stated) or other physical data |
|---|---|---|
| T153 | 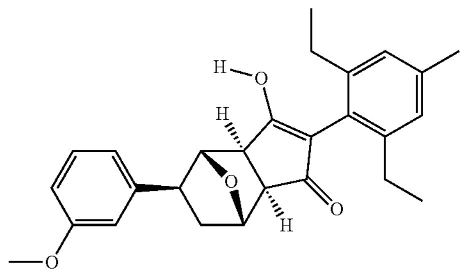 | δ_H 7.21-7.18 (1H, m), 6.94 (1H, s), 6.93 (1H, s), 6.90-6.84 (2H, m), 6.76-6.74 (1H, m), 4.81 (1H, br. s), 4.60 (1H, s), 3.80 (3H, s), 2.97-2.83 (2H, m), 2.83-2.35 (5H, m), 2.30 (3H, s), 2.16-2.14 (1H, m), 2.00-1.96 (1H, m), 1.09-1.04 (6H, m). |
| T154 | 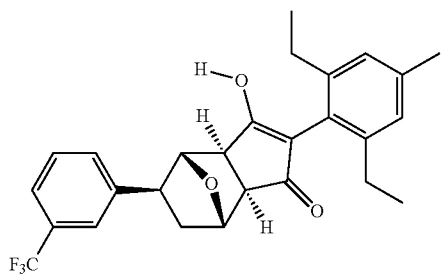 | δ_H 7.53-7.39 (4H, m), 6.94-6.93 (2H, m), 4.82 (1H, br. s), 4.59 (1H, d), 3.04-3.02 (1H, m), 2.93-2.89 (2H, br. m), 2.38-2.33 (4H, m), 2.30 (3H, s), 2.18 (3H, s), 2.16 (3H, s), 1.92-1.90 (1H, m), 1.08-1.04 (6H, m). |
| T155 | 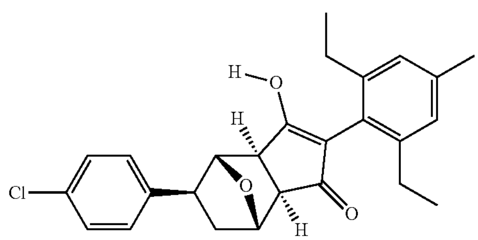 [SMILES: CCc1cc(C)cc(CC)c1C1=C(O)[C@@H]2[C@@H]3O[C@@H](C[C@H]3c3ccc(Cl)cc3)[C@@H]2C1=O] | δ_H 7.26-7.25 (4H, m), 6.95-6.94 (2H, m), 4.84 (1H, s), 4.60-4.57 (1H, m), 3.09-3.06 (1H, m), 2.99-2.97 (1H, m), 2.85-2.80 (1H, m), 2.40-2.36 (4H, m), 2.31 (3H, s), 2.22-2.17 (1H, m), 1.93-1.89 (1H, m), 1.09-1.05 (6H, m). |
| T156 | 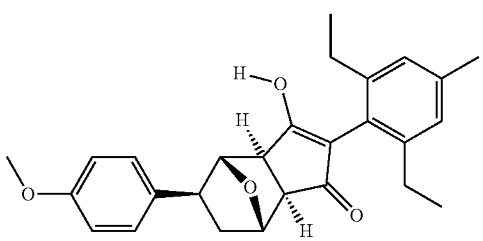 | δ_H 7.22-7.20 (2H, m), 6.95-6.93 (2H, m), 6.84-6.82 (2H, m), 4.83-4.82 (1H, br. m), 4.56 (1H, s), 3.78 (3H, s), 2.98-2.95 (1H, m), 2.90-2.75 (2H, br. s), 2.39-2.35 (4H, m), 2.30 (3H, s), 2.19-2.13 (1H, m), 1.95-1.89 (1H, m), 1.09-1.05 (6H, m). |
| T157 | 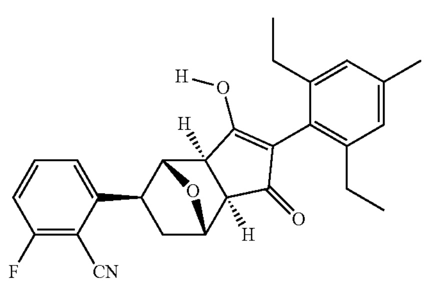 [SMILES: CCc1cc(C)cc(CC)c1C1=C(O)[C@@H]2[C@@H]3O[C@@H](C[C@H]3c3cccc(F)c3C#N)[C@@H]2C1=O] | δ_H 7.57-7.53 (1H, m), 7.44-7.42 (1H, m), 7.09-7.05 (1H, m), 6.93 (2H, s), 4.84 (1H, br. s), 4.70 (1H, br. s), 3.45-3.33 (1H, m), 3.10-2.90 (2H, m), 2.37-2.32 (4H, m), 2.29 (3H, s), 1.85-1.83 (2H, m), 1.09-1.04 (6H, m). |
| T158 | 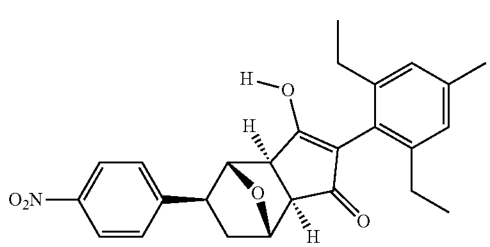 [SMILES: CCc1cc(C)cc(CC)c1C1=C(O)[C@@H]2[C@@H]3O[C@@H](C[C@H]3c3ccc([N+](=O)[O-])cc3)[C@@H]2C1=O] | δ_H 8.15 (2H, d), 7.46 (2H, dd), 6.95 (1H, s), 6.94 (1H, s), 4.88 (1H, s with fine splitting), 4.62 (1H, s), 4.62 (1H, s), 3.12-3.10 (1H, m), 2.99-2.90 (2H, br. m), 2.40-2.35 (4H, m), 2.31 (3H, s), 2.25-2.22 (1H, m), 1.93-1.89 (1H, m), 1.08-1.05 (6H, m). |

TABLE T1-continued

| Compound Number | Structure | ¹H nmr (CDCl₃ unless stated) or other physical data |
|---|---|---|
| T159 | 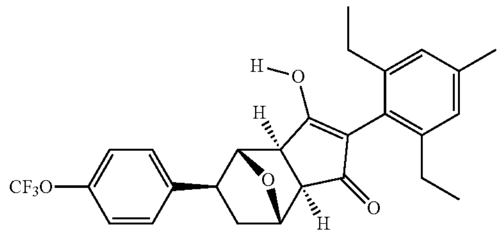 | $\delta_H$ 7.31-7.28 (2H, m), 7.13-7.12 (2H, m), 6.94-6.93 (2H, m), 4.84-4.81 (1H, m), 4.57 (1H, d), 3.00-2.99 (4H, m), 2.98-2.85 (2H, br. m), 2.38-2.33 (4H, m), 2.30 (3H, s), 2.17-2.14 (1H, m), 1.90-1.87 (1H, m), 1.08-1.04 (6H, m). |
| T160 | 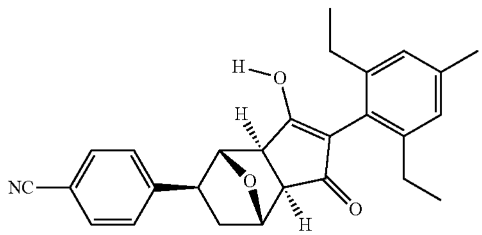 [SMILES: CCc1cc(C)cc(CC)c1C1=C(O)[C@@H]2[C@@H]3O[C@@H](C[C@H]3c3ccc(C#N)cc3)[C@@H]2C1=O] | $\delta_H$ 7.58 (2H, dd), 7.41-7.40 (2H, m), 6.95 (1H, s), 4.87-4.85 (1H, m), 4.60 (1H, d), 3.06-3.03 (1H, m), 3.04-2.95 (2H, br. m), 2.40-2.33 (4H, m), 2.30 (3H, s), 2.25-2.20 (1H, m), 1.93-1.88 (1H, m), 1.09-1.05 (6H, m). |
| T161 | 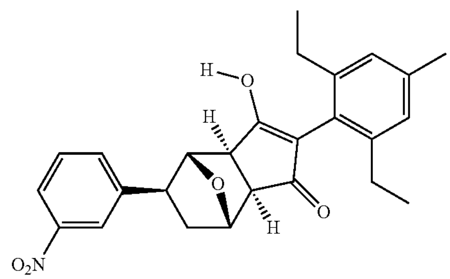 [SMILES: CCc1cc(C)cc(CC)c1C1=C(O)[C@@H]2[C@@H]3O[C@@H](C[C@H]3c3cccc([N+](=O)[O-])c3)[C@@H]2C1=O] | $\delta_H$ 8.18 (1H, s), 8.10-8.08 (1H, m), 7.69-7.67 (1H, m), 7.48 (1H, t), 6.97 (1H, s), 6.95 (1H, s), 4.91 (1H, d), 4.64 (1H, s), 3.18-3.13 (1H, m), 3.10-2.95 (2H, br. m), 2.40-2.36 (4H, m), 2.31 (3H, s), 1.08 (6H, t). |
| T162 | 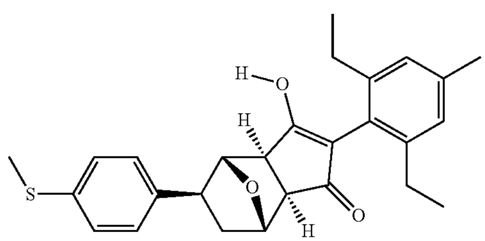 | $\delta_H$ 7.25-7.15 (4H, m), 6.96 (1H, s), 6.94 (1H, s), 4.85 (1H, s), 4.58 (1H, br. s), 3.10-3.05 (1H, br. m), 3.00-2.97 (1H, m), 2.87-2.85 (1H, m), 2.47 (3H, s), 2.42-2.34 (4H, m), 2.31 (3H, s), 2.21-2.17 (1H, m), 1.96-1.91 (1H, m), 1.00-1.05 (6H, m). |
| T163 | 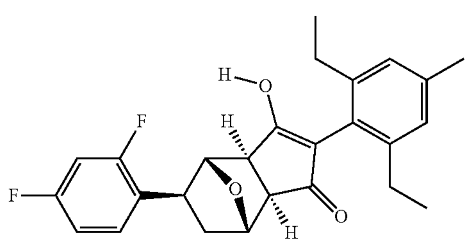 [SMILES: CCc1cc(C)cc(CC)c1C1=C(O)[C@@H]2[C@@H]3O[C@@H](C[C@H]3c3ccc(F)cc3F)[C@@H]2C1=O] | $\delta_H$ 7.42-7.38 (1H, m), 6.94-6.92 (2H, m), 6.85-6.83 (1H, m), 6.77-6.73 (1H, m), 4.82-4.80 (1H, m), 4.59 (1H, d), 3.38-3.34 (1H, m), 3.05-2.91 (2H, br. m), 2.37-2.34 (4H, m), 2.30 (3H, s), 2.19-2.15 (1H, m), 1.85-1.80 (1H, m), 1.08-1.04 (6H, m). |
| T164 | 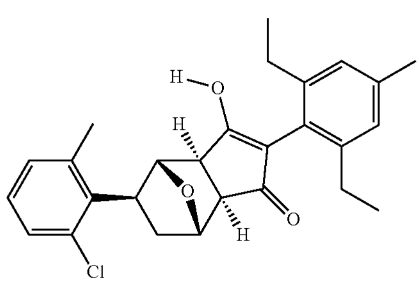 [SMILES: CCc1cc(C)cc(CC)c1C1=C(O)[C@@H]2[C@@H]3O[C@@H](C[C@H]3c3c(C)cccc3Cl)[C@@H]2C1=O] | $\delta_H$ 7.22-7.20 (1H, m), 7.05-7.00 (2H, m), 6.94 (1H, s), 6.92 (1H, s), 4.83 (1H, s), 4.79 (1H, br. s), 3.85-3.82 (1H, m), 3.06-2.89 (2H, br. m), 2.51 (3H, s), 2.39-2.33 (4H, m), 2.30 (3H, s), 2.18-2.14 (1H, m), 1.99-1.95 (1H, m), 1.05 (6H, t). |

TABLE T1-continued

| Compound Number | Structure | $^1$H nmr (CDCl$_3$ unless stated) or other physical data |
|---|---|---|
| T165 | 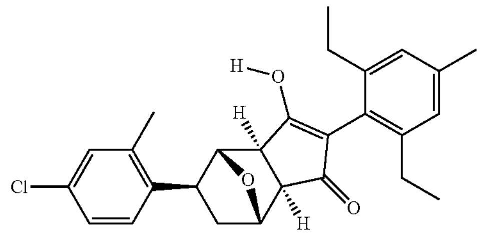 [SMILES: CCc1cc(C)cc(CC)c1C1=C(O)[C@@H]2[C@@H]3O[C@@H](C[C@H]3c3ccc(Cl)cc3C)[C@@H]2C1=O] | $\delta_H$ 7.35 (1H, t), 7.16-7.12 (1H, m), 6.96 (1H, s), 6.61-6.53 (1H, m), 4.86 (1H, br. s), 4.66 (1H, s), 3.17-3.09 (2H, m), 2.87-2.85 (1H, m), 2.42-2.35 (4H, m), 2.32 (6H, s), 2.26-2.18 (1H, m), 1.83-1.76 (1H, m), 1.08 (6H, t). |
| T166 | 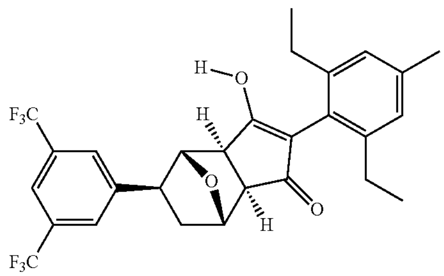 [SMILES: CCc1cc(C)cc(CC)c1C1=C(O)[C@@H]2[C@@H]3O[C@@H](C[C@H]3c3cc(C(F)(F)F)cc(C(F)(F)F)c3)[C@@H]2C1=O] | $\delta_H$ 7.76-7.74 (3H, m), 6.96 (1H, s), 6.94 (1H, s), 4.89 (1H, br. s), 4.62 (1H, s), 3.15-3.13 (1H, m), 3.12-3.07 (1H, br. m), 2.87 (1H, br. s), 2.43-2.36 (4H, m), 2.30 (3H, s), 2.28-2.25 (1H, m), 1.92-1.90 (1H, m), 1.09-1.06 (6H, m). |
| T167 | 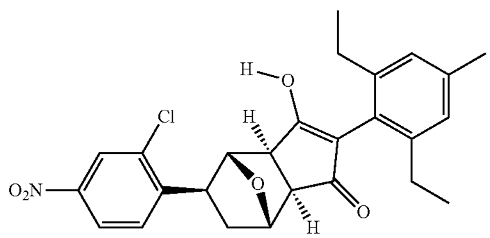 [SMILES: CCc1cc(C)cc(CC)c1C1=C(O)[C@@H]2[C@@H]3O[C@@H](C[C@H]3c3ccc([N+](=O)[O-])cc3Cl)[C@@H]2C1=O] | $\delta_H$ 8.26-8.24 (1H, m), 8.10 (1H, dd), 7.71 (1H, d), 6.96 (1H, s), 9.95 (1H, s), 4.89 (1H, br. s), 4.73 (1H, br. s), 3.62 (1H, br. s), 3.13 (1H, br. s), 2.94 (1H, br. s), 2.39-2.33 (4H, m), 2.31 (3H, s), 1.82-1.80 (1H, m), 1.67-1.65 (1H, m), 1.08 (6H, t). |
| T168 | 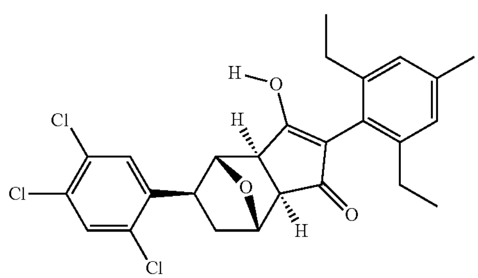 [SMILES: CCc1cc(C)cc(CC)c1C1=C(O)[C@@H]2[C@@H]3O[C@@H](C[C@H]3c3cc(Cl)c(Cl)cc3Cl)[C@@H]2C1=O] | $\delta_H$ 7.58 (1H, s), 7.46 (1H, d), 6.97 (1H, s), 6.95 (1H, s), 4.88 (1H, br. s), 4.64 (1H, s), 3.49-3.47 (1H, m), 3.17-2.86 (2H, br. m), 2.40-2.35 (4H, m), 2.32 (3H, s), 1.81-1.79 (1H, m), .158-1.56 (1H, m), 1.10-1.06 (6H, m). |
| T169 | 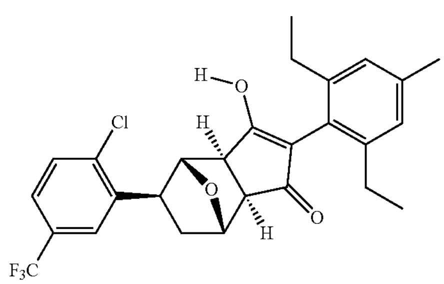 | $\delta_H$ 7.73 (1H, s), 7.48-7.41 (2H, m), 6.96 (1H, s), 6.93 (1H, s), 4.84 (1H, br. s), 4.69 (1H, s), 3.58 (1H, br. s), 3.08-2.93 (2H, br. m), 2.38-2.32 (4H, m), 2.31 (3H, s), 2.27-2.35 (1H, m), 1.84-1.80 (1H, m), 1.10-1.05 (6H, m). |
| T170 | 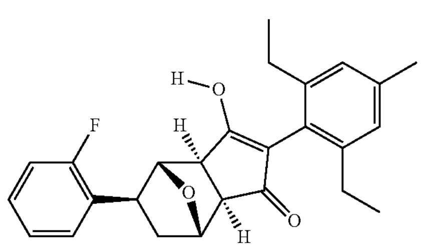 [SMILES: CCc1cc(C)cc(CC)c1C1=C(O)[C@@H]2[C@@H]3O[C@@H](C[C@H]3c3ccccc3F)[C@@H]2C1=O] | $\delta_H$ 7.43-7.38 (1H, m), 7.19-7.14 (1H, m), 7.11-7.07 (1H, m), 7.01-6.96 (1H, m), 6.90-6.89 (2H, m), 4.75 (1H, d), 4.60 (1H, s), 3.35 (1H, dd), 2.90-2.83 (2H, m), 2.37-2.29 (4H, m), 2.28 (3H, s), 2.12-2.07 (1H, m), 1.84-1.78 (1H, m), 1.06-1.01 (6H, m). |

TABLE T1-continued

| Compound Number | Structure | ¹H nmr (CDCl₃ unless stated) or other physical data |
|---|---|---|
| T171 | 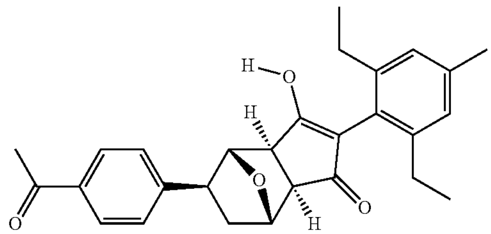 [SMILES: CCc1cc(C)cc(CC)c1C1=C(O)[C@@H]2[C@@H]3O[C@@H](C[C@H]3c3ccc(C(C)=O)cc3)[C@@H]2C1=O] | $δ_H$ 7.86 (2H, d), 7.34 (2H, d), 6.91-6.90 (2H, m), 4.76 (1H, d), 4.57 (1H, s), 2.97 (1H, dd), 2.87-2.83 (2H, m), 2.58 (3H, s), 2.42-2.32 (4H, m), 2.28 (3H, s), 2.10-2.02 (1H, m), 1.87-1.82 (1H, m), 1.09-1.05 (6H, m). |
| T172 | 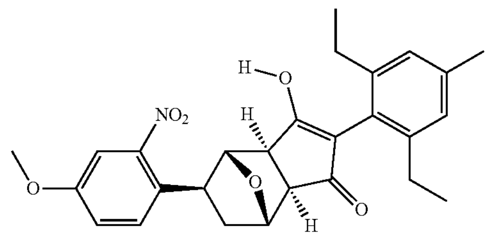 | $δ_H$ 7.61 (1H, d), 7.30 (1H, d), 7.12 (1H, dd), 6.94-6.93 (2H, m), 4.81 (1H, d), 4.67 (1H, s), 3.85 (3H, s), 3.40 (1H, dd), 3.04-2.88 (2H, br. s), 2.40-2.31 (4H, m), 2.30 (3H, s), 2.29-2.26 (1H, m), 1.89-1.86 (1H, m), 1.06 (6H, t). |
| T173 | 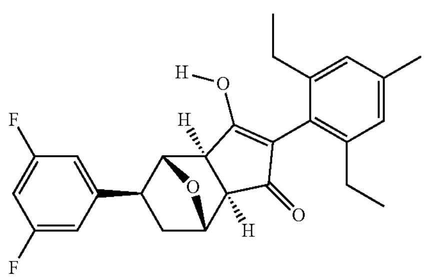 [SMILES: CCc1cc(C)cc(CC)c1C1=C(O)[C@@H]2[C@@H]3O[C@@H](C[C@H]3c3cc(F)cc(F)c3)[C@@H]2C1=O] | $δ_H$ 6.89 (1H, s), 6.88 (1H, s), 6.78-6.73 (2H, m), 6.67-6.61 (1H, m), 4.66 (1H, d), 4.48 (1H, s), 2.81 (1H, dd), 2.74 (2H, br. s), 2.33-2.27 (4H, m), 2.26 (3H, s), 2.05-1.98 (1H, m), 1.77-1.71 (1H, m), 1.02 (6H, t). |
| T174 | 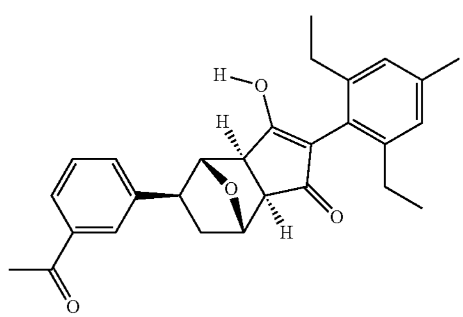 [SMILES: CCc1cc(C)cc(CC)c1C1=C(O)[C@@H]2[C@@H]3O[C@@H](C[C@H]3c3cccc(C(C)=O)c3)[C@@H]2C1=O] | $δ_H$ 7.78-7.73 (2H, m), 7.44-7.42 (1H, m), 7.35 (1H, t), 6.84 (2H, s), 4.69 (1H, d), 4.50 (1H, s), 2.93 (1H, dd), 2.79-2.76 (2H, m), 2.54 (3H, s), 2.35-2.26 (4H, m), 2.22 (3H, s), 2.05-2.00 (1H, m), 1.82-1.76 (1H, m), 1.04-0.99 (6H, m). |
| T175 | 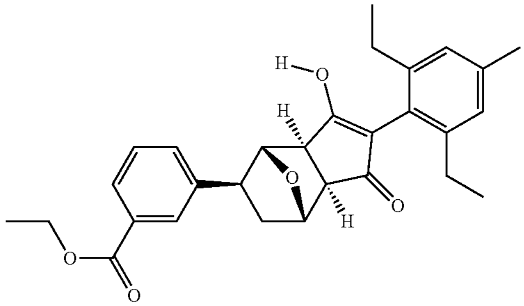 [SMILES: CCOC(=O)c1cccc([C@@H]2C[C@@H]3O[C@H]2[C@H]2C(O)=C(c4c(CC)cc(C)cc4CC)C(=O)[C@H]23)c1] | $δ_H$ 7.95 (2H, d), 7.28 (2H, d), 6.91-6.90 (2H, m), 4.69 (1H, d), 4.53 (1H, s), 4.38 (2H, q), 2.91 (1H, dd), 2.79-2.76 (2H, m), 2.40-2.31 (4H, m), 2.30 (3H, s), 2.03-1.97 (1H, m), 1.83-1.77 (1H, m), 1.43 (2H, t), 1.06 (6H, t). |

TABLE T1-continued

| Compound Number | Structure | $^1$H nmr (CDCl$_3$ unless stated) or other physical data |
|---|---|---|
| T176 | 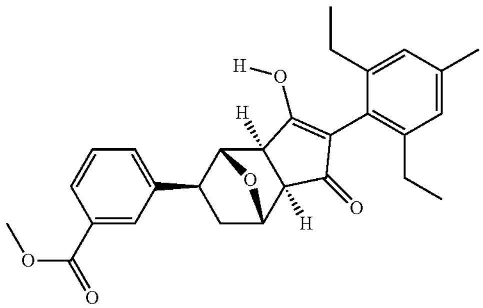 | δ$_H$ 7.94 (2H, d), 7.33 (2H, d), 6.92-6.91 (2H, m), 4.81 (1H, d), 4.60 (1H, s), 3.89 (3H, s), 3.02 (1H, dd), 2.97-2.80 (2H, br. m), 2.38-2.30 (4H, m), 2.29 (3H, s), 2.16 (1H, dd), 1.93-1.87 (1H, m), 1.07-1.03 (6H, m). |
| T177 | 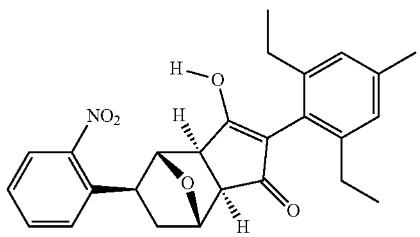 [SMILES: CCc1cc(C)cc(CC)c1C1=C(O)[C@@H]2[C@@H]3O[C@@H](C[C@H]3c3ccccc3[N+](=O)[O-])[C@@H]2C1=O] | δ$_H$ 7.78 (1H, dd), 7.71 (1H, dd), 7.59-7.54 (1H, m), 7.37-7.33 (1H, m), 6.91-6.90 (2H, m), 4.79 (1H, d), 4.69 (1H, s), 3.42 (1H, dd), 2.93 (1H, br. s), 2.88-2.86 (1H, m), 2.93-2.30 (4H, m), 2.28 (3H, s), 2.28-2.26 (1H, m), 1.91-1.85 (1H, m), 1.05 (6H, t). |
| T178 | 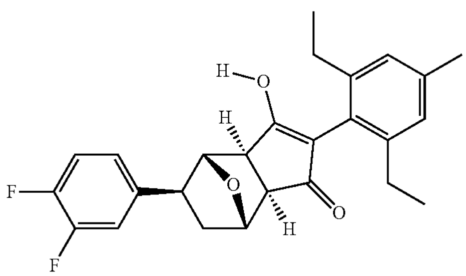 [SMILES: CCc1cc(C)cc(CC)c1C1=C(O)[C@@H]2[C@@H]3O[C@@H](C[C@H]3c3ccc(F)c(F)c3)[C@@H]2C1=O] | δ$_H$ 7.05-6.97 (2H, m), 6.87-6.83 (3H, m), 4.62 (1H, d), 4.41 (1H, s), 2.76 (1H, dd), 2.70 (2H, br. s), 2.34-2.24 (5H, m), 2.26 (3H, s), 1.97-1.92 (1H, m), 1.71-1.66 (1H, m), 1.00 (6H, t). |
| T179 | 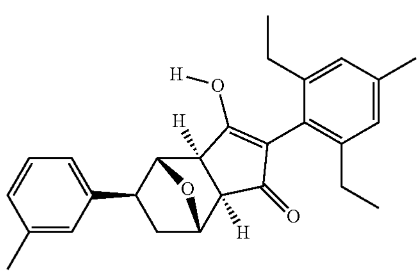 [SMILES: CCc1cc(C)cc(CC)c1C1=C(O)[C@@H]2[C@@H]3O[C@@H](C[C@H]3c3cccc(C)c3)[C@@H]2C1=O] | δ$_H$ 7.15 (1H, t), 7.07 (1H, s), 7.02-7.00 (2H, m), 6.89 (1H, s), 6.88 (1H, s), 4.70 (1H, d), 4.51 (1H, s), 2.85 (1H, dd), 2.80-2.76 (2H, m), 2.37-2.31 (4H, m), 2.32 (3H, s), 2.27 (3H, s), 2.04-1.98 (1H, m), 1.87-1.82 (1H, m), 1.05-1.01 (6H, m). |
| T180 | 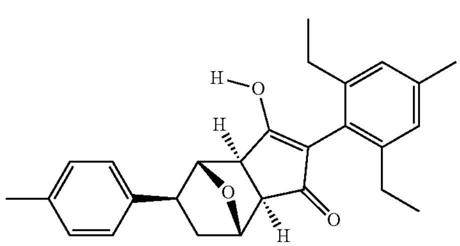 | δ$_H$ 7.11-7.05 (4H, m), 6.88-6.87 (2H, m), 4.67 (1H, d), 4.47 (1H, s), 2.84 (1H, dd), 2.77-2.73 (2H, m), 2.36-2.28 (4H, m), 2.30 (3H, s), 2.27 (3H, s), 2.01-1.96 (1H, m), 1.84-1.79 (1H, m), 1.05-1.00 (6H, m). |

TABLE T1-continued

| Compound Number | Structure | ¹H nmr (CDCl₃ unless stated) or other physical data |
|---|---|---|
| T181 | 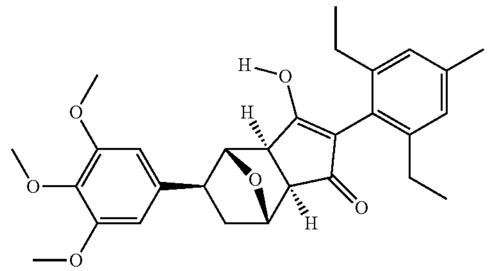 | $\delta_H$ 6.90 (1H, s), 6.89 (1H, s), 6.47 (2H, s), 4.70 (1H, d), 4.51 (1H, s), 3.84 (6H, s), 3.80 (3H, s), 2.84-2.79 (3H, m), 2.37-2.30 (4H, m), 2.28 (3H, s), 2.07-2.02 (1H, m), 1.86-1.80 (1H, m), 1.07-1.02 (6H, m). |
| T182 | 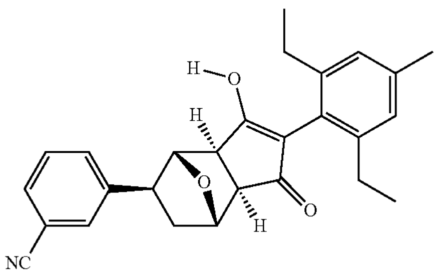 [SMILES: CCc1cc(C)cc(CC)c1C1=C(O)[C@@H]2[C@@H]3O[C@@H](C[C@H]3c3cccc(C#N)c3)[C@@H]2C1=O] | $\delta_H$ 7.53 (1H, s), 7.49-7.43 (2H, m), 7.38-7.34 (1H, m), 6.89 (1H, s), 6.88 (1H, s), 4.71 (1H, d), 4.47 (1H, s), 289 (1H, dd), 2.82-2.78 (2H, m), 2.36-2.26 (4H, m), 2.25 (3H, s), 2.05 (1H, dd), 1.78-1.72 (1H, m), 1.02 (6H, t) |
| T183 | 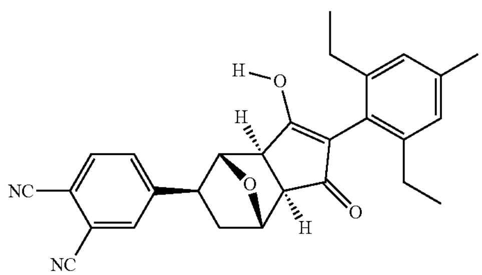 [SMILES: CCc1cc(C)cc(CC)c1C1=C(O)[C@@H]2[C@@H]3O[C@@H](C[C@H]3c3ccc(C#N)c(C#N)c3)[C@@H]2C1=O] | $\delta_H$ 7.79 (1H, d), 7.74-7.72 (1H, m), 7.69-7.66 (1H, m), 6.96 (1H, s), 6.95 (1H, s), 4.90 (1H, d), 4.60 (1H, s), 3.11 (1H, dd), 2.99 (2H, br. s), 2.40-2.32 (4H, m), 2.30 (3H, s), 2.29-2.26 (1H, m), 1.90-1.84 (1H, m), 1.09-1.05 (6H, m). |
| T184 | 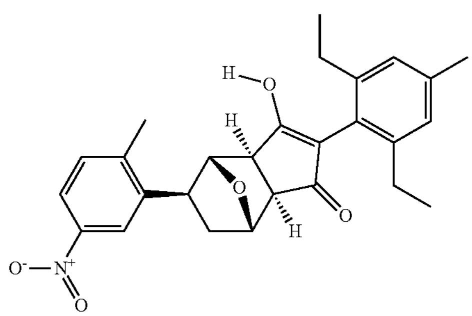 [SMILES: CCc1cc(C)cc(CC)c1C1=C(O)[C@@H]2[C@@H]3O[C@@H](C[C@H]3c3cc([N+](=O)[O-])ccc3C)[C@@H]2C1=O] | $\delta_H$ 8.29 (1H, d), 7.97 (1H, dd), 7.29 (1H, d), 6.97 (1H, s), 6.95 (1H, s), 4.92 (1H, d), 4.72 (1H, s), 3.26 (1H, dd), 3.03 (2H, br. s), 2.43 (3H, s), 2.40-2.33 (4H, m), 2.32 (3H, s), 2.26 (1H, dd), 1.87-1.85 (1H, m), 1.12-1.06 (6H, m). |
| T185 | 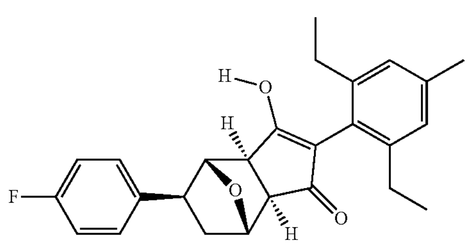 [SMILES: CCc1cc(C)cc(CC)c1C1=C(O)[C@@H]2[C@@H]3O[C@@H](C[C@H]3c3ccc(F)cc3)[C@@H]2C1=O] | $\delta_H$ 7.19-7.16 (2H, m), 6.97-6.90 (4H, m), 4.71 (1H, d), 4.48 (1H, s), 2.88 (1H, dd), 2.82-2.78 (2H, m), 2.37-2.30 (4H, m), 2.28 (3H, s), 2.05 (1H, dd), 1.83-1.77 (1H, m), 1.05-1.01 (6H, m). |
| T186 | 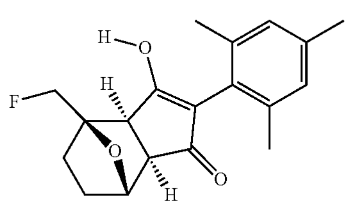 [SMILES: Cc1cc(C)c(C2=C(O)[C@H]3[C@@H](C2=O)[C@@H]2CC[C@@]3(CF)O2)c(C)c1] | d₄-MeOH $\delta_H$ 6.82 (1H, s), 6.80 (1H, s), 4.87 (1H, d), 4.77 (1H, d), 4.63 (1H, d), 2.72 (1H, d), 2.65 (1H, d), 2.23 (3H, s), 2.12 (3H, s), 2.08 (3H, s), 2.07-2.03 (1H, m), 1.95-1.86 (1H, m), 1.76-1.70 (1H, m), 1.62-1.55 (1H, m). |

TABLE T1-continued

| Compound Number | Structure | ¹H nmr (CDCl₃ unless stated) or other physical data |
|---|---|---|
| T187 | 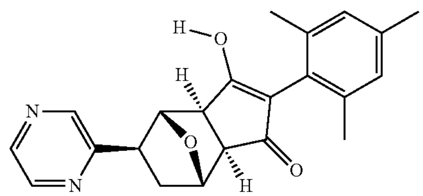 [SMILES: Cc1cc(C)c(C2=C(O)[C@@H]3[C@@H]4O[C@@H](C[C@H]4c4cnccn4)[C@@H]3C2=O)c(C)c1] | d₄-MeOH δ$_H$ 8.65 (1H, s), 8.54 (1H, br. s), 8.46 (1H, br. s), 6.87 (2H, s), 4.82 (1H, d), 4.72 (1H, s), 3.48-3.46 (1H, m), 3.13 (1H, d), 3.04 (1H, d), 2.25 (3H, s), 2.25-2.18 (2H, m), 2.09 (3H, s), 2.07 (3H, s), 1.79-1.74 (1H, m), 1.72-1.67 (1H, m). |
| T188 | 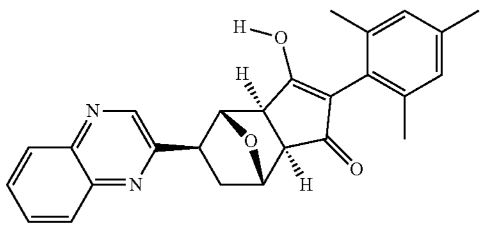 [SMILES: Cc1cc(C)c(C2=C(O)[C@@H]3[C@@H]4O[C@@H](C[C@H]4c4cnc5ccccc5n4)[C@@H]3C2=O)c(C)c1] | d₄-MeOH δ$_H$ 8.93 (1H, s, 8.09-8.06 (2H, m), 7.85-7.78 (2H, m), 6.87 (2H, s), 4.90 (1H, s), 4.87 (1H, d), 3.66 (1H, dd), 3.19 (1H, d), 3.09 (1H, d), 2.44-2.33 (2H, m), 2.25 (3H, s), 2.09 (3H, s), 2.08 (3H, s). |
| T189 | 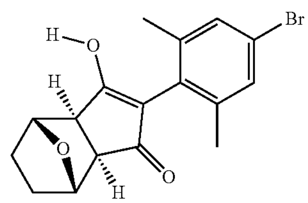 [SMILES: Cc1cc(Br)cc(C)c1C1=C(O)[C@H]2[C@@H](C1=O)[C@@H]1CC[C@H]2O1] | d₄-MeOH δ$_H$ 7.23 (2H, s), 4.61 (2H, t), 2.88 (2H, s), 2.09 (6H, s), 1.83 (2H, m), 1.69 (2H, m) |
| T190 | 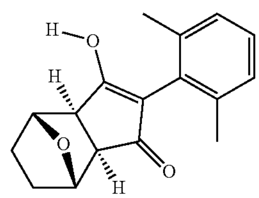 [SMILES: Cc1cccc(C)c1C1=C(O)[C@H]2[C@@H](C1=O)[C@@H]1CC[C@H]2O1] | d₄-MeOH δ$_H$ 7.14-7.04 (3H, m), 4.61 (2H, t), 2.88 (2H, s), 2.11 (6H, s), 1.83 (2H, m), 1.69 (2H, m) |
| T191 | 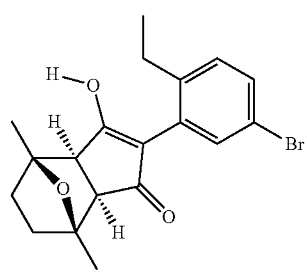 [SMILES: CCc1ccc(Br)cc1C1=C(O)[C@H]2[C@@H](C1=O)[C@]1(C)CC[C@@]2(C)O1] | d₄-MeOH δ$_H$ 7.36 (1H, dd), 7.17 (1H, d), 7.15 (1H, d), 2.81 (2H, s), 2.48-2.43 (2H, m), 1.84-1.79 (2H, m), 1.69-1.65 (2H, m), 1.51 (6H, s), 1.08 (3H, t). |
| T192 | 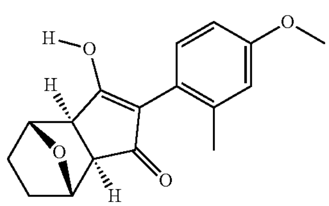 [SMILES: COc1ccc(C2=C(O)[C@H]3[C@@H](C2=O)[C@@H]2CC[C@H]3O2)c(C)c1] | d₄-MeOH δ$_H$ 6.94 (1H, d), 6.78 (1H, d), 6.73 (1H, dd), 4.59 (2H, s), 3.77 (3H, s), 2.82 (2H, s), 2.10 (3H, s), 1.84-1.79 (2H, m), 1.69-1.62 (2H, m). |
| T193 | 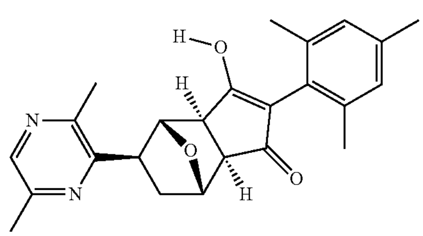 [SMILES: Cc1cc(C)c(C2=C(O)[C@@H]3[C@@H]4O[C@@H](C[C@H]4c4nc(C)cnc4C)[C@@H]3C2=O)c(C)c1] | d₄-MeOH δ$_H$ 7.84 (1H, br. s), 6.78 (2H, s), 4.89 (1H, br. s), 4.84 (1H, s), 3.28 (1H, br. s), 3.02 (1H, br. s), 2.94 (1H, br. s), 2.57-2.46 (2H, m), 2.53 (3H, s), 2.18 (3H, s), 2.05 (3H, s), 2.03 (3H, s), 2.02 (3H, s). |

TABLE T1-continued

| Compound Number | Structure | ¹H nmr (CDCl₃ unless stated) or other physical data |
|---|---|---|
| T194 | 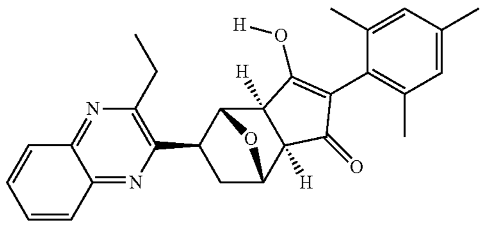 [SMILES: CCc1nc2ccccc2nc1[C@@H]1C[C@@H]2O[C@H]1[C@H]1C(O)=C(c3c(C)cc(C)cc3C)C(=O)[C@H]12] | d₄-MeOH $\delta_H$ 8.09-8.06 (1H, m), 8.00-7.98 (1H, m), 7.73-7.70 (2H, m), 6.86 (2H, s), 4.99 (1H, s), 4.80 (1H, d), 3.19-3.10 (3H, m), 2.49-2.43 (1H, m), 2.34-2.28 (1H, m), 2.25 (3H, s), 2.07 (3H, s), 2.06 (3H, s), 1.46 (3H, t). |
| T195 | 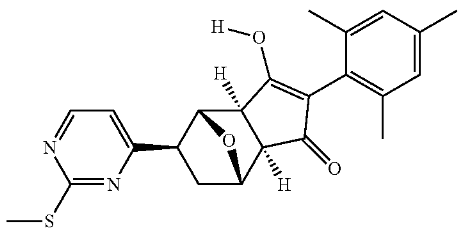 | d₄-MeOH $\delta_H$ 7.04 (1H, br. s), 6.86 (2H, s), 5.93 (1H, br. s), 4.86 (1H, br. s), 4.78 (1H, s), 3.18 (1H, br. s), 3.02 (1H, br. s), 2.94 (1H, br. s), 2.59 (3H, s), 2.37 (3H, s), 2.24 (3H, s), 2.16 (3H, s), 2.07 (6H, m). |
| T196 | 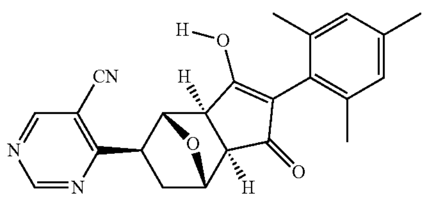 [SMILES: Cc1cc(C)c(C2=C(O)[C@@H]3[C@@H]4O[C@@H](C[C@H]4c4ncncc4C#N)[C@@H]3C2=O)c(C)c1] | d₄-MeOH $\delta_H$ 8.79 (1H, s), 8.59 (1H, s), 6.87 (1H, s), 4.95 (1H, s), 4.92 (1H, d), 3.74-3.71 (1H, m), 2.87 (2H, m), 2.26 (2H, m), 2.18 (3H, s), 2.10 (3H, s), 2.07 (3H, s). |
| T197 | 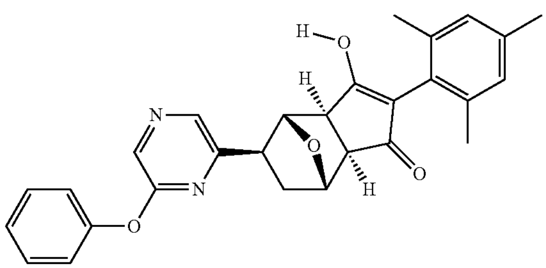 [SMILES: Cc1cc(C)c(C2=C(O)[C@@H]3[C@@H]4O[C@@H](C[C@H]4c4cncc(Oc5ccccc5)n4)[C@@H]3C2=O)c(C)c1] | d₄-MeOH $\delta_H$ 7.45-7.42 (3H, m), 7.29-7.23 (2H, m), 7.17-7.15 (2H, m), 6.80 (2H, s), 4.82 (1H, br. s), 4.73 (1H, br. s), 3.21 (1H, br. s), 2.90 (1H, br. s), 2.84 (1H, br. s), 2.20 (3H s), 2.09-2.07 (2H, m), 2.05 (6H, s). |
| T198 | 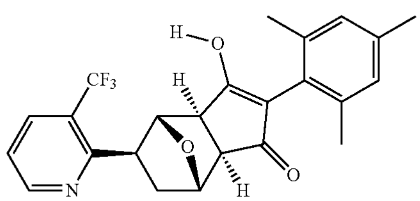 [SMILES: Cc1cc(C)c(C2=C(O)[C@@H]3[C@@H]4O[C@@H](C[C@H]4c4ncccc4C(F)(F)F)[C@@H]3C2=O)c(C)c1] | d₄-MeOH $\delta_H$ 8.78 (1H, br. s), 7.96 (1H, br. s), 6.84 (3H, s), 4.82 (2H, br. s), 3.51 (1H, br. s), 2.98 (1H, br. s), 2.90 (1H, br. s), 2.35 (1H, br. s), 2.22 (3H, s), 2.04-2.02 (7H, m). |
| T199 | 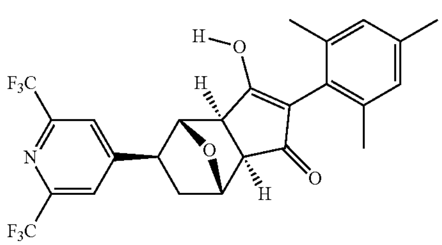 [SMILES: Cc1cc(C)c(C2=C(O)[C@@H]3[C@@H]4O[C@@H](C[C@H]4c4cc(C(F)(F)F)nc(C(F)(F)F)c4)[C@@H]3C2=O)c(C)c1] | d₄-MeOH $\delta_H$ 7.81 (1H, s), 7.26 (1H, s), 6.92 (1H, s), 6.90 (1H, s), 4.91 (1H, d), 4.64 (1H, s), 3.19-3.17 (1H, m), 2.99-2.95 (2H, m), 2.32-2.27 (1H, m), 2.26 (3H, s), 2.09 (3H, s), 2.07 (3H, s), 1.93-1.90 (1H, m). |
| T200 | 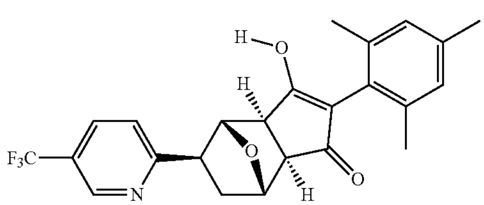 [SMILES: Cc1cc(C)c(C2=C(O)[C@@H]3[C@@H]4O[C@@H](C[C@H]4c4ccc(C(F)(F)F)cn4)[C@@H]3C2=O)c(C)c1] | d₄-MeOH $\delta_H$ 7.95 (1H, br. s), 7.86 (1H, br. s), 7.44 (1H, br. s), 6.88 (1H, s), 6.84 (1H, s), 4.86 (1H, br. s), 4.71 (1H, br. s), 3.44-3.40 (1H, br. s), 3.07 (1H, br. s), 2.85 (1H, br. s), 2.22 (3H, s), 2.15-2.11 (2H, m), 2.10 (3H, s), 2.05 (3H, s). |

TABLE T1-continued

| Compound Number | Structure | ¹H nmr (CDCl₃ unless stated) or other physical data |
|---|---|---|
| T201 | 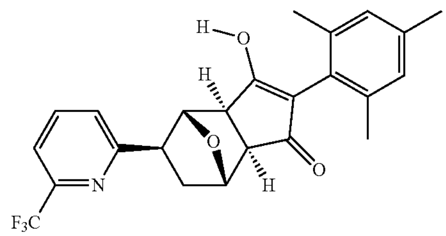 [SMILES: Cc1cc(C)c(C2=C(O)[C@@H]3[C@@H]4O[C@@H](C[C@H]4c4cccc(C(F)(F)F)n4)[C@@H]3C2=O)c(C)c1] | d₄-MeOH δ$_H$ 7.79 (1H, t), 7.53 (2H, d), 6.86 (2H, s), 4.78 (1H, s), 4.71 (1H, s), 3.35-3.31 (1H, m), 2.88 (1H, br. s), 2.79 (1H, br. s), 2.22 (3H, s), 2.17-2.09(2H, m), 2.04 (3H, s), 2.02 (3H, s). |
| T202 | 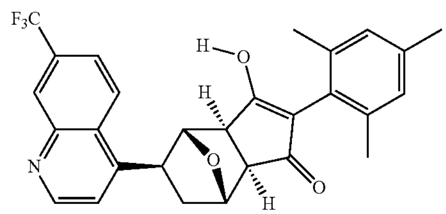 [SMILES: Cc1cc(C)c(C2=C(O)[C@@H]3[C@@H]4O[C@@H](C[C@H]4c4ccnc5cc(C(F)(F)F)ccc45)[C@@H]3C2=O)c(C)c1] | d₄-MeOH δ$_H$ 8.76 (1H, br. s), 8.61 (1H, d), 8.32 (1H, d), 7.96 (1H, d), 7.85 (1H, d), 6.86 (2H, s), 4.84 (1H, s), 4.11 (1H, dd), 3.24 (1H, d), 3.13 (1H, d), 2.58-2.54 (1H, m), 2.24 (3H, s), 2.07 (6H, s), 1.95-1.91 (1H, m). |
| T203 | 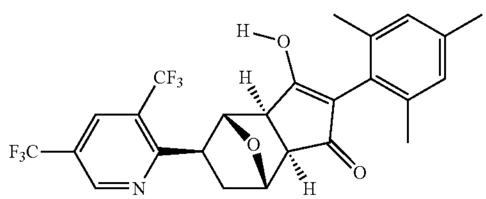 [SMILES: Cc1cc(C)c(C2=C(O)[C@@H]3[C@@H]4O[C@@H](C[C@H]4c4ncc(C(F)(F)F)cc4C(F)(F)F)[C@@H]3C2=O)c(C)c1] | d₄-MeOH δ$_H$ 9.07 (1H, s), 8.38 (1H, s), 6.87 (2H, s), 4.77 (1H, s), 3.77-3.74 (1H, m), 3.04 (2H, br. s), 2.40-2.37 (1H, m), 2.29-2.25 (1H, m), 2.25 (3H, s), 2.06 (3H, s), 2.04 (3H, s). |
| T204 | 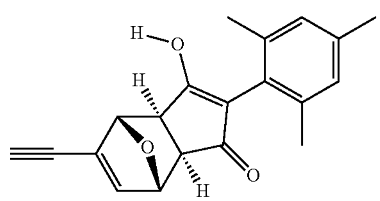 [SMILES: C#CC1=C[C@@H]2O[C@H]1[C@H]1C(O)=C(c3c(C)cc(C)cc3C)C(=O)[C@H]12] | d₄-MeOH δ$_H$ 6.85 (2H, s), 6.72 (1H, d), 5.03 (1H, d), 3.96 (1H, s), 2.92-2.88 (2H, m), 2.24 (3H, s), 2.06 (3H, s), 2.01 (3H, s). |
| T205 | 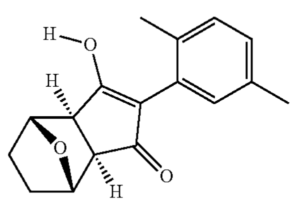 [SMILES: Cc1ccc(C)c(C2=C(O)[C@H]3[C@@H](C2=O)[C@@H]2CC[C@H]3O2)c1] | d₆-DMSO δ$_H$ 11.92 (1H, s), 7.05 (1H, d), 6.96 (1H, d), 6.77 (1H, s), 4.50 (2H, s), 2.74 (2H, br. s), 2.23 (3H, s), 2.03 (3H, s), 1.71-1.65 (2H, m), 1.57-1.53 (2H, m). |
| T206 | 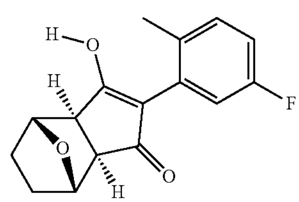 [SMILES: Cc1ccc(F)cc1C1=C(O)[C@H]2[C@@H](C1=O)[C@@H]1CC[C@H]2O1] | d₆-DMSO δ$_H$ 12.21 (1H, s), 7.20 (1H, dd), 6.99 (1H, td), 6.75 (1H, dd), 4.51 (2H, s), 2.76 (2H, br. s), 2.04 (3H, s), 1.71-1.65 (2H, m), 1.60-1.52 (2H, m). |
| T207 | 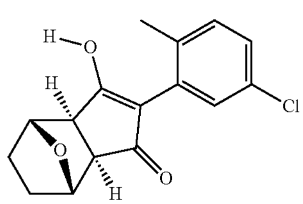 [SMILES: Cc1ccc(Cl)cc1C1=C(O)[C@H]2[C@@H](C1=O)[C@@H]1CC[C@H]2O1] | d₆-DMSO δ$_H$ 12.27 (1H, s), 7.21 (2H, s), 6.97 (1H, s), 4.51 (2H, s), 2.78 (2H, br. s), 2.05 (3H, s), 1.73-1.63 (2H, m), 1.60-1.51 (2H, m). |

TABLE T1-continued

| Compound Number | Structure | ¹H nmr (CDCl₃ unless stated) or other physical data |
|---|---|---|
| T208 | 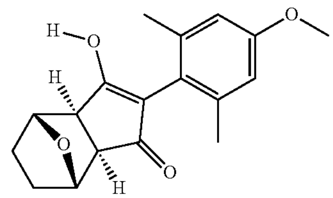 [SMILES: COc1cc(C)c(C2=C(O)[C@H]3[C@@H](C2=O)[C@@H]2CC[C@H]3O2)c(C)c1] | d₄-MeOH δ$_H$ 6.61 (2H, s), 4.64-4.50 (2H, m), 3.74 (3H, s), 2.83 (2H, s), 2.04 (6H, d), 1.87-1.77 (2H, m), 1.70-1.59 (2H, m). |
| T209 | 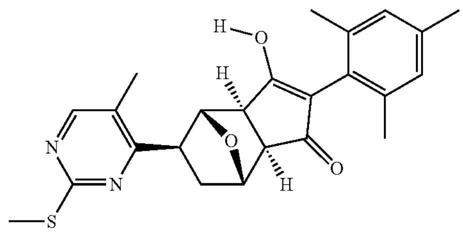 | d₄-MeOH δ$_H$ 8.30 (1H, s), 6.86 (2H, s), 4.89 (1H, s), 4.73 (1H, d), 3.47 (1H, dd), 3.09 (1H, d), 3.04 (1H, d), 2.55 (3H, s), 2.39-2.35 (1H, m), 2.30 (3H, s), 2.25 (3H, s), 2.17 (1H, dd), 2.06 (3H, s), 2.04 (3H, s). |
| T210 | 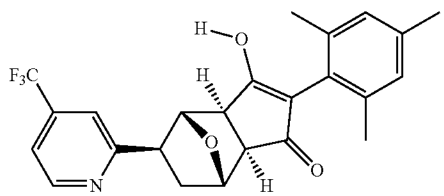 [SMILES: Cc1cc(C)c(C2=C(O)[C@@H]3[C@@H]4O[C@@H](C[C@H]4c4cc(C(F)(F)F)ccn4)[C@@H]3C2=O)c(C)c1] | d₄-MeOH δ$_H$ 8.72 (1H, d), 7.72 (1H, s), 7.58 (1H, d), 6.86 (2H, s), 4.81 (1H, d), 4.68 (1H, s), 3.51 (1H, dd), 3.10 (1H, d), 3.03 (1H, d), 2.33 (1H, dd), 2.25 (3H, s), 2.16-2.11 (1H, m), 2.06 (3H, s), 2.05 (3H, s). |
| T211 | 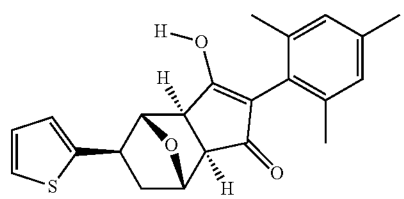 [SMILES: Cc1cc(C)c(C2=C(O)[C@@H]3[C@@H]4O[C@@H](C[C@H]4c4cccs4)[C@@H]3C2=O)c(C)c1] | d₄-MeOH δ$_H$ 7.21-7.19 (1H, m), 6.92-6.90 (2H, m), 6.86 (2H, s), 4.72 (1H, d), 4.43 (1H, s), 3.49 (1H, dd), 3.02 (1H, d), 2.93 (1H, d), 2.29 (1H, dd), 2.25 (3H, s), 2.05 (6H, s), 1.98-1.93 (1H, m). |
| T212 | 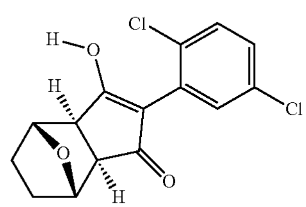 [SMILES: O=C1C(c2cc(Cl)ccc2Cl)=C(O)[C@H]2[C@@H]1[C@@H]1CC[C@H]2O1] | d₄-MeOH δ$_H$ 7.41 (1H, d), 7.29 (1H, dd), 7.19 (1H, d), 4.65-4.60 (2H, m), 2.87 (2H, s), 1.86-1.79 (2H, m), 1.70-1.63 (2H, m). |
| T213 | 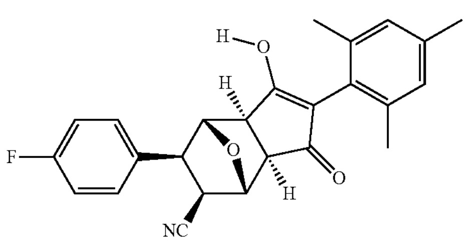 [SMILES: Cc1cc(C)c(C2=C(O)[C@@H]3[C@@H]4O[C@@H]([C@@H](C#N)[C@H]4c4ccc(F)cc4)[C@@H]3C2=O)c(C)c1] | d₄-MeOH δ$_H$ 7.44-7.41 (2H, m), 7.08 (2H, t), 6.88 (1H, s), 6.87 (1H, s), 4.89(1H, s), 4.73 (1H, s), 3.68 (1H, d), 3.59 (1H, d), 3.10-3.06 (2H, m), 2.25 (3H, s), 2.07 (3H, s), 2.5 (3H, s). |
| T214 | 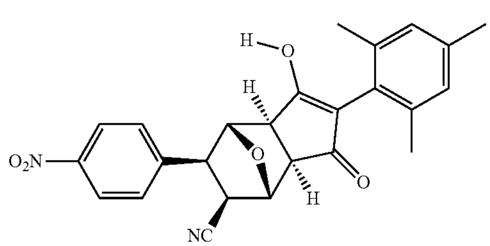 [SMILES: Cc1cc(C)c(C2=C(O)[C@@H]3[C@@H]4O[C@@H]([C@@H](C#N)[C@H]4c4ccc([N+](=O)[O-])cc4)[C@@H]3C2=O)c(C)c1] | d₄-MeOH δ$_H$ 8.24 (2H, d), 7.66 (2H, d), 6.88 (2H, s), 4.93 (1H, s), 4.68 (1H, s), 3.76 (2H, s), 3.13-3.11 (2H, m), 2.25 (3H, s), 2.07 (3H, s), 2.05 (3H, s). |

TABLE T1-continued

| Compound Number | Structure | ¹H nmr (CDCl₃ unless stated) or other physical data |
|---|---|---|
| T215 | 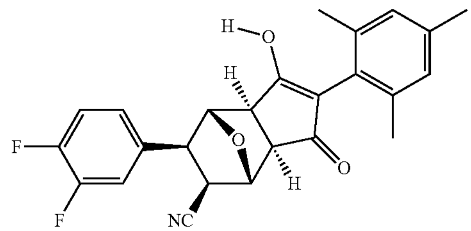 [SMILES: Cc1cc(C)c(C2=C(O)[C@@H]3[C@@H]4O[C@@H]([C@@H](C#N)[C@H]4c4ccc(F)c(F)c4)[C@@H]3C2=O)c(C)c1] | d₄-MeOH δ$_H$ 7.34-7.30 (1H, m), 7.25-7.18 (2H, m), 6.89 (1H, s), 6.87 (1H, s), 4.90 (1H, s), 4.75 (1H, s), 3.67 (1H, d), 3.58 (1H, d), 3.10-3.05 (2H, m), 2.26 (3H, s), 2.07 (3H, s), 2.05 (3H, s). |
| T216 | 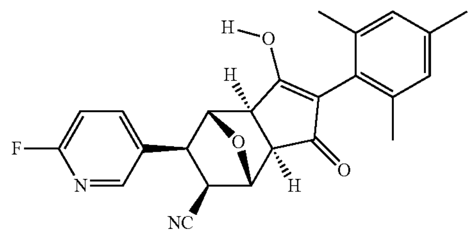 [SMILES: Cc1cc(C)c(C2=C(O)[C@@H]3[C@@H]4O[C@@H]([C@@H](C#N)[C@H]4c4ccc(F)nc4)[C@@H]3C2=O)c(C)c1] | d₄-MeOH δ$_H$ 8.53 (1H, s), 7.83 (1H, d), 7.64 (1H, d), 6.91 (2H, s), 3.12 (1H, dd), 2.97 (2H, br. s), 2.47 (1H, dd), 2.27 (3H, s), 1.84-1.79 (1H, m), 2.11 (3H, s), 2.08 (3H, s), 1.71 (3H, s), 1.10 (3H, s). |
| T217 | 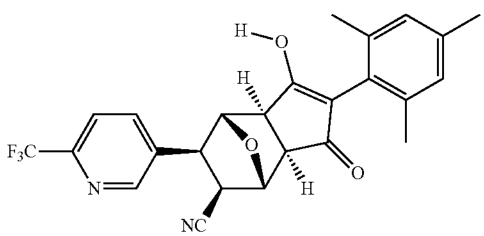 [SMILES: Cc1cc(C)c(C2=C(O)[C@@H]3[C@@H]4O[C@@H]([C@@H](C#N)[C@H]4c4ccc(C(F)(F)F)nc4)[C@@H]3C2=O)c(C)c1] | d₄-MeOH δ$_H$ 7.92 (1H, d), 7.77-7.73 (1H, m), 6.91-6.88(3H, m), 3.04 (1H, dd), 2.96-2.92 (2H, m), 2.43(1H, dd), 2.25 (3H, s), 2.11 (3H, s), 2.08 (3H, s), 1.76 (1H, dd), 1.70 (3H, s), 1.09 (3H, s). |
| T218 | 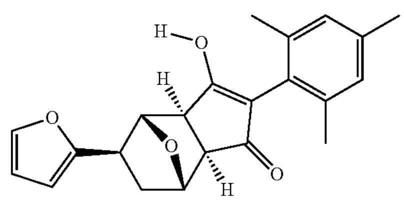 [SMILES: Cc1cc(C)c(C2=C(O)[C@@H]3[C@@H]4O[C@@H](C[C@H]4c4ccco4)[C@@H]3C2=O)c(C)c1] | d₄-MeOH δ$_H$ 7.41 (1H, d), 6.88 (2H, s), 6.35-6.34 (1H, m), 6.14 (1H, d), 4.72 (1H, d), 4.59 (1H, s), 3.26(1H, dd), 3.02 (1H, d), 2.94 (1H, d), 2.27 (3H, s), 2.18-2.12 (1H, m), 2.08 (3H, s), 2.06 (3H, s), 2.05-2.01 (1H, m). |
| T219 | 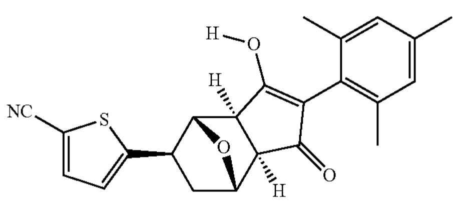 [SMILES: Cc1cc(C)c(C2=C(O)[C@@H]3[C@@H]4O[C@@H](C[C@H]4c4ccc(C#N)s4)[C@@H]3C2=O)c(C)c1] | d₄-MeOH δ$_H$ 7.60 (1H, d), 7.06 (1H, d), 6.89 (2H, s), 4.79 (1H, d), 4.47 (1H, s), 3.63 (1H, dd), 3.06 (1H, d), 3.00 (1H, d), 2.36 (1H, dd), 2.27 (3H, s), 2.07 (6H, s), 1.97-1.91 (1H, m). |
| T220 | 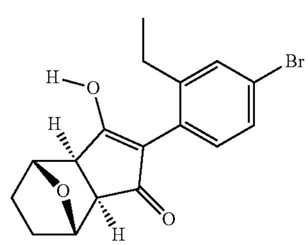 [SMILES: CCc1cc(Br)ccc1C1=C(O)[C@H]2[C@@H](C1=O)[C@@H]1CC[C@H]2O1] | δ$_H$ 7.39 (1H, dd), 7.27-7.33 (1H, m), 6.97 (1H, dd), 4.68 (2H, m), 2.74 (2H, br. s), 2.48 (2H, q), 1.78-1.87 (2H, m), 1.56 (2H, m), 1.11 (3H, t). |
| T221 | 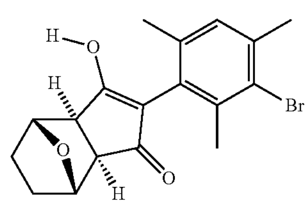 [SMILES: Cc1cc(C)c(C2=C(O)[C@H]3[C@@H](C2=O)[C@@H]2CC[C@H]3O2)c(C)c1Br] | δ$_H$ 7.05-6.99 (1H, m), 4.76-4.67 (2H, m), 2.84 (2H, br. s), 2.38 (3H, s), 2.24 (3H, d), 2.05 (3H, d), 1.88-1.85 (2H, m), 1.64-1.58 (2H, m). |

TABLE T1-continued

| Compound Number | Structure | $^1$H nmr (CDCl$_3$ unless stated) or other physical data |
|---|---|---|
| T222 | 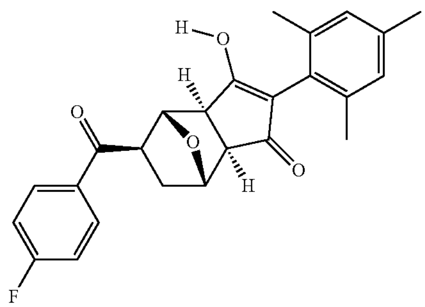 [SMILES: Cc1cc(C)c(C2=C(O)[C@@H]3[C@@H]4O[C@@H](C[C@H]4C(=O)c4ccc(F)cc4)[C@@H]3C2=O)c(C)c1] | d$_4$-MeOH δ$_H$ 8.11 (2H, dd), 8.61 (2H, t), 6.86 (2H, s), 4.81 (1H, s), 4.67 (1H, d), 3.81 (1H, dd), 3.14 (1H, d), 3.03 (1H, d), 2.24 (3H, s), 2.23-2.19 (1H, m), 2.11-2.09 (1H, m), 2.06 (3H, s), 2.02 (3H, s). |
| T223 | 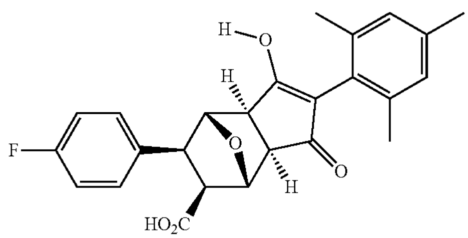 [SMILES: Cc1cc(C)c(C2=C(O)[C@@H]3[C@@H]4O[C@@H]([C@@H](C(=O)O)[C@H]4c4ccc(F)cc4)[C@@H]3C2=O)c(C)c1] | d$_4$-MeOH δ$_H$ 7.39-7.36 (2H, m), 6.98-6.94 (2H, m), 6.88 (1H, s), 6.86 (1H, s), 4.95 (1H, s), 4.53 (1H, s), 3.63 (1H, d), 3.08 (1H, d), 3.03 (1H, d), 2.88-2.86 (1H, m), 2.25 (3H, s), 2.09 (3H, s), 2.06 (3H, s). |
| T224 | 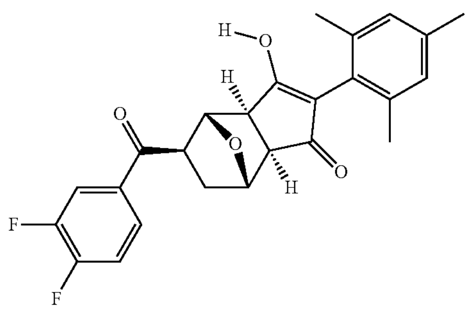 [SMILES: Cc1cc(C)c(C2=C(O)[C@@H]3[C@@H]4O[C@@H](C[C@H]4C(=O)c4ccc(F)c(F)c4)[C@@H]3C2=O)c(C)c1] | d$_4$-MeOH δ$_H$ 7.81-7.76 (1H, m), 7.73-7.70 (1H, m), 7.29-7.23 (1H, m), 6.88 (2H, s), 4.96 (1H, s), 4.79 (1H, d), 3.47 (1H, dd), 3.04-2.92 (2H, m), 2.25 (3H, s), 2.11-2.07(1H, m), 2.07 (3H, s), 2.04 (3H, s), 1.96-1.88 (1H, m). |
| T225 | 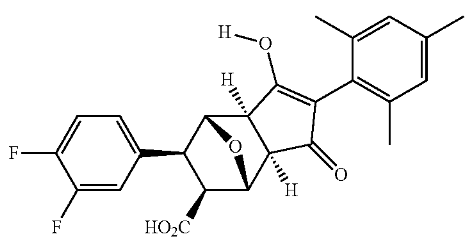 [SMILES: Cc1cc(C)c(C2=C(O)[C@@H]3[C@@H]4O[C@@H]([C@@H](C(=O)O)[C@H]4c4ccc(F)c(F)c4)[C@@H]3C2=O)c(C)c1] | d$_4$-MeOH δ$_H$ 7.16-7.12 (1H, m), 7.01-6.90 (2H, m), 6.78 (1H, s), 6.76 (1H, s), 4.94 (1H, s), 4.54 (1H, s), 3.39 (1H, d), 3.12 (1H, d), 2.28-2.80 (2H, br. m), 2.14 (3H, s), 2.00 (3H, s), 1.96 (3H, s). |
| T226 | 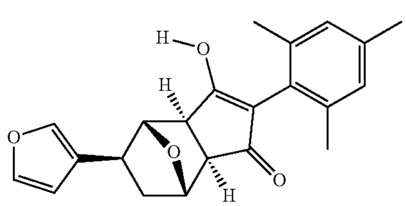 [SMILES: Cc1cc(C)c(C2=C(O)[C@@H]3[C@@H]4O[C@@H](C[C@H]4c4ccoc4)[C@@H]3C2=O)c(C)c1] | d$_4$-MeOH δ$_H$ 7.43 (1H, s), 7.38 (1H, s), 6.88 (2H, s), 6.42 (1H, d), 4.93 (1H, s), 4.71 (1H, d), 3.09 (1H, dd), 2.99 (1H, d), 2.93 (1H, d), 2.27 (3H, s), 2.17 (1H, dd), 2.08 (6H, m), 1.85-1.80 (1H, m). |
| T227 | 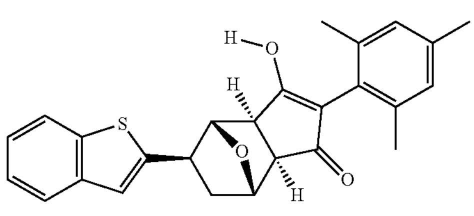 [SMILES: Cc1cc(C)c(C2=C(O)[C@@H]3[C@@H]4O[C@@H](C[C@H]4c4cc5ccccc5s4)[C@@H]3C2=O)c(C)c1] | δ$_H$ 7.92-7.81 (3H, m), 7.42-7.29 (2H, m), 6.85 (2H, s), 4.78 (1H, d), 4.59 (1H, s), 3.57 (1H, dd), 3.14 (1H, d), 3.00 (1H, d), 2.31 (1H, dd), 2.24 (3H, s), 2.07 (3H, s), 2.05 (3H, s), 2.04-1.98 (1H, m). |

TABLE T1-continued

| Compound Number | Structure | $^1$H nmr (CDCl$_3$ unless stated) or other physical data |
|---|---|---|
| T228 | 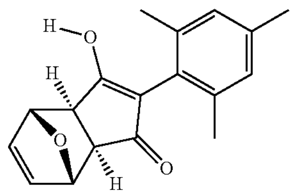 [SMILES: Cc1cc(C)c(C2=C(O)[C@H]3[C@@H](C2=O)[C@@H]2C=C[C@H]3O2)c(C)c1] | $\delta_H$ 6.86 (2H, s), 6.47 (2H, s), 5.01 (2H, s), 2.74 (2H, s), 2.23 (3H, s), 2.08 (3H, s), 2.06 (3H, s). |
| T229 | 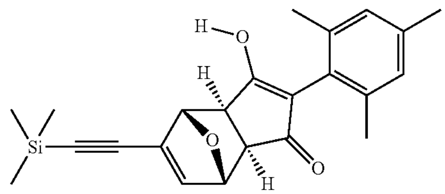 | $\delta_H$ 6.65 (2H, s), 6.26 (1H, s), 4.75 (1H, s), 4.67 (1H, s), 2.62 (1H, d), 2.52 (1H, d), 2.03 (3H, s), 1.84 (3H, s), 1.80 (3H, s), 0.00 (9H, s). |

The compounds of the following Tables 1 to 146 can be obtained in an analogous manner.

Table 1 covers compounds of formula (A)

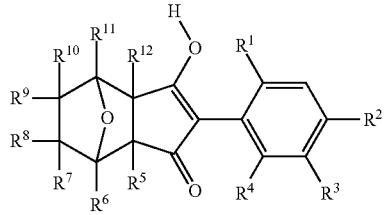

(I)

wherein $R^1$, $R^2$ and $R^4$ are methyl, $R^3$, $R^5$ and $R^{12}$ are hydrogen and $R^6$, $R^7$, $R^8$, $R^9$, $R^{10}$, and $R^{11}$ are as defined in Table 1.

TABLE 1

| | $R^6$ | $R^7$ | $R^8$ | $R^9$ | $R^{10}$ | $R^{11}$ |
|---|---|---|---|---|---|---|
| 1.001 | H | H | H | H | H | H |
| 1.002 | H | H | H | H | H | CH$_3$ |
| 1.003 | H | H | H | H | H | CH$_2$OH |
| 1.004 | H | H | H | H | H | CH$_2$OCH$_3$ |
| 1.005 | H | H | H | H | H | CH$_2$OCH$_2$CH$_3$ |
| 1.006 | H | H | H | H | H | CH$_2$OCH$_2$OCH$_3$ |
| 1.007 | H | H | H | H | H | CH$_2$OCH$_2$OCH$_2$CH$_3$ |
| 1.007 | H | H | H | H | H | CH$_2$OCH$_2$CO$_2$CH$_3$ |
| 1.008 | H | H | H | H | H | CH$_2$OCH$_2$CO$_2$CH$_2$CH$_3$ |
| 1.009 | H | H | H | H | H | CH$_2$OCH$_2$CN |
| 1.010 | H | H | H | H | H | CH(OH)CH$_3$ |
| 1.011 | H | H | H | H | H | CH(CH$_3$)OCH$_3$ |
| 1.012 | H | H | H | H | H | CH(CH$_3$)OCH$_2$CH$_3$ |
| 1.013 | H | H | H | H | H | CHO |
| 1.014 | H | H | H | H | H | COCH$_3$ |
| 1.015 | H | H | H | H | H | CH$_2$COCH$_3$ |
| 1.016 | H | H | H | H | H | CH$_2$CH$_2$COCH$_3$ |
| 1.017 | H | H | H | H | H | CO$_2$H |
| 1.018 | H | H | H | H | H | CO$_2$CH$_3$ |
| 1.019 | H | H | H | H | H | CO$_2$CH$_2$CH$_3$ |
| 1.020 | H | H | H | H | H | CH$_2$CO$_2$CH$_3$ |
| 1.021 | H | H | H | H | H | CH$_2$CO$_2$CH$_2$CH$_3$ |
| 1.022 | H | H | H | H | H | CH$_2$CH$_2$CO$_2$CH$_3$ |
| 1.023 | H | H | H | H | H | CH$_2$CH$_2$CO$_2$CH$_2$CH$_3$ |
| 1.024 | H | H | H | H | H | CONH$_2$ |
| 1.025 | H | H | H | H | H | CONHCH$_3$ |
| 1.026 | H | H | H | H | H | CONHCH$_2$CH$_3$ |
| 1.027 | H | H | H | H | H | CON(CH$_3$)$_2$ |
| 1.030 | H | H | H | H | H | CON(CH$_2$CH$_3$)$_2$ |
| 1.031 | H | H | H | H | H | CON(CH$_3$)OCH$_3$ |

TABLE 1-continued

|  | R⁶ | R⁷ | R⁸ | R⁹ | R¹⁰ | R¹¹ |
|---|---|---|---|---|---|---|
| 1.032 | H | H | H | H | H | CH=NOH |
| 1.033 | H | H | H | H | H | CH=NOCH$_3$ |
| 1.034 | H | H | H | H | H | CH=NOCH$_2$CH$_3$ |
| 1.035 | H | H | H | H | H | C(CH$_3$)=NOH |
| 1.036 | H | H | H | H | H | C(CH$_3$)=NOCH$_3$ |
| 1.037 | H | H | H | H | H | CH$_2$OC(O)CH$_3$ |
| 1.038 | H | H | H | H | H | CH$_2$OC(O)CH$_2$CH$_3$ |
| 1.039 | H | H | H | H | H | CH$_2$OC(O)CH(CH$_3$)$_2$ |
| 1.040 | H | H | H | H | H | CH$_2$OC(O)C(CH$_3$)$_3$ |
| 1.039 | H | H | H | H | H | CH$_2$OC(O)NHCH$_3$ |
| 1.040 | H | H | H | H | H | CH$_2$OC(O)NHCH$_2$CH$_3$ |
| 1.041 | H | H | H | H | H | CH$_2$OC(O)NHCH$_2$CH$_2$CH$_3$ |
| 1.042 | H | H | H | H | H | CH$_2$OC(O)NHC(CH$_3$)$_3$ |
| 1.043 | H | H | H | H | H | CH$_2$NH$_2$ |
| 1.044 | H | H | H | H | H | CH$_2$NHCHO |
| 1.045 | H | H | H | H | H | CH$_2$NHC(O)CH$_3$ |
| 1.046 | H | H | H | H | H | CH$_2$NHC(O)OCH$_3$ |
| 1.047 | H | H | H | H | H | NHCO$_2$CH$_3$ |
| 1.048 | H | H | H | H | H | NHCO$_2$C(CH$_3$)$_3$ |
| 1.049 | H | H | H | H | H | CN |
| 1.050 | H | H | H | H | H | CH$_2$SCH$_3$ |
| 1.051 | H | H | H | H | H | CH$_2$SCH$_2$CH$_3$ |
| 1.052 | H | H | H | H | H | CH$_2$SCH$_2$CH$_2$CH$_3$ |
| 1.053 | H | H | H | H | H | CH$_2$SCH(CH$_3$)$_2$ |
| 1.054 | H | H | H | H | H | CH$_2$S(O)CH$_3$ |
| 1.055 | H | H | H | H | H | CH$_2$SO$_2$CH$_3$ |
| 1.056 | H | H | H | H | H | CH$_2$SCH$_2$CH$_3$ |
| 1.057 | H | H | H | H | H | CH$_2$S(O)CH$_2$CH$_3$ |
| 1.058 | H | H | H | H | H | CH$_2$SO$_2$CH$_2$CH$_3$ |
| 1.059 | H | H | H | H | H | OCH$_3$ |
| 1.060 | H | H | H | H | H | OCH$_2$CH$_3$ |
| 1.061 | H | H | H | H | H | CH(OCH$_3$)$_2$ |
| 1.062 | H | H | H | H | H | CH(OCH$_2$CH$_3$)$_2$ |
| 1.063 | H | H | H | H | H | 1,3-dioxolan-2-yl |
| 1.064 | 11 | H | H | H | H | 1,3-dioxan-2-yl |
| 1.065 | H | H | H | H | H | 5,5-dimethyl-1,3-dioxan-2-yl |
| 1.066 | H | H | H | H | H | CH$_2$CH$_3$ |
| 1.067 | H | H | H | H | H | n-propyl |
| 1.068 | H | H | H | H | H | isopropyl |
| 1.069 | H | H | H | H | H | n-butyl |
| 1.070 | H | H | H | H | H | isobutyl |
| 1.071 | H | H | H | H | H | sec-butyl |
| 1.072 | H | H | H | H | H | tert-butyl |
| 1.073 | H | H | H | H | H | n-pentyl |
| 1.074 | H | H | H | H | H | neopentyl |
| 1.075 | H | H | H | H | H | n-hexyl |
| 1.076 | H | H | H | H | H | n-heptyl |
| 1.077 | H | H | H | H | H | CH$_2$CN |
| 1.078 | H | H | H | H | H | cyclopropyl |
| 1.079 | H | H | H | H | H | cyclobutyl |
| 1.080 | H | H | H | H | H | cyclopentyl |
| 1.081 | H | H | H | H | H | cyclohexyl |
| 1.082 | H | H | H | H | H | CH$_2$-cyclopropyl |
| 1.083 | H | H | H | H | H | benzyl |
| 1.084 | H | H | H | H | H | CH$_2$CF$_3$ |
| 1.085 | H | H | H | H | H | CH$_2$F |
| 1.086 | H | H | H | H | H | CHF$_2$ |
| 1.087 | H | H | H | H | H | CF$_3$ |
| 1.088 | H | H | H | H | CH$_3$ | H |
| 1.089 | H | H | H | H | CH$_2$CH$_3$ | H |
| 1.090 | H | H | H | H | n-propyl | H |
| 1.091 | H | H | H | H | isopropyl | H |
| 1.092 | H | H | H | H | n-butyl | H |
| 1.093 | H | H | H | H | isobutyl | H |
| 1.094 | H | H | H | H | sec-butyl | H |
| 1.095 | H | H | H | H | tert-butyl | H |
| 1.096 | H | H | H | H | vinyl | H |
| 1.097 | H | H | H | H | ethynyl | H |
| 1.098 | H | H | H | H | trimethylsilylethynyl | H |
| 1.099 | H | H | H | H | CH$_2$OH | H |
| 1.100 | H | H | H | H | CH$_2$OCH$_3$ | H |
| 1.101 | H | H | H | H | CH$_2$OCH$_2$CH$_3$ | H |
| 1.102 | H | H | H | H | CH$_2$OCH$_2$OCH$_3$ | H |
| 1.103 | H | H | H | H | CH$_2$OCH$_2$OCH$_2$CH$_3$ | H |
| 1.104 | H | H | 11 | H | CH$_2$OCH$_2$CH$_2$OCH$_3$ | H |
| 1.105 | H | H | H | H | CHO | H |
| 1.106 | H | H | H | H | COCH$_3$ | H |

TABLE 1-continued

|  | $R^6$ | $R^7$ | $R^8$ | $R^9$ | $R^{10}$ | $R^{11}$ |
|---|---|---|---|---|---|---|
| 1.107 | H | H | H | H | $CO_2H$ | H |
| 1.108 | H | H | H | H | $CO_2CH_3$ | H |
| 1.109 | H | H | H | H | $CO_2CH_2CH_3$ | H |
| 1.110 | H | H | H | H | $CONH_2$ | H |
| 1.111 | H | H | H | H | $CONHCH_3$ | H |
| 1.112 | H | H | H | H | $CONHCH_2CH_3$ | H |
| 1.113 | H | H | H | H | $CON(CH_3)_2$ | H |
| 1.114 | H | H | H | H | $CON(CH_2{-}CH_3)_2$ | H |
| 1.115 | H | H | H | H | $CON(CH_3)OCH_3$ | H |
| 1.116 | H | H | H | H | $CH{=}NOH$ | H |
| 1.117 | H | H | H | H | $CH{=}N{-}OCH_3$ | H |
| 1.118 | H | H | H | H | $CH{=}N{-}OCH_2CH_3$ | H |
| 1.119 | H | H | H | H | $C(CH_3){=}N{-}OH$ | H |
| 1.120 | H | H | H | H | $C(CH_3){=}N{-}OCH_3$ | H |
| 1.121 | H | H | H | H | $CH_2OC(O){-}NHCH_3$ | H |
| 1.122 | H | H | H | H | $CH_2NH_2$ | H |
| 1.123 | H | H | H | H | $CH_2NHCHO$ | H |
| 1.124 | H | H | H | H | $CH_2NHC(O)CH_3$ | H |
| 1.125 | H | H | H | H | $CH_2NHC(O)OCH_3$ | H |
| 1.126 | H | H | H | H | $NHCO_2CH_3$ | H |
| 1.127 | H | H | H | H | $NHCO_2C(CH_3)_3$ | H |
| 1.128 | H | H | H | H | $CH(OH)CH_3$ | H |
| 1.129 | H | H | H | H | $CH(CH_3)OCH_3$ | H |
| 1.130 | H | H | H | H | CN | H |
| 1.131 | H | H | H | H | $CH_2SCH_3$ | H |
| 1.132 | H | H | H | H | $CH_2S(O)CH_3$ | H |
| 1.133 | H | H | H | H | $CH_2SO_2CH_3$ | H |
| 1.134 | H | H | H | H | $CH_2SCH_2CH_3$ | H |
| 1.135 | H | H | H | H | $CH_2S(O)CH_2CH_3$ | H |
| 1.136 | H | H | H | H | $CH_2SO_2CH_2CH_3$ | H |
| 1.137 | H | H | H | H | $OCH_3$ | H |
| 1.138 | H | H | H | H | $OCH_2CH_3$ | H |
| 1.139 | H | H | H | H | $CH(OCH_3)_2$ | H |
| 1.140 | H | H | H | H | $CH(OCH_2CH_3)_2$ | H |
| 1.141 | H | H | H | H | cyclopropyl | H |
| 1.142 | H | H | H | H | cyclobutyl | H |
| 1.143 | H | H | H | H | cyclopentyl | H |
| 1.144 | H | H | H | H | cyclohexyl | H |
| 1.145 | H | H | H | H | F | H |
| 1.146 | H | H | H | H | Cl | H |
| 1.147 | H | H | H | H | Br | H |
| 1.148 | H | H | H | H | I | H |
| 1.149 | H | H | H | H | OH | H |
| 1.150 | H | H | H | H | phenyl | H |
| 1.151 | H | H | H | H | 2-acetylphenyl | H |
| 1.152 | H | H | H | H | 3-acetylphenyl | H |
| 1.153 | H | H | H | H | 4-acetylphenyl | H |
| 1.154 | H | H | H | H | 2-chlorophenyl | H |
| 1.155 | H | H | H | H | 3-chlorophenyl | H |
| 1.156 | H | H | H | H | 4-chlorophenyl | H |
| 1.157 | H | H | H | H | 2-cyanophenyl | H |
| 1.158 | H | H | H | H | 3-cyanophenyl | H |
| 1.159 | H | H | H | H | 4-cyanophenyl | H |
| 1.160 | H | H | H | H | 2-fluorophenyl | H |
| 1.161 | H | H | H | H | 3-fluorophenyl | H |
| 1.162 | H | H | H | H | 4-fluorophenyl | H |
| 1.163 | H | H | H | H | 2-methoxyphenyl | H |
| 1.164 | H | H | H | H | 3-methoxyphenyl | H |
| 1.165 | H | H | H | H | 4-methoxyphenyl | H |
| 1.166 | H | H | H | H | 2-methylphenyl | H |
| 1.167 | H | H | H | H | 3-methylphenyl | H |
| 1.168 | H | H | H | H | 4-methylphenyl | H |
| 1.169 | H | H | H | H | 2-nitrophenyl | H |
| 1.170 | H | H | H | H | 3-nitrophenyl | H |
| 1.171 | H | H | H | H | 4-nitrophenyl | H |
| 1.172 | H | H | H | H | 2-thiomethylphenyl | H |
| 1.173 | H | H | H | H | 3-thiomethylphenyl | H |
| 1.174 | H | H | H | H | 4-thiomethylphenyl | H |
| 1.175 | H | H | H | H | 2-trifluoromethoxyphenyl | H |
| 1.176 | H | H | H | H | 3-trifluoromethoxyphenyl | H |
| 1.177 | H | H | H | H | 4-trifluoromethoxyphenyl | H |
| 1.178 | H | H | H | H | 2-trifluoromethylphenyl | H |
| 1.179 | H | H | H | H | 3-trifluoromethylphenyl | H |
| 1.180 | H | H | H | H | 4-trifluoromethylphenyl | H |
| 1.181 | H | H | H | H | 2,3-dichlorophenyl | H |
| 1.182 | H | H | H | H | 2,4-dichlorophenyl | H |
| 1.183 | H | H | H | H | 2,5-dichlorophenyl | H |
| 1.184 | H | H | H | H | 2,6-dichlorophenyl | H |

TABLE 1-continued

| | R⁶ | R⁷ | R⁸ | R⁹ | R¹⁰ | R¹¹ |
|---|---|---|---|---|---|---|
| 1.185 | H | H | H | H | 3,4-dichlorophenyl | H |
| 1.186 | H | H | H | H | 3,5-dichlorophenyl | H |
| 1.187 | H | H | H | H | 2,3-difluorophenyl | H |
| 1.188 | H | H | H | H | 2,4-difluorophenyl | H |
| 1.189 | H | H | H | H | 2,5-difluorophenyl | H |
| 1.190 | H | H | H | H | 2,6-difluorophenyl | H |
| 1.191 | H | H | H | H | 3,4-difluorophenyl | H |
| 1.192 | H | H | H | H | 3,5-difluorophenyl | H |
| 1.193 | H | H | H | H | 2,4,6-trifluorophenyl | H |
| 1.194 | H | H | H | H | 2,4-dimethylphenyl | H |
| 1.195 | H | H | H | H | 2,4,6-trimethylphenyl | H |
| 1.196 | H | H | H | H | 3,4,5-trimethoxyphenyl | h |
| 1.197 | H | H | H | H | 2-chloro-3-cyanophenyl | H |
| 1.198 | H | H | H | H | 2-chloro-4-cyanophenyl | H |
| 1.199 | H | H | H | H | 2-chloro-5-cyanophenyl | H |
| 1.200 | H | H | H | H | 2-chloro-6-cyanophenyl | H |
| 1.201 | H | H | H | H | 3-chloro-2-cyanophenyl | H |
| 1.202 | H | H | H | H | 3-chloro-4-cyanophenyl | H |
| 1.203 | H | H | H | H | 3-chloro-5-cyanophenyl | H |
| 1.204 | H | H | H | H | 5-chloro-2-cyanophenyl | H |
| 1.205 | H | H | H | H | 4-chloro-2-cyanophenyl | H |
| 1.206 | H | H | H | H | 4-chloro-3-cyanophenyl | H |
| 1.207 | H | H | H | H | 2-chloro-3-fluorophenyl | H |
| 1.208 | H | H | H | H | 2-chloro-4-fluorophenyl | H |
| 1.209 | H | H | H | H | 2-chloro-5-fluorophenyl | H |
| 1.210 | H | H | H | H | 2-chloro-6-fluorophenyl | H |
| 1.211 | H | H | H | H | 3-chloro-2-fluorophenyl | H |
| 1.212 | H | H | H | H | 3-chloro-4-fluorophenyl | H |
| 1.213 | H | H | H | H | 3-chloro-5-fluorophenyl | H |
| 1.214 | H | H | H | H | 5-chloro-2-fluorophenyl | H |
| 1.215 | H | H | H | H | 4-chloro-2-fluorophenyl | H |
| 1.216 | H | H | H | H | 4-chloro-3-fluorophenyl | H |
| 1.217 | H | H | H | H | 2-chloro-3-methylphenyl | H |
| 1.218 | H | H | H | H | 2-chloro-4-methylphenyl | H |
| 1.219 | H | H | H | H | 2-chloro-5-methylphenyl | H |
| 1.220 | H | H | H | H | 2-chloro-6-methylphenyl | H |
| 1.221 | H | H | H | H | 3-chloro-2-methylphenyl | H |
| 1.222 | H | H | H | H | 3-chloro-4-methylphenyl | H |
| 1.223 | H | H | H | H | 3-chloro-5-methylphenyl | H |
| 1.224 | H | H | H | H | 5-chloro-2-methylphenyl | H |
| 1.225 | H | H | H | H | 4-chloro-2-methylphenyl | H |
| 1.226 | H | H | H | H | 4-chloro-3-methylphenyl | H |
| 1.227 | H | H | H | H | 2-cyano-3-fluorophenyl | H |
| 1.228 | H | H | H | H | 2-cyano-4-fluorophenyl | H |
| 1.229 | H | H | H | H | 2-cyano-5-fluorophenyl | H |
| 1.230 | H | H | H | H | 2-cyano-6-fluorophenyl | H |
| 1.231 | H | H | H | H | 3-cyano-2-fluorophenyl | H |
| 1.232 | H | H | H | H | 3-cyano-4-fluorophenyl | H |
| 1.233 | H | H | H | H | 3-cyano-5-fluorophenyl | H |
| 1.234 | H | H | H | H | 5-cyano-2-fluorophenyl | H |
| 1.235 | H | H | H | H | 4-cyano-2-fluorophenyl | H |
| 1.236 | H | H | H | H | 4-cyano-3-fluorophenyl | H |
| 1.237 | H | H | H | H | 2-fluoro-3-methylphenyl | H |
| 1.238 | H | H | H | H | 2-fluoro-4-methylphenyl | H |
| 1.239 | H | H | H | H | 2-fluoro-5-methylphenyl | H |
| 1.240 | H | H | H | H | 2-fluoro-6-methylphenyl | H |
| 1.241 | H | H | H | H | 3-fluoro-2-methylphenyl | H |
| 1.242 | H | H | H | H | 3-fluoro-4-methylphenyl | H |
| 1.243 | H | H | H | H | 3-fluoro-5-methylphenyl | H |
| 1.244 | H | H | H | H | 5-fluoro-2-methylphenyl | H |
| 1.245 | H | H | H | H | 4-fluoro-2-methylphenyl | H |
| 1.246 | H | H | H | H | 4-fluoro-3-methylphenyl | H |
| 1.247 | H | H | H | H | pyridin-2-yl | H |
| 1.248 | H | H | H | H | pyridin-3-yl | H |
| 1.249 | H | H | H | H | pyridin-4-yl | H |
| 1.250 | H | H | H | H | 3-chloropyridin-2-yl | H |
| 1.251 | H | H | H | H | 4-chloropyridin-2-yl | H |
| 1.252 | H | H | H | H | 5-chloropyridin-2-yl | H |
| 1.253 | H | H | H | H | 6-chloropyridin-2-yl | H |
| 1.254 | H | H | H | H | 2-chloropyridin-3-yl | H |
| 1.255 | H | H | H | H | 4-chloropyridin-3-yl | H |
| 1.256 | H | H | H | H | 5-chloropyridin-3-yl | H |
| 1.257 | H | H | H | H | 2-chloropyridin-4-yl | H |
| 1.258 | H | H | H | H | 3-chloropyridin-4-yl | H |
| 1.259 | H | H | H | H | 2-chloropyridin-5-yl | H |
| 1.260 | H | H | H | H | 3-cyanopyridin-2-yl | H |
| 1.261 | H | H | H | H | 4-cyanopyridin-2-yl | H |
| 1.262 | H | H | H | H | 5-cyanopyridin-2-yl | H |

TABLE 1-continued

|  | R⁶ | R⁷ | R⁸ | R⁹ | R¹⁰ | R¹¹ |
|---|---|---|---|---|---|---|
| 1.263 | H | H | H | H | 6-cyanopyridin-2-yl | H |
| 1.264 | H | H | H | H | 2-cyanopyridin-3-yl | H |
| 1.265 | H | H | H | H | 4-cyanopyridin-3-yl | H |
| 1.266 | H | H | H | H | 5-cyanopyridin-3-yl | H |
| 1.267 | H | H | H | H | 2-cyanopyridin-5-yl | H |
| 1.268 | H | H | H | H | 3-fluoropyridin-2-yl | H |
| 1.269 | H | H | H | H | 4-fluoropyridin-2-yl | H |
| 1.270 | H | H | H | H | 5-fluoropyridin-2-yl | H |
| 1.271 | H | H | H | H | 6-fluoropyridin-2-yl | H |
| 1.272 | H | H | H | H | 2-fluoropyridin-3-yl | H |
| 1.273 | H | H | H | H | 4-fluoropyridin-3-yl | H |
| 1.274 | H | H | H | H | 5-fluoropyridin-3-yl | H |
| 1.275 | H | H | H | H | 2-fluoropyridin-5-yl | H |
| 1.276 | H | H | H | H | 3-nitropyridin-2-yl | H |
| 1.277 | H | H | H | H | 4-nitropyridin-2-yl | H |
| 1.278 | H | H | H | H | 5-nitropyridin-2-yl | H |
| 1.279 | H | H | H | H | 6-nitropyridin-2-yl | H |
| 1.280 | H | H | H | H | 2-nitropyridin-3-yl | H |
| 1.281 | H | H | H | H | 4-nitropyridin-3-yl | H |
| 1.282 | H | H | H | H | 5-nitropyridin-3-yl | H |
| 1.283 | H | H | H | H | 2-nitropyridin-5-yl | H |
| 1.284 | H | H | H | H | 3-trifluoromethylpyridin-2-yl | H |
| 1.285 | H | H | H | H | 4-trifluoromethylpyridin-2-yl | H |
| 1.286 | H | H | H | H | 5-trifluoromethylpyridin-2-yl | H |
| 1.287 | H | H | H | H | 6-trifluoromethylpyridin-2-yl | H |
| 1.288 | H | H | H | H | 2-trifluoromethylpyridin-3-yl | H |
| 1.289 | H | H | H | H | 4-trifluoromethylpyridin-3-yl | H |
| 1.290 | H | H | H | H | 5-trifluoromethylpyridin-3-yl | H |
| 1.291 | H | H | H | H | 2-trifluoromethylpyridin-5-yl | H |
| 1.292 | H | H | H | H | 2,6-bis(trifluoromethyl)-pyridin-3-yl | H |
| 1.293 | H | H | H | H | 2,6-bis(trifluoromethyl)-pyridin-4-yl | H |
| 1.294 | H | H | H | H | 3,5-bis(trifluoromethyl)-pyridin-2-yl | H |
| 1.295 | H | H | H | H | 2-thienyl | H |
| 1.296 | H | H | H | H | 3-thienyl | H |
| 1.297 | H | H | H | H | 5-cyanothien-2-yl | H |
| 1.298 | H | H | H | H | 2-furyl | H |
| 1.299 | H | H | H | H | 3-furyl | H |
| 1.300 | H | H | H | H | 1-methyl-1,2,3-triazol-4-yl | H |
| 1.301 | H | H | H | H | 2-methylthiopyrimidin-4-yl | H |
| 1.302 | H | H | H | H | 5-methyl-2-methyl-thiopyrimidin-4-yl | H |
| 1.303 | H | H | H | H | pyrazin-2-yl | H |
| 1.304 | H | H | H | H | 3,6-dimethylpyrazin-2-yl | H |
| 1.305 | H | H | H | H | 3-cyanopyrazin-2-yl | H |
| 1.306 | H | H | H | H | quinolin-2-yl | H |
| 1.307 | H | H | H | H | 3-ethylquinolin-2-yl | H |
| 1.308 | H | H | H | H | benzyl | H |
| 1.309 | H | H | H | H | 4-fluorobenzyl | H |
| 1.310 | H | H | H | H | 4-chlorobenzyl | H |
| 1.311 | H | H | H | H | 4-methylbenzyl | H |
| 1.312 | H | H | H | H | 2,4-dimethylbenzyl | H |
| 1.313 | H | H | H | H | 2,4,6-trimethylbenzyl | H |
| 1.314 | H | H | H | H | $CH_3$ | $CH_3$ |
| 1.315 | H | H | H | H | $CH_2CH_3$ | $CH_3$ |
| 1.316 | H | H | H | H | n-propyl | $CH_3$ |
| 1.317 | H | H | H | H | isopropyl | $CH_3$ |
| 1.318 | H | H | H | H | n-butyl | $CH_3$ |
| 1.319 | H | H | H | H | isobutyl | $CH_3$ |
| 1.320 | H | H | H | H | sec-butyl | $CH_3$ |
| 1.321 | H | H | H | H | tert-butyl | $CH_3$ |
| 1.322 | H | H | H | H | vinyl | $CH_3$ |
| 1.323 | H | H | H | H | ethynyl | $CH_3$ |
| 1.324 | H | H | H | H | trimethylsilylethynyl | $CH_3$ |
| 1.325 | H | H | H | H | $CH_2OH$ | $CH_3$ |
| 1.326 | H | H | H | H | $CH_2OCH_3$ | $CH_3$ |
| 1.327 | H | H | H | H | $CH_2OCH_2CH_3$ | $CH_3$ |
| 1.328 | H | H | H | H | $CH_2OCH_2OCH_3$ | $CH_3$ |
| 1.329 | H | H | H | H | $CH_2OCH_2OCH_2CH_3$ | $CH_3$ |
| 1.330 | H | H | H | H | $CH_2OCH_2CH_2OCH_3$ | $CH_3$ |
| 1.331 | H | H | H | H | CHO | $CH_3$ |
| 1.332 | H | H | H | H | $COCH_3$ | $CH_3$ |
| 1.333 | H | H | H | H | $CO_2H$ | $CH_3$ |
| 1.337 | H | H | H | H | $CO_2CH_3$ | $CH_3$ |
| 1.335 | H | H | H | H | $CO_2CH_2CH_3$ | $CH_3$ |
| 1.336 | H | H | H | H | $CONH_2$ | $CH_3$ |

TABLE 1-continued

| | R⁶ | R⁷ | R⁸ | R⁹ | R¹⁰ | R¹¹ |
|---|---|---|---|---|---|---|
| 1.337 | H | H | H | H | CONHCH₃ | CH₃ |
| 1.338 | H | H | H | H | CONHCH₂CH₃ | CH₃ |
| 1.339 | H | H | H | H | CON(CH₃)₂ | CH₃ |
| 1.340 | H | H | H | H | CON(CH₂—CH₃)₂ | CH₃ |
| 1.341 | H | H | H | H | CON(CH₃)OCH₃ | CH₃ |
| 1.342 | H | H | H | H | CH=NOH | CH₃ |
| 1.343 | H | H | H | H | CH=N—OCH₃ | CH₃ |
| 1.344 | H | H | H | H | CH=N—OCH₂CH₃ | CH₃ |
| 1.345 | H | H | H | H | C(CH₃)=N—OH | CH₃ |
| 1.346 | H | H | H | H | C(CH₃)=N—OCH₃ | CH₃ |
| 1.347 | H | H | H | H | CH₂OC(O)—NHCH₃ | CH₃ |
| 1.348 | H | H | H | H | CH₂NH₂ | CH₃ |
| 1.349 | H | H | H | H | CH₂NHCHO | CH₃ |
| 1.350 | H | H | H | H | CH₂NHC(O)CH₃ | CH₃ |
| 1.351 | H | H | H | H | CH₂NHC(O)OCH₃ | CH₃ |
| 1.352 | H | H | H | H | NHCO₂CH₃ | CH₃ |
| 1.353 | H | H | H | H | NHCO₂C(CH₃)₃ | CH₃ |
| 1.354 | H | H | H | H | CH(OH)CH₃ | CH₃ |
| 1.355 | H | H | H | H | CH(CH₃)OCH₃ | CH₃ |
| 1.356 | H | H | H | H | CN | CH₃ |
| 1.357 | H | H | H | H | CH₂SCH₃ | CH₃ |
| 1.358 | H | H | H | H | CH₂S(O)CH₃ | CH₃ |
| 1.359 | H | H | H | H | CH₂SO₂CH₃ | CH₃ |
| 1.360 | H | H | H | H | CH₂SCH₂CH₃ | CH₃ |
| 1.361 | H | H | H | H | CH₂S(O)CH₂CH₃ | CH₃ |
| 1.362 | H | H | H | H | CH₂SO₂CH₂CH₃ | CH₃ |
| 1.363 | H | H | H | H | OCH₃ | CH₃ |
| 1.364 | H | H | H | H | OCH₂CH₃ | CH₃ |
| 1.365 | H | H | H | H | CH(OCH₃)₂ | CH₃ |
| 1.366 | H | H | H | H | CH(OCH₂CH₃)₂ | CH₃ |
| 1.367 | H | H | H | H | cyclopropyl | CH₃ |
| 1.368 | H | H | H | H | cyclobutyl | CH₃ |
| 1.369 | H | H | H | H | cyclopentyl | CH₃ |
| 1.370 | H | H | H | H | cyclohexyl | CH₃ |
| 1.371 | H | H | H | H | F | CH₃ |
| 1.372 | H | H | H | H | Cl | CH₃ |
| 1.373 | H | H | H | H | Br | CH₃ |
| 1.374 | H | H | H | H | I | CH₃ |
| 1.375 | H | H | H | H | OH | CH₃ |
| 1.376 | H | H | H | H | phenyl | CH₃ |
| 1.377 | H | H | H | H | 2-acetylphenyl | CH₃ |
| 1.378 | H | H | H | H | 3-acetylphenyl | CH₃ |
| 1.379 | H | H | H | H | 4-acetylphenyl | CH₃ |
| 1.380 | H | H | H | H | 2-chlorophenyl | CH₃ |
| 1.381 | H | H | H | H | 3-chlorophenyl | CH₃ |
| 1.382 | H | H | H | H | 4-chlorophenyl | CH₃ |
| 1.383 | H | H | H | H | 2-cyanophenyl | CH₃ |
| 1.384 | H | H | H | H | 3-cyanophenyl | CH₃ |
| 1.385 | H | H | H | H | 4-cyanophenyl | CH₃ |
| 1.386 | H | H | H | H | 2-fluorophenyl | CH₃ |
| 1.387 | H | H | H | H | 3-fluorophenyl | CH₃ |
| 1.388 | H | H | H | H | 4-fluorophenyl | CH₃ |
| 1.389 | H | H | H | H | 2-methoxyphenyl | CH₃ |
| 1.390 | H | H | H | H | 3-methoxyphenyl | CH₃ |
| 1.391 | H | H | H | H | 4-methoxyphenyl | CH₃ |
| 1.392 | H | H | H | H | 2-methylphenyl | CH₃ |
| 1.393 | H | H | H | H | 3-methylphenyl | CH₃ |
| 1.394 | H | H | H | H | 4-methylphenyl | CH₃ |
| 1.395 | H | H | H | H | 2-nitrophenyl | CH₃ |
| 1.396 | H | H | H | H | 3-nitrophenyl | CH₃ |
| 1.397 | H | H | H | H | 4-nitrophenyl | CH₃ |
| 1.398 | H | H | H | H | 2-thiomethylphenyl | CH₃ |
| 1.399 | H | H | H | H | 3-thiomethylphenyl | CH₃ |
| 1.400 | H | H | H | H | 4-thiomethylphenyl | CH₃ |
| 1.401 | H | H | H | H | 2-trifluoromethoxyphenyl | CH₃ |
| 1.402 | H | H | H | H | 3-trifluoromethoxyphenyl | CH₃ |
| 1.403 | H | H | H | H | 4-trifluoromethoxyphenyl | CH₃ |
| 1.404 | H | H | H | H | 2-trifluoromethylphenyl | CH₃ |
| 1.405 | H | H | H | H | 3-trifluoromethylphenyl | CH₃ |
| 1.406 | H | H | H | H | 4-trifluoromethylphenyl | CH₃ |
| 1.407 | H | H | H | H | 2,3-dichlorophenyl | CH₃ |
| 1.408 | H | H | H | H | 2,4-dichlorophenyl | CH₃ |
| 1.409 | H | H | H | H | 2,5-dichlorophenyl | CH₃ |
| 1.410 | H | H | H | H | 2,6-dichlorophenyl | CH₃ |
| 1.411 | H | H | H | H | 3,4-dichlorophenyl | CH₃ |
| 1.412 | H | H | H | H | 3,5-dichlorophenyl | CH₃ |
| 1.413 | H | H | H | H | 2,3-difluorophenyl | CH₃ |
| 1.414 | H | H | H | H | 2,4-difluorophenyl | CH₃ |

TABLE 1-continued

| | R⁶ | R⁷ | R⁸ | R⁹ | R¹⁰ | R¹¹ |
|---|---|---|---|---|---|---|
| 1.415 | H | H | H | H | 2,5-difluorophenyl | CH₃ |
| 1.416 | H | H | H | H | 2,6-difluorophenyl | CH₃ |
| 1.417 | H | H | H | H | 3,4-difluorophenyl | CH₃ |
| 1.418 | H | H | H | H | 3,5-difluorophenyl | CH₃ |
| 1.419 | H | H | H | H | 2,4,6-trifluorophenyl | CH₃ |
| 1.420 | H | H | H | H | 2,4-dimethylphenyl | CH₃ |
| 1.421 | H | H | H | H | 2,4,6-trimethylphenyl | CH₃ |
| 1.422 | H | H | H | H | 3,4,5-trimethoxyphenyl | CH₃ |
| 1.423 | H | H | H | H | 2-chloro-3-cyanophenyl | CH₃ |
| 1.424 | H | H | H | H | 2-chloro-4-cyanophenyl | CH₃ |
| 1.425 | H | H | H | H | 2-chloro-5-cyanophenyl | CH₃ |
| 1.426 | H | H | H | H | 2-chloro-6-cyanophenyl | CH₃ |
| 1.427 | H | H | H | H | 3-chloro-2-cyanophenyl | CH₃ |
| 1.428 | H | H | H | H | 3-chloro-4-cyanophenyl | CH₃ |
| 1.429 | H | H | H | H | 3-chloro-5-cyanophenyl | CH₃ |
| 1.430 | H | H | H | H | 5-chloro-2-cyanophenyl | CH₃ |
| 1.431 | H | H | H | H | 4-chloro-2-cyanophenyl | CH₃ |
| 1.432 | H | H | H | H | 4-chloro-3-cyanophenyl | CH₃ |
| 1.433 | H | H | H | H | 2-chloro-3-fluorophenyl | CH₃ |
| 1.434 | H | H | H | H | 2-chloro-4-fluorophenyl | CH₃ |
| 1.435 | H | H | H | H | 2-chloro-5-fluorophenyl | CH₃ |
| 1.436 | H | H | H | H | 2-chloro-6-fluorophenyl | CH₃ |
| 1.437 | H | H | H | H | 3-chloro-2-fluorophenyl | CH₃ |
| 1.438 | H | H | H | H | 3-chloro-4-fluorophenyl | CH₃ |
| 1.439 | H | H | H | H | 3-chloro-5-fluorophenyl | CH₃ |
| 1.440 | H | H | H | H | 5-chloro-2-fluorophenyl | CH₃ |
| 1.441 | H | H | H | H | 4-chloro-2-fluorophenyl | CH₃ |
| 1.442 | H | H | H | H | 4-chloro-3-fluorophenyl | CH₃ |
| 1.443 | H | H | H | H | 2-chloro-3-methylphenyl | CH₃ |
| 1.444 | H | H | H | H | 2-chloro-4-methylphenyl | CH₃ |
| 1.445 | H | H | H | H | 2-chloro-5-methylphenyl | CH₃ |
| 1.446 | H | H | H | H | 2-chloro-6-methylphenyl | CH₃ |
| 1.447 | H | H | H | H | 3-chloro-2-methylphenyl | CH₃ |
| 1.448 | H | H | H | H | 3-chloro-4-methylphenyl | CH₃ |
| 1.449 | H | H | H | H | 3-chloro-5-methylphenyl | CH₃ |
| 1.450 | H | H | H | H | 5-chloro-2-methylphenyl | CH₃ |
| 1.451 | H | H | H | H | 4-chloro-2-methylphenyl | CH₃ |
| 1.452 | H | H | H | H | 4-chloro-3-methylphenyl | CH₃ |
| 1.453 | H | H | H | H | 2-cyano-3-fluorophenyl | CH₃ |
| 1.454 | H | H | H | H | 2-cyano-4-fluorophenyl | CH₃ |
| 1.455 | H | H | H | H | 2-cyano-5-fluorophenyl | CH₃ |
| 1.456 | H | H | H | H | 2-cyano-6-fluorophenyl | CH₃ |
| 1.457 | H | H | H | H | 3-cyano-2-fluorophenyl | CH₃ |
| 1.458 | H | H | H | H | 3-cyano-4-fluorophenyl | CH₃ |
| 1.459 | H | H | H | H | 3-cyano-5-fluorophenyl | CH₃ |
| 1.460 | H | H | H | H | 5-cyano-2-fluorophenyl | CH₃ |
| 1.461 | H | H | H | H | 4-cyano-2-fluorophenyl | CH₃ |
| 1.462 | H | H | H | H | 4-cyano-3-fluorophenyl | CH₃ |
| 1.463 | H | H | H | H | 2-fluoro-3-methylphenyl | CH₃ |
| 1.464 | H | H | H | H | 2-fluoro-4-methylphenyl | CH₃ |
| 1.465 | H | H | H | H | 2-fluoro-5-methylphenyl | CH₃ |
| 1.466 | H | H | H | H | 2-fluoro-6-methylphenyl | CH₃ |
| 1.467 | H | H | H | H | 3-fluoro-2-methylphenyl | CH₃ |
| 1.468 | H | H | H | H | 3-fluoro-4-methylphenyl | CH₃ |
| 1.469 | H | H | H | H | 3-fluoro-5-methylphenyl | CH₃ |
| 1.470 | H | H | H | H | 5-fluoro-2-methylphenyl | CH₃ |
| 1.471 | H | H | H | H | 4-fluoro-2-methylphenyl | CH₃ |
| 1.472 | H | H | H | H | 4-fluoro-3-methylphenyl | CH₃ |
| 1.473 | H | H | H | H | pyridin-2-yl | CH₃ |
| 1.474 | H | H | H | H | pyridin-3-yl | CH₃ |
| 1.475 | H | H | H | H | pyridin-4-yl | CH₃ |
| 1.476 | H | H | H | H | 3-chloropyridin-2-yl | CH₃ |
| 1.477 | H | H | H | H | 4-chloropyridin-2-yl | CH₃ |
| 1.478 | H | H | H | H | 5-chloropyridin-2-yl | CH₃ |
| 1.479 | H | H | H | H | 6-chloropyridin-2-yl | CH₃ |
| 1.480 | H | H | H | H | 2-chloropyridin-3-yl | CH₃ |
| 1.481 | H | H | H | H | 4-chloropyridin-3-yl | CH₃ |
| 1.482 | H | H | H | H | 5-chloropyridin-3-yl | CH₃ |
| 1.483 | H | H | H | H | 2-chloropyridin-4-yl | CH₃ |
| 1.484 | H | H | H | H | 3-chloropyridin-4-yl | CH₃ |
| 1.485 | H | H | H | H | 2-chloropyridin-5-yl | CH₃ |
| 1.486 | H | H | H | H | 3-cyanopyridin-2-yl | CH₃ |
| 1.487 | H | H | H | H | 4-cyanopyridin-2-yl | CH₃ |
| 1.488 | H | H | H | H | 5-cyanopyridin-2-yl | CH₃ |
| 1.489 | H | H | H | H | 6-cyanopyridin-2-yl | CH₃ |
| 1.490 | H | H | H | H | 2-cyanopyridin-3-yl | CH₃ |
| 1.491 | H | H | H | H | 4-cyanopyridin-3-yl | CH₃ |
| 1.492 | H | H | H | H | 5-cyanopyridin-3-yl | CH₃ |

TABLE 1-continued

| | R⁶ | R⁷ | R⁸ | R⁹ | R¹⁰ | R¹¹ |
|---|---|---|---|---|---|---|
| 1.493 | H | H | H | H | 2-cyanopyridin-5-yl | CH₃ |
| 1.494 | H | H | H | H | 3-fluoropyridin-2-yl | CH₃ |
| 1.495 | H | H | H | H | 4-fluoropyridin-2-yl | CH₃ |
| 1.496 | H | H | H | H | 5-fluoropyridin-2-yl | CH₃ |
| 1.497 | H | H | H | H | 6-fluoropyridin-2-yl | CH₃ |
| 1.498 | H | H | H | H | 2-fluoropyridin-3-yl | CH₃ |
| 1.499 | H | H | H | H | 4-fluoropyridin-3-yl | CH₃ |
| 1.500 | H | H | H | H | 5-fluoropyridin-3-yl | CH₃ |
| 1.501 | H | H | H | H | 2-fluoropyridin-5-yl | CH₃ |
| 1.502 | H | H | H | H | 3-nitropyridin-2-yl | CH₃ |
| 1.503 | H | H | H | H | 4-nitropyridin-2-yl | CH₃ |
| 1.504 | H | H | H | H | 5-nitropyridin-2-yl | CH₃ |
| 1.505 | H | H | H | H | 6-nitropyridin-2-yl | CH₃ |
| 1.506 | H | H | H | H | 2-nitropyridin-3-yl | CH₃ |
| 1.507 | H | H | H | H | 4-nitropyridin-3-yl | CH₃ |
| 1.508 | H | H | H | H | 5-nitropyridin-3-yl | CH₃ |
| 1.509 | H | H | H | H | 2-nitropyridin-5-yl | CH₃ |
| 1.510 | H | H | H | H | 3-trifluoromethylpyridin-2-yl | CH₃ |
| 1.511 | H | H | H | H | 4-trifluoromethylpyridin-2-yl | CH₃ |
| 1.512 | H | H | H | H | 5-trifluoromethylpyridin-2-yl | CH₃ |
| 1.513 | H | H | H | H | 6-trifluoromethylpyridin-2-yl | CH₃ |
| 1.514 | H | H | H | H | 2-trifluoromethylpyridin-3-yl | CH₃ |
| 1.515 | H | H | H | H | 4-trifluoromethylpyridin-3-yl | CH₃ |
| 1.516 | H | H | H | H | 5-trifluoromethylpyridin-3-yl | CH₃ |
| 1.517 | H | H | H | H | 2-trifluoromethylpyridin-5-yl | CH₃ |
| 1.518 | H | H | H | H | 2,6-bis(trifluoromethyl)pyridin-3-yl | CH₃ |
| 1.519 | H | H | H | H | 2,6-bis(trifluoromethyl)pyridin-4-yl | CH₃ |
| 1.520 | H | H | H | H | 3,5-bis(trifluoromethyl)-pyridin-2-yl | CH₃ |
| 1.521 | H | H | H | H | 2-thienyl | CH₃ |
| 1.522 | H | H | H | H | 3-thienyl | CH₃ |
| 1.523 | H | H | H | H | 5-cyanothien-2-yl | CH₃ |
| 1.524 | H | H | H | H | 2-furyl | CH₃ |
| 1.525 | H | H | H | H | 3-furyl | CH₃ |
| 1.526 | H | H | H | H | 1-methyl-1,2,3-triazol-4-yl | CH₃ |
| 1.527 | H | H | H | H | 2-methylthiopyrimidin-4-yl | CH₃ |
| 1.528 | H | H | H | H | 5-methyl-2-methyl-thiopyrimidin-4-yl | CH₃ |
| 1.529 | H | H | H | H | pyrazin-2-yl | CH₃ |
| 1.530 | H | H | H | H | 3,6-dimethylpyrazin-2-yl | CH₃ |
| 1.531 | H | H | H | H | 3-cyanopyrazin-2-yl | CH₃ |
| 1.532 | H | H | H | H | quinolin-2-yl | CH₃ |
| 1.533 | H | H | H | H | 3-ethylquinolin-2-yl | CH₃ |
| 1.534 | H | H | H | H | benzyl | CH₃ |
| 1.535 | H | H | H | H | 4-fluorobenzyl | CH₃ |
| 1.536 | H | H | H | H | 4-chlorobenzyl | CH₃ |
| 1.537 | H | H | H | H | 4-methylbenzyl | CH₃ |
| 1.538 | H | H | H | H | 2,4-dimethylbenzyl | CH₃ |
| 1.539 | H | H | H | H | 2,4,6-trimethylbenzyl | CH₃ |
| 1.540 | CH₃ | H | H | H | CH₃ | H |
| 1.541 | CH₃ | H | H | H | CH₂CH₃ | H |
| 1.542 | CH₃ | H | H | H | n-propyl | H |
| 1.543 | CH₃ | H | H | H | isopropyl | H |
| 1.544 | CH₃ | H | H | H | n-butyl | H |
| 1.545 | CH₃ | H | H | H | isobutyl | H |
| 1.546 | CH₃ | H | H | H | sec-butyl | H |
| 1.547 | CH₃ | H | H | H | tert-butyl | H |
| 1.548 | CH₃ | H | H | H | vinyl | H |
| 1.549 | CH₃ | H | H | H | ethynyl | H |
| 1.550 | CH₃ | H | H | H | trimethylsilylethynyl | H |
| 1.551 | CH₃ | H | H | H | CH₂OH | H |
| 1.552 | CH₃ | H | H | H | CH₂OCH₃ | H |
| 1.553 | CH₃ | H | H | H | CH₂OCH₂CH₃ | H |
| 1.554 | CH₃ | H | H | H | CH₂OCH₂OCH₃ | H |
| 1.555 | CH₃ | H | H | H | CH₂OCH₂OCH₂CH₃ | H |
| 1.556 | CH₃ | H | H | H | CH₂OCH₂CH₂OCH₃ | H |
| 1.557 | CH₃ | H | H | H | CHO | H |
| 1.558 | CH₃ | H | H | H | COCH₃ | H |
| 1.559 | CH₃ | H | H | H | CO₂H | H |
| 1.560 | CH₃ | H | H | H | CO₂CH₃ | H |
| 1.561 | CH₃ | H | H | H | CO₂CH₂CH₃ | H |
| 1.562 | CH₃ | H | H | H | CONH₂ | H |
| 1.563 | CH₃ | H | H | H | CONHCH₃ | H |
| 1.564 | CH₃ | H | H | H | CONHCH₂CH₃ | H |
| 1.565 | CH₃ | H | H | H | CON(CH₃)₂ | H |
| 1.566 | CH₃ | H | H | H | CON(CH₂—CH₃)₂ | H |

TABLE 1-continued

| | $R^6$ | $R^7$ | $R^8$ | $R^9$ | $R^{10}$ | $R^{11}$ |
|---|---|---|---|---|---|---|
| 1.567 | $CH_3$ | H | H | H | $CON(CH_3)OCH_3$ | H |
| 1.568 | $CH_3$ | H | H | H | CH=NOH | H |
| 1.569 | $CH_3$ | H | H | H | CH=N—$OCH_3$ | H |
| 1.570 | $CH_3$ | H | H | H | CH=N—$OCH_2CH_3$ | H |
| 1.571 | $CH_3$ | H | H | H | $C(CH_3)$=N—OH | H |
| 1.572 | $CH_3$ | H | H | H | $C(CH_3)$=N—$OCH_3$ | H |
| 1.573 | $CH_3$ | H | H | H | $CH_2OC(O)$—$NHCH_3$ | H |
| 1.574 | $CH_3$ | H | H | H | $CH_2NH_2$ | H |
| 1.575 | $CH_3$ | H | H | H | $CH_2NHCHO$ | H |
| 1.576 | $CH_3$ | H | H | H | $CH_2NHC(O)CH_3$ | H |
| 1.577 | $CH_3$ | H | H | H | $CH_2NHC(O)OCH_3$ | H |
| 1.578 | $CH_3$ | H | H | H | $NHCO_2CH_3$ | H |
| 1.579 | $CH_3$ | H | H | H | $NHCO_2C(CH_3)_3$ | H |
| 1.580 | $CH_3$ | H | H | H | $CH(OH)CH_3$ | H |
| 1.581 | $CH_3$ | H | H | H | $CH(CH_3)OCH_3$ | H |
| 1.582 | $CH_3$ | H | H | H | CN | H |
| 1.583 | $CH_3$ | H | H | H | $CH_2SCH_3$ | H |
| 1.584 | $CH_3$ | H | H | H | $CH_2S(O)CH_3$ | H |
| 1.585 | $CH_3$ | H | H | H | $CH_2SO_2CH_3$ | H |
| 1.586 | $CH_3$ | H | H | H | $CH_2SCH_2CH_3$ | H |
| 1.587 | $CH_3$ | H | H | H | $CH_2S(O)CH_2CH_3$ | H |
| 1.588 | $CH_3$ | H | H | H | $CH_2SO_2CH_2CH_3$ | H |
| 1.589 | $CH_3$ | H | H | H | $OCH_3$ | H |
| 1.590 | $CH_3$ | H | H | H | $OCH_2CH_3$ | H |
| 1.591 | $CH_3$ | H | H | H | $CH(OCH_3)_2$ | H |
| 1.592 | $CH_3$ | H | H | H | $CH(OCH_2CH_3)_2$ | H |
| 1.593 | $CH_3$ | H | H | H | cyclopropyl | H |
| 1.594 | $CH_3$ | H | H | H | cyclobutyl | H |
| 1.595 | $CH_3$ | H | H | H | cyclopentyl | H |
| 1.596 | $CH_3$ | H | H | H | cyclohexyl | H |
| 1.597 | $CH_3$ | H | H | H | F | H |
| 1.598 | $CH_3$ | H | H | H | Cl | H |
| 1.599 | $CH_3$ | H | H | H | Br | H |
| 1.600 | $CH_3$ | H | H | H | I | H |
| 1.601 | $CH_3$ | H | H | H | OH | H |
| 1.602 | $CH_3$ | H | H | H | phenyl | H |
| 1.603 | $CH_3$ | H | H | H | 2-acetylphenyl | H |
| 1.604 | $CH_3$ | H | H | H | 3-acetylphenyl | H |
| 1.605 | $CH_3$ | H | H | H | 4-acetylphenyl | H |
| 1.606 | $CH_3$ | H | H | H | 2-chlorophenyl | H |
| 1.607 | $CH_3$ | H | H | H | 3-chlorophenyl | H |
| 1.608 | $CH_3$ | H | H | H | 4-chlorophenyl | H |
| 1.609 | $CH_3$ | H | H | H | 2-cyanophenyl | H |
| 1.610 | $CH_3$ | H | H | H | 3-cyanophenyl | H |
| 1.611 | $CH_3$ | H | H | H | 4-cyanophenyl | H |
| 1.612 | $CH_3$ | H | H | H | 2-fluorophenyl | H |
| 1.613 | $CH_3$ | H | H | H | 3-fluorophenyl | H |
| 1.614 | $CH_3$ | H | H | H | 4-fluorophenyl | H |
| 1.615 | $CH_3$ | H | H | H | 2-methoxyphenyl | H |
| 1.616 | $CH_3$ | H | H | H | 3-methoxyphenyl | H |
| 1.617 | $CH_3$ | H | H | H | 4-methoxyphenyl | H |
| 1.618 | $CH_3$ | H | H | H | 2-methylphenyl | H |
| 1.619 | $CH_3$ | H | H | H | 3-methylphenyl | H |
| 1.620 | $CH_3$ | H | H | H | 4-methylphenyl | H |
| 1.621 | $CH_3$ | H | H | H | 2-nitrophenyl | H |
| 1.622 | $CH_3$ | H | H | H | 3-nitrophenyl | H |
| 1.623 | $CH_3$ | H | H | H | 4-nitrophenyl | H |
| 1.624 | $CH_3$ | H | H | H | 2-thiomethylphenyl | H |
| 1.625 | $CH_3$ | H | H | H | 3-thiomethylphenyl | H |
| 1.626 | $CH_3$ | H | H | H | 4-thiomethylphenyl | H |
| 1.627 | $CH_3$ | H | H | H | 2-trifluoromethoxyphenyl | H |
| 1.628 | $CH_3$ | H | H | H | 3-trifluoromethoxyphenyl | H |
| 1.629 | $CH_3$ | H | H | H | 4-trifluoromethoxyphenyl | H |
| 1.630 | $CH_3$ | H | H | H | 2-trifluoromethylphenyl | H |
| 1.631 | $CH_3$ | H | H | H | 3-trifluoromethylphenyl | H |
| 1.632 | $CH_3$ | H | H | H | 4-trifluoromethylphenyl | H |
| 1.633 | $CH_3$ | H | H | H | 2,3-dichlorophenyl | H |
| 1.634 | $CH_3$ | H | H | H | 2,4-dichlorophenyl | H |
| 1.635 | $CH_3$ | H | H | H | 2,5-dichlorophenyl | H |
| 1.636 | $CH_3$ | H | H | H | 2,6-dichlorophenyl | H |
| 1.637 | $CH_3$ | H | H | H | 3,4-dichlorophenyl | H |
| 1.638 | $CH_3$ | H | H | H | 3,5-dichlorophenyl | H |
| 1.639 | $CH_3$ | H | H | H | 2,3-difluorophenyl | H |
| 1.640 | $CH_3$ | H | H | H | 2,4-difluorophenyl | H |
| 1.641 | $CH_3$ | H | H | H | 2,5-difluorophenyl | H |
| 1.642 | $CH_3$ | H | H | H | 2,6-difluorophenyl | H |
| 1.643 | $CH_3$ | H | H | H | 3,4-difluorophenyl | H |
| 1.644 | $CH_3$ | H | H | H | 3,5-difluorophenyl | H |

TABLE 1-continued

| | R⁶ | R⁷ | R⁸ | R⁹ | R¹⁰ | R¹¹ |
|---|---|---|---|---|---|---|
| 1.645 | CH₃ | H | H | H | 2,4,6-trifluorophenyl | H |
| 1.646 | CH₃ | H | H | H | 2,4-dimethylphenyl | H |
| 1.647 | CH₃ | H | H | H | 2,4,6-trimethylphenyl | H |
| 1.648 | CH₃ | H | H | H | 3,4,5-trimethoxy-phenyl | H |
| 1.649 | CH₃ | H | H | H | 2-chloro-3-cyanophenyl | H |
| 1.650 | CH₃ | H | H | H | 2-chloro-4-cyanophenyl | H |
| 1.651 | CH₃ | H | H | H | 2-chloro-5-cyanophenyl | H |
| 1.652 | CH₃ | H | H | H | 2-chloro-6-cyanophenyl | H |
| 1.653 | CH₃ | H | H | H | 3-chloro-2-cyanophenyl | H |
| 1.654 | CH₃ | H | H | H | 3-chloro-4-cyanophenyl | H |
| 1.655 | CH₃ | H | H | H | 3-chloro-5-cyanophenyl | H |
| 1.656 | CH₃ | H | H | H | 5-chloro-2-cyanophenyl | H |
| 1.657 | CH₃ | H | H | H | 4-chloro-2-cyanophenyl | H |
| 1.658 | CH₃ | H | H | H | 4-chloro-3-cyanophenyl | H |
| 1.659 | CH₃ | H | H | H | 2-chloro-3-fluorophenyl | H |
| 1.660 | CH₃ | H | H | H | 2-chloro-4-fluorophenyl | H |
| 1.661 | CH₃ | H | H | H | 2-chloro-5-fluorophenyl | H |
| 1.662 | CH₃ | H | H | H | 2-chloro-6-fluorophenyl | H |
| 1.663 | CH₃ | H | H | H | 3-chloro-2-fluorophenyl | H |
| 1.664 | CH₃ | H | H | H | 3-chloro-4-fluorophenyl | H |
| 1.665 | CH₃ | H | H | H | 3-chloro-5-fluorophenyl | H |
| 1.666 | CH₃ | H | H | H | 5-chloro-2-fluorophenyl | H |
| 1.667 | CH₃ | H | H | H | 4-chloro-2-fluorophenyl | H |
| 1.668 | CH₃ | H | H | H | 4-chloro-3-fluorophenyl | H |
| 1.669 | CH₃ | H | H | H | 2-chloro-3-methylphenyl | H |
| 1.670 | CH₃ | H | H | H | 2-chloro-4-methylphenyl | H |
| 1.671 | CH₃ | H | H | H | 2-chloro-5-methylphenyl | H |
| 1.672 | CH₃ | H | H | H | 2-chloro-6-methylphenyl | H |
| 1.673 | CH₃ | H | H | H | 3-chloro-2-methylphenyl | H |
| 1.674 | CH₃ | H | H | H | 3-chloro-4-methylphenyl | H |
| 1.675 | CH₃ | H | H | H | 3-chloro-5-methylphenyl | H |
| 1.676 | CH₃ | H | H | H | 5-chloro-2-methylphenyl | H |
| 1.677 | CH₃ | H | H | H | 4-chloro-2-methylphenyl | H |
| 1.678 | CH₃ | H | H | H | 4-chloro-3-methylphenyl | H |
| 1.679 | CH₃ | H | H | H | 2-cyano-3-fluorophenyl | H |
| 1.680 | CH₃ | H | H | H | 2-cyano-4-fluorophenyl | H |
| 1.681 | CH₃ | H | H | H | 2-cyano-5-fluorophenyl | H |
| 1.682 | CH₃ | H | H | H | 2-cyano-6-fluorophenyl | H |
| 1.683 | CH₃ | H | H | H | 3-cyano-2-fluorophenyl | H |
| 1.684 | CH₃ | H | H | H | 3-cyano-4-fluorophenyl | H |
| 1.685 | CH₃ | H | H | H | 3-cyano-5-fluorophenyl | H |
| 1.686 | CH₃ | H | H | H | 5-cyano-2-fluorophenyl | H |
| 1.687 | CH₃ | H | H | H | 4-cyano-2-fluorophenyl | H |
| 1.688 | CH₃ | H | H | H | 4-cyano-3-fluorophenyl | H |
| 1.689 | CH₃ | H | H | H | 2-fluoro-3-methylphenyl | H |
| 1.690 | CH₃ | H | H | H | 2-fluoro-4-methylphenyl | H |
| 1.691 | CH₃ | H | H | H | 2-fluoro-5-methylphenyl | H |
| 1.692 | CH₃ | H | H | H | 2-fluoro-6-methylphenyl | H |
| 1.693 | CH₃ | H | H | H | 3-fluoro-2-methylphenyl | H |
| 1.694 | CH₃ | H | H | H | 3-fluoro-4-methylphenyl | H |
| 1.695 | CH₃ | H | H | H | 3-fluoro-5-methylphenyl | H |
| 1.696 | CH₃ | H | H | H | 5-fluoro-2-methylphenyl | H |
| 1.697 | CH₃ | H | H | H | 4-fluoro-2-methylphenyl | H |
| 1.698 | CH₃ | H | H | H | 4-fluoro-3-methylphenyl | H |
| 1.699 | CH₃ | H | H | H | pyridin-2-yl | H |
| 1.700 | CH₃ | H | H | H | pyridin-3-yl | H |
| 1.701 | CH₃ | H | H | H | pyridin-4-yl | H |
| 1.702 | CH₃ | H | H | H | 3-chloropyridin-2-yl | H |
| 1.703 | CH₃ | H | H | H | 4-chloropyridin-2-yl | H |
| 1.704 | CH₃ | H | H | H | 5-chloropyridin-2-yl | H |
| 1.705 | CH₃ | H | H | H | 6-chloropyridin-2-yl | H |
| 1.706 | CH₃ | H | H | H | 2-chloropyridin-3-yl | H |
| 1.707 | CH₃ | H | H | H | 4-chloropyridin-3-yl | H |
| 1.708 | CH₃ | H | H | H | 5-chloropyridin-3-yl | H |
| 1.709 | CH₃ | H | H | H | 2-chloropyridin-4-yl | H |
| 1.710 | CH₃ | H | H | H | 3-chloropyridin-4-yl | H |
| 1.711 | CH₃ | H | H | H | 2-chloropyridin-5-yl | H |
| 1.712 | CH₃ | H | H | H | 3-cyanopyridin-2-yl | H |
| 1.713 | CH₃ | H | H | H | 4-cyanopyridin-2-yl | H |
| 1.714 | CH₃ | H | H | H | 5-cyanopyridin-2-yl | H |
| 1.715 | CH₃ | H | H | H | 6-cyanopyridin-2-yl | H |
| 1.716 | CH₃ | H | H | H | 2-cyanopyridin-3-yl | H |
| 1.717 | CH₃ | H | H | H | 4-cyanopyridin-3-yl | H |
| 1.718 | CH₃ | H | H | H | 5-cyanopyridin-3-yl | H |
| 1.719 | CH₃ | H | H | H | 2-cyanopyridin-5-yl | H |
| 1.720 | CH₃ | H | H | H | 3-fluoropyridin-2-yl | H |
| 1.721 | CH₃ | H | H | H | 4-fluoropyridin-2-yl | H |
| 1.722 | CH₃ | H | H | H | 5-fluoropyridin-2-yl | H |

TABLE 1-continued

|  | $R^6$ | $R^7$ | $R^8$ | $R^9$ | $R^{10}$ | $R^{11}$ |
|---|---|---|---|---|---|---|
| 1.723 | $CH_3$ | H | H | H | 6-fluoropyridin-2-yl | H |
| 1.724 | $CH_3$ | H | H | H | 2-fluoropyridin-3-yl | H |
| 1.725 | $CH_3$ | H | H | H | 4-fluoropyridin-3-yl | H |
| 1.726 | $CH_3$ | H | H | H | 5-fluoropyridin-3-yl | H |
| 1.727 | $CH_3$ | H | H | H | 2-fluoropyridin-5-yl | H |
| 1.728 | $CH_3$ | H | H | H | 3-nitropyridin-2-yl | H |
| 1.729 | $CH_3$ | H | H | H | 4-nitropyridin-2-yl | H |
| 1.730 | $CH_3$ | H | H | H | 5-nitropyridin-2-yl | H |
| 1.731 | $CH_3$ | H | H | H | 6-nitropyridin-2-yl | H |
| 1.732 | $CH_3$ | H | H | H | 2-nitropyridin-3-yl | H |
| 1.733 | $CH_3$ | H | H | H | 4-nitropyridin-3-yl | H |
| 1.734 | $CH_3$ | H | H | H | 5-nitropyridin-3-yl | H |
| 1.735 | $CH_3$ | H | H | H | 2-nitropyridin-5-yl | H |
| 1.736 | $CH_3$ | H | H | H | 3-trifluoromethylpyridin-2-yl | H |
| 1.737 | $CH_3$ | H | H | H | 4-trifluoromethylpyridin-2-yl | H |
| 1.738 | $CH_3$ | H | H | H | 5-trifluoromethylpyridin-2-yl | H |
| 1.739 | $CH_3$ | H | H | H | 6-trifluoromethylpyridin-2-yl | H |
| 1.740 | $CH_3$ | H | H | H | 2-trifluoromethylpyridin-3-yl | H |
| 1.741 | $CH_3$ | H | H | H | 4-trifluoromethylpyridin-3-yl | H |
| 1.742 | $CH_3$ | H | H | H | 5-trifluoromethylpyridin-3-yl | H |
| 1.743 | $CH_3$ | H | H | H | 2-trifluoromethylpyridin-5-yl | H |
| 1.744 | $CH_3$ | H | H | H | 2,6-bis(trifluoromethyl)-pyridin-3-yl | H |
| 1.745 | $CH_3$ | H | H | H | 2,6-bis(trifluoromethyl)-pyridin-4-yl | H |
| 1.746 | $CH_3$ | H | H | H | 3,5-bis(trifluoromethyl)-pyridin-2-yl | H |
| 1.747 | $CH_3$ | H | H | H | 2-thienyl | H |
| 1.748 | $CH_3$ | H | H | H | 3-thienyl | H |
| 1.749 | $CH_3$ | H | H | H | 5-cyanothien-2-yl | H |
| 1.750 | $CH_3$ | H | H | H | 2-furyl | H |
| 1.751 | $CH_3$ | H | H | H | 3-furyl | H |
| 1.752 | $CH_3$ | H | H | H | 1-methyl-1,2,3-triazol-4-yl | H |
| 1.753 | $CH_3$ | H | H | H | 2-methylthiopyrimidin-4-yl | H |
| 1.754 | $CH_3$ | H | H | H | 5-methyl-2-methyl-thiopyrimidin-4-yl | H |
| 1.755 | $CH_3$ | H | H | H | pyrazin-2-yl | H |
| 1.756 | $CH_3$ | H | H | H | 3,6-dimethylpyrazin-2-yl | H |
| 1.757 | $CH_3$ | H | H | H | 3-cyanopyrazin-2-yl | H |
| 1.758 | $CH_3$ | H | H | H | quinolin-2-yl | H |
| 1.759 | $CH_3$ | H | H | H | 3-ethylquinolin-2-yl | H |
| 1.760 | $CH_3$ | H | H | H | benzyl | H |
| 1.761 | $CH_3$ | H | H | H | 4-fluorobenzyl | H |
| 1.762 | $CH_3$ | H | H | H | 4-chlorobenzyl | H |
| 1.763 | $CH_3$ | H | H | H | 4-methylbenzyl | H |
| 1.764 | $CH_3$ | H | H | H | 2,4-dimethylbenzyl | H |
| 1.765 | $CH_3$ | H | H | H | 2,4,6-trimethylbenzyl | H |
| 1.766 | $CH_3$ | H | H | H | H | $CH_3$ |
| 1.767 | $CH_3$ | H | H | H | $CH_3$ | $CH_3$ |
| 1.768 | $CH_3$ | H | H | H | $CH_2CH_3$ | $CH_3$ |
| 1.769 | $CH_3$ | H | H | H | n-propyl | $CH_3$ |
| 1.770 | $CH_3$ | H | H | H | isopropyl | $CH_3$ |
| 1.771 | $CH_3$ | H | H | H | n-butyl | $CH_3$ |
| 1.772 | $CH_3$ | H | H | H | isobutyl | $CH_3$ |
| 1.773 | $CH_3$ | H | H | H | sec-butyl | $CH_3$ |
| 1.774 | $CH_3$ | H | H | H | tert-butyl | $CH_3$ |
| 1.775 | $CH_3$ | H | H | H | vinyl | $CH_3$ |
| 1.776 | $CH_3$ | H | H | H | ethynyl | $CH_3$ |
| 1.777 | $CH_3$ | H | H | H | trimethylsilylethynyl | $CH_3$ |
| 1.778 | $CH_3$ | H | H | H | $CH_2OH$ | $CH_3$ |
| 1.779 | $CH_3$ | H | H | H | $CH_2OCH_3$ | $CH_3$ |
| 1.780 | $CH_3$ | H | H | H | $CH_2OCH_2CH_3$ | $CH_3$ |
| 1.781 | $CH_3$ | H | H | H | $CH_2OCH_2OCH_3$ | $CH_3$ |
| 1.782 | $CH_3$ | H | H | H | $CH_2OCH_2OCH_2CH_3$ | $CH_3$ |
| 1.783 | $CH_3$ | H | H | H | $CH_2OCH_2CH_2OCH_3$ | $CH_3$ |
| 1.784 | $CH_3$ | H | H | H | CHO | $CH_3$ |
| 1.785 | $CH_3$ | H | H | H | $COCH_3$ | $CH_3$ |
| 1.786 | $CH_3$ | H | H | H | $CO_2H$ | $CH_3$ |
| 1.787 | $CH_3$ | H | H | H | $CO_2CH_3$ | $CH_3$ |
| 1.788 | $CH_3$ | H | H | H | $CO_2CH_2CH_3$ | $CH_3$ |
| 1.789 | $CH_3$ | H | H | H | $CONH_2$ | $CH_3$ |
| 1.790 | $CH_3$ | H | H | H | $CONHCH_3$ | $CH_3$ |
| 1.791 | $CH_3$ | H | H | H | $CONHCH_2CH_3$ | $CH_3$ |
| 1.792 | $CH_3$ | H | H | H | $CON(CH_3)_2$ | $CH_3$ |
| 1.793 | $CH_3$ | H | H | H | $CON(CH_2{-}CH_3)_2$ | $CH_3$ |
| 1.794 | $CH_3$ | H | H | H | $CON(CH_3)OCH_3$ | $CH_3$ |
| 1.795 | $CH_3$ | H | H | H | CH=NOH | $CH_3$ |
| 1.796 | $CH_3$ | H | H | H | CH=N—$OCH_3$ | $CH_3$ |

TABLE 1-continued

|  | $R^6$ | $R^7$ | $R^8$ | $R^9$ | $R^{10}$ | $R^{11}$ |
|---|---|---|---|---|---|---|
| 1.797 | $CH_3$ | H | H | H | CH=N—$OCH_2CH_3$ | $CH_3$ |
| 1.798 | $CH_3$ | H | H | H | C($CH_3$)=N—OH | $CH_3$ |
| 1.799 | $CH_3$ | H | H | H | C($CH_3$)=N—$OCH_3$ | $CH_3$ |
| 1.800 | $CH_3$ | H | H | H | $CH_2OC(O)$—$NHCH_3$ | $CH_3$ |
| 1.801 | $CH_3$ | H | H | H | $CH_2NH_2$ | $CH_3$ |
| 1.802 | $CH_3$ | H | H | H | $CH_2NHCHO$ | $CH_3$ |
| 1.803 | $CH_3$ | H | H | H | $CH_2NHC(O)CH_3$ | $CH_3$ |
| 1.804 | $CH_3$ | H | H | H | $CH_2NHC(O)OCH_3$ | $CH_3$ |
| 1.805 | $CH_3$ | H | H | H | $NHCO_2CH_3$ | $CH_3$ |
| 1.806 | $CH_3$ | H | H | H | $NHCO_2C(CH_3)_3$ | $CH_3$ |
| 1.807 | $CH_3$ | H | H | H | $CH(OH)CH_3$ | $CH_3$ |
| 1.808 | $CH_3$ | H | H | H | $CH(CH_3)OCH_3$ | $CH_3$ |
| 1.809 | $CH_3$ | H | H | H | CN | $CH_3$ |
| 1.810 | $CH_3$ | H | H | H | $CH_2SCH_3$ | $CH_3$ |
| 1.811 | $CH_3$ | H | H | H | $CH_2S(O)CH_3$ | $CH_3$ |
| 1.812 | $CH_3$ | H | H | H | $CH_2SO_2CH_3$ | $CH_3$ |
| 1.813 | $CH_3$ | H | H | H | $CH_2SCH_2CH_3$ | $CH_3$ |
| 1.814 | $CH_3$ | H | H | H | $CH_2S(O)CH_2CH_3$ | $CH_3$ |
| 1.815 | $CH_3$ | H | H | H | $CH_2SO_2CH_2CH_3$ | $CH_3$ |
| 1.816 | $CH_3$ | H | H | H | $OCH_3$ | $CH_3$ |
| 1.817 | $CH_3$ | H | H | H | $OCH_2CH_3$ | $CH_3$ |
| 1.818 | $CH_3$ | H | H | H | $CH(OCH_3)_2$ | $CH_3$ |
| 1.819 | $CH_3$ | H | H | H | $CH(OCH_2CH_3)_2$ | $CH_3$ |
| 1.820 | $CH_3$ | H | H | H | Cyclopropyl | $CH_3$ |
| 1.821 | $CH_3$ | H | H | H | Cyclobutyl | $CH_3$ |
| 1.822 | $CH_3$ | H | H | H | Cyclopentyl | $CH_3$ |
| 1.823 | $CH_3$ | H | H | H | Cyclohexyl | $CH_3$ |
| 1.824 | $CH_3$ | H | H | H | F | $CH_3$ |
| 1.825 | $CH_3$ | H | H | H | Cl | $CH_3$ |
| 1.826 | $CH_3$ | H | H | H | Br | $CH_3$ |
| 1.827 | $CH_3$ | H | H | H | I | $CH_3$ |
| 1.828 | $CH_3$ | H | H | H | OH | $CH_3$ |
| 1.829 | $CH_3$ | H | H | H | phenyl | $CH_3$ |
| 1.830 | $CH_3$ | H | H | H | 2-acetylphenyl | $CH_3$ |
| 1.831 | $CH_3$ | H | H | H | 3-acetylphenyl | $CH_3$ |
| 1.832 | $CH_3$ | H | H | H | 4-acetylphenyl | $CH_3$ |
| 1.833 | $CH_3$ | H | H | H | 2-chlorophenyl | $CH_3$ |
| 1.834 | $CH_3$ | H | H | H | 3-chlorophenyl | $CH_3$ |
| 1.835 | $CH_3$ | H | H | H | 4-chlorophenyl | $CH_3$ |
| 1.836 | $CH_3$ | H | H | H | 2-cyanophenyl | $CH_3$ |
| 1.837 | $CH_3$ | H | H | H | 3-cyanophenyl | $CH_3$ |
| 1.838 | $CH_3$ | H | H | H | 4-cyanophenyl | $CH_3$ |
| 1.839 | $CH_3$ | H | H | H | 2-fluorophenyl | $CH_3$ |
| 1.840 | $CH_3$ | H | H | H | 3-fluorophenyl | $CH_3$ |
| 1.841 | $CH_3$ | H | H | H | 4-fluorophenyl | $CH_3$ |
| 1.842 | $CH_3$ | H | H | H | 2-methoxyphenyl | $CH_3$ |
| 1.843 | $CH_3$ | H | H | H | 3-methoxyphenyl | $CH_3$ |
| 1.844 | $CH_3$ | H | H | H | 4-methoxyphenyl | $CH_3$ |
| 1.845 | $CH_3$ | H | H | H | 2-methylphenyl | $CH_3$ |
| 1.846 | $CH_3$ | H | H | H | 3-methylphenyl | $CH_3$ |
| 1.847 | $CH_3$ | H | H | H | 4-methylphenyl | $CH_3$ |
| 1.848 | $CH_3$ | H | H | H | 2-nitrophenyl | $CH_3$ |
| 1.849 | $CH_3$ | H | H | H | 3-nitrophenyl | $CH_3$ |
| 1.850 | $CH_3$ | H | H | H | 4-nitrophenyl | $CH_3$ |
| 1.851 | $CH_3$ | H | H | H | 2-thiomethylphenyl | $CH_3$ |
| 1.852 | $CH_3$ | H | H | H | 3-thiomethylphenyl | $CH_3$ |
| 1.853 | $CH_3$ | H | H | H | 4-thiomethylphenyl | $CH_3$ |
| 1.854 | $CH_3$ | H | H | H | 2-trifluoromethoxyphenyl | $CH_3$ |
| 1.855 | $CH_3$ | H | H | H | 3-trifluoromethoxyphenyl | $CH_3$ |
| 1.856 | $CH_3$ | H | H | H | 4-trifluoromethoxyphenyl | $CH_3$ |
| 1.857 | $CH_3$ | H | H | H | 2-trifluoromethylphenyl | $CH_3$ |
| 1.858 | $CH_3$ | H | H | H | 3-trifluoromethylphenyl | $CH_3$ |
| 1.859 | $CH_3$ | H | H | H | 4-trifluoromethylphenyl | $CH_3$ |
| 1.860 | $CH_3$ | H | H | H | 2,3-dichlorophenyl | $CH_3$ |
| 1.861 | $CH_3$ | H | H | H | 2,4-dichlorophenyl | $CH_3$ |
| 1.862 | $CH_3$ | H | H | H | 2,5-dichlorophenyl | $CH_3$ |
| 1.863 | $CH_3$ | H | H | H | 2,6-dichlorophenyl | $CH_3$ |
| 1.864 | $CH_3$ | H | H | H | 3,4-dichlorophenyl | $CH_3$ |
| 1.865 | $CH_3$ | H | H | H | 3,5-dichlorophenyl | $CH_3$ |
| 1.866 | $CH_3$ | H | H | H | 2,3-difluorophenyl | $CH_3$ |
| 1.867 | $CH_3$ | H | H | H | 2,4-difluorophenyl | $CH_3$ |
| 1.868 | $CH_3$ | H | H | H | 2,5-difluorophenyl | $CH_3$ |
| 1.869 | $CH_3$ | H | H | H | 2,6-difluorophenyl | $CH_3$ |
| 1.870 | $CH_3$ | H | H | H | 3,4-difluorophenyl | $CH_3$ |
| 1.871 | $CH_3$ | H | H | H | 3,5-difluorophenyl | $CH_3$ |
| 1.872 | $CH_3$ | H | H | H | 2,4,6-trifluorophenyl | $CH_3$ |
| 1.873 | $CH_3$ | H | H | H | 2,4-dimethylphenyl | $CH_3$ |
| 1.874 | $CH_3$ | H | H | H | 2,4,6-trimethylphenyl | $CH_3$ |

TABLE 1-continued

| | $R^6$ | $R^7$ | $R^8$ | $R^9$ | $R^{10}$ | $R^{11}$ |
|---|---|---|---|---|---|---|
| 1.875 | $CH_3$ | H | H | H | 3,4,5-trimethoxyphenyl | $CH_3$ |
| 1.876 | $CH_3$ | H | H | H | 2-chloro-3-cyanophenyl | $CH_3$ |
| 1.877 | $CH_3$ | H | H | H | 2-chloro-4-cyanophenyl | $CH_3$ |
| 1.878 | $CH_3$ | H | H | H | 2-chloro-5-cyanophenyl | $CH_3$ |
| 1.879 | $CH_3$ | H | H | H | 2-chloro-6-cyanophenyl | $CH_3$ |
| 1.880 | $CH_3$ | H | H | H | 3-chloro-2-cyanophenyl | $CH_3$ |
| 1.881 | $CH_3$ | H | H | H | 3-chloro-4-cyanophenyl | $CH_3$ |
| 1.882 | $CH_3$ | H | H | H | 3-chloro-5-cyanophenyl | $CH_3$ |
| 1.883 | $CH_3$ | H | H | H | 5-chloro-2-cyanophenyl | $CH_3$ |
| 1.884 | $CH_3$ | H | H | H | 4-chloro-2-cyanophenyl | $CH_3$ |
| 1.885 | $CH_3$ | H | H | H | 4-chloro-3-cyanophenyl | $CH_3$ |
| 1.886 | $CH_3$ | H | H | H | 2-chloro-3-fluorophenyl | $CH_3$ |
| 1.887 | $CH_3$ | H | H | H | 2-chloro-4-fluorophenyl | $CH_3$ |
| 1.888 | $CH_3$ | H | H | H | 2-chloro-5-fluorophenyl | $CH_3$ |
| 1.889 | $CH_3$ | H | H | H | 2-chloro-6-fluorophenyl | $CH_3$ |
| 1.890 | $CH_3$ | H | H | H | 3-chloro-2-fluorophenyl | $CH_3$ |
| 1.891 | $CH_3$ | H | H | H | 3-chloro-4-fluorophenyl | $CH_3$ |
| 1.892 | $CH_3$ | H | H | H | 3-chloro-5-fluorophenyl | $CH_3$ |
| 1.893 | $CH_3$ | H | H | H | 5-chloro-2-fluorophenyl | $CH_3$ |
| 1.894 | $CH_3$ | H | H | H | 4-chloro-2-fluorophenyl | $CH_3$ |
| 1.895 | $CH_3$ | H | H | H | 4-chloro-3-fluorophenyl | $CH_3$ |
| 1.896 | $CH_3$ | H | H | H | 2-chloro-3-methylphenyl | $CH_3$ |
| 1.897 | $CH_3$ | H | H | H | 2-chloro-4-methylphenyl | $CH_3$ |
| 1.898 | $CH_3$ | H | H | H | 2-chloro-5-methylphenyl | $CH_3$ |
| 1.899 | $CH_3$ | H | H | H | 2-chloro-6-methylphenyl | $CH_3$ |
| 1.900 | $CH_3$ | H | H | H | 3-chloro-2-methylphenyl | $CH_3$ |
| 1.901 | $CH_3$ | H | H | H | 3-chloro-4-methylphenyl | $CH_3$ |
| 1.902 | $CH_3$ | H | H | H | 3-chloro-5-methylphenyl | $CH_3$ |
| 1.903 | $CH_3$ | H | H | H | 5-chloro-2-methylphenyl | $CH_3$ |
| 1.904 | $CH_3$ | H | H | H | 4-chloro-2-methylphenyl | $CH_3$ |
| 1.905 | $CH_3$ | H | H | H | 4-chloro-3-methylphenyl | $CH_3$ |
| 1.906 | $CH_3$ | H | H | H | 2-cyano-3-fluorophenyl | $CH_3$ |
| 1.907 | $CH_3$ | H | H | H | 2-cyano-4-fluorophenyl | $CH_3$ |
| 1.908 | $CH_3$ | H | H | H | 2-cyano-5-fluorophenyl | $CH_3$ |
| 1.909 | $CH_3$ | H | H | H | 2-cyano-6-fluorophenyl | $CH_3$ |
| 1.910 | $CH_3$ | H | H | H | 3-cyano-2-fluorophenyl | $CH_3$ |
| 1.911 | $CH_3$ | H | H | H | 3-cyano-4-fluorophenyl | $CH_3$ |
| 1.912 | $CH_3$ | H | H | H | 3-cyano-5-fluorophenyl | $CH_3$ |
| 1.913 | $CH_3$ | H | H | H | 5-cyano-2-fluorophenyl | $CH_3$ |
| 1.914 | $CH_3$ | H | H | H | 4-cyano-2-fluorophenyl | $CH_3$ |
| 1.915 | $CH_3$ | H | H | H | 4-cyano-3-fluorophenyl | $CH_3$ |
| 1.916 | $CH_3$ | H | H | H | 2-fluoro-3-methylphenyl | $CH_3$ |
| 1.917 | $CH_3$ | H | H | H | 2-fluoro-4-methylphenyl | $CH_3$ |
| 1.918 | $CH_3$ | H | H | H | 2-fluoro-5-methylphenyl | $CH_3$ |
| 1.919 | $CH_3$ | H | H | H | 2-fluoro-6-methylphenyl | $CH_3$ |
| 1.920 | $CH_3$ | H | H | H | 3-fluoro-2-methylphenyl | $CH_3$ |
| 1.921 | $CH_3$ | H | H | H | 3-fluoro-4-methylphenyl | $CH_3$ |
| 1.922 | $CH_3$ | H | H | H | 3-fluoro-5-methylphenyl | $CH_3$ |
| 1.923 | $CH_3$ | H | H | H | 5-fluoro-2-methylphenyl | $CH_3$ |
| 1.924 | $CH_3$ | H | H | H | 4-fluoro-2-methylphenyl | $CH_3$ |
| 1.925 | $CH_3$ | H | H | H | 4-fluoro-3-methylphenyl | $CH_3$ |
| 1.926 | $CH_3$ | H | H | H | pyridin-2-yl | $CH_3$ |
| 1.927 | $CH_3$ | H | H | H | pyridin-3-yl | $CH_3$ |
| 1.928 | $CH_3$ | H | H | H | pyridin-4-yl | $CH_3$ |
| 1.929 | $CH_3$ | H | H | H | 3-chloropyridin-2-yl | $CH_3$ |
| 1.930 | $CH_3$ | H | H | H | 4-chloropyridin-2-yl | $CH_3$ |
| 1.931 | $CH_3$ | H | H | H | 5-chloropyridin-2-yl | $CH_3$ |
| 1.932 | $CH_3$ | H | H | H | 6-chloropyridin-2-yl | $CH_3$ |
| 1.933 | $CH_3$ | H | H | H | 2-chloropyridin-3-yl | $CH_3$ |
| 1.934 | $CH_3$ | H | H | H | 4-chloropyridin-3-yl | $CH_3$ |
| 1.935 | $CH_3$ | H | H | H | 5-chloropyridin-3-yl | $CH_3$ |
| 1.936 | $CH_3$ | H | H | H | 2-chloropyridin-4-yl | $CH_3$ |
| 1.937 | $CH_3$ | H | H | H | 3-chloropyridin-4-yl | $CH_3$ |
| 1.938 | $CH_3$ | H | H | H | 2-chloropyridin-5-yl | $CH_3$ |
| 1.939 | $CH_3$ | H | H | H | 3-cyanopyridin-2-yl | $CH_3$ |
| 1.940 | $CH_3$ | H | H | H | 4-cyanopyridin-2-yl | $CH_3$ |
| 1.941 | $CH_3$ | H | H | H | 5-cyanopyridin-2-yl | $CH_3$ |
| 1.942 | $CH_3$ | H | H | H | 6-cyanopyridin-2-yl | $CH_3$ |
| 1.943 | $CH_3$ | H | H | H | 2-cyanopyridin-3-yl | $CH_3$ |
| 1.944 | $CH_3$ | H | H | H | 4-cyanopyridin-3-yl | $CH_3$ |
| 1.945 | $CH_3$ | H | H | H | 5-cyanopyridin-3-yl | $CH_3$ |
| 1.946 | $CH_3$ | H | H | H | 2-cyanopyridin-5-yl | $CH_3$ |
| 1.947 | $CH_3$ | H | H | H | 3-fluoropyridin-2-yl | $CH_3$ |
| 1.948 | $CH_3$ | H | H | H | 4-fluoropyridin-2-yl | $CH_3$ |
| 1.949 | $CH_3$ | H | H | H | 5-fluoropyridin-2-yl | $CH_3$ |
| 1.950 | $CH_3$ | H | H | H | 6-fluoropyridin-2-yl | $CH_3$ |
| 1.951 | $CH_3$ | H | H | H | 2-fluoropyridin-3-yl | $CH_3$ |
| 1.952 | $CH_3$ | H | H | H | 4-fluoropyridin-3-yl | $CH_3$ |

TABLE 1-continued

| | R⁶ | R⁷ | R⁸ | R⁹ | R¹⁰ | R¹¹ |
|---|---|---|---|---|---|---|
| 1.953 | CH₃ | H | H | H | 5-fluoropyridin-3-yl | CH₃ |
| 1.954 | CH₃ | H | H | H | 2-fluoropyridin-5-yl | CH₃ |
| 1.955 | CH₃ | H | H | H | 3-nitropyridin-2-yl | CH₃ |
| 1.956 | CH₃ | H | H | H | 4-nitropyridin-2-yl | CH₃ |
| 1.957 | CH₃ | H | H | H | 5-nitropyridin-2-yl | CH₃ |
| 1.958 | CH₃ | H | H | H | 6-nitropyridin-2-yl | CH₃ |
| 1.959 | CH₃ | H | H | H | 2-nitropyridin-3-yl | CH₃ |
| 1.960 | CH₃ | H | H | H | 4-nitropyridin-3-yl | CH₃ |
| 1.961 | CH₃ | H | H | H | 5-nitropyridin-3-yl | CH₃ |
| 1.962 | CH₃ | H | H | H | 2-nitropyridin-5-yl | CH₃ |
| 1.963 | CH₃ | H | H | H | 3-trifluoromethylpyridin-2-yl | CH₃ |
| 1.964 | CH₃ | H | H | H | 4-trifluoromethylpyridin-2-yl | CH₃ |
| 1.965 | CH₃ | H | H | H | 5-trifluoromethylpyridin-2-yl | CH₃ |
| 1.966 | CH₃ | H | H | H | 6-trifluoromethylpyridin-2-yl | CH₃ |
| 1.967 | CH₃ | H | H | H | 2-trifluoromethylpyridin-3-yl | CH₃ |
| 1.968 | CH₃ | H | H | H | 4-trifluoromethylpyridin-3-yl | CH₃ |
| 1.969 | CH₃ | H | H | H | 5-trifluoromethylpyridin-3-yl | CH₃ |
| 1.970 | CH₃ | H | H | H | 2-trifluoromethylpyridin-5-yl | CH₃ |
| 1.971 | CH₃ | H | H | H | 2,6-bis(trifluoromethyl)-pyridin-3-yl | CH₃ |
| 1.972 | CH₃ | H | H | H | 2,6-bis(trifluoromethyl)-pyridin-4-yl | CH₃ |
| 1.973 | CH₃ | H | H | H | 3,5-bis(trifluoromethyl)-pyridin-2-yl | CH₃ |
| 1.974 | CH₃ | H | H | H | 2-thienyl | CH₃ |
| 1.975 | CH₃ | H | H | H | 3-thienyl | CH₃ |
| 1.976 | CH₃ | H | H | H | 5-cyanothien-2-yl | CH₃ |
| 1.977 | CH₃ | H | H | H | 2-furyl | CH₃ |
| 1.978 | CH₃ | H | H | H | 3-furyl | CH₃ |
| 1.979 | CH₃ | H | H | H | 1-methyl-1,2,3-triazol-4-yl | CH₃ |
| 1.980 | CH₃ | H | H | H | 2-methylthiopyrimidin-4-yl | CH₃ |
| 1.981 | CH₃ | H | H | H | 5-methyl-2-methyl-thiopyrimidin-4-yl | CH₃ |
| 1.982 | CH₃ | H | H | H | pyrazin-2-yl | CH₃ |
| 1.983 | CH₃ | H | H | H | 3,6-dimethylpyrazin-2-yl | CH₃ |
| 1.984 | CH₃ | H | H | H | 3-cyanopyrazin-2-yl | CH₃ |
| 1.985 | CH₃ | H | H | H | quinolin-2-yl | CH₃ |
| 1.986 | CH₃ | H | H | H | 3-ethylquinolin-2-yl | CH₃ |
| 1.987 | CH₃ | H | H | H | benzyl | CH₃ |
| 1.988 | CH₃ | H | H | H | 4-fluorobenzyl | CH₃ |
| 1.989 | CH₃ | H | H | H | 4-chlorobenzyl | CH₃ |
| 1.990 | CH₃ | H | H | H | 4-methylbenzyl | CH₃ |
| 1.991 | CH₃ | H | H | H | 2,4-dimethylbenzyl | CH₃ |
| 1.992 | CH₃ | H | H | H | 2,4,6-trimethylbenzyl | CH₃ |
| 1.993 | CH₃ | H | H | H | H | CH₂OH |
| 1.994 | CH₃ | H | H | H | H | CH₂OCH₃ |
| 1.995 | CH₃ | H | H | H | H | CH₂OCH₂CH₃ |
| 1.996 | CH₃ | H | H | H | H | CHO |
| 1.997 | CH₃ | H | H | H | H | COCH₃ |
| 1.998 | CH₃ | H | H | H | H | CO₂H |
| 1.999 | CH₃ | H | H | H | H | CO₂CH₃ |
| 1.1000 | CH₃ | H | H | H | H | CO₂CH₂CH₃ |
| 1.1001 | CH₃ | H | H | H | H | CONH₂ |
| 1.1002 | CH₃ | H | H | H | H | CONHCH₃ |
| 1.1003 | CH₃ | H | H | H | H | CONHCH₂CH₃ |
| 1.1004 | CH₃ | H | H | H | H | CON(CH₃)₂ |
| 1.1005 | CH₃ | H | H | H | H | CON—(CH₂CH₃)₂ |
| 1.1006 | CH₃ | H | H | H | H | CON(CH₃)O—CH₃ |
| 1.1007 | CH₃ | H | H | H | H | CH=NOH |
| 1.1008 | CH₃ | H | H | H | H | CH=NOCH₃ |
| 1.1009 | CH₃ | H | H | H | H | CH=NOCH₂—CH₃ |
| 1.1010 | CH₃ | H | H | H | H | C(CH₃)=NOH |
| 1.1011 | CH₃ | H | H | H | H | C(CH₃)=NO—CH₃ |
| 1.1012 | CH₃ | H | H | H | H | CH₂OC(O)NH—CH₃ |
| 1.1013 | CH₃ | H | H | H | H | CH₂NH₂ |
| 1.1014 | CH₃ | H | H | H | H | CH₂NHCHO |
| 1.1015 | CH₃ | H | H | H | H | CH₂NHC(O)—CH₃ |
| 1.1016 | CH₃ | H | H | H | H | CH₂NHC(O)OCH₃ |
| 1.1017 | CH₃ | H | H | H | H | NHCO₂CH₃ |
| 1.1018 | CH₃ | H | H | H | H | NHCO₂—C(CH₃)₃ |
| 1.1019 | CH₃ | H | H | H | H | CH(OH)CH₃ |
| 1.1020 | CH₃ | H | H | H | H | CH(CH₃)OCH₃ |
| 1.1021 | CH₃ | H | H | H | H | CN |
| 1.1022 | CH₃ | H | H | H | H | CH₂SCH₃ |
| 1.1023 | CH₃ | H | H | H | H | CH₂S(O)CH₃ |
| 1.1024 | CH₃ | H | H | H | H | CH₂SO₂CH₃ |
| 1.1025 | CH₃ | H | H | H | H | CH₂SCH₂CH₃ |
| 1.1026 | CH₃ | H | H | H | H | CH₂S(O)CH₂—CH₃ |

TABLE 1-continued

| | $R^6$ | $R^7$ | $R^8$ | $R^9$ | $R^{10}$ | $R^{11}$ |
|---|---|---|---|---|---|---|
| 1.1027 | $CH_3$ | H | H | H | H | $CH_2SO_2CH_2$—$CH_3$ |
| 1.1028 | $CH_3$ | H | H | H | H | $OCH_3$ |
| 1.1029 | $CH_3$ | H | H | H | H | $OCH_2CH_3$ |
| 1.1030 | $CH_3$ | H | H | H | H | $CH(OCH_3)_2$ |
| 1.1031 | $CH_3$ | H | H | H | H | $CH$—$(OCH_2CH_3)_2$ |
| 1.1032 | $CH_3$ | H | H | H | H | $CH_2CH_3$ |
| 1.1033 | $CH_3$ | H | H | H | H | $CH_2CH_2CH_3$ |
| 1.1034 | $CH_3$ | H | H | H | H | $CH(CH_3)_2$ |
| 1.1035 | $CH_3$ | H | H | H | H | $C(CH_3)_3$ |
| 1.1036 | $CH_3$ | H | H | H | H | $CH_2CH(CH_3)_2$ |
| 1.1037 | $CH_3$ | H | H | H | H | $CH_2C(CH_3)_3$ |
| 1.1038 | $CH_3$ | H | H | H | H | $CH_2CN$ |
| 1.1039 | $CH_3$ | H | H | H | H | cyclopropyl |
| 1.1040 | $CH_3$ | H | H | H | H | cyclobutyl |
| 1.1041 | $CH_3$ | H | H | H | H | cyclopentyl |
| 1.1042 | $CH_3$ | H | H | H | H | cyclohexyl |
| 1.1043 | $CH_3$ | H | H | H | H | $CH_2$-cyclopropyl |
| 1.1044 | $CH_3$ | H | H | H | H | benzyl |
| 1.1045 | $CH_3$ | H | H | H | H | $CH_2CF_3$ |
| 1.1046 | $CH_3$ | $CH_3$ | H | H | $CH_3$ | $CH_3$ |
| 1.1047 | H | H | Cl | Cl | H | H |
| 1.1048 | H | H | Cl | Cl | H | $CH_3$ |
| 1.1049 | $CH_3$ | H | Cl | Cl | H | $CH_3$ |
| 1.1050 | H | H | Br | Br | H | H |
| 1.1051 | H | H | Br | Br | H | $CH_3$ |
| 1.1052 | $CH_3$ | H | Br | Br | H | $CH_3$ |
| 1.1053 | H | H | OH | OH | H | H |
| 1.1054 | H | H | OH | OH | H | $CH_3$ |
| 1.1055 | $CH_3$ | H | OH | OH | H | $CH_3$ |
| 1.1056 | H | H | —O—$C(CH_3)_2$—O— | | H | H |
| 1.1057 | H | H | —O—$C(CH_3)_2$—O— | | H | $CH_3$ |
| 1.1058 | $CH_3$ | H | —O—$C(CH_3)_2$—O— | | H | $CH_3$ |
| 1.1059 | H | $R^7$ and $R^8$ form unit =O | | H | H |
| 1.1060 | H | $R^7$ and $R^8$ form unit =O | | H | $CH_3$ |
| 1.1061 | $CH_3$ | $R^7$ and $R^8$ form unit =O | | H | H |
| 1.1062 | $CH_3$ | $R^7$ and $R^8$ form unit =O | | H | $CH_3$ |
| 1.1063 | H | $R^7$ and $R^8$ form unit =$NOCH_3$ | | H | H |
| 1.1064 | H | $R^7$ and $R^8$ form unit =$NOCH_3$ | | H | $CH_3$ |
| 1.1065 | $CH_3$ | $R^7$ and $R^8$ form unit =$NOCH_3$ | | H | H |
| 1.1066 | $CH_3$ | $R^7$ and $R^8$ form unit =$NOCH_3$ | | H | $CH_3$ |
| 1.1067 | H | $R^7$ and $R^8$ form unit =$NOCH_2CH_3$ | | H | H |
| 1.1068 | H | $R^7$ and $R^8$ form unit =$NOCH_2CH_3$ | | H | $CH_3$ |
| 1.1069 | $CH_3$ | $R^7$ and $R^8$ form unit =$NOCH_2CH_3$ | | H | H |
| 1.1070 | $CH_3$ | $R^7$ and $R^8$ form unit =$NOCH_2CH_3$ | | H | $CH_3$ |
| 1.1071 | H | H | H | —O—$(CH_2)_2$—O— | | H |
| 1.1072 | H | H | H | —O—$(CH_2)_2$—O— | | $CH_3$ |
| 1.1073 | $CH_3$ | H | H | —O—$(CH_2)_2$—O— | | H |
| 1.1074 | $CH_3$ | H | H | —O—$(CH_2)_2$—O— | | $CH_3$ |
| 1.1075 | H | H | H | —O—$(CH_2)_3$—O— | | H |
| 1.1076 | H | H | H | —O—$(CH_2)_3$—O— | | $CH_3$ |
| 1.1077 | $CH_3$ | H | H | —O—$(CH_2)_3$—O— | | H |
| 1.1078 | $CH_3$ | H | H | —O—$(CH_2)_3$—O— | | $CH_3$ |

Table 2 covers compounds of formula (A), wherein $R^1$ is ethyl, $R^2$ and $R^4$ are methyl, $R^3$, $R^5$ and $R^{12}$ are hydrogen and $R^6$, $R^7$, $R^8$, $R^9$, $R^{10}$, and $R^{11}$ are as defined in Table 1.

Table 3 covers compounds of formula (A), wherein $R^1$ and $R^4$ are ethyl, $R^2$ is methyl, $R^3$, $R^5$ and $R^{12}$ are hydrogen and $R^6$, $R^7$, $R^8$, $R^9$, $R^{10}$, and $R^{11}$ are as defined in Table 1.

Table 4 covers compounds of formula (A), wherein $R^1$, $R^2$ and $R^4$ are ethyl, $R^3$, $R^5$ and $R^{12}$ are hydrogen and $R^6$, $R^7$, $R^8$, $R^9$, $R^{10}$, and $R^{11}$ are as defined in Table 1.

Table 5 covers compounds of formula (A), wherein $R^1$ and $R^2$ are methyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 6 covers compounds of formula (A), wherein $R^1$ and $R^2$ are methyl, $R^4$ is methoxy, $R^3$, $R^5$ and $R^{12}$ are hydrogen and $R^6$, $R^7$, $R^8$, $R^9$, $R^{10}$, and $R^{11}$ are as defined in Table 1.

Table 7 covers compounds of formula (A), wherein $R^1$ and $R^2$ are methyl, $R^4$ is chlorine, $R^3$, $R^5$ and $R^{12}$ are hydrogen and $R^6$, $R^7$, $R^8$, $R^9$, $R^{10}$, and $R^{11}$ are as defined in Table 1.

Table 8 covers compounds of formula (A), wherein $R^1$ and $R^2$ are methyl, $R^4$ is bromine, $R^3$, $R^5$ and $R^{12}$ are hydrogen and $R^6$, $R^7$, $R^8$, $R^9$, $R^{10}$, and $R^{11}$ are as defined in Table 1.

Table 9 covers compounds of formula (A), wherein $R^1$ and $R^2$ are methyl, $R^4$ is iodine, $R^3$, $R^5$ and $R^{12}$ are hydrogen and $R^6$, $R^7$, $R^8$, $R^9$, $R^{10}$, and $R^{11}$ are as defined in Table 1.

Table 10 covers compounds of formula (A), wherein $R^1$ and $R^2$ are methyl, $R^4$ is ethynyl, $R^3$, $R^5$ and $R^{12}$ are hydrogen and $R^6$, $R^7$, $R^8$, $R^9$, $R^{10}$, and $R^{11}$ are as defined in Table 1.

Table 11 covers compounds of formula (A), wherein $R^1$ and $R^2$ are methyl, $R^4$ is vinyl, $R^3$, $R^5$ and $R^{12}$ are hydrogen and $R^6$, $R^7$, $R^8$, $R^9$, $R^{10}$, and $R^{11}$ are as defined in Table 1.

Table 12 covers compounds of formula (A), wherein $R^1$ is ethyl, $R^2$ is methyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 13 covers compounds of formula (A), wherein $R^1$ is ethyl, $R^2$ is methyl, $R^4$ is methoxy, $R^3$, $R^5$ and $R^{12}$ are hydrogen and $R^6$, $R^7$, $R^8$, $R^9$, $R^{10}$, and $R^{11}$ are as defined in Table 1.

Table 14 covers compounds of formula (A), wherein $R^1$ is ethyl, $R^2$ is methyl, $R^4$ is chlorine, $R^3$, $R^5$ and $R^{12}$ are hydrogen and $R^6$, $R^7$, $R^8$, $R^9$, $R^{10}$, and $R^{11}$ are as defined in Table 1.

Table 15 covers compounds of formula (A), wherein $R^1$ is ethyl, $R^2$ is methyl, $R^4$ is bromine, $R^3$, $R^5$ and $R^{12}$ are hydrogen and $R^6$, $R^7$, $R^8$, $R^9$, $R^{10}$, and $R^{11}$ are as defined in Table 1.

Table 16 covers compounds of formula (A), wherein $R^1$ is ethyl, $R^2$ is methyl, $R^4$ is iodine, $R^3$, $R^5$ and $R^{12}$ are hydrogen and $R^6$, $R^7$, $R^8$, $R^9$, $R^{10}$, and $R^{11}$ are as defined in Table 1.

Table 17 covers compounds of formula (A), wherein $R^1$ is ethyl, $R^2$ is methyl, $R^4$ is ethynyl, $R^3$, $R^5$ and $R^{12}$ are hydrogen and $R^6$, $R^7$, $R^8$, $R^9$, $R^{10}$, and $R^{11}$ are as defined in Table 1.

Table 18 covers compounds of formula (A), wherein $R^1$ is ethyl, $R^2$ is methyl, $R^4$ is vinyl, $R^3$, $R^5$ and $R^{12}$ are hydrogen and $R^6$, $R^7$, $R^8$, $R^9$, $R^{10}$, and $R^{11}$ are as defined in Table 1.

Table 19 covers compounds of formula (A), wherein $R^1$ is ethynyl, $R^2$ is methyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 20 covers compounds of formula (A), wherein $R^1$ is ethynyl, $R^2$ is methyl, $R^4$ is methoxy, $R^3$, $R^5$ and $R^{12}$ are hydrogen and $R^6$, $R^7$, $R^8$, $R^9$, $R^{10}$, and $R^{11}$ are as defined in Table 1.

Table 21 covers compounds of formula (A), wherein $R^1$ is ethynyl, $R^2$ is methyl, $R^4$ is chlorine, $R^3$, $R^5$ and $R^{12}$ are hydrogen and $R^6$, $R^7$, $R^8$, $R^9$, $R^{10}$, and $R^{11}$ are as defined in Table 1.

Table 22 covers compounds of formula (A), wherein $R^1$ is ethynyl, $R^2$ is methyl, $R^4$ is bromine, $R^3$, $R^5$ and $R^{12}$ are hydrogen and $R^6$, $R^7$, $R^8$, $R^9$, $R^{10}$, and $R^{11}$ are as defined in Table 1.

Table 23 covers compounds of formula (A), wherein $R^1$ is ethynyl, $R^2$ is methyl, $R^4$ is iodine, $R^3$, $R^5$ and $R^{12}$ are hydrogen and $R^6$, $R^7$, $R^8$, $R^9$, $R^{10}$, and $R^{11}$ are as defined in Table 1.

Table 24 covers compounds of formula (A), wherein $R^1$ and $R^4$ are ethynyl, $R^2$ is methyl, $R^3$, $R^5$ and $R^{12}$ are hydrogen and $R^6$, $R^7$, $R^8$, $R^9$, $R^{10}$, and $R^{11}$ are as defined in Table 1.

Table 25 covers compounds of formula (A), wherein $R^1$ is vinyl, $R^2$ is methyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 26 covers compounds of formula (A), wherein $R^1$ is vinyl, $R^2$ is methyl, $R^4$ is methoxy, $R^3$, $R^5$ and $R^{12}$ are hydrogen and $R^6$, $R^7$, $R^8$, $R^9$, $R^{10}$, and $R^{11}$ are as defined in Table 1.

Table 27 covers compounds of formula (A), wherein $R^1$ is vinyl, $R^2$ is methyl, $R^4$ is chlorine, $R^3$, $R^5$ and $R^{12}$ are hydrogen and $R^6$, $R^7$, $R^8$, $R^9$, $R^{10}$, and $R^{11}$ are as defined in Table 1.

Table 28 covers compounds of formula (A), wherein $R^1$ is vinyl, $R^2$ is methyl, $R^4$ is bromine, $R^3$, $R^5$ and $R^{12}$ are hydrogen and $R^6$, $R^7$, $R^8$, $R^9$, $R^{10}$, and $R^{11}$ are as defined in Table 1.

Table 29 covers compounds of formula (A), wherein $R^1$ is vinyl, $R^2$ is methyl, $R^4$ is iodine, $R^3$, $R^5$ and $R^{12}$ are hydrogen and $R^6$, $R^7$, $R^8$, $R^9$, $R^{10}$, and $R^{11}$ are as defined in Table 1.

Table 30 covers compounds of formula (A), wherein $R^1$ and $R^4$ are vinyl, $R^2$ is methyl, $R^3$, $R^5$ and $R^{12}$ are hydrogen and $R^6$, $R^7$, $R^8$, $R^9$, $R^{10}$, and $R^{11}$ are as defined in Table 1.

Table 31 covers compounds of formula (A), wherein $R^1$ is methyl, $R^2$, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 32 covers compounds of formula (A), wherein $R^1$ is methyl, $R^2$ is methoxy, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 33 covers compounds of formula (A), wherein $R^1$ is methyl, $R^2$ is trifluoromethyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 34 covers compounds of formula (A), wherein $R^1$ is methyl, $R^2$ is ethyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 35 covers compounds of formula (A), wherein $R^1$ is methyl, $R^2$ is ethynyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 36 covers compounds of formula (A), wherein $R^1$ is methyl, $R^2$ is vinyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 37 covers compounds of formula (A), wherein $R^1$ is methyl, $R^2$ is chlorine, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 38 covers compounds of formula (A), wherein $R^1$ is methyl, $R^2$ is bromine, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 39 covers compounds of formula (A), wherein $R^1$ is methyl, $R^2$ is iodine, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 40 covers compounds of formula (A), wherein $R^1$ is ethyl, $R^2$, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 41 covers compounds of formula (A), wherein $R^1$ is ethyl, $R^2$ is methoxy, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 42 covers compounds of formula (A), wherein $R^1$ is ethyl, $R^2$ is trifluoromethyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 43 covers compounds of formula (A), wherein $R^1$ is ethyl, $R^2$ is methyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 44 covers compounds of formula (A), wherein $R^1$ is ethyl, $R^2$ is ethynyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 45 covers compounds of formula (A), wherein $R^1$ is ethyl, $R^2$ is vinyl, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 46 covers compounds of formula (A), wherein $R^1$ is ethyl, $R^2$ is chlorine, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 47 covers compounds of formula (A), wherein $R^1$ is ethyl, $R^2$ is bromine, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 48 covers compounds of formula (A), wherein $R^1$ is ethyl, $R^2$ is iodine, $R^3$, $R^4$, $R^5$ and $R^{12}$ are hydrogen and $R^6$, $R^7$, $R^8$, $R^9$, $R^{10}$, and $R^{11}$ are as defined in Table 1.

Table 49 covers compounds of formula (A), wherein $R^1$ and $R^4$ are methyl, $R^2$ is chlorine, $R^3$, $R^5$ and $R^{12}$ are hydrogen and $R^6$, $R^7$, $R^8$, $R^9$, $R^{10}$, and $R^{11}$ are as defined in Table 1.

Table 50 covers compounds of formula (A), wherein $R^1$ and $R^4$ are methyl, $R^2$ is bromine, $R^3$, $R^5$ and $R^{12}$ are hydrogen and $R^6$, $R^7$, $R^8$, $R^9$, $R^{10}$, and $R^{11}$ are as defined in Table 1.

Table 51 covers compounds of formula (A), wherein $R^1$ and $R^4$ are methyl, $R^2$ is iodine, $R^3$, $R^5$ and $R^{12}$ are hydrogen and $R^6$, $R^7$, $R^8$, $R^9$, $R^{10}$, and $R^{11}$ are as defined in Table 1.

Table 52 covers compounds of formula (A), wherein $R^1$ is methyl, $R^2$ is chlorine, $R^3$ is hydrogen, $R^4$ is ethyl, $R^5$ and $R^{12}$ are hydrogen and $R^6$, $R^7$, $R^8$, $R^9$, $R^{10}$, and $R^{11}$ are as defined in Table 1.

Table 53 covers compounds of formula (A), wherein $R^1$ is methyl, $R^2$ is bromine, $R^3$ is hydrogen, $R^4$ is ethyl, $R^5$ and $R^{12}$ are hydrogen and $R^6$, $R^7$, $R^8$, $R^9$, $R^{10}$, and $R^{11}$ are as defined in Table 1.

Table 54 covers compounds of formula (A), wherein $R^1$ is methyl, $R^2$ is iodine, $R^3$ is hydrogen, $R^4$ is ethyl, $R^5$ and $R^{12}$ are hydrogen and $R^6$, $R^7$, $R^8$, $R^9$, $R^{10}$, and $R^{11}$ are as defined in Table 1.

Table 55 covers compounds of formula (A), wherein $R^1$ and $R^4$ are ethyl, $R^2$ is chlorine, $R^3$, $R^5$ and $R^{12}$ are hydrogen and $R^6$, $R^7$, $R^8$, $R^9$, $R^{10}$, and $R^{11}$ are as defined in Table 1.

Table 56 covers compounds of formula (A), wherein $R^1$ and $R^4$ are ethyl, $R^2$ is bromine, $R^3$, $R^5$ and $R^{12}$ are hydrogen and $R^6$, $R^7$, $R^8$, $R^9$, $R^{10}$, and $R^{11}$ are as defined in Table 1.

Table 57 covers compounds of formula (A), wherein $R^1$ and $R^4$ are ethyl, $R^2$ is iodine, $R^3$, $R^5$ and $R^{12}$ are hydrogen and $R^6$, $R^7$, $R^8$, $R^9$, $R^{10}$, and $R^{11}$ are as defined in Table 1.

Table 58 covers compounds of formula (A), wherein $R^1$ is methyl, $R^2$ is chlorine, $R^3$ is hydrogen, $R^4$ is methoxy, $R^5$ and $R^{12}$ are hydrogen and $R^6$, $R^7$, $R^8$, $R^9$, $R^{10}$, and $R^{11}$ are as defined in Table 1.

Table 59 covers compounds of formula (A), wherein $R^1$ is methyl, $R^2$ is bromine, $R^3$ is hydrogen, $R^4$ is methoxy, $R^5$ and $R^{12}$ are hydrogen and $R^6$, $R^7$, $R^8$, $R^9$, $R^{10}$, and $R^{11}$ are as defined in Table 1.

Table 60 covers compounds of formula (A), wherein $R^1$ is ethyl, $R^2$ is chlorine, $R^3$ is hydrogen, $R^4$ is methoxy, $R^5$ and $R^{12}$ are hydrogen and $R^6$, $R^7$, $R^8$, $R^9$, $R^{10}$, and $R^{11}$ are as defined in Table 1.

Table 61 covers compounds of formula (A), wherein $R^1$ is ethyl, $R^2$ is bromine, $R^3$ is hydrogen, $R^4$ is methoxy, $R^5$ and $R^{12}$ are hydrogen and $R^6$, $R^7$, $R^8$, $R^9$, $R^{10}$, and $R^{11}$ are as defined in Table 1.

Table 62 covers compounds of formula (A), wherein $R^1$ and $R^4$ are methyl, $R^2$ is methoxy, $R^3$, $R^5$ and $R^{12}$ are hydrogen and $R^6$, $R^7$, $R^8$, $R^9$, $R^{10}$, and $R^{11}$ are as defined in Table 1.

Table 63 covers compounds of formula (A), wherein $R^1$ is methyl, $R^2$ is methoxy, $R^3$ is hydrogen, $R^4$ is ethyl, $R^5$ and $R^{12}$ are hydrogen and $R^6$, $R^7$, $R^8$, $R^9$, $R^{10}$, and $R^{11}$ are as defined in Table 1.

Table 64 covers compounds of formula (A), wherein $R^1$ and $R^4$ are ethyl, $R^2$ is methoxy, $R^3$, $R^5$ and $R^{12}$ are hydrogen and $R^6$, $R^7$, $R^8$, $R^9$, $R^{10}$, and $R^{11}$ are as defined in Table 1.

Table 65 covers compounds of formula (A), wherein $R^1$, $R^2$, $R^3$ and $R^4$ are methyl, $R^5$ and $R^{12}$ are hydrogen and $R^6$, $R^7$, $R^8$, $R^9$, $R^{10}$, and $R^{11}$ are as defined in Table 1.

Table 66 covers compounds of formula (A), wherein $R^1$ is difluoromethoxy, $R^2$ and $R^4$ are methyl, $R^3$, $R^5$ and $R^{12}$ are hydrogen and $R^6$, $R^7$, $R^8$, $R^9$, $R^{10}$, and $R^{11}$ are as defined in Table 1.

Table 67 covers compounds of formula (A), wherein $R^1$ is difluoromethoxy, $R^2$ is methyl, $R^4$ is ethyl, $R^3$, $R^5$ and $R^{12}$ are hydrogen and $R^6$, $R^7$, $R^8$, $R^9$, $R^{10}$, and $R^{11}$ are as defined in Table 1.

Table 68 covers compounds of formula (A), wherein $R^1$ is trifluoromethoxy, $R^2$ and $R^4$ are methyl, $R^3$, $R^5$ and $R^{12}$ are hydrogen and $R^6$, $R^7$, $R^8$, $R^9$, $R^{10}$, and $R^{11}$ are as defined in Table 1.

Table 67 covers compounds of formula (A), wherein $R^1$ is trifluoromethoxy, $R^2$ is methyl, $R^4$ is ethyl, $R^3$, $R^5$ and $R^{12}$ are hydrogen and $R^6$, $R^7$, $R^8$, $R^9$, $R^{10}$, and $R^{11}$ are as defined in Table 1.

Table 70 covers compounds of formula (A), wherein $R^1$ is cyclopropyl, $R^2$ and $R^4$ are methyl, $R^3$, $R^5$ and $R^{12}$ are hydrogen and $R^6$, $R^7$, $R^8$, $R^9$, $R^{10}$, and $R^{11}$ are as defined in Table 1.

Table 71 covers compounds of formula (A), wherein $R^1$ is cyclopropyl, $R^2$ is methyl, $R^4$ is ethyl, $R^3$, $R^5$ and $R^{12}$ are hydrogen and $R^6$, $R^7$, $R^8$, $R^9$, $R^{10}$, and $R^{11}$ are as defined in Table 1.

Table 72 covers compounds of formula (A), wherein $R^1$ and $R^2$ are methyl, $R^3$, $R^5$ and $R^{12}$ are hydrogen, $R^4$ is cyclopropyl and $R^6$, $R^7$, $R^8$, $R^9$, $R^{10}$, and $R^{11}$ are as defined in Table 1.

Table 73 covers compounds of formula (A), wherein $R^1$ and $R^2$ are ethyl, $R^3$, $R^5$ and $R^{12}$ are hydrogen, $R^4$ is cyclopropyl and $R^6$, $R^7$, $R^8$, $R^9$, $R^{10}$, and $R^{11}$ are as defined in Table 1.

Table 74 covers compounds of formula (AH)

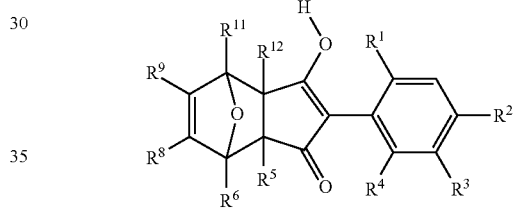

wherein $R^1$, $R^2$ and $R^4$ are methyl, $R^3$, $R^5$ and $R^{12}$ are hydrogen and $R^6$, $R^8$, $R^9$, and $R^{11}$ are as defined in Table 74.

TABLE 74

| | $R^6$ | $R^8$ | $R^9$ | $R^{11}$ |
|---|---|---|---|---|
| 74.001 | H | H | H | H |
| 74.002 | H | H | H | $CH_3$ |
| 74.003 | H | H | H | $CH_2OH$ |
| 74.004 | H | H | H | $CH_2OCH_3$ |
| 74.005 | H | H | H | $CH_2OCH_2CH_3$ |
| 74.006 | H | H | H | $CH_2OCH_2OCH_3$ |
| 74.007 | H | H | H | $CH_2OCH_2OCH_2CH_3$ |
| 74.007 | H | H | H | $CH_2OCH_2CO_2CH_3$ |
| 74.008 | H | H | H | $CH_2OCH_2CO_2CH_2CH_3$ |
| 74.009 | H | H | H | $CH_2OCH_2CN$ |
| 74.010 | H | H | H | $CH(OH)CH_3$ |
| 74.011 | H | H | H | $CH(CH_3)OCH_3$ |
| 74.012 | H | H | H | $CH(CH_3)OCH_2CH_3$ |
| 74.013 | H | H | H | CHO |
| 74.014 | H | H | H | $COCH_3$ |
| 74.015 | H | H | H | $CH_2COCH_3$ |
| 74.016 | H | H | H | $CH_2CH_2COCH_3$ |
| 74.017 | H | H | H | $CO_2H$ |
| 74.018 | H | H | H | $CO_2CH_3$ |
| 74.019 | H | H | H | $CO_2CH_2CH_3$ |
| 74.020 | H | H | H | $CH_2CO_2CH_3$ |
| 74.021 | H | H | H | $CH_2CO_2CH_2CH_3$ |
| 74.022 | H | H | H | $CH_2CH_2CO_2CH_3$ |
| 74.023 | H | H | H | $CH_2CH_2CO_2CH_2CH_3$ |
| 74.024 | H | H | H | $CONH_2$ |
| 74.025 | H | H | H | $CONHCH_3$ |
| 74.026 | H | H | H | $CONHCH_2CH_3$ |

TABLE 74-continued

| | $R^6$ | $R^8$ | $R^9$ | $R^{11}$ |
|---|---|---|---|---|
| 74.027 | H | H | H | $CON(CH_3)_2$ |
| 74.028 | H | H | H | $CON(CH_2CH_3)_2$ |
| 74.029 | H | H | H | $CON(CH_3)OCH_3$ |
| 74.030 | H | H | H | $CH=NOH$ |
| 74.031 | H | H | H | $CH=NOCH_3$ |
| 74.032 | H | H | H | $CH=NOCH_2CH_3$ |
| 74.033 | H | H | H | $C(CH_3)=NOH$ |
| 74.034 | H | H | H | $C(CH_3)=NOCH_3$ |
| 74.035 | H | H | H | $CH_2OC(O)CH_3$ |
| 74.036 | H | H | H | $CH_2OC(O)CH_2CH_3$ |
| 74.037 | H | H | H | $CH_2OC(O)CH(CH_3)_2$ |
| 74.038 | H | H | H | $CH_2OC(O)C(CH_3)_3$ |
| 74.039 | H | H | H | $CH_2OC(O)NHCH_3$ |
| 74.040 | H | H | H | $CH_2OC(O)NHCH_2CH_3$ |
| 74.041 | H | H | H | $CH_2OC(O)NHCH_2CH_2CH_3$ |
| 74.042 | H | H | H | $CH_2OC(O)NHC(CH_3)_3$ |
| 74.043 | H | H | H | $CH_2NH_2$ |
| 74.044 | H | H | H | $CH_2NHCHO$ |
| 74.045 | H | H | H | $CH_2NHC(O)CH_3$ |
| 74.046 | H | H | H | $CH_2NHC(O)OCH_3$ |
| 74.047 | H | H | H | $NHCO_2CH_3$ |
| 74.048 | H | H | H | $NHCO_2C(CH_3)_3$ |
| 74.049 | H | H | H | $CN$ |
| 74.050 | H | H | H | $CH_2SCH_3$ |
| 74.051 | H | H | H | $CH_2SCH_2CH_3$ |
| 74.052 | H | H | H | $CH_2SCH_2CH_2CH_3$ |
| 74.053 | H | H | H | $CH_2SCH(CH_3)_2$ |
| 74.054 | H | H | H | $CH_2S(O)CH_3$ |
| 74.055 | H | H | H | $CH_2SO_2CH_3$ |
| 74.056 | H | H | H | $CH_2SCH_2CH_3$ |
| 74.057 | H | H | H | $CH_2S(O)CH_2CH_3$ |
| 74.058 | H | H | H | $CH_2SO_2CH_2CH_3$ |
| 74.059 | H | H | H | $OCH_3$ |
| 74.060 | H | H | H | $OCH_2CH_3$ |
| 74.061 | H | H | H | $CH(OCH_3)_2$ |
| 74.062 | H | H | H | $CH(OCH_2CH_3)_2$ |
| 74.063 | H | H | H | 1,3-dioxolan-2-yl |
| 74.064 | H | H | H | 1,3-dioxan-2-yl |
| 74.065 | H | H | H | 5,5-dimethyl-1,3-dioxan-2-yl |
| 74.066 | H | H | H | $CH_2CH_3$ |
| 74.067 | H | H | H | n-propyl |
| 74.068 | H | H | H | isopropyl |
| 74.069 | H | H | H | n-butyl |
| 74.070 | H | H | H | isobutyl |
| 74.071 | H | H | H | sec-butyl |
| 74.072 | H | H | H | tert-butyl |
| 74.073 | H | H | H | n-pentyl |
| 74.074 | H | H | H | neopentyl |
| 74.075 | H | H | H | n-hexyl |
| 74.076 | H | H | H | n-heptyl |
| 74.077 | H | H | H | $CH_2CN$ |
| 74.078 | H | H | H | cyclopropyl |
| 74.079 | H | H | H | cyclobutyl |
| 74.080 | H | H | H | cyclopentyl |
| 74.081 | H | H | H | cyclohexyl |
| 74.082 | H | H | H | $CH_2$-cyclopropyl |
| 74.083 | H | H | H | benzyl |
| 74.084 | H | H | H | $CH_2CF_3$ |
| 74.085 | H | H | H | $CH_2F$ |
| 74.086 | H | H | H | $CHF_2$ |
| 74.087 | H | H | H | $CF_3$ |
| 74.088 | H | H | $CH_3$ | H |
| 74.089 | H | H | $CH_2CH_3$ | H |
| 74.090 | H | H | n-propyl | H |
| 74.091 | H | H | isopropyl | H |
| 74.092 | H | H | n-butyl | H |
| 74.093 | H | H | isobutyl | H |
| 74.094 | H | H | sec-butyl | H |
| 74.095 | H | H | tert-butyl | H |
| 74.096 | H | H | vinyl | H |
| 74.097 | H | H | ethynyl | H |
| 74.098 | H | H | trimethylsilylethynyl | H |
| 74.099 | H | H | $CH_2OH$ | H |
| 74.100 | H | H | $CH_2OCH_3$ | H |
| 74.101 | H | H | $CH_2OCH_2CH_3$ | H |
| 74.102 | H | H | $CH_2OCH_2OCH_3$ | H |
| 74.103 | H | H | $CH_2OCH_2OCH_2CH_3$ | H |
| 74.104 | H | H | $CH_2OCH_2CH_2OCH_3$ | H |

TABLE 74-continued

| | R⁶ | R⁸ | R⁹ | R¹¹ |
|---|---|---|---|---|
| 74.105 | H | H | CHO | H |
| 74.106 | H | H | COCH₃ | H |
| 74.107 | H | H | CO₂H | H |
| 74.108 | H | H | CO₂CH₃ | H |
| 74.109 | H | H | CO₂CH₂CH₃ | H |
| 74.110 | H | H | CONH₂ | H |
| 74.111 | H | H | CONHCH₃ | H |
| 74.112 | H | H | CONHCH₂CH₃ | H |
| 74.113 | H | H | CON(CH₃)₂ | H |
| 74.114 | H | H | CON(CH₂—CH₃)₂ | H |
| 74.115 | H | H | CON(CH₃)OCH₃ | H |
| 74.116 | H | H | CH=NOH | H |
| 74.117 | H | H | CH=N—OCH₃ | H |
| 74.118 | H | H | CH=N—OCH₂CH₃ | H |
| 74.119 | H | H | C(CH₃)=N—OH | H |
| 74.120 | H | H | C(CH₃)=N—OCH₃ | H |
| 74.121 | H | H | CH₂OC(O)—NHCH₃ | H |
| 74.122 | H | H | CH₂NH₂ | H |
| 74.123 | H | H | CH₂NHCHO | H |
| 74.124 | H | H | CH₂NHC(O)CH₃ | H |
| 74.125 | H | H | CH₂NHC(O)OCH₃ | H |
| 74.126 | H | H | CH(OH)CH₃ | H |
| 74.127 | H | H | CH(CH₃)OCH₃ | H |
| 74.128 | H | H | CN | H |
| 74.129 | H | H | CH₂SCH₃ | H |
| 74.130 | H | H | CH₂S(O)CH₃ | H |
| 74.131 | H | H | CH₂SO₂CH₃ | H |
| 74.132 | H | H | CH₂SCH₂CH₃ | H |
| 74.133 | H | H | CH₂S(O)CH₂CH₃ | H |
| 74.134 | H | H | CH₂SO₂CH₂CH₃ | H |
| 74.135 | H | H | OCH₃ | H |
| 74.136 | H | H | OCH₂CH₃ | H |
| 74.137 | H | H | CH(OCH₃)₂ | H |
| 74.138 | H | H | CH(OCH₂CH₃)₂ | H |
| 74.139 | H | H | cyclopropyl | H |
| 74.140 | H | H | cyclobutyl | H |
| 74.141 | H | H | cyclopentyl | H |
| 74.142 | H | H | cyclohexyl | H |
| 74.143 | H | H | F | H |
| 74.144 | H | H | Cl | H |
| 74.145 | H | H | Br | H |
| 74.146 | H | H | I | H |
| 74.147 | H | H | phenyl | H |
| 74.148 | H | H | 2-acetylphenyl | H |
| 74.149 | H | H | 3-acetylphenyl | H |
| 74.150 | H | H | 4-acetylphenyl | H |
| 74.151 | H | H | 2-chlorophenyl | H |
| 74.152 | H | H | 3-chlorophenyl | H |
| 74.153 | H | H | 4-chlorophenyl | H |
| 74.154 | H | H | 2-cyanophenyl | H |
| 74.155 | H | H | 3-cyanophenyl | H |
| 74.156 | H | H | 4-cyanophenyl | H |
| 74.157 | H | H | 2-fluorophenyl | H |
| 74.158 | H | H | 3-fluorophenyl | H |
| 74.159 | H | H | 4-fluorophenyl | H |
| 74.160 | H | H | 2-methoxyphenyl | H |
| 74.161 | H | H | 3-methoxyphenyl | H |
| 74.162 | H | H | 4-methoxyphenyl | H |
| 74.163 | H | H | 2-methylphenyl | H |
| 74.164 | H | H | 3-methylphenyl | H |
| 74.165 | H | H | 4-methylphenyl | H |
| 74.166 | H | H | 2-nitrophenyl | H |
| 74.167 | H | H | 3-nitrophenyl | H |
| 74.168 | H | H | 4-nitrophenyl | H |
| 74.169 | H | H | 2-thiomethylphenyl | H |
| 74.170 | H | H | 3-thiomethylphenyl | H |
| 74.171 | H | H | 4-thiomethylphenyl | H |
| 74.172 | H | H | 2-trifluoromethoxyphenyl | H |
| 74.173 | H | H | 3-trifluoromethoxyphenyl | H |
| 74.174 | H | H | 4-trifluoromethoxyphenyl | H |
| 74.175 | H | H | 2-trifluoromethylphenyl | H |
| 74.176 | H | H | 3-trifluoromethylphenyl | H |
| 74.177 | H | H | 4-trifluoromethylphenyl | H |
| 74.178 | H | H | 2,3-dichlorophenyl | H |
| 74.179 | H | H | 2,4-dichlorophenyl | H |
| 74.180 | H | H | 2,5-dichlorophenyl | H |
| 74.181 | H | H | 2,6-dichlorophenyl | H |
| 74.182 | H | H | 3,4-dichlorophenyl | H |

TABLE 74-continued

| | R⁶ | R⁸ | R⁹ | R¹¹ |
|---|---|---|---|---|
| 74.183 | H | H | 3,5-dichlorophenyl | H |
| 74.184 | H | H | 2,3-difluorophenyl | H |
| 74.185 | H | H | 2,4-difluorophenyl | H |
| 74.186 | H | H | 2,5-difluorophenyl | H |
| 74.187 | H | H | 2,6-difluorophenyl | H |
| 74.188 | H | H | 3,4-difluorophenyl | H |
| 74.189 | H | H | 3,5-difluorophenyl | H |
| 74.190 | H | H | 2,4,6-trifluorophenyl | H |
| 74.191 | H | H | 2,4-dimethylphenyl | H |
| 74.192 | H | H | 2,4,6-trimethylphenyl | H |
| 74.193 | H | H | 3,4,5-trimethoxyphenyl | H |
| 74.194 | H | H | 2-chloro-3-cyanophenyl | H |
| 74.195 | H | H | 2-chloro-4-cyanophenyl | H |
| 74.196 | H | H | 2-chloro-5-cyanophenyl | h |
| 74.197 | H | H | 2-chloro-6-cyanophenyl | H |
| 74.198 | H | H | 3-chloro-2-cyanophenyl | H |
| 74.199 | H | H | 3-chloro-4-cyanophenyl | H |
| 74.200 | H | H | 3-chloro-5-cyanophenyl | H |
| 74.201 | H | H | 5-chloro-2-cyanophenyl | H |
| 74.202 | H | H | 4-chloro-2-cyanophenyl | H |
| 74.203 | H | H | 4-chloro-3-cyanophenyl | H |
| 74.204 | H | H | 2-chloro-3-fluorophenyl | H |
| 74.205 | H | H | 2-chloro-4-fluorophenyl | H |
| 74.206 | H | H | 2-chloro-5-fluorophenyl | H |
| 74.207 | H | H | 2-chloro-6-fluorophenyl | H |
| 74.208 | H | H | 3-chloro-2-fluorophenyl | H |
| 74.209 | H | H | 3-chloro-4-fluorophenyl | H |
| 74.210 | H | H | 3-chloro-5-fluorophenyl | H |
| 74.211 | H | H | 5-chloro-2-fluorophenyl | H |
| 74.212 | H | H | 4-chloro-2-fluorophenyl | H |
| 74.213 | H | H | 4-chloro-3-fluorophenyl | H |
| 74.214 | H | H | 2-chloro-3-methylphenyl | H |
| 74.215 | H | H | 2-chloro-4-methylphenyl | H |
| 74.216 | H | H | 2-chloro-5-methylphenyl | H |
| 74.217 | H | H | 2-chloro-6-methylphenyl | H |
| 74.218 | H | H | 3-chloro-2-methylphenyl | H |
| 74.219 | H | H | 3-chloro-4-methylphenyl | H |
| 74.220 | H | H | 3-chloro-5-methylphenyl | H |
| 74.221 | H | H | 5-chloro-2-methylphenyl | H |
| 74.222 | H | H | 4-chloro-2-methylphenyl | H |
| 74.223 | H | H | 4-chloro-3-methylphenyl | H |
| 74.224 | H | H | 2-cyano-3-fluorophenyl | H |
| 74.225 | H | H | 2-cyano-4-fluorophenyl | H |
| 74.226 | H | H | 2-cyano-5-fluorophenyl | H |
| 74.227 | H | H | 2-cyano-6-fluorophenyl | H |
| 74.228 | H | H | 3-cyano-2-fluorophenyl | H |
| 74.229 | H | H | 3-cyano-4-fluorophenyl | H |
| 74.230 | H | H | 3-cyano-5-fluorophenyl | H |
| 74.231 | H | H | 5-cyano-2-fluorophenyl | H |
| 74.232 | H | H | 4-cyano-2-fluorophenyl | H |
| 74.233 | H | H | 4-cyano-3-fluorophenyl | H |
| 74.234 | H | H | 2-fluoro-3-methylphenyl | H |
| 74.235 | H | H | 2-fluoro-4-methylphenyl | H |
| 74.236 | H | H | 2-fluoro-5-methylphenyl | H |
| 74.237 | H | H | 2-fluoro-6-methylphenyl | H |
| 74.238 | H | H | 3-fluoro-2-methylphenyl | H |
| 74.239 | H | H | 3-fluoro-4-methylphenyl | H |
| 74.240 | H | H | 3-fluoro-5-methylphenyl | H |
| 74.241 | H | H | 5-fluoro-2-methylphenyl | H |
| 74.242 | H | H | 4-fluoro-2-methylphenyl | H |
| 74.243 | H | H | 4-fluoro-3-methylphenyl | H |
| 74.244 | H | H | pyridin-2-yl | H |
| 74.245 | H | H | pyridin-3-yl | H |
| 74.246 | H | H | pyridin-4-yl | H |
| 74.247 | H | H | 3-chloropyridin-2-yl | H |
| 74.248 | H | H | 4-chloropyridin-2-yl | H |
| 74.249 | H | H | 5-chloropyridin-2-yl | H |
| 74.250 | H | H | 6-chloropyridin-2-yl | H |
| 74.251 | H | H | 2-chloropyridin-3-yl | H |
| 74.252 | H | H | 4-chloropyridin-3-yl | H |
| 74.253 | H | H | 5-chloropyridin-3-yl | H |
| 74.254 | H | H | 2-chloropyridin-4-yl | H |
| 74.255 | H | H | 3-chloropyridin-4-yl | H |
| 74.256 | H | H | 2-chloropyridin-5-yl | H |
| 74.257 | H | H | 3-cyanopyridin-2-yl | H |
| 74.258 | H | H | 4-cyanopyridin-2-yl | H |
| 74.259 | H | H | 5-cyanopyridin-2-yl | H |
| 74.260 | H | H | 6-cyanopyridin-2-yl | H |

TABLE 74-continued

| | R⁶ | R⁸ | R⁹ | R¹¹ |
|---|---|---|---|---|
| 74.261 | H | H | 2-cyanopyridin-3-yl | H |
| 74.262 | H | H | 4-cyanopyridin-3-yl | H |
| 74.263 | H | H | 5-cyanopyridin-3-yl | H |
| 74.264 | H | H | 2-cyanopyridin-5-yl | H |
| 74.265 | H | H | 3-fluoropyridin-2-yl | H |
| 74.266 | H | H | 4-fluoropyridin-2-yl | H |
| 74.267 | H | H | 5-fluoropyridin-2-yl | H |
| 74.268 | H | H | 6-fluoropyridin-2-yl | H |
| 74.269 | H | H | 2-fluoropyridin-3-yl | H |
| 74.270 | H | H | 4-fluoropyridin-3-yl | H |
| 74.271 | H | H | 5-fluoropyridin-3-yl | H |
| 74.272 | H | H | 2-fluoropyridin-5-yl | H |
| 74.273 | H | H | 3-nitropyridin-2-yl | H |
| 74.274 | H | H | 4-nitropyridin-2-yl | H |
| 74.275 | H | H | 5-nitropyridin-2-yl | H |
| 74.276 | H | H | 6-nitropyridin-2-yl | H |
| 74.277 | H | H | 2-nitropyridin-3-yl | H |
| 74.278 | H | H | 4-nitropyridin-3-yl | H |
| 74.279 | H | H | 5-nitropyridin-3-yl | H |
| 74.280 | H | H | 2-nitropyridin-5-yl | H |
| 74.281 | H | H | 3-trifluoromethylpyridin-2-yl | H |
| 74.282 | H | H | 4-trifluoromethylpyridin-2-yl | H |
| 74.283 | H | H | 5-trifluoromethylpyridin-2-yl | H |
| 74.284 | H | H | 6-trifluoromethylpyridin-2-yl | H |
| 74.285 | H | H | 2-trifluoromethylpyridin-3-yl | H |
| 74.286 | H | H | 4-trifluoromethylpyridin-3-yl | H |
| 74.287 | H | H | 5-trifluoromethylpyridin-3-yl | H |
| 74.288 | H | H | 2-trifluoromethylpyridin-5-yl | H |
| 74.289 | H | H | 2,6-bis(trifluoromethyl)pyridin-3-yl | H |
| 74.290 | H | H | 2,6-bis(trifluoromethyl)pyridin-4-yl | H |
| 74.291 | H | H | 3,5-bis(trifluoromethyl)pyridin-2-yl | H |
| 74.292 | H | H | 2-thienyl | H |
| 74.293 | H | H | 3-thienyl | H |
| 74.294 | H | H | 5-cyanothien-2-yl | H |
| 74.295 | H | H | 2-furyl | H |
| 74.296 | H | H | 3-furyl | H |
| 74.297 | H | H | 1-methyl-1,2,3-triazol-4-yl | H |
| 74.298 | H | H | 2-methylthiopyrimidin-4-yl | H |
| 74.299 | H | H | 5-methyl-2-methylthiopyrimidin-4-yl | H |
| 74.300 | H | H | pyrazin-2-yl | H |
| 74.301 | H | H | 3,6-dimethylpyrazin-2-yl | H |
| 74.302 | H | H | 3-cyanopyrazin-2-yl | H |
| 74.303 | H | H | quinolin-2-yl | H |
| 74.304 | H | H | 3-ethylquinolin-2-yl | H |
| 74.305 | H | H | benzyl | H |
| 74.306 | H | H | 4-fluorobenzyl | H |
| 74.307 | H | H | 4-chlorobenzyl | H |
| 74.308 | H | H | 4-methylbenzyl | H |
| 74.309 | H | H | 2,4-dimethylbenzyl | H |
| 74.310 | H | H | 2,4,6-trimethylbenzyl | H |
| 74.311 | H | H | CH₃ | CH₃ |
| 74.312 | H | H | CH₂CH₃ | CH₃ |
| 74.313 | H | H | n-propyl | CH₃ |
| 74.314 | H | H | isopropyl | CH₃ |
| 74.315 | H | H | n-butyl | CH₃ |
| 74.316 | H | H | isobutyl | CH₃ |
| 74.317 | H | H | sec-butyl | CH₃ |
| 74.318 | H | H | tert-butyl | CH₃ |
| 74.319 | H | H | vinyl | CH₃ |
| 74.320 | H | H | ethynyl | CH₃ |
| 74.321 | H | H | trimethylsilylethynyl | CH₃ |
| 74.322 | H | H | CH₂OH | CH₃ |
| 74.323 | H | H | CH₂OCH₃ | CH₃ |
| 74.324 | H | H | CH₂OCH₂CH₃ | CH₃ |
| 74.325 | H | H | CH₂OCH₂OCH₃ | CH₃ |
| 74.326 | H | H | CH₂OCH₂OCH₂CH₃ | CH₃ |
| 74.327 | H | H | CH₂OCH₂CH₂OCH₃ | CH₃ |
| 74.328 | H | H | CHO | CH₃ |
| 74.329 | H | H | COCH₃ | CH₃ |
| 74.330 | H | H | CO₂H | CH₃ |
| 74.331 | H | H | CO₂CH₃ | CH₃ |
| 74.332 | H | H | CO₂CH₂CH₃ | CH₃ |
| 74.333 | H | H | CONH₂ | CH₃ |
| 74.334 | H | H | CONHCH₃ | CH₃ |
| 74.335 | H | H | CONHCH₂CH₃ | CH₃ |
| 74.336 | H | H | CON(CH₃)₂ | CH₃ |
| 74.337 | H | H | CON(CH₂—CH₃)₂ | CH₃ |
| 74.338 | H | H | CON(CH₃)OCH₃ | CH₃ |

TABLE 74-continued

| | $R^6$ | $R^8$ | $R^9$ | $R^{11}$ |
|---|---|---|---|---|
| 74.339 | H | H | CH=NOH | $CH_3$ |
| 74.340 | H | H | CH=N—$OCH_3$ | $CH_3$ |
| 74.341 | H | H | CH=N—$OCH_2CH_3$ | $CH_3$ |
| 74.342 | H | H | $C(CH_3)$=N—OH | $CH_3$ |
| 74.343 | H | H | $C(CH_3)$=N—$OCH_3$ | $CH_3$ |
| 74.344 | H | H | $CH_2OC(O)$—$NHCH_3$ | $CH_3$ |
| 74.345 | H | H | $CH_2NH_2$ | $CH_3$ |
| 74.346 | H | H | $CH_2NHCHO$ | $CH_3$ |
| 74.347 | H | H | $CH_2NHC(O)CH_3$ | $CH_3$ |
| 74.348 | H | H | $CH_2NHC(O)OCH_3$ | $CH_3$ |
| 74.349 | H | H | $CH(OH)CH_3$ | $CH_3$ |
| 74.350 | H | H | $CH(CH_3)OCH_3$ | $CH_3$ |
| 74.351 | H | H | CN | $CH_3$ |
| 74.352 | H | H | $CH_2SCH_3$ | $CH_3$ |
| 74.353 | H | H | $CH_2S(O)CH_3$ | $CH_3$ |
| 74.354 | H | H | $CH_2SO_2CH_3$ | $CH_3$ |
| 74.355 | H | H | $CH_2SCH_2CH_3$ | $CH_3$ |
| 74.356 | H | H | $CH_2S(O)CH_2CH_3$ | $CH_3$ |
| 74.357 | H | H | $CH_2SO_2CH_2CH_3$ | $CH_3$ |
| 74.358 | H | H | $OCH_3$ | $CH_3$ |
| 74.359 | H | H | $OCH_2CH_3$ | $CH_3$ |
| 74.360 | H | H | $CH(OCH_3)_2$ | $CH_3$ |
| 74.361 | H | H | $CH(OCH_2CH_3)_2$ | $CH_3$ |
| 74.362 | H | H | cyclopropyl | $CH_3$ |
| 74.363 | H | H | cyclobutyl | $CH_3$ |
| 74.364 | H | H | cyclopentyl | $CH_3$ |
| 74.365 | H | H | cyclohexyl | $CH_3$ |
| 74.366 | H | H | F | $CH_3$ |
| 74.367 | H | H | Cl | $CH_3$ |
| 74.368 | H | H | Br | $CH_3$ |
| 74.369 | H | H | I | $CH_3$ |
| 74.370 | H | H | phenyl | $CH_3$ |
| 74.371 | H | H | 2-acetylphenyl | $CH_3$ |
| 74.372 | H | H | 3-acetylphenyl | $CH_3$ |
| 74.373 | H | H | 4-acetylphenyl | $CH_3$ |
| 74.374 | H | H | 2-chlorophenyl | $CH_3$ |
| 74.375 | H | H | 3-chlorophenyl | $CH_3$ |
| 74.376 | H | H | 4-chlorophenyl | $CH_3$ |
| 74.377 | H | H | 2-cyanophenyl | $CH_3$ |
| 74.378 | H | H | 3-cyanophenyl | $CH_3$ |
| 74.379 | H | H | 4-cyanophenyl | $CH_3$ |
| 74.380 | H | H | 2-fluorophenyl | $CH_3$ |
| 74.381 | H | H | 3-fluorophenyl | $CH_3$ |
| 74.382 | H | H | 4-fluorophenyl | $CH_3$ |
| 74.383 | H | H | 2-methoxyphenyl | $CH_3$ |
| 74.384 | H | H | 3-methoxyphenyl | $CH_3$ |
| 74.385 | H | H | 4-methoxyphenyl | $CH_3$ |
| 74.386 | H | H | 2-methylphenyl | $CH_3$ |
| 74.387 | H | H | 3-methylphenyl | $CH_3$ |
| 74.388 | H | H | 4-methylphenyl | $CH_3$ |
| 74.389 | H | H | 2-nitrophenyl | $CH_3$ |
| 74.390 | H | H | 3-nitrophenyl | $CH_3$ |
| 74.391 | H | H | 4-nitrophenyl | $CH_3$ |
| 74.392 | H | H | 2-thiomethylphenyl | $CH_3$ |
| 74.393 | H | H | 3-thiomethylphenyl | $CH_3$ |
| 74.394 | H | H | 4-thiomethylphenyl | $CH_3$ |
| 74.395 | H | H | 2-trifluoromethoxyphenyl | $CH_3$ |
| 74.396 | H | H | 3-trifluoromethoxyphenyl | $CH_3$ |
| 74.397 | H | H | 4-trifluoromethoxyphenyl | $CH_3$ |
| 74.398 | H | H | 2-trifluoromethylphenyl | $CH_3$ |
| 74.399 | H | H | 3-trifluoromethylphenyl | $CH_3$ |
| 74.400 | H | H | 4-trifluoromethylphenyl | $CH_3$ |
| 74.401 | H | H | 2,3-dichlorophenyl | $CH_3$ |
| 74.402 | H | H | 2,4-dichlorophenyl | $CH_3$ |
| 74.403 | H | H | 2,5-dichlorophenyl | $CH_3$ |
| 74.404 | H | H | 2,6-dichlorophenyl | $CH_3$ |
| 74.405 | H | H | 3,4-dichlorophenyl | $CH_3$ |
| 74.406 | H | H | 3,5-dichlorophenyl | $CH_3$ |
| 74.407 | H | H | 2,3-difluorophenyl | $CH_3$ |
| 74.408 | H | H | 2,4-difluorophenyl | $CH_3$ |
| 74.409 | H | H | 2,5-difluorophenyl | $CH_3$ |
| 74.410 | H | H | 2,6-difluorophenyl | $CH_3$ |
| 74.411 | H | H | 3,4-difluorophenyl | $CH_3$ |
| 74.412 | H | H | 3,5-difluorophenyl | $CH_3$ |
| 74.413 | H | H | 2,4,6-trifluorophenyl | $CH_3$ |
| 74.414 | H | H | 2,4-dimethylphenyl | $CH_3$ |
| 74.415 | H | H | 2,4,6-trimethylphenyl | $CH_3$ |
| 74.416 | H | H | 3,4,5-trimethoxyphenyl | $CH_3$ |

TABLE 74-continued

| | R⁶ | R⁸ | R⁹ | R¹¹ |
|---|---|---|---|---|
| 74.417 | H | H | 2-chloro-3-cyanophenyl | CH₃ |
| 74.418 | H | H | 2-chloro-4-cyanophenyl | CH₃ |
| 74.419 | H | H | 2-chloro-5-cyanophenyl | CH₃ |
| 74.420 | H | H | 2-chloro-6-cyanophenyl | CH₃ |
| 74.421 | H | H | 3-chloro-2-cyanophenyl | CH₃ |
| 74.422 | H | H | 3-chloro-4-cyanophenyl | CH₃ |
| 74.423 | H | H | 3-chloro-5-cyanophenyl | CH₃ |
| 74.424 | H | H | 5-chloro-2-cyanophenyl | CH₃ |
| 74.425 | H | H | 4-chloro-2-cyanophenyl | CH₃ |
| 74.426 | H | H | 4-chloro-3-cyano-phenyl | CH₃ |
| 74.427 | H | H | 2-chloro-3-fluorophenyl | CH₃ |
| 74.428 | H | H | 2-chloro-4-fluorophenyl | CH₃ |
| 74.429 | H | H | 2-chloro-5-fluoro-phenyl | CH₃ |
| 74.430 | H | H | 2-chloro-6-fluorophenyl | CH₃ |
| 74.431 | H | H | 3-chloro-2-fluorophenyl | CH₃ |
| 74.432 | H | H | 3-chloro-4-fluorophenyl | CH₃ |
| 74.433 | H | H | 3-chloro-5-fluorophenyl | CH₃ |
| 74.434 | H | H | 5-chloro-2-fluorophenyl | CH₃ |
| 74.435 | H | H | 4-chloro-2-fluorophenyl | CH₃ |
| 74.436 | H | H | 4-chloro-3-fluorophenyl | CH₃ |
| 74.437 | H | H | 2-chloro-3-methylphenyl | CH₃ |
| 74.438 | H | H | 2-chloro-4-methyl phenyl | CH₃ |
| 74.439 | H | H | 2-chloro-5-methylphenyl | CH₃ |
| 74.440 | H | H | 2-chloro-6-methylphenyl | CH₃ |
| 74.441 | H | H | 3-chloro-2-methylphenyl | CH₃ |
| 74.442 | H | H | 3-chloro-4-methylphenyl | CH₃ |
| 74.443 | H | H | 3-chloro-5-methylphenyl | CH₃ |
| 74.444 | H | H | 5-chloro-2-methylphenyl | CH₃ |
| 74.445 | H | H | 4-chloro-2-methylphenyl | CH₃ |
| 74.446 | H | H | 4-chloro-3-methyl phenyl | CH₃ |
| 74.447 | H | H | 2-cyano-3-fluorophenyl | CH₃ |
| 74.448 | H | H | 2-cyano-4-fluorophenyl | CH₃ |
| 74.449 | H | H | 2-cyano-5-fluorophenyl | CH₃ |
| 74.450 | H | H | 2-cyano-6-fluorophenyl | CH₃ |
| 74.451 | H | H | 3-cyano-2-fluorophenyl | CH₃ |
| 74.452 | H | H | 3-cyano-4-fluorophenyl | CH₃ |
| 74.453 | H | H | 3-cyano-5-fluorophenyl | CH₃ |
| 74.454 | H | H | 5-cyano-2-fluorophenyl | CH₃ |
| 74.455 | H | H | 4-cyano-2-fluorophenyl | CH₃ |
| 74.456 | H | H | 4-cyano-3-fluorophenyl | CH₃ |
| 74.457 | H | H | 2-fluoro-3-methylphenyl | CH₃ |
| 74.458 | H | H | 2-fluoro-4-methylphenyl | CH₃ |
| 74.459 | H | H | 2-fluoro-5-methylphenyl | CH₃ |
| 74.460 | H | H | 2-fluoro-6-methylphenyl | CH₃ |
| 74.461 | H | H | 3-fluoro-2-methylphenyl | CH₃ |
| 74.462 | H | H | 3-fluoro-4-methylphenyl | CH₃ |
| 74.463 | H | H | 3-fluoro-5-methylphenyl | CH₃ |
| 74.464 | H | H | 5-fluoro-2-methylphenyl | CH₃ |
| 74.465 | H | H | 4-fluoro-2-methylphenyl | CH₃ |
| 74.466 | H | H | 4-fluoro-3-methylphenyl | CH₃ |
| 74.467 | H | H | pyridin-2-yl | CH₃ |
| 74.468 | H | H | pyridin-3-yl | CH₃ |
| 74.469 | H | H | pyridin-4-yl | CH₃ |
| 74.470 | H | H | 3-chloropyridin-2-yl | CH₃ |
| 74.471 | H | H | 4-chloropyridin-2-yl | CH₃ |
| 74.472 | H | H | 5-chloropyridin-2-yl | CH₃ |
| 74.473 | H | H | 6-chloropyridin-2-yl | CH₃ |
| 74.474 | H | H | 2-chloropyridin-3-yl | CH₃ |
| 74.475 | H | H | 4-chloropyridin-3-yl | CH₃ |
| 74.476 | H | H | 5-chloropyridin-3-yl | CH₃ |
| 74.477 | H | H | 2-chloropyridin-4-yl | CH₃ |
| 74.478 | H | H | 3-chloropyridin-4-yl | CH₃ |
| 74.479 | H | H | 2-chloropyridin-5-yl | CH₃ |
| 74.480 | H | H | 3-cyanopyridin-2-yl | CH₃ |
| 74.481 | H | H | 4-cyanopyridin-2-yl | CH₃ |
| 74.482 | H | H | 5-cyanopyridin-2-yl | CH₃ |
| 74.483 | H | H | 6-cyanopyridin-2-yl | CH₃ |
| 74.484 | H | H | 2-cyanopyridin-3-yl | CH₃ |
| 74.485 | H | H | 4-cyanopyridin-3-yl | CH₃ |
| 74.486 | H | H | 5-cyanopyridin-3-yl | CH₃ |
| 74.487 | H | H | 2-cyanopyridin-5-yl | CH₃ |
| 74.488 | H | H | 3-fluoropyridin-2-yl | CH₃ |
| 74.489 | H | H | 4-fluoropyridin-2-yl | CH₃ |
| 74.490 | H | H | 5-fluoropyridin-2-yl | CH₃ |
| 74.491 | H | H | 6-fluoropyridin-2-yl | CH₃ |
| 74.492 | H | H | 2-fluoropyridin-3-yl | CH₃ |
| 74.493 | H | H | 4-fluoropyridin-3-yl | CH₃ |
| 74.494 | H | H | 5-fluoropyridin-3-yl | CH₃ |

TABLE 74-continued

| | $R^6$ | $R^8$ | $R^9$ | $R^{11}$ |
|---|---|---|---|---|
| 74.495 | H | H | 2-fluoropyridin-5-yl | $CH_3$ |
| 74.496 | H | H | 3-nitropyridin-2-yl | $CH_3$ |
| 74.497 | H | H | 4-nitropyridin-2-yl | $CH_3$ |
| 74.498 | H | H | 5-nitropyridin-2-yl | $CH_3$ |
| 74.499 | H | H | 6-nitropyridin-2-yl | $CH_3$ |
| 74.500 | H | H | 2-nitropyridin-3-yl | $CH_3$ |
| 74.501 | H | H | 4-nitropyridin-3-yl | $CH_3$ |
| 74.502 | H | H | 5-nitropyridin-3-yl | $CH_3$ |
| 74.503 | H | H | 2-nitropyridin-5-yl | $CH_3$ |
| 74.504 | H | H | 3-trifluoromethylpyridin-2-yl | $CH_3$ |
| 74.505 | H | H | 4-trifluoromethylpyridin-2-yl | $CH_3$ |
| 74.506 | H | H | 5-trifluoromethylpyridin-2-yl | $CH_3$ |
| 74.507 | H | H | 6-trifluoromethylpyridin-2-yl | $CH_3$ |
| 74.508 | H | H | 2-trifluoromethylpyridin-3-yl | $CH_3$ |
| 74.509 | H | H | 4-trifluoromethylpyridin-3-yl | $CH_3$ |
| 74.510 | H | H | 5-trifluoromethylpyridin-3-yl | $CH_3$ |
| 74.511 | H | H | 2-trifluoromethylpyridin-5-yl | $CH_3$ |
| 74.512 | H | H | 2,6-bis(trifluoromethyl)pyridin-3-yl | $CH_3$ |
| 74.513 | H | H | 2,6-bis(trifluoromethyl)pyridin-4-yl | $CH_3$ |
| 74.514 | H | H | 3,5-bis(trifluoromethyl)pyridin-2-yl | $CH_3$ |
| 74.515 | H | H | 2-thienyl | $CH_3$ |
| 74.516 | H | H | 3-thienyl | $CH_3$ |
| 74.517 | H | H | 5-cyanothien-2-yl | $CH_3$ |
| 74.518 | H | H | 2-furyl | $CH_3$ |
| 74.519 | H | H | 3-furyl | $CH_3$ |
| 74.520 | H | H | 1-methyl-1,2,3-triazol-4-yl | $CH_3$ |
| 74.521 | H | H | 2-methylthiopyrimidin-4-yl | $CH_3$ |
| 74.522 | H | H | 5-methyl-2-methylthiopyrimidin-4-yl | $CH_3$ |
| 74.523 | H | H | pyrazin-2-yl | $CH_3$ |
| 74.524 | H | H | 3,6-dimethylpyrazin-2-yl | $CH_3$ |
| 74.525 | H | H | 3-cyanopyrazin-2-yl | $CH_3$ |
| 74.526 | H | H | quinolin-2-yl | $CH_3$ |
| 74.527 | H | H | 3-ethylquinolin-2-yl | $CH_3$ |
| 74.528 | H | H | benzyl | $CH_3$ |
| 74.529 | H | H | 4-fluorobenzyl | $CH_3$ |
| 74.530 | H | H | 4-chlorobenzyl | $CH_3$ |
| 74.531 | H | H | 4-methylbenzyl | $CH_3$ |
| 74.532 | H | H | 2,4-dimethylbenzyl | $CH_3$ |
| 74.533 | H | H | 2,4,6-trimethylbenzyl | $CH_3$ |
| 74.534 | $CH_3$ | H | $CH_3$ | H |
| 74.535 | $CH_3$ | H | $CH_2CH_3$ | H |
| 74.536 | $CH_3$ | H | n-propyl | H |
| 74.537 | $CH_3$ | H | isopropyl | H |
| 74.538 | $CH_3$ | H | n-butyl | H |
| 74.539 | $CH_3$ | H | isobutyl | H |
| 74.540 | $CH_3$ | H | sec-butyl | H |
| 74.541 | $CH_3$ | H | tert-butyl | H |
| 74.542 | $CH_3$ | H | vinyl | H |
| 74.543 | $CH_3$ | H | ethynyl | H |
| 74.544 | $CH_3$ | H | trimethylsilylethynyl | H |
| 74.545 | $CH_3$ | H | $CH_2OH$ | H |
| 74.546 | $CH_3$ | H | $CH_2OCH_3$ | H |
| 74.547 | $CH_3$ | H | $CH_2OCH_2CH_3$ | H |
| 74.548 | $CH_3$ | H | $CH_2OCH_2OCH_3$ | H |
| 74.549 | $CH_3$ | H | $CH_2OCH_2OCH_2CH_3$ | H |
| 74.550 | $CH_3$ | H | $CH_2OCH_2CH_2OCH_3$ | H |
| 74.551 | $CH_3$ | H | CHO | H |
| 74.552 | $CH_3$ | H | $COCH_3$ | H |
| 74.553 | $CH_3$ | H | $CO_2H$ | H |
| 74.554 | $CH_3$ | H | $CO_2CH_3$ | H |
| 74.555 | $CH_3$ | H | $CO_2CH_2CH_3$ | H |
| 74.556 | $CH_3$ | H | $CONH_2$ | H |
| 74.557 | $CH_3$ | H | $CONHCH_3$ | H |
| 74.558 | $CH_3$ | H | $CONHCH_2CH_3$ | H |
| 74.559 | $CH_3$ | H | $CON(CH_3)_2$ | H |
| 74.560 | $CH_3$ | H | $CON(CH_2-CH_3)_2$ | H |
| 74.561 | $CH_3$ | H | $CON(CH_3)OCH_3$ | H |
| 74.562 | $CH_3$ | H | CH=NOH | H |
| 74.563 | $CH_3$ | H | CH=N—$OCH_3$ | H |
| 74.564 | $CH_3$ | H | CH=N—$OCH_2CH_3$ | H |
| 74.565 | $CH_3$ | H | $C(CH_3)$=N—OH | H |
| 74.566 | $CH_3$ | H | $C(CH_3)$=N—$OCH_3$ | H |
| 74.567 | $CH_3$ | H | $CH_2OC(O)$—$NHCH_3$ | H |
| 74.568 | $CH_3$ | H | $CH_2NH_2$ | H |
| 74.569 | $CH_3$ | H | $CH_2NHCHO$ | H |
| 74.570 | $CH_3$ | H | $CH_2NHC(O)CH_3$ | H |
| 74.571 | $CH_3$ | H | $CH_2NHC(O)OCH_3$ | H |
| 74.572 | $CH_3$ | H | $CH(OH)CH_3$ | H |

TABLE 74-continued

| | $R^6$ | $R^8$ | $R^9$ | $R^{11}$ |
|---|---|---|---|---|
| 74.573 | CH$_3$ | H | CH(CH$_3$)OCH$_3$ | H |
| 74.574 | CH$_3$ | H | CN | H |
| 74.575 | CH$_3$ | H | CH$_2$SCH$_3$ | H |
| 74.576 | CH$_3$ | H | CH$_2$S(O)CH$_3$ | H |
| 74.577 | CH$_3$ | H | CH$_2$SO$_2$CH$_3$ | H |
| 74.578 | CH$_3$ | H | CH$_2$SCH$_2$CH$_3$ | H |
| 74.579 | CH$_3$ | H | CH$_2$S(O)CH$_2$CH$_3$ | H |
| 74.580 | CH$_3$ | H | CH$_2$SO$_2$CH$_2$CH$_3$ | H |
| 74.581 | CH$_3$ | H | OCH$_3$ | H |
| 74.582 | CH$_3$ | H | OCH$_2$CH$_3$ | H |
| 74.583 | CH$_3$ | H | CH(OCH$_3$)$_2$ | H |
| 74.584 | CH$_3$ | H | CH(OCH$_2$CH$_3$)$_2$ | H |
| 74.585 | CH$_3$ | H | cyclopropyl | H |
| 74.586 | CH$_3$ | H | cyclobutyl | H |
| 74.587 | CH$_3$ | H | cyclopentyl | H |
| 74.588 | CH$_3$ | H | cyclohexyl | H |
| 74.589 | CH$_3$ | H | F | H |
| 74.590 | CH$_3$ | H | Cl | H |
| 74.591 | CH$_3$ | H | Br | H |
| 74.592 | CH$_3$ | H | I | H |
| 74.593 | CH$_3$ | H | phenyl | H |
| 74.594 | CH$_3$ | H | 2-acetylphenyl | H |
| 74.595 | CH$_3$ | H | 3-acetylphenyl | H |
| 74.596 | CH$_3$ | H | 4-acetylphenyl | H |
| 74.597 | CH$_3$ | H | 2-chlorophenyl | H |
| 74.598 | CH$_3$ | H | 3-chlorophenyl | H |
| 74.599 | CH$_3$ | H | 4-chlorophenyl | H |
| 74.600 | CH$_3$ | H | 2-cyanophenyl | H |
| 74.601 | CH$_3$ | H | 3-cyanophenyl | H |
| 74.602 | CH$_3$ | H | 4-cyanophenyl | H |
| 74.603 | CH$_3$ | H | 2-fluorophenyl | H |
| 74.604 | CH$_3$ | H | 3-fluorophenyl | H |
| 74.605 | CH$_3$ | H | 4-fluorophenyl | H |
| 74.606 | CH$_3$ | H | 2-methoxyphenyl | H |
| 74.607 | CH$_3$ | H | 3-methoxyphenyl | H |
| 74.608 | CH$_3$ | H | 4-methoxyphenyl | H |
| 74.609 | CH$_3$ | H | 2-methylphenyl | H |
| 74.610 | CH$_3$ | H | 3-methylphenyl | H |
| 74.611 | CH$_3$ | H | 4-methylphenyl | H |
| 74.612 | CH$_3$ | H | 2-nitrophenyl | H |
| 74.613 | CH$_3$ | H | 3-nitrophenyl | H |
| 74.614 | CH$_3$ | H | 4-nitrophenyl | H |
| 74.615 | CH$_3$ | H | 2-thiomethylphenyl | H |
| 74.616 | CH$_3$ | H | 3-thiomethylphenyl | H |
| 74.617 | CH$_3$ | H | 4-thiomethylphenyl | H |
| 74.618 | CH$_3$ | H | 2-trifluoromethoxyphenyl | H |
| 74.619 | CH$_3$ | H | 3-trifluoromethoxyphenyl | H |
| 74.620 | CH$_3$ | H | 4-trifluoromethoxyphenyl | H |
| 74.621 | CH$_3$ | H | 2-trifluoromethylphenyl | H |
| 74.622 | CH$_3$ | H | 3-trifluoromethylphenyl | H |
| 74.623 | CH$_3$ | H | 4-trifluoromethylphenyl | H |
| 74.624 | CH$_3$ | H | 2,3-dichlorophenyl | H |
| 74.625 | CH$_3$ | H | 2,4-dichlorophenyl | H |
| 74.626 | CH$_3$ | H | 2,5-dichlorophenyl | H |
| 74.627 | CH$_3$ | H | 2,6-dichlorophenyl | H |
| 74.628 | CH$_3$ | H | 3,4-dichlorophenyl | H |
| 74.629 | CH$_3$ | H | 3,5-dichlorophenyl | H |
| 74.630 | CH$_3$ | H | 2,3-difluorophenyl | H |
| 74.631 | CH$_3$ | H | 2,4-difluorophenyl | H |
| 74.632 | CH$_3$ | H | 2,5-difluorophenyl | H |
| 74.633 | CH$_3$ | H | 2,6-difluorophenyl | H |
| 74.634 | CH$_3$ | H | 3,4-difluorophenyl | H |
| 74.635 | CH$_3$ | H | 3,5-difluorophenyl | H |
| 74.636 | CH$_3$ | H | 2,4,6-trifluorophenyl | H |
| 74.637 | CH$_3$ | H | 2,4-dimethylphenyl | H |
| 74.638 | CH$_3$ | H | 2,4,6-trimethylphenyl | H |
| 74.639 | CH$_3$ | H | 3,4,5-trimethoxyphenyl | H |
| 74.640 | CH$_3$ | H | 2-chloro-3-cyanophenyl | H |
| 74.641 | CH$_3$ | H | 2-chloro-4-cyanophenyl | H |
| 74.642 | CH$_3$ | H | 2-chloro-5-cyanophenyl | H |
| 74.643 | CH$_3$ | H | 2-chloro-6-cyanophenyl | H |
| 74.644 | CH$_3$ | H | 3-chloro-2-cyanophenyl | H |
| 74.645 | CH$_3$ | H | 3-chloro-4-cyanophenyl | H |
| 74.646 | CH$_3$ | H | 3-chloro-5-cyanophenyl | H |
| 74.647 | CH$_3$ | H | 5-chloro-2-cyanophenyl | H |
| 74.648 | CH$_3$ | H | 4-chloro-2-cyanophenyl | H |
| 74.649 | CH$_3$ | H | 4-chloro-3-cyanophenyl | H |
| 74.650 | CH$_3$ | H | 2-chloro-3-fluorophenyl | H |

TABLE 74-continued

| | R⁶ | R⁸ | R⁹ | R¹¹ |
|---|---|---|---|---|
| 74.651 | CH₃ | H | 2-chloro-4-fluorophenyl | H |
| 74.652 | CH₃ | H | 2-chloro-5-fluorophenyl | H |
| 74.653 | CH₃ | H | 2-chloro-6-fluorophenyl | H |
| 74.654 | CH₃ | H | 3-chloro-2-fluorophenyl | H |
| 74.655 | CH₃ | H | 3-chloro-4-fluorophenyl | H |
| 74.656 | CH₃ | H | 3-chloro-5-fluorophenyl | H |
| 74.657 | CH₃ | H | 5-chloro-2-fluorophenyl | H |
| 74.658 | CH₃ | H | 4-chloro-2-fluorophenyl | H |
| 74.659 | CH₃ | H | 4-chloro-3-fluorophenyl | H |
| 74.660 | CH₃ | H | 2-chloro-3-methylphenyl | H |
| 74.661 | CH₃ | H | 2-chloro-4-methylphenyl | H |
| 74.662 | CH₃ | H | 2-chloro-5-methylphenyl | H |
| 74.663 | CH₃ | H | 2-chloro-6-methylphenyl | H |
| 74.664 | CH₃ | H | 3-chloro-2-methylphenyl | H |
| 74.665 | CH₃ | H | 3-chloro-4-methylphenyl | H |
| 74.666 | CH₃ | H | 3-chloro-5-methylphenyl | H |
| 74.667 | CH₃ | H | 5-chloro-2-methylphenyl | H |
| 74.668 | CH₃ | H | 4-chloro-2-methylphenyl | H |
| 74.669 | CH₃ | H | 4-chloro-3-methylphenyl | H |
| 74.670 | CH₃ | H | 2-cyano-3-fluorophenyl | H |
| 74.671 | CH₃ | H | 2-cyano-4-fluorophenyl | H |
| 74.672 | CH₃ | H | 2-cyano-5-fluorophenyl | H |
| 74.673 | CH₃ | H | 2-cyano-6-fluorophenyl | H |
| 74.674 | CH₃ | H | 3-cyano-2-fluorophenyl | H |
| 74.675 | CH₃ | H | 3-cyano-4-fluorophenyl | H |
| 74.676 | CH₃ | H | 3-cyano-5-fluorophenyl | H |
| 74.677 | CH₃ | H | 5-cyano-2-fluorophenyl | H |
| 74.678 | CH₃ | H | 4-cyano-2-fluorophenyl | H |
| 74.679 | CH₃ | H | 4-cyano-3-fluorophenyl | H |
| 74.680 | CH₃ | H | 2-fluoro-3-methylphenyl | H |
| 74.681 | CH₃ | H | 2-fluoro-4-methylphenyl | H |
| 74.682 | CH₃ | H | 2-fluoro-5-methylphenyl | H |
| 74.683 | CH₃ | H | 2-fluoro-6-methylphenyl | H |
| 74.684 | CH₃ | H | 3-fluoro-2-methylphenyl | H |
| 74.685 | CH₃ | H | 3-fluoro-4-methylphenyl | H |
| 74.686 | CH₃ | H | 3-fluoro-5-methylphenyl | H |
| 74.687 | CH₃ | H | 5-fluoro-2-methylphenyl | H |
| 74.688 | CH₃ | H | 4-fluoro-2-methylphenyl | H |
| 74.689 | CH₃ | H | 4-fluoro-3-methylphenyl | H |
| 74.690 | CH₃ | H | pyridin-2-yl | H |
| 74.691 | CH₃ | H | pyridin-3-yl | H |
| 74.692 | CH₃ | H | pyridin-4-yl | H |
| 74.693 | CH₃ | H | 3-chloropyridin-2-yl | H |
| 74.694 | CH₃ | H | 4-chloropyridin-2-yl | H |
| 74.695 | CH₃ | H | 5-chloropyridin-2-yl | H |
| 74.696 | CH₃ | H | 6-chloropyridin-2-yl | H |
| 74.697 | CH₃ | H | 2-chloropyridin-3-yl | H |
| 74.698 | CH₃ | H | 4-chloropyridin-3-yl | H |
| 74.699 | CH₃ | H | 5-chloropyridin-3-yl | H |
| 74.700 | CH₃ | H | 2-chloropyridin-4-yl | H |
| 74.701 | CH₃ | H | 3-chloropyridin-4-yl | H |
| 74.702 | CH₃ | H | 2-chloropyridin-5-yl | H |
| 74.703 | CH₃ | H | 3-cyanopyridin-2-yl | H |
| 74.704 | CH₃ | H | 4-cyanopyridin-2-yl | H |
| 74.705 | CH₃ | H | 5-cyanopyridin-2-yl | H |
| 74.706 | CH₃ | H | 6-cyanopyridin-2-yl | H |
| 74.707 | CH₃ | H | 2-cyanopyridin-3-yl | H |
| 74.708 | CH₃ | H | 4-cyanopyridin-3-yl | H |
| 74.709 | CH₃ | H | 5-cyanopyridin-3-yl | H |
| 74.710 | CH₃ | H | 2-cyanopyridin-5-yl | H |
| 74.711 | CH₃ | H | 3-fluoropyridin-2-yl | H |
| 74.712 | CH₃ | H | 4-fluoropyridin-2-yl | H |
| 74.713 | CH₃ | H | 5-fluoropyridin-2-yl | H |
| 74.714 | CH₃ | H | 6-fluoropyridin-2-yl | H |
| 74.715 | CH₃ | H | 2-fluoropyridin-3-yl | H |
| 74.716 | CH₃ | H | 4-fluoropyridin-3-yl | H |
| 74.717 | CH₃ | H | 5-fluoropyridin-3-yl | H |
| 74.718 | CH₃ | H | 2-fluoropyridin-5-yl | H |
| 74.719 | CH₃ | H | 3-nitropyridin-2-yl | H |
| 74.720 | CH₃ | H | 4-nitropyridin-2-yl | H |
| 74.721 | CH₃ | H | 5-nitropyridin-2-yl | H |
| 74.722 | CH₃ | H | 6-nitropyridin-2-yl | H |
| 74.723 | CH₃ | H | 2-nitropyridin-3-yl | H |
| 74.724 | CH₃ | H | 4-nitropyridin-3-yl | H |
| 74.725 | CH₃ | H | 5-nitropyridin-3-yl | H |
| 74.726 | CH₃ | H | 2-nitropyridin-5-yl | H |
| 74.727 | CH₃ | H | 3-trifluoromethylpyridin-2-yl | H |
| 74.728 | CH₃ | H | 4-trifluoromethylpyridin-2-yl | H |

TABLE 74-continued

| | R⁶ | R⁸ | R⁹ | R¹¹ |
|---|---|---|---|---|
| 74.729 | CH₃ | H | 5-trifluoromethylpyridin-2-yl | H |
| 74.730 | CH₃ | H | 6-trifluoromethylpyridin-2-yl | H |
| 74.731 | CH₃ | H | 2-trifluoromethylpyridin-3-yl | H |
| 74.732 | CH₃ | H | 4-trifluoromethylpyridin-3-yl | H |
| 74.733 | CH₃ | H | 5-trifluoromethylpyridin-3-yl | H |
| 74.734 | CH₃ | H | 2-trifluoromethylpyridin-5-yl | H |
| 74.735 | CH₃ | H | 2,6-bis(trifluoromethyl)pyridin-3-yl | H |
| 74.736 | CH₃ | H | 2,6-bis(trifluoromethyl)pyridin-4-yl | H |
| 74.737 | CH₃ | H | 3,5-bis(trifluoromethyl)pyridin-2-yl | H |
| 74.738 | CH₃ | H | 2-thienyl | H |
| 74.739 | CH₃ | H | 3-thienyl | H |
| 74.740 | CH₃ | H | 5-cyanothien-2-yl | H |
| 74.741 | CH₃ | H | 2-furyl | H |
| 74.742 | CH₃ | H | 3-furyl | H |
| 74.743 | CH₃ | H | 1-methyl-1,2,3-triazol-4-yl | H |
| 74.744 | CH₃ | H | 2-methylthiopyrimidin-4-yl | H |
| 74.745 | CH₃ | H | 5-methyl-2-methylthiopyrimidin-4-yl | H |
| 74.746 | CH₃ | H | pyrazin-2-yl | H |
| 74.747 | CH₃ | H | 3,6-dimethylpyrazin-2-yl | H |
| 74.748 | CH₃ | H | 3-cyanopyrazin-2-yl | H |
| 74.749 | CH₃ | H | quinolin-2-yl | H |
| 74.750 | CH₃ | H | 3-ethylquinolin-2-yl | H |
| 74.751 | CH₃ | H | benzyl | H |
| 74.752 | CH₃ | H | 4-fluorobenzyl | H |
| 74.753 | CH₃ | H | 4-chlorobenzyl | H |
| 74.754 | CH₃ | H | 4-methylbenzyl | H |
| 74.755 | CH₃ | H | 2,4-dimethylbenzyl | H |
| 74.756 | CH₃ | H | 2,4,6-trimethylbenzyl | H |
| 74.757 | CH₃ | H | H | CH₃ |
| 74.758 | CH₃ | H | CH₃ | CH₃ |
| 74.759 | CH₃ | H | CH₂CH₃ | CH₃ |
| 74.760 | CH₃ | H | n-propyl | CH₃ |
| 74.761 | CH₃ | H | isopropyl | CH₃ |
| 74.762 | CH₃ | H | n-butyl | CH₃ |
| 74.763 | CH₃ | H | isobutyl | CH₃ |
| 74.764 | CH₃ | H | sec-butyl | CH₃ |
| 74.765 | CH₃ | H | tert-butyl | CH₃ |
| 74.766 | CH₃ | H | vinyl | CH₃ |
| 74.767 | CH₃ | H | ethynyl | CH₃ |
| 74.768 | CH₃ | H | trimethylsilylethynyl | CH₃ |
| 74.769 | CH₃ | H | CH₂OH | CH₃ |
| 74.770 | CH₃ | H | CH₂OCH₃ | CH₃ |
| 74.771 | CH₃ | H | CH₂OCH₂CH₃ | CH₃ |
| 74.772 | CH₃ | H | CH₂OCH₂OCH₃ | CH₃ |
| 74.773 | CH₃ | H | CH₂OCH₂OCH₂CH₃ | CH₃ |
| 74.774 | CH₃ | H | CH₂OCH₂CH₂OCH₃ | CH₃ |
| 74.775 | CH₃ | H | CHO | CH₃ |
| 74.776 | CH₃ | H | COCH₃ | CH₃ |
| 74.777 | CH₃ | H | CO₂H | CH₃ |
| 74.778 | CH₃ | H | CO₂CH₃ | CH₃ |
| 74.779 | CH₃ | H | CO₂CH₂CH₃ | CH₃ |
| 74.780 | CH₃ | H | CONH₂ | CH₃ |
| 74.781 | CH₃ | H | CONHCH₃ | CH₃ |
| 74.782 | CH₃ | H | CONHCH₂CH₃ | CH₃ |
| 74.783 | CH₃ | H | CON(CH₃)₂ | CH₃ |
| 74.784 | CH₃ | H | CON(CH₂—CH₃)₂ | CH₃ |
| 74.785 | CH₃ | H | CON(CH₃)OCH₃ | CH₃ |
| 74.786 | CH₃ | H | CH=NOH | CH₃ |
| 74.787 | CH₃ | H | CH=N—OCH₃ | CH₃ |
| 74.788 | CH₃ | H | CH=N—OCH₂CH₃ | CH₃ |
| 74.789 | CH₃ | H | C(CH₃)=N—OH | CH₃ |
| 74.790 | CH₃ | H | C(CH₃)=N—OCH₃ | CH₃ |
| 74.791 | CH₃ | H | CH₂OC(O)—NHCH₃ | CH₃ |
| 74.792 | CH₃ | H | CH₂NH₂ | CH₃ |
| 74.793 | CH₃ | H | CH₂NHCHO | CH₃ |
| 74.794 | CH₃ | H | CH₂NHC(O)CH₃ | CH₃ |
| 74.795 | CH₃ | H | CH₂NHC(O)OCH₃ | CH₃ |
| 74.796 | CH₃ | H | CH(OH)CH₃ | CH₃ |
| 74.797 | CH₃ | H | CH(CH₃)OCH₃ | CH₃ |
| 74.798 | CH₃ | H | CN | CH₃ |
| 74.799 | CH₃ | H | CH₂SCH₃ | CH₃ |
| 74.800 | CH₃ | H | CH₂S(O)CH₃ | CH₃ |
| 74.801 | CH₃ | H | CH₂SO₂CH₃ | CH₃ |
| 74.802 | CH₃ | H | CH₂SCH₂CH₃ | CH₃ |
| 74.803 | CH₃ | H | CH₂S(O)CH₂CH₃ | CH₃ |
| 74.804 | CH₃ | H | CH₂SO₂CH₂CH₃ | CH₃ |
| 74.805 | CH₃ | H | OCH₃ | CH₃ |
| 74.806 | CH₃ | H | OCH₂CH₃ | CH₃ |

TABLE 74-continued

| | $R^6$ | $R^8$ | $R^9$ | $R^{11}$ |
|---|---|---|---|---|
| 74.807 | $CH_3$ | H | $CH(OCH_3)_2$ | $CH_3$ |
| 74.808 | $CH_3$ | H | $CH(OCH_2CH_3)_2$ | $CH_3$ |
| 74.809 | $CH_3$ | H | cyclopropyl | $CH_3$ |
| 74.810 | $CH_3$ | H | cyclobutyl | $CH_3$ |
| 74.811 | $CH_3$ | H | cyclopentyl | $CH_3$ |
| 74.812 | $CH_3$ | H | cyclohexyl | $CH_3$ |
| 74.813 | $CH_3$ | H | F | $CH_3$ |
| 74.814 | $CH_3$ | H | Cl | $CH_3$ |
| 74.815 | $CH_3$ | H | Br | $CH_3$ |
| 74.816 | $CH_3$ | H | I | $CH_3$ |
| 74.817 | $CH_3$ | H | phenyl | $CH_3$ |
| 74.818 | $CH_3$ | H | 2-acetylphenyl | $CH_3$ |
| 74.819 | $CH_3$ | H | 3-acetylphenyl | $CH_3$ |
| 74.820 | $CH_3$ | H | 4-acetylphenyl | $CH_3$ |
| 74.821 | $CH_3$ | H | 2-chlorophenyl | $CH_3$ |
| 74.822 | $CH_3$ | H | 3-chlorophenyl | $CH_3$ |
| 74.823 | $CH_3$ | H | 4-chlorophenyl | $CH_3$ |
| 74.824 | $CH_3$ | H | 2-cyanophenyl | $CH_3$ |
| 74.825 | $CH_3$ | H | 3-cyanophenyl | $CH_3$ |
| 74.826 | $CH_3$ | H | 4-cyanophenyl | $CH_3$ |
| 74.827 | $CH_3$ | H | 2-fluorophenyl | $CH_3$ |
| 74.828 | $CH_3$ | H | 3-fluorophenyl | $CH_3$ |
| 74.829 | $CH_3$ | H | 4-fluorophenyl | $CH_3$ |
| 74.830 | $CH_3$ | H | 2-methoxyphenyl | $CH_3$ |
| 74.831 | $CH_3$ | H | 3-methoxyphenyl | $CH_3$ |
| 74.832 | $CH_3$ | H | 4-methoxyphenyl | $CH_3$ |
| 74.833 | $CH_3$ | H | 2-methylphenyl | $CH_3$ |
| 74.834 | $CH_3$ | H | 3-methylphenyl | $CH_3$ |
| 74.835 | $CH_3$ | H | 4-methylphenyl | $CH_3$ |
| 74.836 | $CH_3$ | H | 2-nitrophenyl | $CH_3$ |
| 74.837 | $CH_3$ | H | 3-nitrophenyl | $CH_3$ |
| 74.838 | $CH_3$ | H | 4-nitrophenyl | $CH_3$ |
| 74.839 | $CH_3$ | H | 2-thiomethylphenyl | $CH_3$ |
| 74.840 | $CH_3$ | H | 3-thiomethylphenyl | $CH_3$ |
| 74.841 | $CH_3$ | H | 4-thiomethylphenyl | $CH_3$ |
| 74.842 | $CH_3$ | H | 2-trifluoromethoxyphenyl | $CH_3$ |
| 74.843 | $CH_3$ | H | 3-trifluoromethoxyphenyl | $CH_3$ |
| 74.844 | $CH_3$ | H | 4-trifluoromethoxyphenyl | $CH_3$ |
| 74.845 | $CH_3$ | H | 2-trifluoromethylphenyl | $CH_3$ |
| 74.846 | $CH_3$ | H | 3-trifluoromethylphenyl | $CH_3$ |
| 74.847 | $CH_3$ | H | 4-trifluoromethylphenyl | $CH_3$ |
| 74.848 | $CH_3$ | H | 2,3-dichlorophenyl | $CH_3$ |
| 74.849 | $CH_3$ | H | 2,4-dichlorophenyl | $CH_3$ |
| 74.850 | $CH_3$ | H | 2,5-dichlorophenyl | $CH_3$ |
| 74.851 | $CH_3$ | H | 2,6-dichlorophenyl | $CH_3$ |
| 74.852 | $CH_3$ | H | 3,4-dichlorophenyl | $CH_3$ |
| 74.853 | $CH_3$ | H | 3,5-dichlorophenyl | $CH_3$ |
| 74.854 | $CH_3$ | H | 2,3-difluorophenyl | $CH_3$ |
| 74.855 | $CH_3$ | H | 2,4-difluorophenyl | $CH_3$ |
| 74.856 | $CH_3$ | H | 2,5-difluorophenyl | $CH_3$ |
| 74.857 | $CH_3$ | H | 2,6-difluorophenyl | $CH_3$ |
| 74.858 | $CH_3$ | H | 3,4-difluorophenyl | $CH_3$ |
| 74.859 | $CH_3$ | H | 3,5-difluorophenyl | $CH_3$ |
| 74.860 | $CH_3$ | H | 2,4,6-trifluorophenyl | $CH_3$ |
| 74.861 | $CH_3$ | H | 2,4-dimethylphenyl | $CH_3$ |
| 74.862 | $CH_3$ | H | 2,4,6-trimethylphenyl | $CH_3$ |
| 74.863 | $CH_3$ | H | 3,4,5-trimethoxyphenyl | $CH_3$ |
| 74.864 | $CH_3$ | H | 2-chloro-3-cyanophenyl | $CH_3$ |
| 74.865 | $CH_3$ | H | 2-chloro-4-cyanophenyl | $CH_3$ |
| 74.866 | $CH_3$ | H | 2-chloro-5-cyanophenyl | $CH_3$ |
| 74.867 | $CH_3$ | H | 2-chloro-6-cyanophenyl | $CH_3$ |
| 74.868 | $CH_3$ | H | 3-chloro-2-cyanophenyl | $CH_3$ |
| 74.869 | $CH_3$ | H | 3-chloro-4-cyanophenyl | $CH_3$ |
| 74.870 | $CH_3$ | H | 3-chloro-5-cyanophenyl | $CH_3$ |
| 74.871 | $CH_3$ | H | 5-chloro-2-cyanophenyl | $CH_3$ |
| 74.872 | $CH_3$ | H | 4-chloro-2-cyanophenyl | $CH_3$ |
| 74.873 | $CH_3$ | H | 4-chloro-3-cyanophenyl | $CH_3$ |
| 74.874 | $CH_3$ | H | 2-chloro-3-fluorophenyl | $CH_3$ |
| 74.875 | $CH_3$ | H | 2-chloro-4-fluorophenyl | $CH_3$ |
| 74.876 | $CH_3$ | H | 2-chloro-5-fluorophenyl | $CH_3$ |
| 74.877 | $CH_3$ | H | 2-chloro-6-fluorophenyl | $CH_3$ |
| 74.878 | $CH_3$ | H | 3-chloro-2-fluorophenyl | $CH_3$ |
| 74.879 | $CH_3$ | H | 3-chloro-4-fluorophenyl | $CH_3$ |
| 74.880 | $CH_3$ | H | 3-chloro-5-fluorophenyl | $CH_3$ |
| 74.881 | $CH_3$ | H | 5-chloro-2-fluorophenyl | $CH_3$ |
| 74.882 | $CH_3$ | H | 4-chloro-2-fluorophenyl | $CH_3$ |
| 74.883 | $CH_3$ | H | 4-chloro-3-fluorophenyl | $CH_3$ |
| 74.884 | $CH_3$ | H | 2-chloro-3-methylphenyl | $CH_3$ |

TABLE 74-continued

| | R⁶ | R⁸ | R⁹ | R¹¹ |
|---|---|---|---|---|
| 74.885 | CH₃ | H | 2-chloro-4-methylphenyl | CH₃ |
| 74.886 | CH₃ | H | 2-chloro-5-methylphenyl | CH₃ |
| 74.887 | CH₃ | H | 2-chloro-6-methylphenyl | CH₃ |
| 74.888 | CH₃ | H | 3-chloro-2-methylphenyl | CH₃ |
| 74.889 | CH₃ | H | 3-chloro-4-methylphenyl | CH₃ |
| 74.890 | CH₃ | H | 3-chloro-5-methylphenyl | CH₃ |
| 74.891 | CH₃ | H | 5-chloro-2-methylphenyl | CH₃ |
| 74.892 | CH₃ | H | 4-chloro-2-methylphenyl | CH₃ |
| 74.893 | CH₃ | H | 4-chloro-3-methylphenyl | CH₃ |
| 74.894 | CH₃ | H | 2-cyano-3-fluorophenyl | CH₃ |
| 74.895 | CH₃ | H | 2-cyano-4-fluorophenyl | CH₃ |
| 74.896 | CH₃ | H | 2-cyano-5-fluorophenyl | CH₃ |
| 74.897 | CH₃ | H | 2-cyano-6-fluorophenyl | CH₃ |
| 74.898 | CH₃ | H | 3-cyano-2-fluorophenyl | CH₃ |
| 74.899 | CH₃ | H | 3-cyano-4-fluorophenyl | CH₃ |
| 74.901 | CH₃ | H | 3-cyano-5-fluorophenyl | CH₃ |
| 74.902 | CH₃ | H | 5-cyano-2-fluorophenyl | CH₃ |
| 74.903 | CH₃ | H | 4-cyano-2-fluorophenyl | CH₃ |
| 74.904 | CH₃ | H | 4-cyano-3-fluorophenyl | CH₃ |
| 74.905 | CH₃ | H | 2-fluoro-3-methylphenyl | CH₃ |
| 74.906 | CH₃ | H | 2-fluoro-4-methylphenyl | CH₃ |
| 74.907 | CH₃ | H | 2-fluoro-5-methylphenyl | CH₃ |
| 74.908 | CH₃ | H | 2-fluoro-6-methylphenyl | CH₃ |
| 74.909 | CH₃ | H | 3-fluoro-2-methylphenyl | CH₃ |
| 74.910 | CH₃ | H | 3-fluoro-4-methylphenyl | CH₃ |
| 74.911 | CH₃ | H | 3-fluoro-5-methylphenyl | CH₃ |
| 74.912 | CH₃ | H | 5-fluoro-2-methylphenyl | CH₃ |
| 74.913 | CH₃ | H | 4-fluoro-2-methylphenyl | CH₃ |
| 74.914 | CH₃ | H | 4-fluoro-3-methylphenyl | CH₃ |
| 74.915 | CH₃ | H | pyridin-2-yl | CH₃ |
| 74.916 | CH₃ | H | pyridin-3-yl | CH₃ |
| 74.917 | CH₃ | H | pyridin-4-yl | CH₃ |
| 74.918 | CH₃ | H | 3-chloropyridin-2-yl | CH₃ |
| 74.919 | CH₃ | H | 4-chloropyridin-2-yl | CH₃ |
| 74.920 | CH₃ | H | 5-chloropyridin-2-yl | CH₃ |
| 74.921 | CH₃ | H | 6-chloropyridin-2-yl | CH₃ |
| 74.922 | CH₃ | H | 2-chloropyridin-3-yl | CH₃ |
| 74.923 | CH₃ | H | 4-chloropyridin-3-yl | CH₃ |
| 74.924 | CH₃ | H | 5-chloropyridin-3-yl | CH₃ |
| 74.925 | CH₃ | H | 2-chloropyridin-4-yl | CH₃ |
| 74.926 | CH₃ | H | 3-chloropyridin-4-yl | CH₃ |
| 74.927 | CH₃ | H | 2-chloropyridin-5-yl | CH₃ |
| 74.928 | CH₃ | H | 3-cyanopyridin-2-yl | CH₃ |
| 74.929 | CH₃ | H | 4-cyanopyridin-2-yl | CH₃ |
| 74.930 | CH₃ | H | 5-cyanopyridin-2-yl | CH₃ |
| 74.931 | CH₃ | H | 6-cyanopyridin-2-yl | CH₃ |
| 74.932 | CH₃ | H | 2-cyanopyridin-3-yl | CH₃ |
| 74.933 | CH₃ | H | 4-cyanopyridin-3-yl | CH₃ |
| 74.934 | CH₃ | H | 5-cyanopyridin-3-yl | CH₃ |
| 74.935 | CH₃ | H | 2-cyanopyridin-5-yl | CH₃ |
| 74.936 | CH₃ | H | 3-fluoropyridin-2-yl | CH₃ |
| 74.937 | CH₃ | H | 4-fluoropyridin-2-yl | CH₃ |
| 74.938 | CH₃ | H | 5-fluoropyridin-2-yl | CH₃ |
| 74.939 | CH₃ | H | 6-fluoropyridin-2-yl | CH₃ |
| 74.940 | CH₃ | H | 2-fluoropyridin-3-yl | CH₃ |
| 74.941 | CH₃ | H | 4-fluoropyridin-3-yl | CH₃ |
| 74.942 | CH₃ | H | 5-fluoropyridin-3-yl | CH₃ |
| 74.943 | CH₃ | H | 2-fluoropyridin-5-yl | CH₃ |
| 74.944 | CH₃ | H | 3-nitropyridin-2-yl | CH₃ |
| 74.945 | CH₃ | H | 4-nitropyridin-2-yl | CH₃ |
| 74.946 | CH₃ | H | 5-nitropyridin-2-yl | CH₃ |
| 74.947 | CH₃ | H | 6-nitropyridin-2-yl | CH₃ |
| 74.948 | CH₃ | H | 2-nitropyridin-3-yl | CH₃ |
| 74.949 | CH₃ | H | 4-nitropyridin-3-yl | CH₃ |
| 74.950 | CH₃ | H | 5-nitropyridin-3-yl | CH₃ |
| 74.951 | CH₃ | H | 2-nitropyridin-5-yl | CH₃ |
| 74.952 | CH₃ | H | 3-trifluoromethylpyridin-2-yl | CH₃ |
| 74.953 | CH₃ | H | 4-trifluoromethylpyridin-2-yl | CH₃ |
| 74.954 | CH₃ | H | 5-trifluoromethylpyridin-2-yl | CH₃ |
| 74.955 | CH₃ | H | 6-trifluoromethylpyridin-2-yl | CH₃ |
| 74.956 | CH₃ | H | 2-trifluoromethylpyridin-3-yl | CH₃ |
| 74.957 | CH₃ | H | 4-trifluoromethylpyridin-3-yl | CH₃ |
| 74.958 | CH₃ | H | 5-trifluoromethylpyridin-3-yl | CH₃ |
| 74.959 | CH₃ | H | 2-trifluoromethylpyridin-5-yl | CH₃ |
| 74.960 | CH₃ | H | 2,6-bis(trifluoromethyl)pyridin-3-yl | CH₃ |
| 74.961 | CH₃ | H | 2,6-bis(trifluoromethyl)pyridin-4-yl | CH₃ |
| 74.962 | CH₃ | H | 3,5-bis(trifluoromethyl)pyridin-2-yl | CH₃ |
| 74.963 | CH₃ | H | 2-thienyl | CH₃ |

TABLE 74-continued

| | $R^6$ | $R^8$ | $R^9$ | $R^{11}$ |
|---|---|---|---|---|
| 74.964 | $CH_3$ | H | 3-thienyl | $CH_3$ |
| 74.965 | $CH_3$ | H | 5-cyanothien-2-yl | $CH_3$ |
| 74.966 | $CH_3$ | H | 2-furyl | $CH_3$ |
| 74.967 | $CH_3$ | H | 3-furyl | $CH_3$ |
| 74.968 | $CH_3$ | H | 1-methyl-1,2,3-triazol-4-yl | $CH_3$ |
| 74.969 | $CH_3$ | H | 2-methylthiopyrimidin-4-yl | $CH_3$ |
| 74.970 | $CH_3$ | H | 5-methyl-2-methylthiopyrimidin-4-yl | $CH_3$ |
| 74.971 | $CH_3$ | H | pyrazin-2-yl | $CH_3$ |
| 74.972 | $CH_3$ | H | 3,6-dimethylpyrazin-2-yl | $CH_3$ |
| 74.973 | $CH_3$ | H | 3-cyanopyrazin-2-yl | $CH_3$ |
| 74.974 | $CH_3$ | H | quinolin-2-yl | $CH_3$ |
| 74.975 | $CH_3$ | H | 3-ethylquinolin-2-yl | $CH_3$ |
| 74.976 | $CH_3$ | H | benzyl | $CH_3$ |
| 74.977 | $CH_3$ | H | 4-fluorobenzyl | $CH_3$ |
| 74.978 | $CH_3$ | H | 4-chlorobenzyl | $CH_3$ |
| 74.979 | $CH_3$ | H | 4-methylbenzyl | $CH_3$ |
| 74.980 | $CH_3$ | H | 2,4-dimethylbenzyl | $CH_3$ |
| 74.981 | $CH_3$ | H | 2,4,6-trimethylbenzyl | $CH_3$ |
| 74.982 | $CH_3$ | H | H | $CH_2OH$ |
| 74.983 | $CH_3$ | H | H | $CH_2OCH_3$ |
| 74.984 | $CH_3$ | H | H | $CH_2OCH_2CH_3$ |
| 74.985 | $CH_3$ | H | H | CHO |
| 74.986 | $CH_3$ | H | H | $COCH_3$ |
| 74.987 | $CH_3$ | H | H | $CO_2H$ |
| 74.988 | $CH_3$ | H | H | $CO_2CH_3$ |
| 74.989 | $CH_3$ | H | H | $CO_2CH_2CH_3$ |
| 74.990 | $CH_3$ | H | H | $CONH_2$ |
| 74.991 | $CH_3$ | H | H | $CONHCH_3$ |
| 74.992 | $CH_3$ | H | H | $CONHCH_2CH_3$ |
| 74.993 | $CH_3$ | H | H | $CON(CH_3)_2$ |
| 74.994 | $CH_3$ | H | H | $CON-(CH_2CH_3)_2$ |
| 74.995 | $CH_3$ | H | H | $CON(CH_3)O-CH_3$ |
| 74.996 | $CH_3$ | H | H | $CH=NOH$ |
| 74.997 | $CH_3$ | H | H | $CH=NOCH_3$ |
| 74.998 | $CH_3$ | H | H | $CH=NOCH_2-CH_3$ |
| 74.999 | $CH_3$ | H | H | $C(CH_3)=NOH$ |
| 74.1000 | $CH_3$ | H | H | $C(CH_3)=NO-CH_3$ |
| 74.1001 | $CH_3$ | H | H | $CH_2OC(O)NH-CH_3$ |
| 74.1002 | $CH_3$ | H | H | $CH_2NH_2$ |
| 74.1003 | $CH_3$ | H | H | $CH_2NHCHO$ |
| 74.1004 | $CH_3$ | H | H | $CH_2NHC(O)-CH_3$ |
| 74.1005 | $CH_3$ | H | H | $CH_2NHC(O)OCH_3$ |
| 74.1006 | $CH_3$ | H | H | $NHCO_2CH_3$ |
| 74.1007 | $CH_3$ | H | H | $NHCO_2-C(CH_3)_3$ |
| 74.1008 | $CH_3$ | H | H | $CH(OH)CH_3$ |
| 74.1009 | $CH_3$ | H | H | $CH(CH_3)OCH_3$ |
| 74.1010 | $CH_3$ | H | H | CN |
| 74.1011 | $CH_3$ | H | H | $CH_2SCH_3$ |
| 74.1012 | $CH_3$ | H | H | $CH_2S(O)CH_3$ |
| 74.1013 | $CH_3$ | H | H | $CH_2SO_2CH_3$ |
| 74.1014 | $CH_3$ | H | H | $CH_2SCH_2CH_3$ |
| 74.1015 | $CH_3$ | H | H | $CH_2S(O)CH_2-CH_3$ |
| 74.1016 | $CH_3$ | H | H | $CH_2SO_2CH_2-CH_3$ |
| 74.1017 | $CH_3$ | H | H | $OCH_3$ |
| 74.1018 | $CH_3$ | H | H | $OCH_2CH_3$ |
| 74.1019 | $CH_3$ | H | H | $CH(OCH_3)_2$ |
| 74.1020 | $CH_3$ | H | H | $CH-(OCH_2CH_3)_2$ |
| 74.1021 | $CH_3$ | H | H | $CH_2CH_3$ |
| 74.1022 | $CH_3$ | H | H | $CH_2CH_2CH_3$ |
| 74.1023 | $CH_3$ | H | H | $CH(CH_3)_2$ |
| 74.1024 | $CH_3$ | H | H | $C(CH_3)_3$ |
| 74.1025 | $CH_3$ | H | H | $CH_2CH(CH_3)_2$ |
| 74.1026 | $CH_3$ | H | H | $CH_2C(CH_3)_3$ |
| 74.1027 | $CH_3$ | H | H | $CH_2CN$ |
| 74.1028 | $CH_3$ | H | H | cyclopropyl |
| 74.1029 | $CH_3$ | H | H | cyclobutyl |
| 74.1030 | $CH_3$ | H | H | cyclopentyl |
| 74.1031 | $CH_3$ | H | H | cyclohexyl |
| 74.1032 | $CH_3$ | H | H | $CH_2$-cyclopropyl |
| 74.1033 | $CH_3$ | H | H | benzyl |
| 74.1034 | $CH_3$ | H | H | $CH_2CF_3$ |

Table 75 covers compounds of formula (AH), wherein $R^1$ is ethyl, $R^2$ and $R^4$ are methyl, $R^3$, $R^5$ and $R^{12}$ are hydrogen and $R^6$, $R^8$, $R^9$, and $R^{11}$ are as defined in Table 74.

Table 76 covers compounds of formula (AH), wherein Wand $R^4$ are ethyl, $R^2$ is methyl, $R^3$, $R^5$ and $R^{12}$ are hydrogen and $R^6$, $R^8$, $R^9$, and $R^{11}$ are as defined in Table 74.

Table 77 covers compounds of formula (AH), wherein $R^1$, $R^2$ and $R^4$ are ethyl, $R^3$, $R^5$ and $R^{12}$ are hydrogen and $R^6$, $R^8$, $R^9$, and $R^{11}$ are as defined in Table 74.

Table 78 covers compounds of formula (AH), wherein $R^1$ and $R^2$ are methyl, $R^3$, $R^4$, $R^5$ and $R^{12}$ are hydrogen and $R^6$, $R^8$, $R^9$, and $R^{11}$ are as defined in Table 74.

Table 79 covers compounds of formula (AH), wherein $R^1$ and $R^2$ are methyl, $R^4$ is methoxy, $R^3$, $R^5$ and $R^{12}$ are hydrogen and $R^6$, $R^8$, $R^9$, and $R^{11}$ are as defined in Table 74.

Table 80 covers compounds of formula (AH), wherein $R^1$ and $R^2$ are methyl, $R^4$ is chlorine, $R^3$, $R^5$ and $R^{12}$ are hydrogen and $R^6$, $R^8$, $R^9$, and $R^{11}$ are as defined in Table 74.

Table 81 covers compounds of formula (AH), wherein $R^1$ and $R^2$ are methyl, $R^4$ is bromine, $R^3$, $R^5$ and $R^{12}$ are hydrogen and $R^6$, $R^8$, $R^9$, and $R^{11}$ are as defined in Table 74.

Table 82 covers compounds of formula (AH), wherein $R^1$ and $R^2$ are methyl, $R^4$ is iodine, $R^3$, $R^5$ and $R^{12}$ are hydrogen and $R^6$, $R^8$, $R^9$, and $R^{11}$ are as defined in Table 74.

Table 83 covers compounds of formula (AH), wherein $R^1$ and $R^2$ are methyl, $R^4$ is ethynyl, $R^3$, $R^5$ and $R^{12}$ are hydrogen and $R^6$, $R^8$, $R^9$, and $R^{11}$ are as defined in Table 74.

Table 84 covers compounds of formula (AH), wherein $R^1$ and $R^2$ are methyl, $R^4$ is vinyl, $R^3$, $R^5$ and $R^{12}$ are hydrogen and $R^6$, $R^8$, $R^9$, and $R^{11}$ are as defined in Table 74.

Table 85 covers compounds of formula (AH), wherein $R^1$ is ethyl, $R^2$ is methyl, $R^3$, $R^4$, $R^5$ and $R^{12}$ are hydrogen and $R^6$, $R^8$, $R^9$, and $R^{11}$ are as defined in Table 74.

Table 86 covers compounds of formula (AH), wherein $R^1$ is ethyl, $R^2$ is methyl, $R^4$ is methoxy, $R^3$, $R^5$ and $R^{12}$ are hydrogen and $R^6$, $R^8$, $R^9$, and $R^{11}$ are as defined in Table 74.

Table 87 covers compounds of formula (AH), wherein $R^1$ is ethyl, $R^2$ is methyl, $R^4$ is chlorine, $R^3$, $R^5$ and $R^{12}$ are hydrogen and $R^6$, $R^8$, $R^9$, and $R^{11}$ are as defined in Table 74.

Table 88 covers compounds of formula (AH), wherein $R^1$ is ethyl, $R^2$ is methyl, $R^4$ is bromine, $R^3$, $R^5$ and $R^{12}$ are hydrogen and $R^6$, $R^8$, $R^9$, and $R^{11}$ are as defined in Table 74.

Table 89 covers compounds of formula (AH), wherein $R^1$ is ethyl, $R^2$ is methyl, $R^4$ is iodine, $R^3$, $R^5$ and $R^{12}$ are hydrogen and $R^6$, $R^8$, $R^9$, and $R^{11}$ are as defined in Table 74.

Table 90 covers compounds of formula (AH), wherein $R^1$ is ethyl, $R^2$ is methyl, $R^4$ is ethynyl, $R^3$, $R^5$ and $R^{12}$ are hydrogen and $R^6$, $R^8$, $R^9$, and $R^{11}$ are as defined in Table 74.

Table 91 covers compounds of formula (AH), wherein $R^1$ is ethyl, $R^2$ is methyl, $R^4$ is vinyl, $R^3$, $R^5$ and $R^{12}$ are hydrogen and $R^6$, $R^8$, $R^9$, and $R^{11}$ are as defined in Table 74.

Table 92 covers compounds of formula (AH), wherein $R^1$ is ethynyl, $R^2$ is methyl, $R^3$, $R^4$, $R^5$ and $R^{12}$ are hydrogen and $R^6$, $R^8$, $R^9$, and $R^{11}$ are as defined in Table 74.

Table 93 covers compounds of formula (AH), wherein $R^1$ is ethynyl, $R^2$ is methyl, $R^4$ is methoxy, $R^3$, $R^5$ and $R^{12}$ are hydrogen and $R^6$, $R^8$, $R^9$, and $R^{11}$ are as defined in Table 74.

Table 94 covers compounds of formula (AH), wherein $R^1$ is ethynyl, $R^2$ is methyl, $R^4$ is chlorine, $R^3$, $R^5$ and $R^{12}$ are hydrogen and $R^6$, $R^8$, $R^9$, and $R^{11}$ are as defined in Table 74.

Table 95 covers compounds of formula (AH), wherein $R^1$ is ethynyl, $R^2$ is methyl, $R^4$ is bromine, $R^3$, $R^5$ and $R^{12}$ are hydrogen and $R^6$, $R^8$, $R^9$, and $R^{11}$ are as defined in Table 74.

Table 96 covers compounds of formula (AH), wherein $R^1$ is ethynyl, $R^2$ is methyl, $R^4$ is iodine, $R^3$, $R^5$ and $R^{12}$ are hydrogen and $R^6$, $R^8$, $R^9$, and $R^{11}$ are as defined in Table 74.

Table 97 covers compounds of formula (AH), wherein $R^1$ and $R^4$ are ethynyl, $R^2$ is methyl, $R^3$, $R^5$ and $R^{12}$ are hydrogen and $R^6$, $R^8$, $R^9$, and $R^{11}$ are as defined in Table 74.

Table 98 covers compounds of formula (AH), wherein $R^1$ is vinyl, $R^2$ is methyl, $R^3$, $R^4$, $R^5$ and $R^{12}$ are hydrogen and $R^6$, $R^8$, $R^9$, and $R^{11}$ are as defined in Table 74.

Table 99 covers compounds of formula (AH), wherein $R^1$ is vinyl, $R^2$ is methyl, $R^4$ is methoxy, $R^3$, $R^5$ and $R^{12}$ are hydrogen and $R^6$, $R^8$, $R^9$, and $R^{11}$ are as defined in Table 74.

Table 100 covers compounds of formula (AH), wherein $R^1$ is vinyl, $R^2$ is methyl, $R^4$ is chlorine, $R^3$, $R^5$ and $R^{12}$ are hydrogen and $R^6$, $R^8$, $R^9$, and $R^{11}$ are as defined in Table 74.

Table 101 covers compounds of formula (AH), wherein $R^1$ is vinyl, $R^2$ is methyl, $R^4$ is bromine, $R^3$, $R^5$ and $R^{12}$ are hydrogen and $R^6$, $R^8$, $R^9$, and $R^{11}$ are as defined in Table 74.

Table 102 covers compounds of formula (AH), wherein $R^1$ is vinyl, $R^2$ is methyl, $R^4$ is iodine, $R^3$, $R^5$ and $R^{12}$ are hydrogen and $R^6$, $R^8$, $R^9$, and $R^{11}$ are as defined in Table 74.

Table 103 covers compounds of formula (AH), wherein $R^1$ and $R^4$ are vinyl, $R^2$ is methyl, $R^3$, $R^5$ and $R^{12}$ are hydrogen and $R^6$, $R^8$, $R^9$, and $R^{11}$ are as defined in Table 74.

Table 104 covers compounds of formula (AH), wherein $R^1$ is methyl, $R^2$, $R^3$, $R^4$, $R^5$ and $R^{12}$ are hydrogen and $R^6$, $R^8$, $R^9$, and $R^{11}$ are as defined in Table 74.

Table 105 covers compounds of formula (AH), wherein $R^1$ is methyl, $R^2$ is methoxy, $R^3$, $R^4$, $R^5$ and $R^{12}$ are hydrogen and $R^6$, $R^8$, $R^9$, and $R^{11}$ are as defined in Table 74.

Table 106 covers compounds of formula (AH), wherein $R^1$ is methyl, $R^2$ is trifluoromethyl, $R^3$, $R^4$, $R^5$ and $R^{12}$ are hydrogen and $R^6$, $R^8$, $R^9$, and $R^{11}$ are as defined in Table 74.

Table 107 covers compounds of formula (AH), wherein $R^1$ is methyl, $R^2$ is ethyl, $R^3$, $R^4$, $R^5$ and $R^{12}$ are hydrogen and $R^6$, $R^8$, $R^9$, and $R^{11}$ are as defined in Table 74.

Table 108 covers compounds of formula (AH), wherein $R^1$ is methyl, $R^2$ is ethynyl, $R^3$, $R^4$, $R^5$ and $R^{12}$ are hydrogen and $R^6$, $R^8$, $R^9$, and $R^{11}$ are as defined in Table 74.

Table 109 covers compounds of formula (AH), wherein $R^1$ is methyl, $R^2$ is vinyl, $R^3$, $R^4$, $R^5$ and $R^{12}$ are hydrogen and $R^6$, $R^8$, $R^9$, and $R^{11}$ are as defined in Table 74.

Table 110 covers compounds of formula (AH), wherein $R^1$ is methyl, $R^2$ is chlorine, $R^3$, $R^4$, $R^5$ and $R^{12}$ are hydrogen and $R^6$, $R^8$, $R^9$, and $R^{11}$ are as defined in Table 74.

Table 111 covers compounds of formula (AH), wherein $R^1$ is methyl, $R^2$ is bromine, $R^3$, $R^4$, $R^5$ and $R^{12}$ are hydrogen and $R^6$, $R^8$, $R^9$, and $R^{11}$ are as defined in Table 74.

Table 112 covers compounds of formula (AH), wherein $R^1$ is methyl, $R^2$ is iodine, $R^3$, $R^4$, $R^5$ and $R^{12}$ are hydrogen and $R^6$, $R^8$, $R^9$, and $R^{11}$ are as defined in Table 74.

Table 113 covers compounds of formula (AH), wherein $R^1$ is ethyl, $R^2$, $R^3$, $R^4$, $R^5$ and $R^{12}$ are hydrogen and $R^6$, $R^8$, $R^9$, and $R^{11}$ are as defined in Table 74.

Table 114 covers compounds of formula (AH), wherein $R^1$ is ethyl, $R^2$ is methoxy, $R^3$, $R^4$, $R^5$ and $R^{12}$ are hydrogen and $R^6$, $R^8$, $R^9$, and $R^{11}$ are as defined in Table 74.

Table 115 covers compounds of formula (AH), wherein $R^1$ and $R^2$ are ethyl, $R^3$, $R^4$, $R^5$ and $R^{12}$ are hydrogen and $R^6$, $R^8$, $R^9$, and $R^{11}$ are as defined in Table 74.

Table 116 covers compounds of formula (AH), wherein $R^1$ is ethyl, $R^2$ is trifluoromethyl, $R^3$, $R^4$, $R^5$ and $R^{12}$ are hydrogen and $R^6$, $R^8$, $R^9$, and $R^{11}$ are as defined in Table 74.

Table 117 covers compounds of formula (AH), wherein $R^1$ is ethyl, $R^2$ is ethynyl, $R^3$, $R^4$, $R^5$ and $R^{12}$ are hydrogen and $R^6$, $R^8$, $R^9$, and $R^{11}$ are as defined in Table 74.

Table 118 covers compounds of formula (AH), wherein $R^1$ is ethyl, $R^2$ is vinyl, $R^3$, $R^4$, $R^5$ and $R^{12}$ are hydrogen and $R^6$, $R^8$, $R^9$, and $R^{11}$ are as defined in Table 74.

Table 119 covers compounds of formula (AH), wherein $R^1$ is ethyl, $R^2$ is chlorine, $R^3$, $R^4$, $R^5$ and $R^{12}$ are hydrogen and $R^6$, $R^8$, $R^9$, and $R^{11}$ are as defined in Table 74.

Table 120 covers compounds of formula (AH), wherein $R^1$ is ethyl, $R^2$ is bromine, $R^3$, $R^4$, $R^5$ and $R^{12}$ are hydrogen and $R^6$, $R^8$, $R^9$, and $R^{11}$ are as defined in Table 74.

Table 121 covers compounds of formula (AH), wherein $R^1$ is ethyl, $R^2$ is iodine, $R^3$, $R^4$, $R^5$ and $R^{12}$ are hydrogen and $R^6$, $R^8$, $R^9$, and $R^{11}$ are as defined in Table 74.

Table 122 covers compounds of formula (AH), wherein $R^1$ and $R^4$ are methyl, $R^2$ is chlorine, $R^3$, $R^5$ and $R^{12}$ are hydrogen and $R^6$, $R^8$, $R^9$, and $R^{11}$ are as defined in Table 74.

Table 123 covers compounds of formula (AH), wherein $R^1$ and $R^4$ are methyl, $R^2$ is bromine, $R^3$, $R^5$ and $R^{12}$ are hydrogen and $R^6$, $R^8$, $R^9$, and $R^{11}$ are as defined in Table 74.

Table 124 covers compounds of formula (AH), wherein $R^1$ and $R^4$ are methyl, $R^2$ is iodine, $R^3$, $R^5$ and $R^{12}$ are hydrogen and $R^6$, $R^8$, $R^9$, and $R^{11}$ are as defined in Table 74.

Table 125 covers compounds of formula (AH), wherein $R^1$ is methyl, $R^2$ is chlorine, $R^3$ is hydrogen, $R^4$ is ethyl, $R^5$ and $R^{12}$ are hydrogen and $R^6$, $R^8$, $R^9$, and $R^{11}$ are as defined in Table 74.

Table 126 covers compounds of formula (AH), wherein $R^1$ is methyl, $R^2$ is bromine, $R^3$ is hydrogen, $R^4$ is ethyl, $R^5$ and $R^{12}$ are hydrogen and $R^6$, $R^8$, $R^9$, and $R^{11}$ are as defined in Table 74.

Table 127 covers compounds of formula (AH), wherein $R^1$ is methyl, $R^2$ is iodine, $R^3$ is hydrogen, $R^4$ is ethyl, $R^5$ and $R^{12}$ are hydrogen and $R^6$, $R^8$, $R^9$, and $R^{11}$ are as defined in Table 74.

Table 128 covers compounds of formula (AH), wherein $R^1$ and $R^4$ are ethyl, $R^2$ is chlorine, $R^3$, $R^5$ and $R^{12}$ are hydrogen and $R^6$, $R^8$, $R^9$, and $R^{11}$ are as defined in Table 74.

Table 129 covers compounds of formula (AH), wherein $R^1$ and $R^4$ are methyl, $R^2$ is bromine, $R^3$, $R^5$ and $R^{12}$ are hydrogen and $R^6$, $R^8$, $R^9$, and $R^{11}$ are as defined in Table 74.

Table 130 covers compounds of formula (AH), wherein $R^1$ and $R^4$ are ethyl, $R^2$ is iodine, $R^3$, $R^5$ and $R^{12}$ are hydrogen and $R^6$, $R^8$, $R^9$, and $R^{11}$ are as defined in Table 74.

Table 131 covers compounds of formula (AH), wherein $R^1$ is methyl, $R^2$ is chlorine, $R^3$ is hydrogen, $R^4$ is methoxy, $R^5$ and $R^{12}$ are hydrogen and $R^6$, $R^8$, $R^9$, and $R^{11}$ are as defined in Table 74.

Table 132 covers compounds of formula (AH), wherein $R^1$ is methyl, $R^2$ is bromine, $R^3$ is hydrogen, $R^4$ is methoxy, $R^5$ and $R^{12}$ are hydrogen and $R^6$, $R^8$, $R^9$, and $R^{11}$ are as defined in Table 74.

Table 133 covers compounds of formula (AH), wherein $R^1$ is ethyl, $R^2$ is chlorine, $R^3$ is hydrogen, $R^4$ is methoxy, $R^5$ and $R^{12}$ are hydrogen and $R^6$, $R^8$, $R^9$, and $R^{11}$ are as defined in Table 74.

Table 134 covers compounds of formula (AH), wherein $R^1$ is ethyl, $R^2$ is bromine, $R^3$ is hydrogen, $R^4$ is methoxy, $R^5$ and $R^{12}$ are hydrogen and $R^6$, $R^8$, $R^9$, and $R^{11}$ are as defined in Table 74.

Table 135 covers compounds of formula (AH), wherein $R^1$ and $R^4$ are methyl, $R^2$ is methoxy, $R^3$, $R^5$ and $R^{12}$ are hydrogen and $R^6$, $R^8$, $R^9$, and $R^{11}$ are as defined in Table 74.

Table 136 covers compounds of formula (AH), wherein $R^1$ is methyl, $R^2$ is methoxy, $R^3$ is hydrogen, $R^4$ is ethyl, $R^5$ and $R^{12}$ are hydrogen and $R^6$, $R^8$, $R^9$, and $R^{11}$ are as defined in Table 74.

Table 137 covers compounds of formula (AH), wherein $R^1$ and $R^4$ are ethyl, $R^2$ is methoxy, $R^3$, $R^5$ and $R^{12}$ are hydrogen and $R^6$, $R^8$, $R^9$, and $R^{11}$ are as defined in Table 74.

Table 138 covers compounds of formula (AH) wherein $R^1$, $R^2$, $R^3$ and $R^4$ are methyl, $R^5$ and $R^{12}$ are hydrogen and $R^6$, $R^8$, $R^9$, and $R^{11}$ are as defined in Table 74.

Table 139 covers compounds of formula (A), wherein $R^1$ is difluoromethoxy, $R^2$ and $R^4$ are methyl, $R^3$, $R^5$ and $R^{12}$ are hydrogen and $R^6$, $R^8$, $R^9$, and $R^{11}$ are as defined in Table 74.

Table 140 covers compounds of formula (A), wherein $R^1$ is difluoromethoxy, $R^2$ is methyl, $R^4$ is ethyl, $R^3$, $R^5$ and $R^{12}$ are hydrogen and $R^6$, $R^8$, $R^9$, and $R^{11}$ are as defined in Table 74.

Table 141 covers compounds of formula (A), wherein $R^1$ is trifluoromethoxy, $R^2$ and $R^4$ are methyl, $R^3$, $R^5$ and $R^{12}$ are hydrogen and $R^6$, $R^8$, $R^9$, and $R^{11}$ are as defined in Table 74.

Table 142 covers compounds of formula (A), wherein $R^1$ is trifluoromethoxy, $R^2$ is methyl, $R^4$ is ethyl, $R^3$, $R^5$ and $R^{12}$ are hydrogen and $R^6$, $R^8$, $R^9$, and $R^{11}$ are as defined in Table 74.

Table 143 covers compounds of formula (A), wherein $R^1$ is cyclopropyl, $R^2$ and $R^4$ are methyl, $R^3$, $R^5$ and $R^{12}$ are hydrogen and $R^6$, $R^8$, $R^9$, and $R^{11}$ are as defined in Table 74.

Table 144 covers compounds of formula (A), wherein $R^1$ is cyclopropyl, $R^2$ is methyl, $R^4$ is ethyl, $R^3$, $R^5$ and $R^{12}$ are hydrogen and $R^6$, $R^8$, $R^9$, and $R^{11}$ are as defined in Table 74.

Table 145 covers compounds of formula (A), wherein $R^1$ and $R^2$ are methyl, $R^3$, $R^5$ and $R^{12}$ are hydrogen, $R^4$ is cyclopropyl and $R^6$, $R^8$, $R^9$, and $R^{11}$ are as defined in Table 74.

Table 146 covers compounds of formula (A), wherein $R^1$ and $R^2$ are ethyl, $R^3$, $R^5$ and $R^{12}$ are hydrogen, $R^4$ is cyclopropyl and $R^6$, $R^8$, $R^9$, and $R^{11}$ are as defined in Table 74.

Example 25

Preparation of (1RS,2SR,6RS,7SR)-5-oxo-4-(2,4,6-trimethylphenyl)-10-oxatricyclo[5.2.1.0$^{2,6}$]dec-3-en-3-yl 2,2-dimethylpropionate

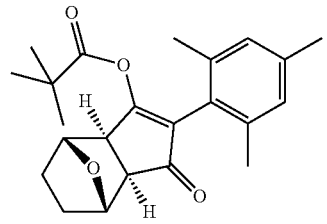 [SMILES: Cc1cc(C)c(C2=C(OC(=O)C(C)(C)C)[C@H]3[C@@H](C2=O)[C@@H]2CC[C@H]3O2)c(C)c1]

A solution of pivaloyl chloride (0.055 g, 0.57 mmol) in dichloromethane (2 ml) is added dropwise to a solution of (1RS,2SR,6RS,7SR)-4-(2,4,6-trimethylphenyl)-10-oxatricyclo[5.2.1.0$^{2,6}$]decane-3,5-dione (0.12 g, 0.42 mmol) in dichloromethane (2 ml) at room temperature and the reaction mixture is stirred for 2 minutes. A solution of triethylamine (0.08 ml) in dichloromethane (1 ml) is added and the reaction mixture is stirred at room temperature for 3 hours. The reaction mixture is diluted with dichloromethane (20 ml) and washed with saturated aqueous sodium bicarbonate solution. The organic phase is dried over anhydrous magnesium sulfate, filtered and the filtrate evaporated under reduced pressure to give (1RS,2SR,6RS,7SR)-5-oxo-4-(2,4,6-trimethylphenyl)-10-oxatricyclo[5.2.1.0$^{2,6}$]dec-3-en-3-yl 2,2-dimethylpropionate as a colourless oil.

$^1$H NMR (400 MHz, CDCl$_3$) $\delta_H$ 6.84 (1H, s), 6.82 (1H, s), 4.75 (1H, d), 4.55 (1H, d), 3.45 (1H, d), 2.78 (1H, d), 2.24 (3H, s), 2.09 (3H, s), 2.02 (3H, s), 1.89-1.83 (2H, m), 1.63-1.59 (2H, m), 1.11 (9H, s).

Example 26

Preparation of carbonic acid (1RS,2SR,6RS,7SR)-5-oxo-4-(2,6-diethyl-4-methylphenyl)-10-oxatricyclo[5.2.1.0$^{2,6}$]-dec-3-en-3-yl ester ethyl ester

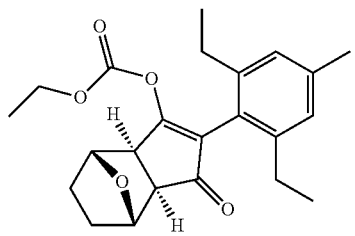 [SMILES: CCOC(=O)OC1=C(c2c(CC)cc(C)cc2CC)C(=O)[C@@H]2[C@H]1[C@H]1CC[C@@H]2O1]

A solution of ethyl chloroformate (0.071 g, 0.65 mmol) in dichloromethane (0.5 ml) is added dropwise to a solution of (1RS,2SR,6RS,7SR)-4-(2,6-diethyl-4-methylphenyl)-10-oxatricyclo[5.2.1.0$^{2,6}$]decane-3,5-dione (0.172 g, 0.55 mmol) in dichloromethane (2 ml) at 0° C. and the reaction mixture is stirred. A solution of triethylamine (0.066 g, 0.65 mmol) in dichloromethane (1 ml) is added and the reaction mixture is stirred at room temperature for 17 hours, warming slowly to room temperature. The reaction mixture is diluted with dichloromethane (3 ml) and washed with saturated aqueous sodium bicarbonate solution. The organic phase is separated, dried over anhydrous magnesium sulfate, filtered and the filtrate evaporated under reduced pressure. The residue is purified by column chromatography on silica gel to give carbonic acid (1RS, 2SR,6RS,7SR)-5-oxo-4-(2,6-diethyl-4-methylphenyl)-10-oxatricyclo-[5.2.1.0$^{2,6}$]-dec-3-en-3-yl ester ethyl ester as a colourless solid.

$^1$H NMR (400 MHz, CDCl$_3$) $\delta_H$ 1.06 (6H, m), 1.28 (3H, t), 1.63 (2H, m), 1.87 (2H, m), 2.3 (3H, s), 2.35 (4H, m), 2.8 (1H, d), 3.63 (1H, d), 4.22 (2H, q), 4.64 (1H, d), 4.77 (1H, d), 6.91 (2H, d).

Additional compounds in Table P1 below were prepared by similar methods using appropriate starting materials.

TABLE P1

| Compound Number | Structure | $^1$H nmr (CDCl$_3$ unless stated) or other physical data |
|---|---|---|
| P1 | 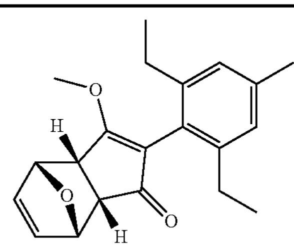 | $\delta_H$ 6.90 (2H, s), 6.45 (1H, dd), 6.35 (1H, dd), 5.30 (1H, d), 5.25 (1H, d), 3.65 (3H, s), 3.65 (1H, dd), 3.45 (1H, dd), 2.35 (4H, m), 2.30 (3H, s), 1.10 (6H, m). |
| P2 | 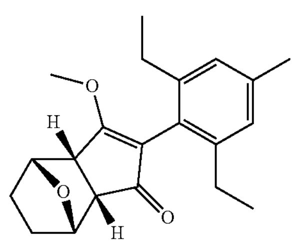 [SMILES: CCc1cc(C)cc(CC)c1C1=C(OC)[C@@H]2[C@H](C1=O)[C@@H]1CC[C@H]2O1] | $\delta_H$ 6.90 (2H, m), 4.85 (2H, m), 3.70 (3H, s), 3.60 (1H, m), 3.35 (1H, dd), 2.50 (2H, m), 2.35 (2H, m), 2.30 (3H, s), 1.90-1.75 (4H, m), 1.20 (3H, t), 1.10 (3H, t) |
| P3 | 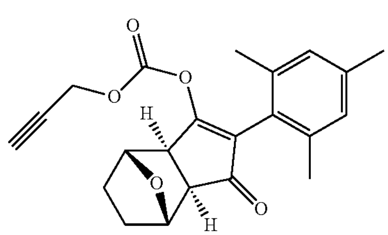 [SMILES: C#CCOC(=O)OC1=C(c2c(C)cc(C)cc2C)C(=O)[C@@H]2[C@H]1[C@H]1CC[C@@H]2O1] | $\delta_H$ 6.87 (1H, s), 6.85 (1H, s), 4.74 (1H, d), 4.68 (2H, t), 4.65 (1H, d), 3.53 (1H, d), 2.79 (1H, d), 2.56 (1H, t), 2.26 (3H, s), 2.09 (3H, s), 2.05 (3H, s), 1.94-1.80 (2H, m), 1.67-1.56 (2H, m). |
| P4 | 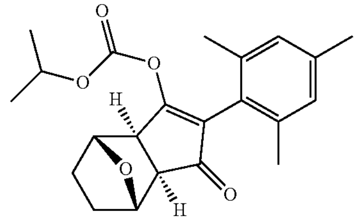 [SMILES: Cc1cc(C)c(C2=C(OC(=O)OC(C)C)[C@H]3[C@@H](C2=O)[C@@H]2CC[C@H]3O2)c(C)c1] | $\delta_H$ 6.87 (1H, s), 6.85 (1H. s), 4.85-4.78 (1H, m), 4.74 (1H, d), 4.64 (1H, d), 3.51 (1H, d), 2.77 (1H, d), 2.25 (3H, s), 2.09 (3H, s), 2.06 (3H, s), 1.93-1.79 (2H, m), 1.67-1.54 (2H, m), 1.25 (3H, d), 1.20 (3H, d). |

TABLE P1-continued

| Compound Number | Structure | $^1$H nmr (CDCl$_3$ unless stated) or other physical data |
|---|---|---|
| P5 | 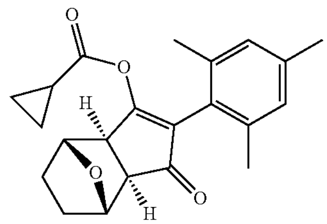 [SMILES: Cc1cc(C)c(C2=C(OC(=O)C3CC3)[C@H]3[C@@H](C2=O)[C@@H]2CC[C@H]3O2)c(C)c1] | $\delta_H$ 6.88 (1H, s), 6.86 (1H, s), 4.73 (1H, d), 4.59 (1H, d), 3.56 (1H, d), 2.76 (1H, d), 2.27 (3H, s), 2.10 (3H, s), 2.04 (3H, s), 1.89-1.80 (2H, m), 1.69-1.56 (3H, m), 1.01-0.92 (4H, m). |
| P6 | 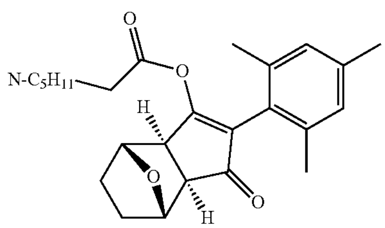 | $\delta_H$ 6.86 (1H, s), 6.84 (1H, s), 4.74 (1H, d), 4.58 (1H, d), 3.48 (1H, d), 2.77 (1H, d), 2.40-2.35 (2H, m), 2.26 (3H, s), 2.09 (3H, s), 2.04 (3H, s), 1.93-1.82 (2H, m), 1.65-1.48 (4H, m), 1.31-1.17 (6H, m), 0.86 (3H, t). |
| P7 | 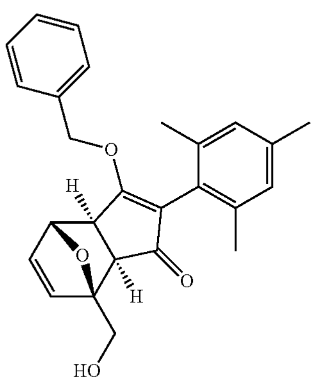 [SMILES: Cc1cc(C)c(C2=C(OCc3ccccc3)[C@H]3[C@@H](C2=O)[C@]2(CO)C=C[C@H]3O2)c(C)c1] | $\delta_H$ 7.38-7.37 (3H, m), 7.19-7.18 (2H, m), 6.97 (2H, s), 6.68 (1H, dd), 6.55 (1H, d), 5.08 (1H, s with fine splitting), 4.82-4.81 (2H, m), 4.13-4.10 (1H, m), 4.03-4.00 (1H, m), 3.13 (1H, dd), 2.89 (1H, dd), 2.54-2.45 (4H, m), 2.37 (3H, s), 1.20-1.16 (6H, m). |
| P8 | 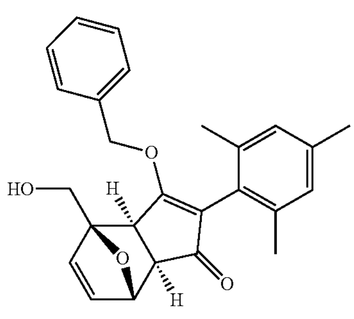 [SMILES: Cc1cc(C)c(C2=C(OCc3ccccc3)[C@H]3[C@@H](C2=O)[C@@H]2C=C[C@@]3(CO)O2)c(C)c1] | $\delta_H$ 7.35-7.32 (3H, m), 7.15-7.13 (2H, m), 6.93 (1H, s), 6.92 (1H, s), 6.54-6.49 (2H, m), 5.14 (1H, d), 4.71-4.64 (2H, m), 4.15-4.08 (2H, m), 2.99 (1H, d), 2.84 (1H, d), 2.59-2.39 (4H, m), 2.32 (3H, s), 1.17-1.13 (6H, m). |
| P9 | 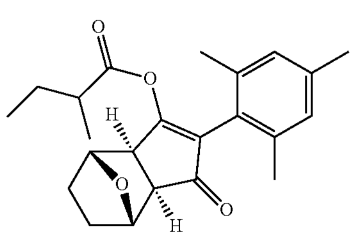 [SMILES: CCC(C)C(=O)OC1=C(c2c(C)cc(C)cc2C)C(=O)[C@@H]2[C@H]1[C@H]1CC[C@@H]2O1] | $\delta_H$ 6.84 (1H, s), 6.82 (1H, s), 4.73 (1H, d), 4.57-4.55 (1H, m), 3.46-3.44 (1H, m), 2.77 (1H, d), 2.46-2.35 (1H, m), 2.23 (3H, s), 2.08 (3H, s), 2.02 (3H, s), 1.92-1.80 (2H, m), 1.04 (3H, d), 0.93 (3H, t). |

TABLE P1-continued

| Compound Number | Structure | ¹H nmr (CDCl₃ unless stated) or other physical data |
|---|---|---|
| P10 | 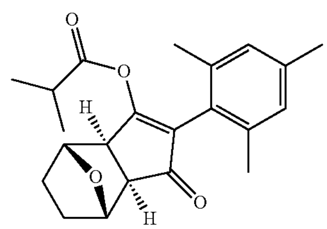 [SMILES: Cc1cc(C)c(C2=C(OC(=O)C(C)C)[C@H]3[C@@H](C2=O)[C@@H]2CC[C@H]3O2)c(C)c1] | $\delta_H$ 6.86 (1H, s), 6.84 (1H, s), 4.74 (1H, d), 4.56 (1H, d), 3.49 (1H, d), 2.78 (1H, d), 2.65-2.58 (1H, m), 2.25 (3H, s), 2.09 (3H, s), 2.03 (3H, s), 1.93-1.79 (2H, m), 1.66-1.56 (2H, m), 1.13 (3H, d), 1.06 (3H, d). |
| P11 | 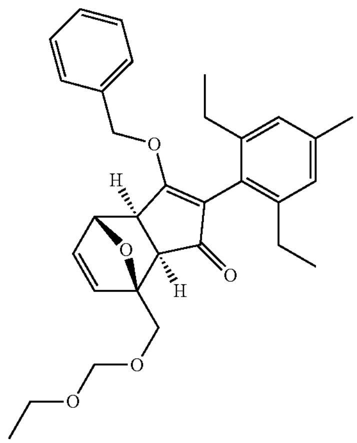 [SMILES: CCOCOC[C@@]12C=C[C@@H](O1)[C@H]1C(OCc3ccccc3)=C(c3c(CC)cc(C)cc3CC)C(=O)[C@H]12] | $\delta_H$ 7.34-7.31 (3H, m), 7.15-7.12 (2H, m), 6.90 (2H, s), 6.50 (2H, s), 5.05 (1H, s), 4.79-4.72 (4H, m), 4.23 (1H, d), 3.97 (1H, d), 3.65-3.58 (2H, m), 3.06 (1H, d), 2.66 (1H, d), 2.54-2.34 (4H, m), 2.31 (3H, s), 1.20 (3H, t), 1.15-1.10 (6H, m). |
| P12 | 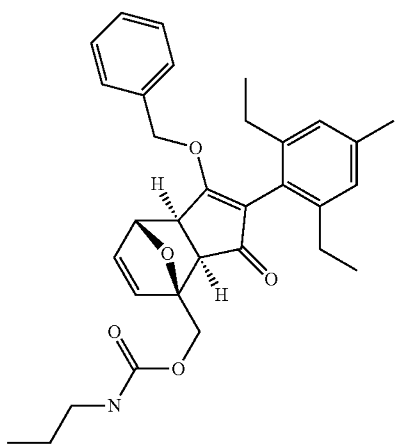 [SMILES: CCCNC(=O)OC[C@@]12C=C[C@@H](O1)[C@H]1C(OCc3ccccc3)=C(c3c(CC)cc(C)cc3CC)C(=O)[C@H]12] | $\delta_H$ 7.33-7.30 (3H, m), 7.14-7.12 (2H, m), 6.90 (2H, s), 6.51 (1H, dd), 6.45 (1H, d), 5.11 (1H, d), 5.05 (1H, d), 4.81-4.76 (1H, m), 4.73-4.72 (2H, m), 4.30 (1H, d), 3.17-3.12 (2H, m), 3.06 (1H, d), 2.69 (1H, d), 2.52-2.35 (4H, m), 2.31 (3H, s), 1.53-1.47 (2H, m), 1.15-1.11 (6H, m), 0.90 (3H, t). |
| P13 | 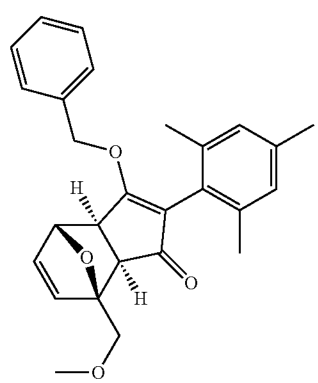 [SMILES: COC[C@@]12C=C[C@@H](O1)[C@H]1C(OCc3ccccc3)=C(c3c(C)cc(C)cc3C)C(=O)[C@H]12] | $\delta_H$ 7.33-7.30 (3H, m), 7.15-7.11 (2H, m), 6.86 (2H, s), 6.50-6.49 (2H, m), 5.11 (0.5H, s), 5.04 (0.5H, s), 4.76-4.66 (2H, m), 4.16-4.11 (1H, m), 3.77-3.74 (1H, m), 3.43 (1.5H, s), 3.34 (1.5H, s), 3.03 (0.5H, s), 2.94 (0.5H, s), 2.77 (0.5H, d), 2.62 (0.5H, d), 2.27 (1.5H, s), 2.19 (1.5H, s), 2.12 (1.5H, s), 2.08 (1.5H, s), 2.07 (3H, s). |

| Compound Number | Structure | ¹H nmr (CDCl₃ unless stated) or other physical data |
|---|---|---|
| P14 | 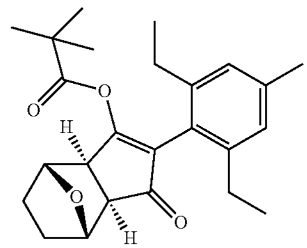 [SMILES: CCc1cc(C)cc(CC)c1C1=C(OC(=O)C(C)(C)C)[C@H]2[C@@H](C1=O)[C@@H]1CC[C@H]2O1] | $\delta_H$ 1.04 (6H, m), 1.08 (9H, s), 1.6 (2H, m), 1.85 (2H, m), 2.3 (3H, s), 2.33 (4H, m), 2.79 (1H, d), 3.58 (1H, d), 4.54 (1H, d), 4.74 (1H, d), 6.85 (1H, s) 6.88 (1H, s). |
| P15 | 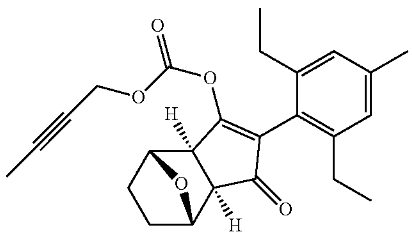 [SMILES: CC#CCOC(=O)OC1=C(c2c(CC)cc(C)cc2CC)C(=O)[C@@H]2[C@H]1[C@H]1CC[C@@H]2O1] | $\delta_H$ 1.04 (6H, m), 1.6 (2H, m), 1.85 (2H, m), 2.3 (3H, s), 2.35 (4H, m), 2.8 (1H, d), 3.63 (1H, d), 4.66 (1H, d), 4.7 (1H, d), 4.75 (1H, d), 6.9 (2H, s). |
| P16 | 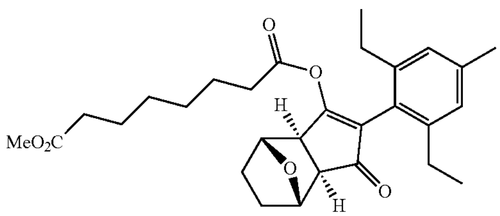 [SMILES: CCc1cc(C)cc(CC)c1C1=C(OC(=O)CCCCCCC(=O)OC)[C@H]2[C@@H](C1=O)[C@@H]1CC[C@H]2O1] | $\delta_H$ 1.04 (6H, m), 1.2 (3H, m), 1.35 (1H, m), 1.6 (8H, m), 1.85 (2H, m), 2.32 (9H, m), 2.8 (1H, d), 3.58 (1H, d), 3.67 (3H, s), 4.58 (1H, d), 4.75 (1H, d), 6.9 (2H, s). |
| P17 | 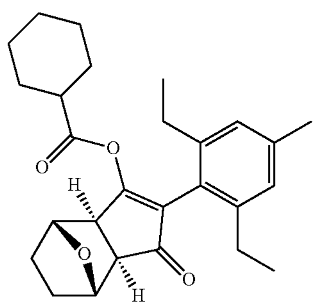 [SMILES: CCc1cc(C)cc(CC)c1C1=C(OC(=O)C2CCCCC2)[C@H]2[C@@H](C1=O)[C@@H]1CC[C@H]2O1] | $\delta_H$ 1.04 (6H, m), 1.3-1.8 (14H, m), 2.3 (3H, s), 2.34 (5H, m), 2.79 (1H, d), 3.6 (1H, d), 4.54 (1H, d), 4.75 (1H, d), 6.89 (2H, d). |
| P18 | 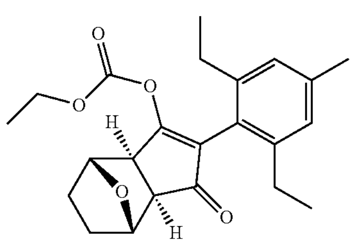 [SMILES: CCOC(=O)OC1=C(c2c(CC)cc(C)cc2CC)C(=O)[C@@H]2[C@H]1[C@H]1CC[C@@H]2O1] | $\delta_H$ 1.06 (6H, m), 1.28 (3H, t), 1.63 (2H, m), 1.87 (2H, m), 2.3 (3H, s), 2.35 (4H, m), 2.8 (1H, d), 3.63 (1H, d), 4.22 (2H, q), 4.64 (1H, d), 4.77 (1H, d), 6.91 (2H, d). |
| P19 | 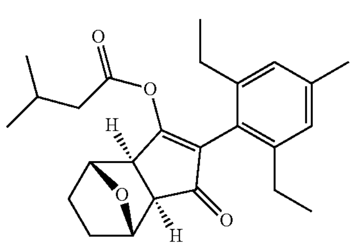 [SMILES: CCc1cc(C)cc(CC)c1C1=C(OC(=O)CC(C)C)[C@H]2[C@@H](C1=O)[C@@H]1CC[C@H]2O1] | $\delta_H$ 0.85 (6H, d), 1.05 (6H, m), 1.61 (2H, m), 1.85 (2H, m), 1.98 (1H, m), 2.28 (2H, d), 2.3 (3H, s), 2.35 (4H, m), 2.8 (1H, d), 3.58 (1H, d), 4.58 (1H, d), 4.75 (1H, d), 6.89 (2H, d). |

TABLE P1-continued

| Compound Number | Structure | ¹H nmr (CDCl₃ unless stated) or other physical data |
|---|---|---|
| P20 | 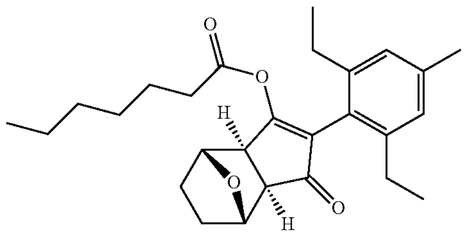 [SMILES: CCCCCCC(=O)OC1=C(c2c(CC)cc(C)cc2CC)C(=O)[C@@H]2[C@H]1[C@H]1CC[C@@H]2O1] | $\delta_H$ 0.84 (3H, t), 1.05 (6H, m), 1.23 (8H, m), 1.62 (2H, m), 1.86 (2H, m), 2.3 (3H, s), 2.37 (6H, m), 2.8 (1H, d), 3.59 (1H, d), 4.58 (1H, d), 4.75 (1H, d), 6.9 (2H, d). |
| P21 | 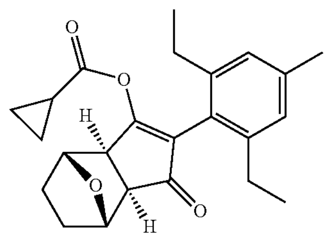 [SMILES: CCc1cc(C)cc(CC)c1C1=C(OC(=O)C2CC2)[C@H]2[C@@H](C1=O)[C@@H]1CC[C@H]2O1] | $\delta_H$ 0.95 (4H, m), 1.05 (6H, m), 1.63 (3H, m), 1.85 (2H, m), 2.3 (3H, s), 2.35 (4H, m), 2.77 (1H, d), 3.65 (1H, d), 4.59 (1H, d), 4.74 (1H, d), 6.9 (2H, d) |
| P22 | 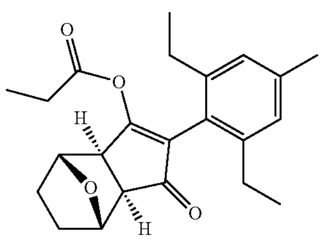 [SMILES: CCC(=O)OC1=C(c2c(CC)cc(C)cc2CC)C(=O)[C@@H]2[C@H]1[C@H]1CC[C@@H]2O1] | $\delta_H$ 1.07 (9H, m), 1.6 (2H, m), 1.85 (2H, m), 2.31 (3H, s), 2.39 (6H, m), 2.79 (1H, d), 3.62 (1H, d), 4.58 (1H, d), 4.74 (1H, d), 6.9 (2H, d). |
| P23 | 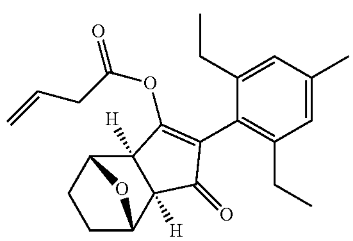 [SMILES: C=CCC(=O)OC1=C(c2c(CC)cc(C)cc2CC)C(=O)[C@@H]2[C@H]1[C@H]1CC[C@@H]2O1] | $\delta_H$ 1.06 (6H, m), 1.62 (2H, m), 1.87 (2H, m), 2.3 (3H, s), 2.35 (4H, m), 2.8 (1H, d), 3.52 (1H, d), 4.62 (3H, m), 4.75 (1H, d), 5.31 (2H, m), 5.85 (1H, m), 6.91 (2H, d). |
| P24 | 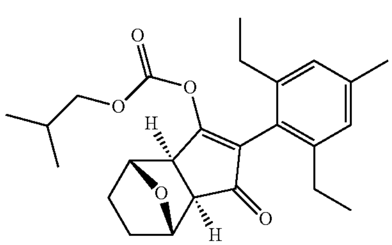 [SMILES: CCc1cc(C)cc(CC)c1C1=C(OC(=O)OCC(C)C)[C@H]2[C@@H](C1=O)[C@@H]1CC[C@H]2O1] | $\delta_H$ 0.9 (6H, d), 1.07 (6H, m), 1.61 (2H, m), 1.86 (2H, m), 1.92 (1H, m), 2.31 (3H, s), 2.32 (4H, m), 2.8 (1H, d), 3.52 (1H, d), 3.94 (2H, m), 4.64 (1H, d), 4.76 (1H, d), 6.91 (2H, d). |
| P25 | 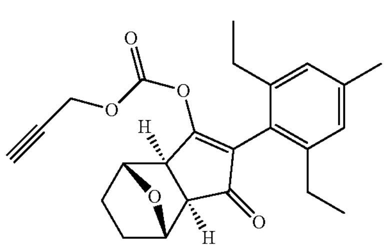 [SMILES: C#CCOC(=O)OC1=C(c2c(CC)cc(C)cc2CC)C(=O)[C@@H]2[C@H]1[C@H]1CC[C@@H]2O1] | $\delta_H$ 1.07 (6H, m), 1.62 (2H, m), 1.87 (2H, m), 2.31 (3H, s), 2.36 (4H, m), 2.56 (1H, m), 2.81 (1H, d), 3.63 (1H, d), 4.67 (1H, d), 4.75 (2H, m), 6.9 (2H, d). |

TABLE P1-continued

| Compound Number | Structure | ¹H nmr (CDCl₃ unless stated) or other physical data |
|---|---|---|
| P26 | 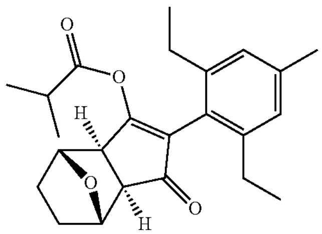 [SMILES: CCc1cc(C)cc(CC)c1C1=C(OC(=O)C(C)C)[C@H]2[C@@H](C1=O)[C@@H]1CC[C@H]2O1] | δ$_H$ 1.05 (9H, m), 1.13 (3H, d), 1.61 (2H, m), 1.87 (2H, m), 2.31 (3H, s), 2.36 (4H, m), 2.6 (1H, m), 2.79 (1H, d) 3.61 (1H, d), 4.57 (1H, d), 4.76 (1H, d), 6.89 (2H, d). |
| P27 | Isomer A / Isomer B | Approximately 1:1 ratio of Isomer A:Isomer B δ$_H$ 6.87-6.86 (2H, m), 4.84-4.77 (1H, m), 4.60 (1H, d), 3.89 (1H, d), 3.70 (1H, d), 3.60 (1H, d), 3.41 (3H, s), 2.80 (1H, d), 2.25 (3H, s), 2.10 (3H, s), 2.05 (3H, s), 2.03-1.96 (2H, m), 1.72-1.65 (2H, m), 1.25 (3H, d), 1.19 (3H, d). |
| P28 | Isomer A | Approximately 1:1 ratio of Isomer A:Isomer B δ$_H$ 6.88-6.86 (2H, m), 4.74-4.60 (3H, m), 3.89-6.63 (3H, m), 3.41 (3H, s), 2.92 (0.5H, d), 2.83-2.81 (0.5H, m), 2.56-2.55 (1H, m), 2.26 (3H, s), 2.10 (1.5H, 5), 2.09 (1.5H, s), 2.04 (1.5H, s), 2.03 (1.5H, s), 2.00-1.65 (4H, m). |

| Compound Number | Structure | ¹H nmr (CDCl₃ unless stated) or other physical data |
|---|---|---|
| | Isomer B | |
| P29 | Isomer A / Isomer B | Approximately 1:1 ratio of Isomer A:Isomer B $\delta_H$ 6.86-6.84 (2H, m), 4.55 (1H, d), 3.89 (1H, d), 3.70 (1H, d), 3.59 (1H, d), 3.41 (3H, s), 2.81 (1H, d), 2.39-2.33 (2H, m), 2.25 (3H, s), 2.09 (3H, s), 2.03 (3H, s), 2.00-1.95 (1H, m), 1.66-1.49 (3H, m), 1.38-1.13 (8H, m), 0.90-0.84 (3H, m). |
| P30 | Isomer A | Approximately 1:1 ratio of Isomer A:Isomer B $\delta_H$ 6.88-6.86 (2H, m), 4.55 (1H, d), 3.89 (1H, d), 3.71-3.65 (2H, m), 3.41 (3H, s), 2.79 (1H, d), 2.27 (3H, s), 2.11 (3H, s), 2.03 (3H, s), 1.78-1.50 (4H, m), 1.07-1.04 (1H, m), 0.99-0.91 (4H, m). |

| Compound Number | Structure | ¹H nmr (CDCl₃ unless stated) or other physical data |
|---|---|---|
| | 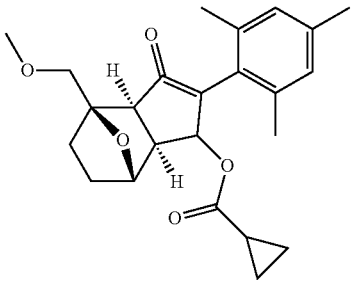<br>Isomer B | |
| P31 | 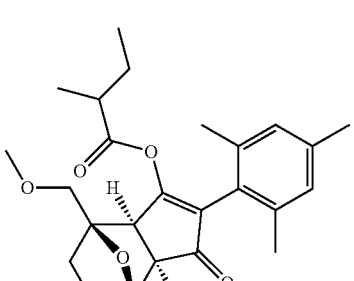<br>Isomer A<br><br>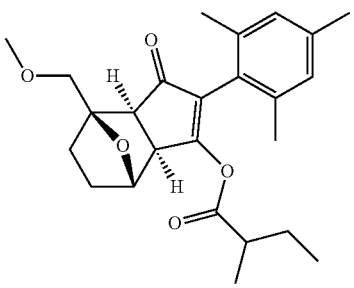<br>Isomer B | Approximately 1:1 ratio of Isomer A:Isomer B<br>$\delta_H$ 6.84-6.82 (2H, m), 4.54-4.52 (1H, m), 3.89 (1H, d), 3.70 (1H, d), 3.56 (1H, t), 3.40 (3H, s), 2.80 (1H, d), 2.44-2.37 (1H, m), 2.24 (3H, s), 2.09 (3H, s), 2.02 (3H, s), 1.71-1.35 (6H, m), 1.17-1.02 (3H, m), 0.95-0.67 (3H, m). |
| P32 | 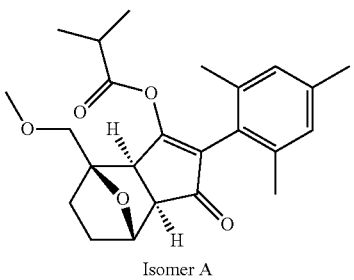<br>Isomer A<br><br>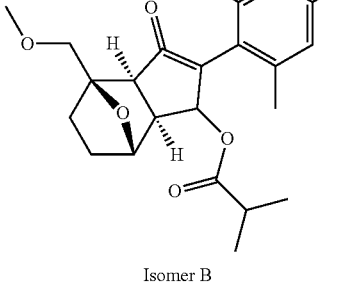<br>Isomer B | Approximately 1:1 ratio of Isomer A:Isomer B<br>$\delta_H$ 6.85-6.83 (2H, m), 4.52 (1H, d), 3.89 (1H, d), 3.70 (1H, d), 3.58 (1H, d), 3.40 (3H, s), 2.80 (1H, d), 2.62-2.57 (1H, m), 2.24 (3H, s), 2.09 (3H, s), 2.02 (3H, s), 1.71-1.52 (4H, m), 1.11 (3H, t), 1.04 (3H, d). |

TABLE P1-continued

| Compound Number | Structure | ¹H nmr (CDCl₃ unless stated) or other physical data |
|---|---|---|
| P33 | 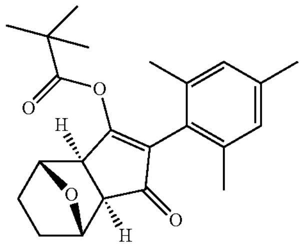 [SMILES: Cc1cc(C)c(C2=C(OC(=O)C(C)(C)C)[C@H]3[C@@H](C2=O)[C@@H]2CC[C@H]3O2)c(C)c1] | δ$_H$ 6.84 (1H, s), 6.82 (1H, s), 4.75 (1H, d), 4.55 (1H, d), 3.45 (1H, d), 2.78 (1H, d), 2.24 (3H, s), 2.09 (3H, s), 2.02 (3H, s), 1.89-1.83 (2H, m), 1.63-1.59 (2H, m), 1.11 (9H, s). |
| P34 | 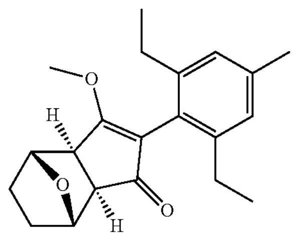 [SMILES: CCc1cc(C)cc(CC)c1C1=C(OC)[C@H]2[C@@H](C1=O)[C@@H]1CC[C@H]2O1] | δ$_H$ 6.90 (1H, s), 6.89 (1H, s), 4.73 (1H, d), 4.66 (1H, d), 3.58 (3H, s), 2.91 (1H, d), 2.66 (1H, d), 2.49-2.39 (4H, m), 2.30 (3H, s), 1.88-1.81 (2H, m), 1.62-1.56 (2H, m), 1.12-1.08 (3H, m). |
| P35 | 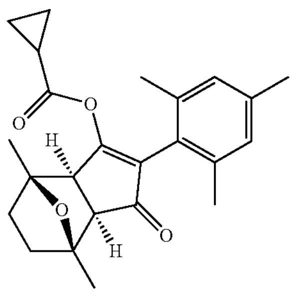 [SMILES: Cc1cc(C)c(C2=C(OC(=O)C3CC3)[C@H]3[C@@H](C2=O)[C@]2(C)CC[C@@]3(C)O2)c(C)c1] | δ$_H$ 6.93 (2H, br. s), 3.71-3.69 (1H, m), 2.81-2.80 (1H, m), 2.33 (3H, s), 2.20 (3H, s), 2.08 (3H, s), 1.87-1.72 (5H, m), 1.64-1.60 (6H, m), 1.05-0.99 (4H, m). |
| P36 | 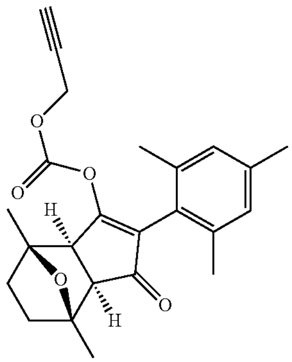 [SMILES: C#CCOC(=O)OC1=C(c2c(C)cc(C)cc2C)C(=O)[C@@H]2[C@H]1[C@@]1(C)CC[C@]2(C)O1] | δ$_H$ 6.88 (1H, s), 6.86 (1H, s), 4.71 (1H, dd), 4.61 (1h, dd), 3.65 (1H, d), 2.77 (1H, d), 2.55 (1H, t), 2.26 (3H, s), 2.12 (3H, s), 2.04 (3H, s), 1.82-1.71 (4H, m), 1.56 (3H, s), 1.53 (3H, s). |
| P37 | Isomer A | Approximately 1:1 ratio of Isomer A:Isomer B δ$_H$ 6.87 (1H, s), 6.85 (1H, s), 4.70 (0.5H, d), 4.55 (0.5H, d), 4.43 (1H, s), 4.26 (1H, s), 3.53 (1H, app t), 2.74 (1H, app t), 2.26 (3H, s), 2.09 (3H, s), 2.04 (3H, s), 1.82-1.63 (3H, m), 1.49-1.41 (2H, m), 1.30-1.26 (1H, m), 0.98-0.90 (7H, m). |

| Compound Number | Structure | ¹H nmr (CDCl₃ unless stated) or other physical data |
|---|---|---|
| | Isomer B | |
| P38 | Isomer A<br><br>Isomer B | Approximately 1:1 ratio of Isomer A:Isomer B<br>$\delta_H$ 6.87 (1H, s), 6.86 (1H, s), 4.72-4.60 (3H, m), 4.45 (0.5H, s), 4.33 (0.5H, d), 3.77 (1H, s), 3.50 (1H, d), 2.79-2.76 (0.5H, m), 2.56-2.54 (0.5H, m), 2.26 (3H, s), 2.08 (3H, s), 2.05 (3H, s), 1.84-1.75 (2H, m), 1.52-1.42 (2H, m), 1.30-1.24 (1H, m), 0.96-0.83 (3H, m). |
| P39 | 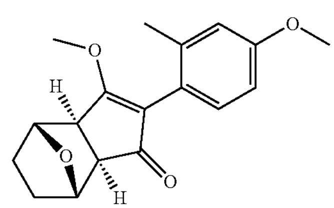 [SMILES: COC1=C(c2ccc(OC)cc2C)C(=O)[C@@H]2[C@H]1[C@H]1CC[C@@H]2O1] | $\delta_H$ 7.01 (1H, br. s), 6.76 (1H, d), 6.72 (1H, dd), 4.72 (1H, d), 4.65 (1H, d), 3.78 (3H, s), 3.65 (3H, s), 2.88 (1H, d), 2.64 (1H, d), 2.15 (3H, s), 1.80-1.89 (2H, m), 1.56-1.62 (2H, m). |
| P40 | 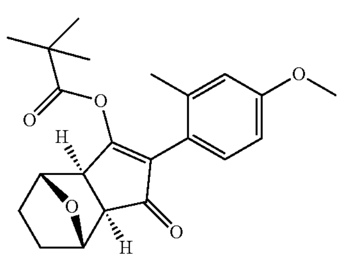 [SMILES: COc1ccc(C2=C(OC(=O)C(C)(C)C)[C@H]3[C@@H](C2=O)[C@@H]2CC[C@H]3O2)c(C)c1] | $\delta_H$ 6.91 (1H, br. s), 6.76 (1H, s), 6.70 (1H, d), 4.73 (1H, d), 4.53 (1H, d), 3.78 (3H, s), 3.43 (1H, s), 2.75 (1H, d), 2.15 (3H, s), 1.93-1.79 (2H, m), 1.65-1.58 (2H, m), 1.16 (9H, s). |

TABLE P1-continued

| Compound Number | Structure | ¹H nmr (CDCl₃ unless stated) or other physical data |
|---|---|---|
| P41 | 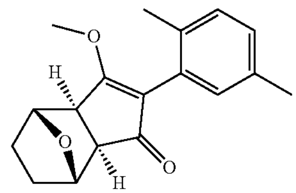 [SMILES: COC1=C(c2cc(C)ccc2C)C(=O)[C@@H]2[C@H]1[C@H]1CC[C@@H]2O1] | δ_H 7.11-7.05 (1H, m), 7.03-6.99 (1H, m), 6.89 (1H, br. s), 4.73 (1H, d), 4.65 (1H, d), 3.64 (1H, s), 2.89 (1H, d), 2.64 (1H, d), 2.28 (3H, s), 2.13 (3H, s), 1.92-1.78 (2H, m), 1.63-1.57 (2H, m). |
| P42 | 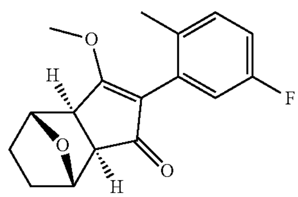 [SMILES: COC1=C(c2cc(F)ccc2C)C(=O)[C@@H]2[C@H]1[C@H]1CC[C@@H]2O1] | δ_H 7.19 (1H, dd), 6.96 (1H, td), 6.91-6.86 (1H, m), 4.77 (1H, d), 4.70 (1H, d), 3.72 (3H, s), 2.96 (1H, d), 2.70 (1H, d), 2.18 (3H, s), 1.97-1.82 (2H, m), 1.68-1.62 (2H, m). |
| P43 | 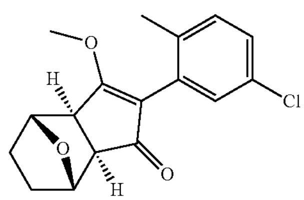 [SMILES: COC1=C(c2cc(Cl)ccc2C)C(=O)[C@@H]2[C@H]1[C@H]1CC[C@@H]2O1] | δ_H 7.16-7.10 (1H, m), 7.08-7.03 (1H, m), 6.94 (1H, br. s), 4.77 (1H, d), 4.70 (11-1, d), 3.68 (3H, s), 2.93 (1H, d), 2.72-2.66 (1H, m), 2.17 (3H, s), 1.97-1.80 (2H, m), 1.62-1.58 (2H, m). |
| P44 | 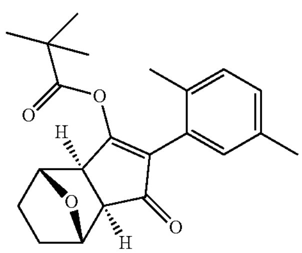 [SMILES: Cc1ccc(C)c(C2=C(OC(=O)C(C)(C)C)[C@H]3[C@@H](C2=O)[C@@H]2CC[C@H]3O2)c1] | δ_H 7.09 (1H, d), 7.04-6.99 (1H, m), 6.76 (1H, br. s), 4.75 (1H, d), 4.54 (1H, d), 3.49-3.41 (1H, m), 2.76 (1H, d), 2.26 (3H, s), 2.17 (3H, s), 1.94-1.79 (2H, m), 1.67-1.59 (2H, m), 1.15 (9H, s). |
| P45 | 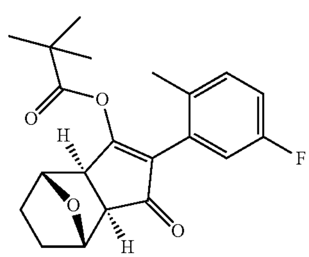 [SMILES: Cc1ccc(F)cc1C1=C(OC(=O)C(C)(C)C)[C@H]2[C@@H](C1=O)[C@@H]1CC[C@H]2O1] | δ_H 7.16 (1H, dd), 6.92 (1H, td), 6.74 (1H, br. s), 4.75 (1H, d), 4.54 (1H, d), 3.46 (1H, d), 2.77 (1H, d), 2.17 (3H, s), 1.93-1.82 (2H, m), 1.67-1.57 (2H, m), 1.17 (9H, s). |
| P46 | 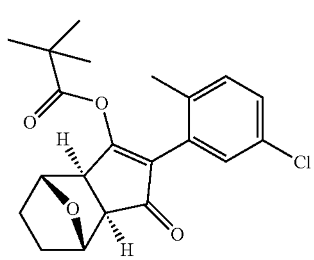 [SMILES: Cc1ccc(Cl)cc1C1=C(OC(=O)C(C)(C)C)[C@H]2[C@@H](C1=O)[C@@H]1CC[C@H]2O1] | δ_H 7.21-7.17 (1H, m), 7.16-7.12 (1H, m), 6.96 (1H, br. s), 4.74 (1H, d), 4.54 (1H, s), 3.45 (1H, d), 2.77 (1H, d), 2.17 (3H, s), 1.94-1.80 (2H, m), 1.67-1.58 (2H, m), 1.17 (9H, s). |

| Compound Number | Structure | $^1$H nmr (CDCl$_3$ unless stated) or other physical data |
|---|---|---|
| P47 | 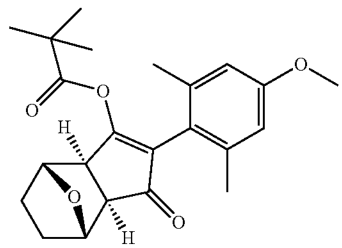 [SMILES: COc1cc(C)c(C2=C(OC(=O)C(C)(C)C)[C@H]3[C@@H](C2=O)[C@@H]2CC[C@H]3O2)c(C)c1] | δ$_H$ 6.58 (2H, d), 4.74 (1H, d), 4.55 (1H, d), 3.76 (3H, s), 3.43 (1H, d), 2.82-2.73 (1H, m), 2.11 (3H, s), 2.04 (3H, s), 1.93-1.78 (2H, m), 1.66-1.57 (2H, m), 1.11 (9H, s). |
| P48 | 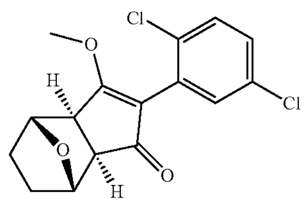 [SMILES: COC1=C(c2cc(Cl)ccc2Cl)C(=O)[C@@H]2[C@H]1[C@H]1CC[C@@H]2O1] | δ$_H$ 7.33 (1H, d), 7.29 (1H, br. s), 7.23 (1H, dd), 4.75 (1H, d), 4.67 (1H, d), 3.76 (3H, s), 2.94 (1H, s), 2.69 (1H, s), 1.93-1.79 (2H, m), 1.65-1.54 (2H, m). |
| P49 | 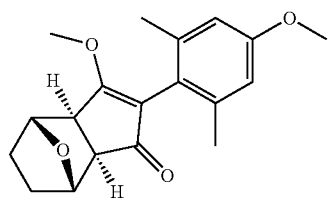 [SMILES: COC1=C(c2c(C)cc(OC)cc2C)C(=O)[C@@H]2[C@H]1[C@H]1CC[C@@H]2O1] | δH 6.60 (2H, d), 4.72 (1H, d), 4.65 (1H, d), 3.76 (3H, s), 3.58 (3H, s), 2.88 (1H, d), 2.64 (1H, d), 2.13 (3H, s), 2.10 (3H, s), 1.90-1.77 (2H, m), 1.64-1.54 (2H, m). |
| P50 | 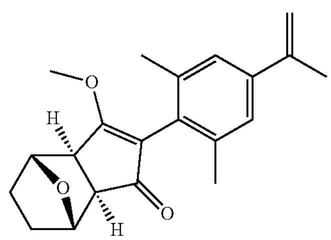 [SMILES: C=C(C)c1cc(C)c(C2=C(OC)[C@H]3[C@@H](C2=O)[C@@H]2CC[C@H]3O2)c(C)c1] | δ$_H$ 7.14 (2H, d), 5.34 (1H, s), 5.04 (1H, s), 4.73 (1H, d), 4.66 (1H, d), 3.58 (3H, s), 2.90 (1H, d), 2.66 (1H, d), 2.17 (3H, s), 2.14 (3H, s), 2.11 (3H, s), 1.92-1.75 (2H, m), 1.66-1.54 (2H, m). |
| P51 | Isomer A <br> 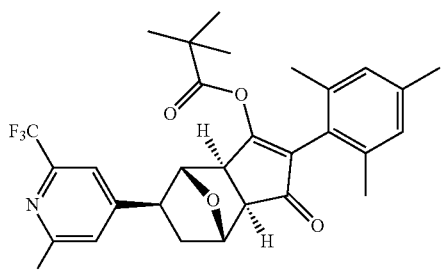 <br> Isomer B | Approximately 1:1 mixture of Isomer A:Isomer B <br> Isomer A: δ$_H$ 7.81 (2H, s), 6.87 (1H, s), 6.83 (1H, s), 4.83 (1H, d), 4.69 (1H, s), 3.64 (1H, d), 3.22 (1H, dd), 2.99 (1H, d), 2.38 (1H, dd), 2.25 (3H, s), 2.11 (3H, s), 2.04 (3H, s), 1.99-1.96 (1H, m), 1.23 (3H, s), 1.13 (6H, s). <br> Isomer B: δ$_H$ 7.84 (2H, s), 6.87 (1H, s), 6.84 (1H, s), 4.99 (1H, d), 4.50 (1H, s), 3.64 (1H, d), 3.24 (1H, dd), 2.94 (1H, d), 2.35 (1H, dd), 2.25 (3H, s), 2.10 (3H, s), 2.04 (3H, s), 1.91-1.89 (1H, m), 1.07 (9H s). |

TABLE P1-continued

| Compound Number | Structure | $^1$H nmr (CDCl$_3$ unless stated) or other physical data |
|---|---|---|
| P52 | 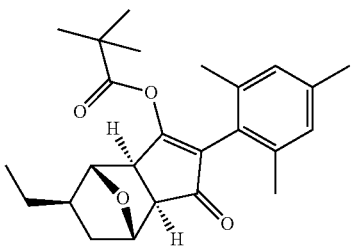<br>Isomer A<br>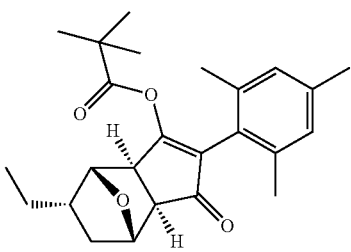<br>Isomer B<br>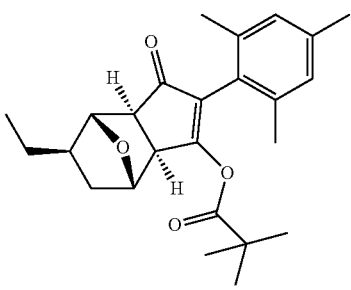<br>Isomer C<br>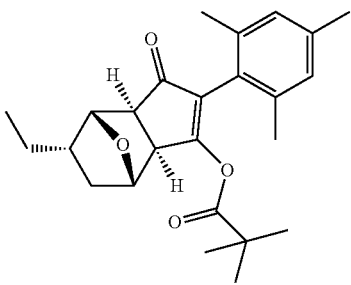<br>Isomer D | Approximately 1:1:1:1 mixture of Isomer A:Isomer B:Isomer C:Isomer D $\delta_H$ 6.84 (1H, s), 6.82 (1H, s), 4.71 (0.25H, d), 4.68 (0.25H, d), 4.60 (0.25H, d), 4.52 (0.25H, d), 4.48 (0.25H, d), 4.45 (0.25H, s), 4.41 (0.25H, d), 4.23 (0.25H, s), 3.79 (0.25H, d), 3.43 (0.514, t), 3.04 (0.25H, d), 2.77-2.73 (0.75H, m), 2.24 (3H, s), 2.19-2.11 (1H, m), 2.09 (3H, s), 2.03 (3H, s), 1.84-1.73 (1H, m), 1.52-1.39 (2H, m), 1.28-1.26 (1H, m), 1.12-1.10 (9H, m), 1.00-0.90 (3H, m). |

Biological Examples

Test Example 1

Monocotyledonous and dicotyledonous test plants were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 15 days later for post-emergence and 20 days for pre-emergence, the test was evaluated (100=total damage to plant; 0=no damage to plant).

Test Plants:

*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

Pre-Emergence Activity

| Compound Number | Rate g/ha | ALOMY | AVEFA | LOLPE | SETFA | DIGSA | ECHCG |
|---|---|---|---|---|---|---|---|
| T1 | 250 | 100 | 100 | 100 | 100 | 100 | 100 |
| T2 | 250 | 100 | 100 | 100 | 90 | 100 | 100 |
| T3 | 250 | 90 | 80 | 100 | 70 | 80 | 100 |
| T4 | 250 | 90 | 90 | 100 | 90 | 100 | 100 |
| T5 | 250 | 100 | 80 | 100 | 80 | 100 | 100 |
| T6 | 250 | 80 | 30 | 100 | 80 | 90 | 90 |
| T7 | 250 | 100 | 80 | 100 | 90 | 80 | 90 |
| T8 | 250 | 100 | 90 | 100 | 100 | 100 | 100 |
| T9 | 250 | 70 | 40 | 100 | 100 | 100 | 100 |
| T10 | 250 | 80 | 70 | 100 | 80 | 80 | 90 |
| T11 | 250 | 30 | 40 | 60 | 20 | 0 | 30 |
| T12 | 250 | 10 | 10 | 40 | 40 | 40 | 0 |
| T13 | 250 | 80 | 80 | 90 | 100 | 100 | 100 |
| T14 | 250 | 90 | 90 | 100 | 100 | 70 | 90 |
| T15 | 250 | 40 | 20 | 40 | 60 | 30 | 80 |
| T16 | 250 | 0 | 10 | 0 | 10 | 0 | 0 |
| T17 | 250 | 100 | 90 | 100 | 100 | 100 | 100 |
| T18 | 250 | 100 | 100 | 100 | 100 | 100 | 100 |
| T19 | 250 | 100 | 90 | 100 | 100 | 90 | 100 |
| T21 | 250 | 90 | 30 | 80 | 70 | 10 | 80 |
| T27 | 250 | 70 | 70 | 70 | 100 | 90 | 100 |
| T34 | 250 | 70 | 30 | 60 | 80 | 60 | 40 |
| T37 | 250 | 60 | 30 | 30 | 0 | 20 | 30 |
| T39 | 250 | 10 | 20 | 30 | 40 | 30 | 30 |
| T40 | 250 | 50 | 60 | 60 | 40 | 60 | 40 |
| T41 | 250 | 50 | 30 | 20 | 60 | 30 | 70 |
| T42 | 250 | 0 | 10 | 0 | 0 | 0 | 30 |
| T43 | 250 | 10 | 20 | 0 | 50 | 20 | 0 |
| T44 | 250 | 80 | 40 | 70 | 80 | 80 | 70 |
| T46 | 250 | 10 | 0 | 30 | 30 | 20 | 70 |
| T47 | 250 | 100 | 80 | 100 | 80 | 70 | 100 |
| T48 | 250 | 100 | 80 | 100 | 100 | 100 | 100 |
| T49 | 250 | 80 | 70 | 100 | 20 | 10 | 80 |
| T52 | 250 | 40 | 30 | 100 | 90 | 90 | 100 |
| T53 | 250 | 10 | 20 | 10 | 10 | 10 | 0 |
| T56 | 250 | 100 | 60 | 100 | 70 | 70 | 100 |
| T57 | 250 | 50 | 30 | 100 | 80 | 60 | 70 |
| T58 | 250 | 0 | 10 | 0 | 0 | 0 | 60 |
| T59 | 250 | 10 | 20 | 30 | 40 | 50 | 30 |
| T60 | 250 | 0 | 40 | 10 | 10 | 30 | 30 |
| T62 | 250 | 70 | 70 | 60 | 80 | 80 | 80 |
| T64 | 250 | 0 | 0 | 10 | 20 | 10 | 50 |
| T65 | 250 | 100 | 90 | 100 | 90 | 100 | 100 |
| T66 | 250 | 30 | 60 | 40 | 100 | 90 | 70 |
| T70 | 250 | 80 | 50 | 100 | 90 | 90 | 100 |
| T71 | 250 | 30 | 0 | 0 | 20 | 50 | 50 |
| T85 | 250 | 40 | 60 | 70 | 70 | 60 | 70 |
| T89 | 250 | 20 | 60 | 40 | 30 | 30 | 20 |
| T90 | 250 | 10 | 60 | 20 | 40 | 60 | 70 |
| T91 | 250 | 20 | 50 | 20 | 50 | 70 | 50 |
| T92 | 250 | 20 | 60 | 30 | 70 | 70 | 90 |
| T93 | 250 | 40 | 30 | 20 | 30 | 30 | 0 |
| T97 | 250 | 100 | 90 | 100 | 90 | 100 | 100 |
| T98 | 250 | 30 | 20 | 20 | 70 | 0 | 30 |
| T99 | 250 | 80 | 60 | 100 | 80 | 80 | 100 |
| T106 | 250 | 90 | 90 | 100 | 100 | 100 | 100 |
| T107 | 250 | 90 | 90 | 100 | 100 | 100 | 100 |
| T125 | 250 | 70 | 70 | 100 | 100 | 100 | 100 |
| T128 | 250 | 70 | 70 | 90 | 100 | 100 | 100 |
| T129 | 250 | 100 | 90 | 90 | 100 | 90 | 100 |
| T134 | 250 | 60 | 20 | 70 | 0 | 50 | 20 |
| T143 | 250 | 50 | 20 | 70 | 70 | 80 | 10 |
| T146 | 250 | 70 | 60 | 90 | 80 | 80 | 80 |
| T147 | 250 | 40 | 0 | 40 | 60 | 40 | 90 |
| T148 | 250 | 60 | 50 | 70 | 60 | 70 | 80 |
| T149 | 250 | 90 | 60 | 80 | 80 | 70 | 90 |
| T150 | 250 | 0 | 0 | 30 | 0 | 0 | 40 |
| T151 | 250 | 50 | 20 | 60 | 20 | 80 | 40 |
| T153 | 250 | 70 | 70 | 80 | 70 | 60 | 70 |
| T154 | 250 | 70 | 50 | 80 | 70 | 70 | 100 |
| T155 | 250 | 60 | 50 | 80 | 60 | 70 | 60 |
| T156 | 250 | 70 | 60 | 70 | 70 | 70 | 70 |
| T157 | 250 | 30 | — | 70 | 0 | 0 | 50 |
| T158 | 250 | 60 | 50 | 70 | 70 | 70 | 50 |
| T159 | 250 | 50 | 60 | 40 | 70 | 70 | 70 |

-continued

| Compound Number | Rate g/ha | ALOMY | AVEFA | LOLPE | SETFA | DIGSA | ECHCG |
|---|---|---|---|---|---|---|---|
| T160 | 250 | 30 | 50 | 40 | 70 | 40 | 40 |
| T162 | 250 | 70 | 70 | 90 | 10 | 40 | 80 |
| T163 | 250 | 70 | 60 | 90 | 90 | 90 | 80 |
| T165 | 250 | 70 | 20 | 80 | 70 | 50 | 80 |
| T167 | 250 | 30 | 40 | 40 | 0 | 30 | 50 |
| T169 | 250 | 20 | 30 | 40 | 0 | 0 | 0 |
| T170 | 250 | 80 | 40 | 90 | 70 | 70 | 80 |
| T171 | 250 | 30 | 0 | 10 | 70 | 40 | 70 |
| T173 | 250 | 90 | 70 | 100 | 60 | 70 | 70 |
| T174 | 250 | 30 | 30 | 30 | 0 | 40 | 0 |
| T177 | 250 | 60 | 50 | 70 | 50 | 10 | 70 |
| T178 | 250 | 70 | 40 | 80 | 100 | 80 | 100 |
| T179 | 250 | 70 | 60 | 80 | 10 | 60 | 70 |
| T180 | 250 | 30 | 20 | 70 | 40 | 80 | 60 |
| T181 | 250 | 40 | 40 | 80 | 70 | 90 | 100 |
| T182 | 250 | 30 | 50 | 40 | 50 | 80 | 90 |
| T184 | 250 | 30 | 60 | 70 | 90 | 70 | 60 |
| T185 | 250 | 80 | 80 | 100 | 80 | 80 | 80 |
| T187 | 250 | 10 | 20 | 60 | 40 | 20 | 10 |
| T188 | 250 | 40 | 0 | 50 | 70 | 100 | 60 |
| T193 | 250 | 20 | 30 | 60 | 40 | 20 | 20 |
| T194 | 250 | 0 | 20 | 20 | 50 | 70 | 50 |
| T199 | 250 | 0 | 50 | 60 | 60 | 100 | 80 |
| T200 | 250 | 0 | 0 | 70 | 70 | 70 | 90 |
| T203 | 250 | 20 | 20 | 60 | 70 | 70 | 90 |
| T208 | 250 | 50 | 70 | 80 | 80 | 70 | 80 |
| P3 | 250 | 100 | 100 | 100 | 90 | 90 | 100 |
| P4 | 250 | 100 | 100 | 100 | 70 | 90 | 90 |
| P5 | 250 | 100 | 100 | 100 | 90 | 100 | 90 |
| P6 | 250 | 100 | 100 | 100 | 80 | 100 | 90 |
| P9 | 250 | 100 | 100 | 100 | 80 | 90 | 80 |
| P10 | 250 | 100 | 100 | 100 | 80 | 100 | 100 |
| P14 | 250 | 100 | 100 | 100 | 100 | 100 | 100 |
| P15 | 250 | 80 | 90 | 90 | 100 | 100 | 100 |
| P16 | 250 | 100 | 90 | 100 | 100 | 100 | 100 |
| P17 | 250 | 90 | 90 | 100 | 100 | 100 | 100 |
| P18 | 250 | 100 | 100 | 100 | 100 | 100 | 100 |
| P19 | 250 | 100 | 100 | 100 | 100 | 100 | 100 |
| P20 | 250 | 100 | 80 | 100 | 100 | 100 | 100 |
| P21 | 250 | 100 | 100 | 100 | 100 | 100 | 100 |
| P22 | 250 | 100 | 100 | 100 | 100 | 100 | 100 |
| P23 | 250 | 80 | 90 | 100 | 100 | 100 | 100 |
| P24 | 250 | 90 | 90 | 100 | 100 | 100 | 100 |
| P25 | 250 | 100 | 100 | 100 | 100 | 100 | 100 |
| P26 | 250 | 100 | 90 | 100 | 100 | 100 | 100 |
| P27 | 250 | 90 | 80 | 90 | 80 | 90 | 100 |
| P28 | 250 | 90 | 80 | 100 | 80 | 90 | 80 |
| P30 | 250 | 80 | 80 | 90 | 80 | 80 | 90 |
| P33 | 250 | 90 | 70 | 100 | 80 | 80 | — |
| P36 | 250 | 70 | 80 | 100 | 80 | 80 | 100 |
| P37 | 250 | 90 | 90 | 100 | 100 | 100 | 100 |

Post-Emergence Activity

| Compound Number | Rate g/ha | ALOMY | AVEFA | LOLPE | SETFA | DIGSA | ECHCG |
|---|---|---|---|---|---|---|---|
| T1 | 125 | 90 | 90 | 80 | 100 | 100 | 100 |
| T2 | 125 | 100 | 90 | 100 | 80 | 100 | 100 |
| T3 | 125 | 60 | 30 | 60 | 90 | 100 | 100 |
| T4 | 125 | 80 | 90 | 90 | 80 | 80 | 100 |
| T5 | 125 | 70 | 70 | 80 | 90 | 100 | 100 |
| T6 | 125 | 80 | 80 | 80 | 80 | 90 | 90 |
| T7 | 125 | 100 | 90 | 90 | 90 | 70 | 90 |
| T8 | 125 | 100 | 100 | 100 | 100 | 100 | 100 |
| T9 | 125 | 80 | 60 | 70 | 80 | 100 | 100 |
| T10 | 125 | 70 | 70 | 80 | 80 | 50 | 80 |
| T11 | 125 | 40 | 20 | 30 | 70 | 80 | 70 |
| T12 | 125 | 70 | 50 | 10 | 70 | 70 | 70 |
| T13 | 125 | 80 | 90 | 90 | 100 | 50 | 100 |
| T14 | 125 | 80 | 80 | 80 | 100 | 90 | 100 |
| T15 | 125 | 50 | 40 | 40 | 50 | 80 | 80 |
| T16 | 125 | 40 | 20 | 50 | 0 | 0 | 30 |

-continued

| Compound Number | Rate g/ha | ALOMY | AVEFA | LOLPE | SETFA | DIGSA | ECHCG |
|---|---|---|---|---|---|---|---|
| T17 | 125 | 100 | 100 | 90 | 100 | 100 | 100 |
| T18 | 125 | 100 | 100 | 80 | 100 | 100 | 100 |
| T19 | 125 | 100 | 100 | 90 | 100 | 90 | 100 |
| T21 | 125 | 90 | 70 | 70 | 60 | 30 | 100 |
| T27 | 125 | 100 | 90 | 80 | 100 | 100 | 100 |
| T34 | 125 | 40 | 30 | 30 | 80 | 80 | 80 |
| T37 | 125 | 50 | 20 | 20 | 70 | 50 | 80 |
| T39 | 125 | 10 | 20 | 0 | 60 | 70 | 70 |
| T40 | 125 | 40 | 30 | 30 | 70 | 70 | 70 |
| T41 | 125 | 40 | 0 | 0 | 80 | 80 | 80 |
| T42 | 125 | 0 | 0 | 10 | 0 | 20 | 60 |
| T43 | 125 | 10 | 0 | 0 | 40 | 20 | 60 |
| T44 | 125 | 80 | 50 | 20 | 80 | 80 | 90 |
| T46 | 125 | 0 | 0 | 0 | 60 | 0 | 80 |
| T47 | 125 | 100 | 90 | 90 | 70 | 60 | 100 |
| T48 | 125 | 80 | 70 | 70 | 90 | 100 | 100 |
| T49 | 125 | 80 | 80 | 70 | 50 | 70 | 80 |
| T52 | 125 | 60 | 70 | 70 | 80 | 80 | 100 |
| T56 | 125 | 100 | 50 | 80 | 60 | 70 | 100 |
| T57 | 125 | 70 | 70 | 40 | 70 | 70 | 80 |
| T58 | 125 | 0 | 10 | 0 | 30 | 40 | 30 |
| T59 | 125 | 50 | 40 | 0 | 70 | 80 | 80 |
| T60 | 125 | 10 | 0 | 0 | 40 | 50 | 0 |
| T62 | 125 | 60 | 0 | 20 | 70 | 70 | 80 |
| T64 | 125 | 10 | 0 | 0 | 30 | 60 | 50 |
| T65 | 125 | 90 | 90 | 80 | 100 | 100 | 100 |
| T66 | 125 | 80 | 80 | 50 | 80 | 90 | 80 |
| T70 | 125 | 90 | 70 | 70 | 70 | 70 | 80 |
| T71 | 125 | 50 | 10 | 20 | 50 | 70 | 60 |
| T85 | 125 | 90 | 20 | 70 | 70 | 20 | 100 |
| T89 | 125 | 80 | 80 | 80 | 90 | 90 | 100 |
| T90 | 125 | 90 | 80 | 60 | 60 | 80 | 80 |
| T91 | 125 | 90 | 90 | 50 | 100 | 100 | 100 |
| T92 | 125 | 100 | 100 | 50 | 100 | 100 | 100 |
| T93 | 125 | 60 | 80 | 60 | 100 | 100 | 100 |
| T97 | 125 | 90 | 90 | 80 | 100 | 100 | 100 |
| T98 | 125 | 70 | 20 | 40 | 70 | 60 | 80 |
| T99 | 125 | 80 | 30 | 10 | 70 | 60 | 100 |
| T106 | 125 | 90 | 80 | 80 | 90 | 80 | 100 |
| T107 | 125 | 100 | 90 | 90 | 100 | 100 | 100 |
| T125 | 125 | 80 | 70 | 70 | 80 | 80 | 90 |
| T128 | 125 | 80 | 90 | 80 | 100 | 100 | 100 |
| T129 | 125 | 80 | 80 | 70 | 100 | 80 | 100 |
| T134 | 125 | 20 | 20 | 20 | 50 | 20 | 70 |
| T143 | 125 | 40 | 60 | 30 | 40 | 60 | 70 |
| T146 | 125 | 80 | 80 | 90 | 70 | 70 | 100 |
| T147 | 125 | 90 | 90 | 40 | 70 | 100 | 90 |
| T149 | 125 | 80 | 90 | 70 | 70 | 80 | 100 |
| T150 | 125 | 60 | 60 | 40 | 90 | 30 | 100 |
| T151 | 125 | 80 | 80 | 30 | 10 | 70 | 80 |
| T153 | 125 | 50 | 80 | 50 | 20 | 30 | 70 |
| T154 | 125 | 90 | 60 | 60 | 70 | 70 | 100 |
| T155 | 125 | 90 | 70 | 60 | 100 | 100 | 100 |
| T156 | 125 | 90 | 80 | 70 | 100 | 70 | 100 |
| T157 | 125 | 60 | 60 | 40 | 60 | 60 | 100 |
| T158 | 125 | 90 | 90 | 80 | 100 | 100 | 100 |
| T159 | 125 | 90 | 70 | 40 | 100 | 100 | 100 |
| T160 | 125 | 90 | 90 | 70 | 100 | 100 | 100 |
| T162 | 125 | 90 | 90 | 70 | 100 | 100 | 100 |
| T163 | 125 | 80 | 80 | 80 | 90 | 70 | 100 |
| T165 | 125 | 80 | 30 | 80 | 90 | 70 | 100 |
| T167 | 125 | 80 | 50 | 50 | 70 | 70 | 100 |
| T169 | 125 | 90 | 10 | 30 | 60 | 40 | 80 |
| T170 | 125 | 80 | 70 | 80 | 40 | 40 | 100 |
| T171 | 125 | 70 | 60 | 20 | 90 | 80 | 100 |
| T173 | 125 | 100 | 90 | 90 | 90 | 70 | 100 |
| T174 | 125 | 70 | 70 | 40 | 50 | 70 | 80 |
| T177 | 125 | 80 | 70 | 30 | 20 | 30 | 80 |
| T178 | 125 | 100 | 90 | 90 | 100 | 100 | 100 |
| T179 | 125 | 80 | 80 | 80 | 10 | 50 | 70 |
| T180 | 125 | 90 | 70 | 70 | 100 | 90 | 100 |
| T181 | 125 | 90 | 90 | 80 | 100 | 80 | 100 |
| T182 | 125 | 100 | 90 | 80 | 100 | 100 | 100 |
| T184 | 125 | 10 | 0 | 10 | 50 | 20 | 100 |
| T185 | 125 | 90 | 80 | 80 | 100 | 100 | 100 |
| T187 | 125 | 70 | 10 | 40 | 60 | 60 | 70 |
| T188 | 125 | 80 | 70 | 30 | 70 | 100 | 100 |

-continued

| Compound Number | Rate g/ha | ALOMY | AVEFA | LOLPE | SETFA | DIGSA | ECHCG |
|---|---|---|---|---|---|---|---|
| T193 | 125 | 60 | 40 | 30 | 30 | 60 | 60 |
| T194 | 125 | 30 | 0 | 20 | 0 | 70 | 80 |
| T199 | 125 | 100 | 100 | 60 | 80 | 100 | 100 |
| T200 | 125 | 70 | 80 | 80 | 100 | 100 | 100 |
| T203 | 125 | 20 | 10 | 10 | 0 | 50 | 50 |
| T208 | 125 | 70 | 70 | 80 | 70 | 50 | 80 |
| P3 | 125 | 100 | 90 | 100 | 80 | 70 | 100 |
| P4 | 125 | 100 | 90 | 100 | 90 | 80 | 100 |
| P5 | 125 | 100 | 90 | 100 | 80 | 60 | 100 |
| P6 | 125 | 100 | 90 | 100 | 80 | 80 | 100 |
| P9 | 125 | 100 | 90 | 100 | 80 | 80 | 90 |
| P10 | 125 | 100 | 90 | 100 | 80 | 80 | 100 |
| P14 | 125 | 90 | 90 | 90 | 100 | 100 | 100 |
| P15 | 125 | 100 | 90 | 90 | 80 | 80 | 100 |
| P16 | 125 | 100 | 90 | 100 | 100 | 100 | 100 |
| P17 | 125 | 100 | 90 | 100 | 100 | 100 | 100 |
| P18 | 125 | 90 | 50 | 80 | 70 | 70 | 100 |
| P19 | 125 | 100 | 100 | 100 | 100 | 100 | 100 |
| P20 | 125 | 100 | 100 | 100 | 90 | 80 | 100 |
| P21 | 125 | 90 | 100 | 100 | 100 | 80 | 100 |
| P22 | 125 | 100 | 100 | 100 | 100 | 100 | 100 |
| P23 | 125 | 100 | 90 | 90 | 80 | 70 | 100 |
| P24 | 125 | 100 | 100 | 100 | 100 | 70 | 100 |
| P25 | 125 | 100 | 90 | 100 | 80 | 80 | 100 |
| P26 | 125 | 100 | 100 | 90 | 100 | 100 | 100 |
| P24 | 125 | 80 | 60 | 70 | 90 | 100 | 90 |
| P28 | 125 | 80 | 80 | 70 | 80 | 80 | 100 |
| P30 | 125 | 80 | NC | 70 | 80 | 90 | 100 |
| P33 | 125 | 80 | 70 | 80 | 70 | 70 | 90 |
| P36 | 125 | 60 | 70 | 60 | 80 | 80 | 90 |
| P37 | 125 | 90 | 80 | 90 | 100 | 90 | 100 |

Test Example 2

Test compounds were applied post-emergence at 60 g ai/ha, alone and in combination with cloquintocet-mexyl at 60 g ai/ha; the adjuvant Adigor (0.5%) was included for every treatment. The application volume was 200 l/ha. Target plants were 2-3 leaf seedlings of winter wheat 'Hereward' and winter barley 'Antoniya' grown in a greenhouse under ambient conditions. Assessments were made at 14-21 days after application.

| Compound | Rate (g/ha) | Cloquintocet-mexyl (g/ha) | Crop Injury (%) Wheat | Crop Injury (%) Barley |
|---|---|---|---|---|
| T1 | 60 | 0 | 85 | 99 |
|  | 60 | 60 | 18 | 73 |
| T3 | 60 | 0 | 28 | 5 |
|  | 60 | 60 | 0 | 5 |
| 1:1 mixture of T106:T107 | 60 | 0 | 63 | 85 |
|  | 60 | 60 | 23 | 45 |

Test Example 3

The test compound T1 was applied at 100 and 200 g ai/ha, alone and in combination with a range of safeners as 1:1 mixtures (for example at 100 g+100 g; 200 g+200 g) to the test plants—wheat and maize—at the 2-3 leaf stage. A 4-way safener mixture (cloquintocet-mexyl, benoxacor, fluxofenim and compound A*) was also applied with the test compound so that each safener was used a 1:1 ratio (for example at 100+100+100+100+100 g ai/ha). Assessments were made at 14-21 days after application.

| Test Sample | Wheat Injury (%) 100 g/ha | Wheat Injury (%) 200 g/ha | Maize Injury (%) 100 g/ha | Maize Injury (%) 200 g/ha |
|---|---|---|---|---|
| T1 alone | 83 | 92 | 90 | 100 |
| T1 + benoxacor at 1:1 ratio | 80 | 85 | 90 | 75 |
| T1 + cloquintocet-mexyl at 1:1 ratio | 5 | 10 | 93 | 95 |
| T1 + isoxadifen at 1:1 ratio | 65 | 73 | 65 | 75 |
| T1 + cyprosulfamide at 1:1 ratio | 68 | 85 | 23 | 28 |
| T1 + compound A* at 1:1 ratio | 73 | 88 | 30 | 35 |
| T1 + fluxofenim at 1:1 ratio | 75 | 90 | 85 | 88 |
| T1 + mefenpyr-diethyl at 1:1 ratio | 23 | 45 | 100 | 100 |
| T1 + dichlormid at 1:1 ratio | 73 | 73 | 80 | 100 |
| T1 + 4-way mix at 1:1:1:1 ratio | 0 | 20 | 30 | 50 |

*Compound A is N-(2-methoxybenzoyl)-4-[(methylaminocarbonyl)amino]benzenesulfonamide.

What is claimed is:

1. A compound of formula I wherein

G is hydrogen or an alkali metal, alkaline earth metal, sulfonium, ammonium or a latentiating group, $R^1$ is methyl, ethyl, n-propyl, isopropyl, cyclopropyl, halomethyl, haloethyl, vinyl, ethynyl, halogen, $C_1$-$C_2$alkoxy or $C_1$-$C_2$haloalkoxy, $R^2$, $R^3$ and $R^4$ are independently of each other hydrogen, methyl, ethyl, n-propyl, isopropyl, cyclopropyl, halomethyl, haloethyl, vinyl, ethynyl, halogen, $C_1$-$C_2$alkoxy or $C_1$-$C_2$ haloalkoxy, $R^5$ and $R^{12}$ are independently of each other hydrogen, $C_1$-$C_3$alkyl, $C_1$-$C_3$haloalkyl, $C_1$-$C_3$alkyoxy, $C_1$-$C_3$alkylthio, halogen or $C_1$-$C_6$alkoxycarbonyl, or $R^5$ and $R^{12}$ join together to form a 3-7 membered carbocyclic ring, optionally containing an oxygen or sulfur atom, and wherein $R^6$ and $R^{11}$ are independently of each other hydrogen, halogen, formyl, cyano or nitro or $R^6$ and $R^{11}$ are independently of each other $C_1$-$C_6$alkyl, $C_2$-$C_6$alkenyl, $C_2$-$C_6$alkynyl, $C_1$-$C_6$alkoxy, $C_3$-$C_7$ cycloalkyl, $C_3$-$C_7$ cycloalkenyl, phenyl, heteroaryl or a 3-7 membered heterocyclyl, where all these substituents are optionally substituted, or $R^6$ and $R^{11}$ are independently of each other a group $COR^{13}$, $CO_2R^{14}$ or $CONR^{15}R^{16}$, $CR^{17}$=$NOR^{18}$, $CR^{19}$=$NNR^{20}R^{21}$, $NHR^{22}$, $NR^{22}R^{23}$ or $OR^{24}$, wherein $R^{13}$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted, $R^{14}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted, $R^{15}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, phenyl, heteroaryl or a 3-7 membered heterocyclyl, where all these substituents are optionally substituted, and $R^{16}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, phenylsulfonyl, heteroarylsulfonyl, $C_1$-$C_6$alkylamino, di$C_1$-$C_6$alkylamino, phenyl, heteroaryl or a 3-7 membered heterocyclyl, where all these substituents are optionally substituted, or amino, or $R^{15}$ and $R^{16}$ are joined to form an optionally substituted 3-7 membered ring, optionally containing an oxygen, sulfur or nitrogen atom, and $R^{17}$ and $R^{19}$ are independently of each other hydrogen, $C_1$-$C_3$alkyl or $C_3$-$C_6$cycloalkyl, $R^{18}$, $R^{20}$ and $R^{21}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, phenyl or heteroaryl, where all these substituents are optionally substituted, or aminocarbonyl, and $R^{22}$ is $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenylcarbonyl, phenoxycarbonyl, phenylaminocarbonyl, phenylthiocarbonyl, phenylsulfonyl, heteroarylcarbonyl, heteroaryloxycarbonyl, heteroarylaminocarbonyl, heteroarylthiocarbonyl or heteroarylsulfonyl, where all these substituents are optionally substituted, and $R^{23}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl, where all these substituents are optionally substituted, or $R^{22}$ and $R^{23}$ are joined to form an optionally substituted 3-7 membered ring, optionally containing an oxygen, sulfur or nitrogen atom, where all these substituents are optionally substituted, and $R^{24}$ is $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, tri($C_1$-$C_6$alkyl)silyl, phenyl or heteroaryl, where all these substituents are optionally substituted, or aminocarbonyl;

and wherein $R^7$, $R^8$, $R^9$ and $R^{10}$ are independently of each other hydrogen, halogen, hydroxyl, formyl, amino, cyano or nitro, or $R^7$, $R^8$, $R^9$ and $R^{10}$ are independently of each other $C_1$-$C_6$alkyl, $C_2$-$C_6$alkenyl, $C_2$-$C_6$alkynyl, $C_1$-$C_6$alkoxy, $C_1$-$C_6$alkoxy$C_1$-$C_6$alkyl, $C_1$-$C_6$alkylthio, $C_1$-$C_6$alkylsulfinyl, $C_1$-$C_6$alkylsulfonyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_3$-$C_7$ cycloalkyl, $C_4$-$C_7$cycloalkenyl, tri($C_1$-$C_6$alkyl)silyl, aryl, heteroaryl or a 3-7 membered heterocyclyl, where all these substituents are optionally substituted, or $R^7$, $R^8$, $R^9$ and $R^{10}$ are independently of each other a group $COR^{13A}$, $CO_2R^{14A}$ or $CONR^{15A}R^{16A}$, $CR^{17A}$=$NOR^{18A}$, $CR^{19A}$=$NNR^{20A}R^{21A}$, $NR^{22A}R^{23A}$ or $OR^{24A}$, or $R^7$ and $R^8$, or $R^9$ and $R^{10}$, together form a unit =O, or form a unit =$CR^{25}R^{26}$, or form a unit =$NR^{27}$, or any two of $R^7$, $R^8$, $R^9$ and $R^{10}$ form a 3-8 membered ring, optionally containing a heteroatom selected from O, S and N and optionally substituted by: $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, $C_1$-$C_3$haloalkyl, halogen, phenyl; phenyl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, $C_1$-$C_4$alkoxycarbonyl, aminocarbonyl, $C_1$-$C_6$alkylaminocarbonyl, di$C_1$-$C_6$alkylaminocarbonyl, halogen, cyano or by nitro; or heteroaryl or heteroaryl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, halogen, cyano or by nitro, or $R^7$ and $R^{10}$ together form a bond;

and wherein $R^{13A}$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted, $R^{14A}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted, $R^{15A}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, phenyl, heteroaryl or a 3-7 membered heterocyclyl, where all these substituents are optionally substituted, and $R^{16A}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, $C_1$-$C_6$alkylamino, di$C_1$-$C_6$alkylamino, phenyl, heteroaryl or a 3-7 membered heterocyclyl, where all these substituents are optionally substituted, or amino, or $R^{15A}$ and $R^{16A}$ are joined to form an optionally substituted 3-7 membered ring, optionally containing an oxygen, sulfur or nitrogen atom, and $R^{17A}$ and $R^{19A}$ are independently of each other hydrogen, $C_1$-$C_3$alkyl or $C_3$-$C_6$cycloalkyl, $R^{18A}$, $R^{20A}$ and $R^{21A}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, phenyl or heteroaryl, where all these substituents are optionally substituted, and $R^{22A}$ and $R^{23A}$ are independently of each other $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl, or $R^{22A}$ and $R^{23A}$ are joined to form an optionally substituted 3-7 membered ring, optionally containing an oxygen, sulfur or nitrogen atom, where all these substituents are optionally substituted, and $R^{24A}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, tri($C_1$-$C_6$alkyl)silyl, phenyl or heteroaryl, where all these substituents are optionally substituted;

and wherein $R^{25}$ and $R^{26}$ are independently of each other hydrogen, halogen, cyano or nitro, or $R^{25}$ and $R^{26}$ are independently of each other $C_1$-$C_6$alkyl, $C_1$-$C_6$alkoxy, $C_1$-$C_6$alkylamino, di$C_1$-$C_6$alkylamino, $C_1$-$C_6$alkylcarbonyl, $C_1$-$C_6$alkoxycarbonyl, $C_1$-$C_6$alkylaminocarbonyl, di$C_1$-$C_6$alkylaminocarbonyl, N-phenyl-N—$C_1$-$C_6$alkylaminocarbonyl, N-phenyl$C_1$-$C_6$alkyl-N—$C_1$-$C_6$alkylaminocarbonyl, N-heteroaryl-N—$C_1$-$C_6$alkylaminocarbonyl, N-heteroaryl$C_1$-$C_6$alkyl-N—$C_1$-$C_6$alkylaminocarbonyl, phenyl, heteroaryl, $C_3$-$C_8$cycloalkyl or 3-7 membered heterocyclyl, where all these substituents are optionally substituted, or $R^{25}$ and $R^{26}$ are joined together to form a 5-8 membered ring optionally containing a heteroatom selected from O, S and N and optionally substituted by $C_1$-$C_2$alkyl or $C_1$-$C_2$alkoxy, and $R^{27}$ is nitro or cyano, or $R^{27}$ is $C_1$-$C_6$alkylamino, di$C_1$-$C_6$alkylamino, $C_1$-$C_6$alkoxy, $C_3$-$C_6$alkenyloxy, $C_3$-$C_6$alkynyloxy, phenoxy, phenylamino, N-phenyl-N—$C_1$-$C_6$alkylamino, N-phenyl$C_1$-$C_6$alkyl-N—$C_1$-$C_6$alkylamino, heteroaryloxy, heteroarylamino, N-heteroaryl-N—$C_1$-$C_6$alkylamino or N-heteroaryl$C_1$-$C_6$alkyl-N—$C_1$-$C_6$alkylamino, where all these substituents are optionally substituted;

and wherein, when G is a latentiating group then G is selected from the groups phenyl$C_1$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro; heteroaryl$C_1$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro; $C_3$ alkenyl, $C_3$ haloalkenyl, $C_3$ alkynyl, $C(X^a\text{—}R^a$, $C(X^b)\text{—}X^c\text{—}R^b$, $C(X^d)\text{—}N(R^c)\text{—}R^d$, —$SO_2$—$R^e$, —$P(X^e)(R^f)$—$R^g$ and $CH_2$—$X^f$—$R^h$;

wherein $X^a$, $X^b$, $X^c$, $X^d$, $X^e$ and $X^f$ are independently of each other oxygen or sulfur; and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl; phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro;

or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl; phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl; phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di-$C_3$-$C_7$cycloalkylamino or $C_3$-$C_7$cycloalkoxy;

or $R^c$ and $R^d$ may join together to form a 3-7 membered ring, optionally containing one heteroatom selected from O and S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl; phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl; phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro; $C_2$-$C_5$haloalkenyl, $C_3$-$C_8$cycloalkyl;

phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl; phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro; heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl,$C_1$-$C_3$ alkylsulfonyl, halogen, cyano or by nitro; phenoxy$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro; heteroaryloxy$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro; $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein, when present, optional substituents on an alkyl moiety, either alone or as part of a larger group, are selected from one or more of halogen, nitro, cyano, $C_{3-7}$ cycloalkyl optionally substituted with $C_{1-6}$ alkyl or halogen, $C_{5-7}$ cycloalkenyl optionally substituted with $C_{1-6}$ alkyl or halogen, hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy where the aryl group is optionally substituted, $C_{3-7}$ cycloalkyloxy where the cycloalkyl group is optionally substituted with $C_{1-6}$ alkyl or halogen, $C_{3-10}$ alkenyloxy, $C_{3-10}$ alkynyloxy, mercapto, $C_{1-10}$ alkylthio, $C_{1-10}$ haloalkylthio, aryl($C_{1-4}$)alkylthio where the aryl group is optionally substituted, $C_{3-7}$ cycloalkylthio where the cycloalkyl group is optionally substituted with $C_{1-6}$ alkyl or halogen, tri($C_{1-4}$)alkylsilyl($C_{1-6}$)alkylthio, arylthio where the aryl group is optionally substituted, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl where the aryl group is optionally substituted, tri($C_{1-4}$)alkylsilyl, aryldi($C_{1-4}$)alkylsilyl, ($C_{1-4}$)alkyldiarylsilyl, triarylsilyl, aryl($C_{1-4}$)alkylthio($C_{1-4}$)alkyl, aryloxy($C_{1-4}$)alkyl, formyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy where the aryl group is optionally substituted, di($C_{1-6}$)alkylaminocarbonyloxy, $C_{1-6}$alkyliminooxy, $C_{3-6}$alkenyloxyimino, aryloxyimino, optionally substituted aryl, optionally substituted heteroaryl heterocyclyl optionally substituted with $C_{1-6}$ alkyl or halogen, aryloxy where the aryl group is optionally substituted, heteroaryloxy where the heteroaryl group is optionally substituted, heterocyclyloxy where the heterocyclyl group is optionally substituted with $C_{1-6}$ alkyl or halogen, amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$) alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl where the aryl group is optionally substituted, and arylcarbonyl where the aryl group is optionally substituted;

wherein, when present, optional substituents on alkenyl or alkynyl are selected from those optional substituents defined above for an alkyl moiety;

wherein, when present, optional substituents on cycloalkyl or cycloalkenyl are selected from $C_{1-3}$ alkyl and those optional substituents defined above for an alkyl moiety;

wherein, when present, the optional substituents on aryl, heteroaryl and carbocycles, unless otherwise indicated, are selected, independently, from: halogen, nitro, cyano, isothiocyanato, $C_{1-6}$ alkyl, $C_{1-6}$ haloalkyl, $C_1$alkoxy($C_{1-6}$)alkyl, $C_{2-6}$ alkenyl, $C_{2-6}$ haloalkenyl, $C_{2-6}$ alkynyl, $C_3$ cycloalkyl optionally substituted with $C_1$ alkyl or halogen, $C_{5-7}$ cycloalkenyl optionally substituted with $C_1$ alkyl or halogen, hydroxy, alkoxy within which the alkyl moiety is $C_1$-$C_3$ alkyl, $C_1$alkoxy($C_1$)alkoxy, $C_1$alkoxycarbonyl($C_1$)alkoxy, $C_1$ haloalkoxy, $C_3$ alkenyloxy, $C_3$ alkynyloxy, mercapto, $C_1$ alkylthio, $C_1$ haloalkylthio, $C_1$ alkylsulfonyl, $C_1$ haloalkylsulfonyl, $C_1$ alkylsulfinyl, $C_1$ haloalkylsulfinyl, $C_1$ alkylcarbonyl, $HO_2C$, $C_1$ alkoxycarbonyl, aminocarbonyl, $C_1$ alkylaminocarbonyl, di($C_1$alkyl)aminocarbonyl, N—($C_1$alkyl)-N—($C_1$alkoxy)aminocarbonyl, $C_1$ alkylcarbonyloxy, di($C_1$)alkylamino-carbonyloxy, amino, $C_1$ alkylamino, di($C_1$)alkylamino, $C_1$ alkylcarbonylamino, and N—$C_1$alkylcarbonyl)—N—($C_1$alkyl)amino;

wherein, for substituted heterocyclyl groups then the one or more substituents are independently selected from halogen, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, nitro and cyano;

and wherein "heterocyclyl" means a non-aromatic monocyclic or bicyclic ring system containing up to 7 atoms including one or two heteroatoms selected from O, S and N;

wherein "aryl" means phenyl;

and wherein "heteroaryl" means an aromatic ring system containing at least one heteroatom and consisting either of a single ring or two fused rings.

2. A compound according to claim 1, wherein $R^1$, $R^2$ and $R^4$ are methyl and $R^3$ is hydrogen.

3. A compound according to claim 1, wherein $R^1$, $R^2$ and $R^4$ are methyl and $R^3$ is hydrogen, and $R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxyC$_1$-$C_6$alkyl, 3-7 membered heterocyclyl, optionally substituted aryl or optionally substituted heteroaryl.

4. A compound according to claim 1, wherein $R^5$ and $R^{12}$ are independently of each other hydrogen or $C_1$-$C_3$alkyl.

5. A compound according to claim 1, wherein $R^1$ is methyl, ethyl, vinyl, ethynyl, cyclopropyl, difluoromethoxy, trifluoromethoxy or $C_1$-$C_2$ alkoxy and $R^2$, $R^3$ and $R^4$ are independently of each other hydrogen, methyl, ethyl, vinyl or ethynyl.

6. A process for the preparation of a compound of formula (AH)

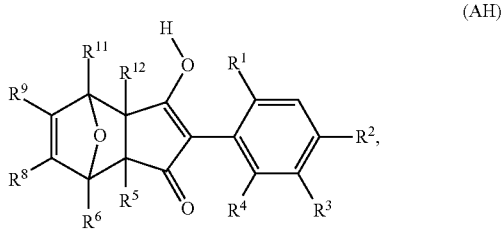

wherein $R^1$, $R^2$, $R^3$, $R^4$, $R^5$, $R^6$, $R^8$, $R^9$, $R^{11}$ and $R^{12}$ are as defined in claim 1, which comprises reacting a compound of formula (H)

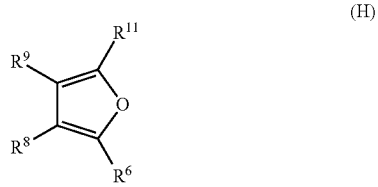

with a compound of formula (AI)

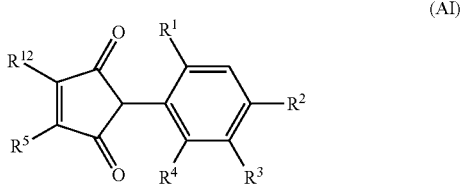

in the presence or absence of a catalyst and in the presence or absence of a solvent.

7. A herbicidal composition, which, in addition to comprising at least one formulation adjuvant, comprises a herbicidally effective amount of a compound of formula I as defined in claim 1.

8. A herbicidal composition according to claim 7, which, in addition to comprising at least one formulation adjuvant, comprises a herbicidally effective amount of a compound of formula I and a further herbicide.

9. A herbicidal composition according to claim 7, which, in addition to comprising at least one formulation adjuvant, comprises a herbicidally effective amount of a compound of formula I, a further herbicide and a safener.

10. A method of controlling grasses and weeds in crops of useful plants, which comprises applying a herbicidally effective amount of a compound of formula I as defined in claim 1, or of a composition comprising such a compound, to the plants or to the locus thereof.

11. A compound according to claim 1, wherein $R^6$ and $R^{11}$ are independently of each other hydrogen, methyl or methyl substituted by $C_1$-$C_3$alkoxy.

12. A compound according to claim 1, wherein $R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxyC$_1$-$C_6$alkyl, 3-7 membered heterocyclyl, optionally substituted phenyl or optionally substituted heteroaryl.

13. A compound according to claim 12, wherein $R^7$, $R^8$, $R^9$ and $R^{10}$ are independently of each other hydrogen, methyl, ethyl or optionally substituted phenyl.

14. A compound according to claim 12, wherein one of $R^7$, $R^8$, $R^9$ and $R^{10}$ is furyl, thienyl, pyrazolyl, 1,2,3-triazolyl, 1,2,4-triazolyl, pyridyl, pyrimidinyl, pyridazinyl, pyrazinyl, quinolinyl, isoquinolinyl, cinnolinyl, quinazolinyl or quinoxalinyl, wherein each of these heteroaryls is optionally substituted.

15. A compound according to claim 14, wherein one of $R^7$, $R^8$, $R^9$ and $R^{10}$ is pyridyl substituted once or twice by trifluoromethyl or halogen.

16. A compound according to claim 1, wherein:
$R^5$ and $R^{12}$ are independently of each other hydrogen or $C_1$-$C_3$alkyl; and
$R^6$ and $R^{11}$ are independently of each other hydrogen, methyl or methyl substituted by $C_1$-$C_3$alkoxy;
and wherein $R^7$, $R^8$, $R^9$ and $R^{13}$ are independently of each other hydrogen, cyano, $C_1$-$C_6$alkyl, $C_2$alkenyl, $C_1$alkoxy, $C_1$alkoxyC$_1$alkyl, optionally substituted phenyl or optionally substituted heteroaryl; provided that:
either (a) $R^7$, $R^8$, $R^9$ and $R^{13}$ are independently of each other hydrogen, methyl, ethyl or optionally substituted phenyl;
or (b) one of $R^7$, $R^8$, $R^9$ and $R^{13}$ is furyl, thienyl, pyrazolyl, 1,2,3-triazolyl, 1,2,4-triazolyl, pyridyl, pyrimidinyl, pyridazinyl, pyrazinyl, quinolinyl, isoquinolinyl, cinnolinyl, quinazolinyl or quinoxalinyl, wherein each of these heteroaryls is optionally substituted.

17. A compound according to claim 16, wherein $R^5$ and $R^{12}$ are hydrogen.

18. A compound according to claim 17, wherein $R^7$, $R^8$, $R^9$ and $R^{10}$ are hydrogen.

19. A compound according to claim 17, wherein $R^1$ is methyl, ethyl, vinyl, ethynyl, cyclopropyl, difluoromethoxy, trifluoromethoxy or $C_1$-$C_2$ alkoxy, and $R^2$, $R^3$ and $R^4$ are independently of each other hydrogen, methyl, ethyl, vinyl or ethynyl.

20. A compound according to claim 18, wherein $R^1$ is methyl, ethyl, vinyl, ethynyl, cyclopropyl, difluoromethoxy, trifluoromethoxy or $C_1$-$C_2$ alkoxy, and $R^2$, $R^3$ and $R^4$ are independently of each other hydrogen, methyl, ethyl, vinyl or ethynyl.

* * * * *